(12) United States Patent
Chien et al.

(10) Patent No.: US 7,303,893 B1
(45) Date of Patent: Dec. 4, 2007

(54) CRYSTALLIZATION OF C-KIT TYROSINE KINASE LEADING TO AUTOINHIBITED CRYSTAL STRUCTURE

(75) Inventors: Ellen Chien, La Jolla, CA (US); Ciaran N. Cronin, San Diego, CA (US); Douglas R. Dougan, Calgary (CA); Clifford D. Mol, San Diego, CA (US); Bi Ching Sang, San Diego, CA (US); Hua Zou, San Diego, CA (US)

(73) Assignee: Takeda San Diego, Inc., San Diego, CA (US)

( * ) Notice: Subject to any disclaimer, the term of this patent is extended or adjusted under 35 U.S.C. 154(b) by 393 days.

(21) Appl. No.: 10/651,494

(22) Filed: Aug. 28, 2003

(51) Int. Cl.
*C12Q 1/48* (2006.01)
*C12N 9/12* (2006.01)
*G06F 19/00* (2006.01)

(52) U.S. Cl. .......................... 435/15; 435/194; 702/27
(58) Field of Classification Search ...................... None
See application file for complete search history.

(56) References Cited

U.S. PATENT DOCUMENTS

2004/0137518 A1  7/2004 Lambert et al.

FOREIGN PATENT DOCUMENTS

WO    WO 01/16181 A2    3/2001

OTHER PUBLICATIONS

Brunger, Axel T. et al., "Crystallography & NMR System: A New Software Suite for Macromolecular Structure Determination", Acta Cryst. (1998) D54, pp. 905-921.
Creighton, Thomas E. et al., Encyclopedia of Molecular Biology, vol. 1, New York, 1999, pp. 586 and 2725.
Drenth, Jan, "Principles of Protein X-ray Crystallography", Springer, New York, 1995, p. 1.
Hegyi, Heidi et al., "The Relationship between Protein Structure and Function: a Comprehensive Survey with Application to the Yeast Genome", J. Mol. Biol. (1999) 288, 147-164.
Kierzek, Andrzej M. et al., Biophysical Chemistry, "Models of protein crystal growth", (2001), pp. 1-20.
Mol, Clifford et al., Accelerated Publication, "Structure of a c-Kit Product Complex Reveals the Basis for Kinase Transactivation", The Journal of Biological Chemistry, vol. 278, No. 34, Aug. 2003, pp. 31461-31464.
Tooze, John et al., "Introduction to Protein Structure" Second Edition; Garland Publishing Inc., New York, (1999), pp. 373-375.
Wiencek, J.M. , "New Strategies for Protein Crystal Growth", Ann. Review Biomed. Enginr 1999, 1, pp. 505-536.

*Primary Examiner*—Nashaat T. Nashed
(74) *Attorney, Agent, or Firm*—David J. Weitz

(57) ABSTRACT

Provided are crystals relating to the autoinhibited structure of c-KIT tyrosine kinase (c-KIT) and its various uses.

15 Claims, 62 Drawing Sheets

FIGURE 1

Amino acid sequence for full-length human wild type c-KIT [SEQ. ID No. 1]
(Residues 544-693 and 753-935 are underlined)

```
   1 MRGARGAWDF LCVLLLLLRV QTGSSQPSVS PGEPSPPSIH PGKSDLIVRV GDEIRLLCTD
  61 PGFVKWTFEI LDETNENKQN EWITEKAEAT NTGKYTCTNK HGLSNSIYVF VRDPAKLFLV
 121 DRSLYGKEDN DTLVRCPLTD PEVTNYSLKG CQGKPLPKDL RFIPDPKAGI MIKSVKRAYH
 181 RLCLHCSVDQ EGKSVLSEKF ILKVRPAFKA VPVVSVSKAS YLLREGEEFT VTCTIKDVSS
 241 SVYSTWKREN SQTKLQEKYN SWHHGDFNYE RQATLTISSA RVNDSGVFMC YANNTFGSAN
 301 VTTTLEVVDK GFINIFPMIN TTVFVNDGEN VDLIVEYEAF PKPEHQQWIY MNRTFTDKWE
 361 DYPKSENESN IRYVSELHLT RLKGTEGGTY TFLVSNSDVN AAIAFNVYVN TKPEILTYDR
 421 LVNGMLQCVA AGFPEPTIDW YFCPGTEQRC SASVLPVDVQ TLNSSGPPFG KLVVQSSIDS
 481 SAFKHNGTVE CKAYNDVGKT SAYFNFAFKG NNKEQIHPHT LFTPLLIGFV IVAGMMCIIV
 541 MILTYKYLQK PMYEVQWKVV EEINGNNYVY IDPTQLPYDH KWEFPRNRLS FGKTLGAGAF
 601 GKVVEATAYG LIKSDAAMTV AVKMLKPSAH LTEREALMSE LKVLSYLGNH MNIVNLLGAC
 661 TIGGPTLVIT EYCCYGDLLN FLRRKRDSFI CSKQEDHAEA ALYKNLLHSK ESSCSDSTNE
 721 YMDMKPGVSY VVPTKADKRR SVRIGSYIER DVTPAIMEDD ELALDLEDLL SFSYQVAKGM
 781 AFLASKNCIH RDLAARNILL THGRITKICD FGLARDIKND SNYVVKGNAR LPVKWMAPES
 841 IFNCVYTFES DVWSYGIFLW ELFSLGSSPY PGMPVDSKFY KMIKEGFRML SPEHAPAEMY
 901 DIMKTCWDAD PLKRPTFKQI VQLIEKQISE STNHIYSNLA NCSPNRQKPV VDHSVRINSV
 961 GSTASSSQPL LVHDDV
```

Human cDNA sequence encoding residues 544-935 of c-KIT [SEQ. ID No. 2]

```
    1 ACCTACAAAT ATTTACAGAA ACCCATGTAT GAAGTACAGT GGAAGGTTGT TGAGGAGATA
   61 AATGGAAACA ATTATGTTTA CATAGACCCA ACACAACTTC CTTATGATCA CAAATGGGAG
  121 TTTCCCAGAA ACAGGCTGAG TTTTGGGAAA ACCCTGGGTG CTGGAGCTTT CGGGAAGGTT
  181 GTTGAGGCAA CTGCTTATGG CTTAATTAAG TCAGATGCGG CCATGACTGT CGCTGTAAAG
  241 ATGCTCAAGC CGAGTGCCCA TTTGACAGAA CGGGAAGCCC TCATGTCTGA ACTCAAAGTC
  301 CTGAGTTACC TTGGTAATCA CATGAATATT GTGAATCTAC TTGGAGCCTG CACCATTGGA
  361 GGGCCCACCC TGGTCATTAC AGAATATTGT TGCTATGGTG ATCTTTTGAA TTTTTTGAGA
  421 AGAAAACGTG ATTCATTTAT TTGTTCAAAG CAGGAAGATC ATGCAGAAGC TGCACTTTAT
  481 AAGAATCTTC TGCATTCAAA GGAGTCTTCC TGCAGCGATA GTACTAATGA GTACATGGAC
  541 ATGAAACCTG GAGTTTCTTA TGTTGTCCCA ACCAAGGCCG ACAAAAGGAG ATCTGTGAGA
  601 ATAGGCTCAT ACATAGAAAG AGATGTGACT CCCGCCATCA TGGAGGATGA CGAGTTGGCC
  661 CTAGACTTAG AAGACTTGCT GAGCTTTTCT TACCAGGTGG CAAAGGGCAT GGCTTTCCTC
  721 GCCTCCAAGA ATTGTATTCA CAGAGACTTG GCAGCCAGAA ATATCCTCCT TACTCATGGT
  781 CGGATCACAA AGATTTGTGA TTTTGGTCTA GCCAGAGACA TCAAGAATGA TTCTAATTAT
  841 GTGGTTAAAG GAAACGCTCG ACTACCTGTG AAGTGGATGG CACCTGAAAG CATTTTCAAC
  901 TGTGTATACA CGTTTGAAAG TGACGTCTGG TCCTATGGGA TTTTTCTTTG GGAGCTGTTC
  961 TCTTTAGGAA GCAGCCCCTA TCCTGGAATG CCGGTCGATT CTAAGTTCTA CAAGATGATC
 1021 AAGGAAGGCT TCCGGATGCT CAGCCCTGAA CACGCACCTG CTGAAATGTA TGACATAATG
 1081 AAGACTTGCT GGGATGCAGA TCCCCTAAAA AGACCAACAT TCAAGCAAAT TGTTCAGCTA
 1141 ATTGAGAAGC AGATTTCAGA GAGCACCAAT CATATT
```

FIGURE 1 (cont.)

Amino acid sequence for residues 544-693 and 753-935 of c-KIT with a
N-terminal 6x-histidine tag, a spacer region, an rTEV protease cleavage site, and a Ser residue
inserted between residues Thr753 and Pro754 [SEQ. ID No. 3]
(6x-histidine tag, spacer region and rTEV protease cleavage site are underlined)

```
  1 MSYYHHHHHH DYDIPTTENL YFQGAMEPGG STYKYLQKPM YEVQWKVVEE INGNNYVYID
 61 PTQLPYDHKW EFPRNRLSFG KTLGAGAFGK VVEATAYGLI KSDAAMTVAV KMLKPSAHLT
121 EREALMSELK VLSYLGNHMN IVNLLGACTI GGPTLVITEY CCYGDLLNFL RRKRDSFICS
181 KTSPAIMEDD ELALDLEDLL SFSYQVAKGM AFLASKNCIH RDLAARNILL THGRITKICD
241 FGLARDIKND SNYVVKGNAR LPVKWMAPES IFNCVYTFES DVWSYGIFLW ELFSLGSSPY
301 PGMPVDSKFY KMIKEGFRML SPEHAPAEMY DIMKTCWDAD PLKRPTFKQI VQLIEKQISE
361 STNHI
```

FIGURE 3

Structure Coordinates of Residues 32-365 of c-KIT (SEQ. ID No. 3)

LEGEND

Column headings from left to right are (A)'Atom Number', (B)'Atom Type', (C)'Amino Acid', (D)'Chain Identifier', (E)'Amino Acid Number', (F)'X Coordinate', (G)'Y Coordinate', (H)'Z Coordinate', (I)'Occupancy' (OCC) and (J)'B factor'.

|      | A  | B   | C   | D | E   | F       | G      | H      | I    | J     |
|------|----|-----|-----|---|-----|---------|--------|--------|------|-------|
| ATOM | 1  | N   | THR | A | 544 | -13.698 | 3.599  | -3.644 | 1.00 | 18.70 |
| ATOM | 2  | CA  | THR | A | 544 | -14.239 | 4.778  | -2.903 | 1.00 | 23.17 |
| ATOM | 3  | CB  | THR | A | 544 | -14.702 | 4.370  | -1.481 | 1.00 | 24.81 |
| ATOM | 4  | OG1 | THR | A | 544 | -15.532 | 3.203  | -1.556 | 1.00 | 26.96 |
| ATOM | 5  | CG2 | THR | A | 544 | -15.643 | 5.418  | -0.896 | 1.00 | 26.64 |
| ATOM | 6  | C   | THR | A | 544 | -13.195 | 5.892  | -2.822 | 1.00 | 22.95 |
| ATOM | 7  | O   | THR | A | 544 | -13.528 | 7.076  | -2.917 | 1.00 | 22.00 |
| ATOM | 8  | N   | TYR | A | 545 | -11.935 | 5.497  | -2.660 | 1.00 | 23.50 |
| ATOM | 9  | CA  | TYR | A | 545 | -10.829 | 6.443  | -2.514 | 1.00 | 25.74 |
| ATOM | 10 | CB  | TYR | A | 545 | -9.690  | 5.809  | -1.706 | 1.00 | 28.77 |
| ATOM | 11 | CG  | TYR | A | 545 | -10.058 | 5.511  | -0.262 | 1.00 | 31.50 |
| ATOM | 12 | CD1 | TYR | A | 545 | -11.048 | 6.250  | 0.397  | 1.00 | 32.84 |
| ATOM | 13 | CE1 | TYR | A | 545 | -11.394 | 5.978  | 1.718  | 1.00 | 34.22 |
| ATOM | 14 | CZ  | TYR | A | 545 | -10.745 | 4.963  | 2.400  | 1.00 | 34.45 |
| ATOM | 15 | OH  | TYR | A | 545 | -11.088 | 4.702  | 3.707  | 1.00 | 35.34 |
| ATOM | 16 | CE2 | TYR | A | 545 | -9.757  | 4.213  | 1.772  | 1.00 | 34.45 |
| ATOM | 17 | CD2 | TYR | A | 545 | -9.420  | 4.491  | 0.444  | 1.00 | 32.86 |
| ATOM | 18 | C   | TYR | A | 545 | -10.331 | 7.012  | -3.848 | 1.00 | 25.40 |
| ATOM | 19 | O   | TYR | A | 545 | -9.417  | 7.837  | -3.875 | 1.00 | 25.57 |
| ATOM | 20 | N   | LYS | A | 546 | -10.942 | 6.568  | -4.947 | 1.00 | 24.53 |
| ATOM | 21 | CA  | LYS | A | 546 | -10.741 | 7.189  | -6.255 | 1.00 | 25.17 |
| ATOM | 22 | CB  | LYS | A | 546 | -10.901 | 6.152  | -7.380 | 1.00 | 28.62 |
| ATOM | 23 | CG  | LYS | A | 546 | -10.080 | 6.446  | -8.644 | 1.00 | 31.78 |
| ATOM | 24 | CD  | LYS | A | 546 | -8.615  | 6.023  | -8.496 | 1.00 | 33.03 |
| ATOM | 25 | CE  | LYS | A | 546 | -7.689  | 7.231  | -8.342 | 1.00 | 34.04 |
| ATOM | 26 | NZ  | LYS | A | 546 | -6.406  | 7.064  | -9.083 | 1.00 | 33.69 |
| ATOM | 27 | C   | LYS | A | 546 | -11.726 | 8.347  | -6.437 | 1.00 | 23.73 |
| ATOM | 28 | O   | LYS | A | 546 | -11.797 | 8.959  | -7.506 | 1.00 | 23.82 |
| ATOM | 29 | N   | TYR | A | 547 | -12.475 | 8.638  | -5.375 | 1.00 | 22.16 |
| ATOM | 30 | CA  | TYR | A | 547 | -13.501 | 9.677  | -5.371 | 1.00 | 22.75 |
| ATOM | 31 | CB  | TYR | A | 547 | -14.894 | 9.044  | -5.382 | 1.00 | 22.17 |
| ATOM | 32 | CG  | TYR | A | 547 | -15.161 | 8.143  | -6.567 | 1.00 | 23.26 |
| ATOM | 33 | CD1 | TYR | A | 547 | -15.723 | 8.649  | -7.739 | 1.00 | 22.59 |
| ATOM | 34 | CE1 | TYR | A | 547 | -15.968 | 7.825  | -8.832 | 1.00 | 23.14 |
| ATOM | 35 | CZ  | TYR | A | 547 | -15.649 | 6.478  | -8.756 | 1.00 | 23.05 |
| ATOM | 36 | OH  | TYR | A | 547 | -15.890 | 5.659  | -9.834 | 1.00 | 24.27 |
| ATOM | 37 | CE2 | TYR | A | 547 | -15.093 | 5.950  | -7.605 | 1.00 | 22.86 |
| ATOM | 38 | CD2 | TYR | A | 547 | -14.853 | 6.782  | -6.517 | 1.00 | 23.50 |
| ATOM | 39 | C   | TYR | A | 547 | -13.373 | 10.569 | -4.138 | 1.00 | 23.40 |
| ATOM | 40 | O   | TYR | A | 547 | -13.682 | 11.764 | -4.192 | 1.00 | 25.54 |
| ATOM | 41 | N   | LEU | A | 548 | -12.925 | 9.972  | -3.033 | 1.00 | 22.31 |

FIGURE 3 (Cont.)

|      | A  | B   | C   | D | E   | F       | G      | H      | I    | J     |
|------|----|-----|-----|---|-----|---------|--------|--------|------|-------|
| ATOM | 42 | CA  | LEU | A | 548 | -12.922 | 10.619 | -1.722 | 1.00 | 22.64 |
| ATOM | 43 | CB  | LEU | A | 548 | -14.042 | 10.045 | -0.845 | 1.00 | 24.86 |
| ATOM | 44 | CG  | LEU | A | 548 | -15.487 | 10.325 | -1.258 | 1.00 | 26.13 |
| ATOM | 45 | CD1 | LEU | A | 548 | -16.362 | 9.098  | -1.044 | 1.00 | 27.13 |
| ATOM | 46 | CD2 | LEU | A | 548 | -16.037 | 11.516 | -0.498 | 1.00 | 26.96 |
| ATOM | 47 | C   | LEU | A | 548 | -11.587 | 10.466 | -1.000 | 1.00 | 20.72 |
| ATOM | 48 | O   | LEU | A | 548 | -10.815 | 9.543  | -1.277 | 1.00 | 18.82 |
| ATOM | 49 | N   | GLN | A | 549 | -11.330 | 11.372 | -0.062 | 1.00 | 19.73 |
| ATOM | 50 | CA  | GLN | A | 549 | -10.092 | 11.360 | 0.709  | 1.00 | 17.49 |
| ATOM | 51 | CB  | GLN | A | 549 | -9.846  | 12.736 | 1.339  | 1.00 | 17.41 |
| ATOM | 52 | CG  | GLN | A | 549 | -8.545  | 12.856 | 2.133  | 1.00 | 16.71 |
| ATOM | 53 | CD  | GLN | A | 549 | -7.312  | 12.569 | 1.297  | 1.00 | 16.32 |
| ATOM | 54 | OE1 | GLN | A | 549 | -7.141  | 13.150 | 0.230  | 1.00 | 16.42 |
| ATOM | 55 | NE2 | GLN | A | 549 | -6.461  | 11.668 | 1.773  | 1.00 | 15.52 |
| ATOM | 56 | C   | GLN | A | 549 | -10.091 | 10.273 | 1.786  | 1.00 | 16.53 |
| ATOM | 57 | O   | GLN | A | 549 | -10.960 | 10.244 | 2.658  | 1.00 | 15.78 |
| ATOM | 58 | N   | LYS | A | 550 | -9.106  | 9.384  | 1.704  | 1.00 | 16.96 |
| ATOM | 59 | CA  | LYS | A | 550 | -8.847  | 8.379  | 2.735  | 1.00 | 18.94 |
| ATOM | 60 | CB  | LYS | A | 550 | -7.920  | 7.288  | 2.181  | 1.00 | 22.65 |
| ATOM | 61 | CG  | LYS | A | 550 | -6.611  | 7.805  | 1.584  | 1.00 | 26.78 |
| ATOM | 62 | CD  | LYS | A | 550 | -5.908  | 6.730  | 0.767  | 1.00 | 30.11 |
| ATOM | 63 | CE  | LYS | A | 550 | -4.447  | 7.094  | 0.532  | 1.00 | 33.20 |
| ATOM | 64 | NZ  | LYS | A | 550 | -4.066  | 6.980  | -0.903 | 1.00 | 36.07 |
| ATOM | 65 | C   | LYS | A | 550 | -8.222  | 9.040  | 3.973  | 1.00 | 16.69 |
| ATOM | 66 | O   | LYS | A | 550 | -7.698  | 10.151 | 3.868  | 1.00 | 15.59 |
| ATOM | 67 | N   | PRO | A | 551 | -8.265  | 8.375  | 5.134  | 1.00 | 15.67 |
| ATOM | 68 | CA  | PRO | A | 551 | -7.615  | 8.903  | 6.343  | 1.00 | 15.35 |
| ATOM | 69 | CB  | PRO | A | 551 | -7.656  | 7.715  | 7.308  | 1.00 | 16.37 |
| ATOM | 70 | CG  | PRO | A | 551 | -8.866  | 6.949  | 6.900  | 1.00 | 15.67 |
| ATOM | 71 | CD  | PRO | A | 551 | -8.942  | 7.090  | 5.399  | 1.00 | 16.92 |
| ATOM | 72 | C   | PRO | A | 551 | -6.172  | 9.328  | 6.078  | 1.00 | 13.68 |
| ATOM | 73 | O   | PRO | A | 551 | -5.467  | 8.684  | 5.293  | 1.00 | 13.86 |
| ATOM | 74 | N   | MET | A | 552 | -5.751  | 10.414 | 6.716  | 1.00 | 12.12 |
| ATOM | 75 | CA  | MET | A | 552 | -4.414  | 10.957 | 6.497  | 1.00 | 12.53 |
| ATOM | 76 | CB  | MET | A | 552 | -4.500  | 12.414 | 6.056  | 1.00 | 12.24 |
| ATOM | 77 | CG  | MET | A | 552 | -4.930  | 12.592 | 4.619  | 1.00 | 18.03 |
| ATOM | 78 | SD  | MET | A | 552 | -5.491  | 14.257 | 4.325  | 1.00 | 23.86 |
| ATOM | 79 | CE  | MET | A | 552 | -4.011  | 15.121 | 4.201  | 1.00 | 18.08 |
| ATOM | 80 | C   | MET | A | 552 | -3.568  | 10.892 | 7.747  | 1.00 | 12.04 |
| ATOM | 81 | O   | MET | A | 552 | -4.079  | 10.984 | 8.862  | 1.00 | 12.03 |
| ATOM | 82 | N   | TYR | A | 553 | -2.267  | 10.752 | 7.543  | 1.00 | 11.40 |
| ATOM | 83 | CA  | TYR | A | 553 | -1.304  | 10.894 | 8.615  | 1.00 | 13.18 |
| ATOM | 84 | CB  | TYR | A | 553 | 0.093   | 10.611 | 8.076  | 1.00 | 13.84 |
| ATOM | 85 | CG  | TYR | A | 553 | 1.188   | 10.767 | 9.094  | 1.00 | 16.64 |
| ATOM | 86 | CD1 | TYR | A | 553 | 2.116   | 11.796 | 8.990  | 1.00 | 17.91 |
| ATOM | 87 | CE1 | TYR | A | 553 | 3.138   | 11.932 | 9.930  | 1.00 | 20.49 |
| ATOM | 88 | CZ  | TYR | A | 553 | 3.217   | 11.036 | 10.987 | 1.00 | 20.70 |
| ATOM | 89 | OH  | TYR | A | 553 | 4.215   | 11.147 | 11.925 | 1.00 | 21.97 |
| ATOM | 90 | CE2 | TYR | A | 553 | 2.304   | 10.013 | 11.109 | 1.00 | 17.94 |
| ATOM | 91 | CD2 | TYR | A | 553 | 1.295   | 9.881  | 10.166 | 1.00 | 17.45 |
| ATOM | 92 | C   | TYR | A | 553 | -1.376  | 12.309 | 9.188  | 1.00 | 15.92 |
| ATOM | 93 | O   | TYR | A | 553 | -1.479  | 13.287 | 8.447  | 1.00 | 11.60 |

FIGURE 3 (Cont.)

| | A | B | C | D | E | F | G | H | I | J |
|---|---|---|---|---|---|---|---|---|---|---|
| ATOM | 94 | N | GLU | A | 554 | -1.355 | 12.408 | 10.512 | 1.00 | 16.37 |
| ATOM | 95 | CA | GLU | A | 554 | -1.317 | 13.708 | 11.171 | 1.00 | 22.20 |
| ATOM | 96 | CB | GLU | A | 554 | -2.644 | 14.010 | 11.871 | 1.00 | 25.43 |
| ATOM | 97 | CG | GLU | A | 554 | -2.951 | 15.502 | 11.920 | 1.00 | 31.79 |
| ATOM | 98 | CD | GLU | A | 554 | -4.204 | 15.842 | 12.705 | 1.00 | 35.17 |
| ATOM | 99 | OE1 | GLU | A | 554 | -4.931 | 16.774 | 12.279 | 1.00 | 36.85 |
| ATOM | 100 | OE2 | GLU | A | 554 | -4.461 | 15.191 | 13.748 | 1.00 | 36.15 |
| ATOM | 101 | C | GLU | A | 554 | -0.173 | 13.726 | 12.168 | 1.00 | 21.81 |
| ATOM | 102 | O | GLU | A | 554 | 0.209 | 12.679 | 12.681 | 1.00 | 20.72 |
| ATOM | 103 | N | VAL | A | 555 | 0.381 | 14.909 | 12.421 | 1.00 | 21.61 |
| ATOM | 104 | CA | VAL | A | 555 | 1.421 | 15.058 | 13.433 | 1.00 | 21.63 |
| ATOM | 105 | CB | VAL | A | 555 | 1.963 | 16.510 | 13.508 | 1.00 | 21.78 |
| ATOM | 106 | CG1 | VAL | A | 555 | 3.167 | 16.590 | 14.447 | 1.00 | 21.10 |
| ATOM | 107 | CG2 | VAL | A | 555 | 2.337 | 17.017 | 12.128 | 1.00 | 23.80 |
| ATOM | 108 | C | VAL | A | 555 | 0.828 | 14.655 | 14.783 | 1.00 | 18.33 |
| ATOM | 109 | O | VAL | A | 555 | -0.238 | 15.131 | 15.161 | 1.00 | 19.27 |
| ATOM | 110 | N | GLN | A | 556 | 1.517 | 13.766 | 15.489 | 1.00 | 16.90 |
| ATOM | 111 | CA | GLN | A | 556 | 1.041 | 13.275 | 16.778 | 1.00 | 17.32 |
| ATOM | 112 | CB | GLN | A | 556 | 1.843 | 12.038 | 17.186 | 1.00 | 21.91 |
| ATOM | 113 | CG | GLN | A | 556 | 1.411 | 11.411 | 18.504 | 1.00 | 24.06 |
| ATOM | 114 | CD | GLN | A | 556 | 0.001 | 10.878 | 18.464 | 1.00 | 26.93 |
| ATOM | 115 | OE1 | GLN | A | 556 | -0.352 | 10.104 | 17.576 | 1.00 | 29.50 |
| ATOM | 116 | NE2 | GLN | A | 556 | -0.814 | 11.288 | 19.428 | 1.00 | 28.84 |
| ATOM | 117 | C | GLN | A | 556 | 1.142 | 14.335 | 17.874 | 1.00 | 12.89 |
| ATOM | 118 | O | GLN | A | 556 | 0.169 | 14.637 | 18.562 | 1.00 | 11.99 |
| ATOM | 119 | N | TRP | A | 557 | 2.340 | 14.878 | 18.032 | 1.00 | 12.17 |
| ATOM | 120 | CA | TRP | A | 557 | 2.601 | 15.867 | 19.066 | 1.00 | 12.95 |
| ATOM | 121 | CB | TRP | A | 557 | 4.102 | 16.088 | 19.223 | 1.00 | 13.40 |
| ATOM | 122 | CG | TRP | A | 557 | 4.853 | 14.864 | 19.621 | 1.00 | 14.72 |
| ATOM | 123 | CD1 | TRP | A | 557 | 4.336 | 13.623 | 19.888 | 1.00 | 15.98 |
| ATOM | 124 | NE1 | TRP | A | 557 | 5.346 | 12.752 | 20.216 | 1.00 | 16.53 |
| ATOM | 125 | CE2 | TRP | A | 557 | 6.540 | 13.422 | 20.178 | 1.00 | 16.30 |
| ATOM | 126 | CD2 | TRP | A | 557 | 6.262 | 14.758 | 19.806 | 1.00 | 15.19 |
| ATOM | 127 | CE3 | TRP | A | 557 | 7.331 | 15.658 | 19.692 | 1.00 | 18.37 |
| ATOM | 128 | CZ3 | TRP | A | 557 | 8.623 | 15.204 | 19.954 | 1.00 | 19.21 |
| ATOM | 129 | CH2 | TRP | A | 557 | 8.860 | 13.873 | 20.328 | 1.00 | 18.24 |
| ATOM | 130 | CZ2 | TRP | A | 557 | 7.835 | 12.970 | 20.444 | 1.00 | 17.79 |
| ATOM | 131 | C | TRP | A | 557 | 1.948 | 17.179 | 18.697 | 1.00 | 11.44 |
| ATOM | 132 | O | TRP | A | 557 | 1.929 | 17.566 | 17.523 | 1.00 | 12.96 |
| ATOM | 133 | N | LYS | A | 558 | 1.410 | 17.855 | 19.702 | 1.00 | 9.44 |
| ATOM | 134 | CA | LYS | A | 558 | 0.783 | 19.150 | 19.484 | 1.00 | 10.59 |
| ATOM | 135 | CB | LYS | A | 558 | -0.699 | 19.113 | 19.870 | 1.00 | 12.13 |
| ATOM | 136 | CG | LYS | A | 558 | -1.535 | 18.103 | 19.093 | 1.00 | 16.94 |
| ATOM | 137 | CD | LYS | A | 558 | -1.764 | 18.547 | 17.651 | 1.00 | 20.49 |
| ATOM | 138 | CE | LYS | A | 558 | -2.804 | 17.680 | 16.945 | 1.00 | 24.38 |
| ATOM | 139 | NZ | LYS | A | 558 | -2.222 | 16.960 | 15.771 | 1.00 | 27.04 |
| ATOM | 140 | C | LYS | A | 558 | 1.506 | 20.209 | 20.299 | 1.00 | 10.97 |
| ATOM | 141 | O | LYS | A | 558 | 1.980 | 19.939 | 21.403 | 1.00 | 12.09 |
| ATOM | 142 | N | VAL | A | 559 | 1.610 | 21.405 | 19.733 | 1.00 | 11.27 |
| ATOM | 143 | CA | VAL | A | 559 | 2.093 | 22.557 | 20.470 | 1.00 | 10.40 |
| ATOM | 144 | CB | VAL | A | 559 | 3.081 | 23.413 | 19.639 | 1.00 | 10.12 |
| ATOM | 145 | CG1 | VAL | A | 559 | 3.619 | 24.563 | 20.478 | 1.00 | 13.11 |

FIGURE 3 (Cont.)

|      | A    | B   | C   | D | E   | F      | G      | H      | I    | J     |
|------|------|-----|-----|---|-----|--------|--------|--------|------|-------|
| ATOM | 146  | CG2 | VAL | A | 559 | 4.232  | 22.556 | 19.127 | 1.00 | 15.30 |
| ATOM | 147  | C   | VAL | A | 559 | 0.846  | 23.353 | 20.822 | 1.00 | 10.11 |
| ATOM | 148  | O   | VAL | A | 559 | -0.030 | 23.540 | 19.973 | 1.00 | 10.72 |
| ATOM | 149  | N   | VAL | A | 560 | 0.742  | 23.775 | 22.076 | 1.00 | 7.55  |
| ATOM | 150  | CA  | VAL | A | 560 | -0.457 | 24.459 | 22.548 | 1.00 | 10.11 |
| ATOM | 151  | CB  | VAL | A | 560 | -1.135 | 23.730 | 23.745 | 1.00 | 12.89 |
| ATOM | 152  | CG1 | VAL | A | 560 | -1.656 | 22.358 | 23.314 | 1.00 | 12.49 |
| ATOM | 153  | CG2 | VAL | A | 560 | -0.187 | 23.616 | 24.945 | 1.00 | 12.02 |
| ATOM | 154  | C   | VAL | A | 560 | -0.172 | 25.909 | 22.912 | 1.00 | 11.34 |
| ATOM | 155  | O   | VAL | A | 560 | 0.968  | 26.268 | 23.215 | 1.00 | 8.76  |
| ATOM | 156  | N   | GLU | A | 561 | -1.219 | 26.728 | 22.879 | 1.00 | 15.47 |
| ATOM | 157  | CA  | GLU | A | 561 | -1.117 | 28.132 | 23.263 | 1.00 | 20.62 |
| ATOM | 158  | CB  | GLU | A | 561 | -2.124 | 28.987 | 22.494 | 1.00 | 17.46 |
| ATOM | 159  | CG  | GLU | A | 561 | -1.960 | 28.954 | 20.990 | 1.00 | 17.68 |
| ATOM | 160  | CD  | GLU | A | 561 | -1.034 | 30.037 | 20.461 | 1.00 | 17.52 |
| ATOM | 161  | OE1 | GLU | A | 561 | -1.157 | 30.361 | 19.268 | 1.00 | 15.91 |
| ATOM | 162  | OE2 | GLU | A | 561 | -0.178 | 30.549 | 21.221 | 1.00 | 16.83 |
| ATOM | 163  | C   | GLU | A | 561 | -1.360 | 28.285 | 24.753 | 1.00 | 28.27 |
| ATOM | 164  | O   | GLU | A | 561 | -2.315 | 27.713 | 25.294 | 1.00 | 30.32 |
| ATOM | 165  | N   | GLU | A | 562 | -0.506 | 29.079 | 25.398 | 1.00 | 34.35 |
| ATOM | 166  | CA  | GLU | A | 562 | -0.538 | 29.274 | 26.847 | 1.00 | 37.49 |
| ATOM | 167  | CB  | GLU | A | 562 | 0.861  | 29.663 | 27.348 | 1.00 | 38.27 |
| ATOM | 168  | CG  | GLU | A | 562 | 1.088  | 29.451 | 28.841 | 1.00 | 40.90 |
| ATOM | 169  | CD  | GLU | A | 562 | 1.242  | 30.754 | 29.614 | 1.00 | 41.85 |
| ATOM | 170  | OE1 | GLU | A | 562 | 0.869  | 30.780 | 30.808 | 1.00 | 42.26 |
| ATOM | 171  | OE2 | GLU | A | 562 | 1.740  | 31.753 | 29.038 | 1.00 | 42.09 |
| ATOM | 172  | C   | GLU | A | 562 | -1.587 | 30.299 | 27.300 | 1.00 | 39.18 |
| ATOM | 173  | O   | GLU | A | 562 | -1.250 | 31.452 | 27.586 | 1.00 | 40.40 |
| ATOM | 174  | N   | ILE | A | 563 | -2.852 | 29.871 | 27.338 | 1.00 | 40.56 |
| ATOM | 175  | CA  | ILE | A | 563 | -3.963 | 30.615 | 27.967 | 1.00 | 41.73 |
| ATOM | 176  | CB  | ILE | A | 563 | -3.878 | 32.172 | 27.733 | 1.00 | 42.32 |
| ATOM | 177  | CG1 | ILE | A | 563 | -4.009 | 32.918 | 29.067 | 1.00 | 42.25 |
| ATOM | 178  | CD1 | ILE | A | 563 | -3.711 | 34.413 | 28.991 | 1.00 | 42.90 |
| ATOM | 179  | CG2 | ILE | A | 563 | -4.935 | 32.664 | 26.728 | 1.00 | 42.05 |
| ATOM | 180  | C   | ILE | A | 563 | -5.348 | 30.077 | 27.582 | 1.00 | 42.06 |
| ATOM | 181  | O   | ILE | A | 563 | -5.509 | 29.442 | 26.534 | 1.00 | 40.98 |
| ATOM | 182  | N   | ASN | A | 564 | -6.317 | 30.335 | 28.466 | 1.00 | 42.20 |
| ATOM | 183  | CA  | ASN | A | 564 | -7.750 | 30.092 | 28.265 | 1.00 | 42.04 |
| ATOM | 184  | CB  | ASN | A | 564 | -8.029 | 28.644 | 27.833 | 1.00 | 42.12 |
| ATOM | 185  | CG  | ASN | A | 564 | -8.512 | 28.533 | 26.390 | 1.00 | 41.60 |
| ATOM | 186  | OD1 | ASN | A | 564 | -8.176 | 29.355 | 25.533 | 1.00 | 41.41 |
| ATOM | 187  | ND2 | ASN | A | 564 | -9.300 | 27.500 | 26.115 | 1.00 | 41.27 |
| ATOM | 188  | C   | ASN | A | 564 | -8.447 | 30.417 | 29.589 | 1.00 | 42.33 |
| ATOM | 189  | O   | ASN | A | 564 | -8.579 | 31.587 | 29.958 | 1.00 | 42.04 |
| ATOM | 190  | N   | GLY | A | 565 | -8.892 | 29.379 | 30.295 | 1.00 | 42.07 |
| ATOM | 191  | CA  | GLY | A | 565 | -9.177 | 29.464 | 31.718 | 1.00 | 41.41 |
| ATOM | 192  | C   | GLY | A | 565 | -8.099 | 28.633 | 32.389 | 1.00 | 41.37 |
| ATOM | 193  | O   | GLY | A | 565 | -8.384 | 27.785 | 33.238 | 1.00 | 41.83 |
| ATOM | 194  | N   | ASN | A | 566 | -6.852 | 28.909 | 31.998 | 1.00 | 39.88 |
| ATOM | 195  | CA  | ASN | A | 566 | -5.713 | 28.000 | 32.162 | 1.00 | 39.00 |
| ATOM | 196  | CB  | ASN | A | 566 | -5.282 | 27.859 | 33.627 | 1.00 | 39.72 |
| ATOM | 197  | CG  | ASN | A | 566 | -3.835 | 28.267 | 33.845 | 1.00 | 40.20 |

FIGURE 3 (Cont.)

|      | A    | B   | C   | D | E   | F      | G      | H      | I    | J     |
|------|------|-----|-----|---|-----|--------|--------|--------|------|-------|
| ATOM | 198  | OD1 | ASN | A | 566 | -2.914 | 27.478 | 33.626 | 1.00 | 39.90 |
| ATOM | 199  | ND2 | ASN | A | 566 | -3.629 | 29.509 | 34.267 | 1.00 | 39.87 |
| ATOM | 200  | C   | ASN | A | 566 | -5.955 | 26.643 | 31.481 | 1.00 | 37.74 |
| ATOM | 201  | O   | ASN | A | 566 | -5.672 | 25.578 | 32.040 | 1.00 | 37.31 |
| ATOM | 202  | N   | ASN | A | 567 | -6.482 | 26.718 | 30.260 | 1.00 | 35.97 |
| ATOM | 203  | CA  | ASN | A | 567 | -6.771 | 25.549 | 29.438 | 1.00 | 33.99 |
| ATOM | 204  | CB  | ASN | A | 567 | -8.284 | 25.359 | 29.281 | 1.00 | 34.31 |
| ATOM | 205  | CG  | ASN | A | 567 | -8.962 | 24.997 | 30.589 | 1.00 | 35.29 |
| ATOM | 206  | OD1 | ASN | A | 567 | -8.701 | 23.939 | 31.165 | 1.00 | 36.15 |
| ATOM | 207  | ND2 | ASN | A | 567 | -9.835 | 25.878 | 31.069 | 1.00 | 34.15 |
| ATOM | 208  | C   | ASN | A | 567 | -6.056 | 25.611 | 28.081 | 1.00 | 31.99 |
| ATOM | 209  | O   | ASN | A | 567 | -5.212 | 26.484 | 27.864 | 1.00 | 32.47 |
| ATOM | 210  | N   | TYR | A | 568 | -6.407 | 24.696 | 27.175 | 1.00 | 28.81 |
| ATOM | 211  | CA  | TYR | A | 568 | -5.559 | 24.368 | 26.026 | 1.00 | 26.09 |
| ATOM | 212  | CB  | TYR | A | 568 | -5.110 | 22.901 | 26.117 | 1.00 | 28.38 |
| ATOM | 213  | CG  | TYR | A | 568 | -4.373 | 22.530 | 27.391 | 1.00 | 30.05 |
| ATOM | 214  | CD1 | TYR | A | 568 | -3.021 | 22.201 | 27.358 | 1.00 | 30.64 |
| ATOM | 215  | CE1 | TYR | A | 568 | -2.340 | 21.855 | 28.515 | 1.00 | 30.86 |
| ATOM | 216  | CZ  | TYR | A | 568 | -3.009 | 21.831 | 29.726 | 1.00 | 31.66 |
| ATOM | 217  | OH  | TYR | A | 568 | -2.333 | 21.489 | 30.873 | 1.00 | 32.73 |
| ATOM | 218  | CE2 | TYR | A | 568 | -4.355 | 22.150 | 29.791 | 1.00 | 31.75 |
| ATOM | 219  | CD2 | TYR | A | 568 | -5.031 | 22.486 | 28.624 | 1.00 | 31.09 |
| ATOM | 220  | C   | TYR | A | 568 | -6.193 | 24.599 | 24.654 | 1.00 | 22.72 |
| ATOM | 221  | O   | TYR | A | 568 | -7.331 | 24.211 | 24.412 | 1.00 | 24.06 |
| ATOM | 222  | N   | VAL | A | 569 | -5.429 | 25.218 | 23.759 | 1.00 | 20.08 |
| ATOM | 223  | CA  | VAL | A | 569 | -5.774 | 25.293 | 22.339 | 1.00 | 17.61 |
| ATOM | 224  | CB  | VAL | A | 569 | -6.459 | 26.652 | 21.968 | 1.00 | 21.99 |
| ATOM | 225  | CG1 | VAL | A | 569 | -5.447 | 27.741 | 21.619 | 1.00 | 20.09 |
| ATOM | 226  | CG2 | VAL | A | 569 | -7.456 | 26.464 | 20.840 | 1.00 | 23.81 |
| ATOM | 227  | C   | VAL | A | 569 | -4.512 | 24.999 | 21.510 | 1.00 | 14.79 |
| ATOM | 228  | O   | VAL | A | 569 | -3.423 | 25.436 | 21.873 | 1.00 | 9.69  |
| ATOM | 229  | N   | TYR | A | 570 | -4.665 | 24.240 | 20.425 | 1.00 | 16.28 |
| ATOM | 230  | CA  | TYR | A | 570 | -3.532 | 23.814 | 19.595 | 1.00 | 19.19 |
| ATOM | 231  | CB  | TYR | A | 570 | -3.896 | 22.577 | 18.763 | 1.00 | 22.39 |
| ATOM | 232  | CG  | TYR | A | 570 | -4.299 | 21.332 | 19.529 | 1.00 | 24.11 |
| ATOM | 233  | CD1 | TYR | A | 570 | -5.200 | 20.423 | 18.972 | 1.00 | 26.30 |
| ATOM | 234  | CE1 | TYR | A | 570 | -5.576 | 19.268 | 19.652 | 1.00 | 26.40 |
| ATOM | 235  | CZ  | TYR | A | 570 | -5.042 | 19.008 | 20.902 | 1.00 | 26.75 |
| ATOM | 236  | OH  | TYR | A | 570 | -5.417 | 17.864 | 21.571 | 1.00 | 27.82 |
| ATOM | 237  | CE2 | TYR | A | 570 | -4.139 | 19.890 | 21.478 | 1.00 | 25.71 |
| ATOM | 238  | CD2 | TYR | A | 570 | -3.769 | 21.043 | 20.788 | 1.00 | 25.24 |
| ATOM | 239  | C   | TYR | A | 570 | -3.061 | 24.903 | 18.636 | 1.00 | 19.26 |
| ATOM | 240  | O   | TYR | A | 570 | -3.869 | 25.642 | 18.079 | 1.00 | 22.96 |
| ATOM | 241  | N   | ILE | A | 571 | -1.751 | 24.993 | 18.444 | 1.00 | 17.67 |
| ATOM | 242  | CA  | ILE | A | 571 | -1.176 | 25.817 | 17.385 | 1.00 | 18.95 |
| ATOM | 243  | CB  | ILE | A | 571 | 0.279  | 26.223 | 17.736 | 1.00 | 21.81 |
| ATOM | 244  | CG1 | ILE | A | 571 | 0.297  | 27.146 | 18.958 | 1.00 | 21.25 |
| ATOM | 245  | CD1 | ILE | A | 571 | 1.686  | 27.516 | 19.454 | 1.00 | 21.90 |
| ATOM | 246  | CG2 | ILE | A | 571 | 0.980  | 26.879 | 16.531 | 1.00 | 23.14 |
| ATOM | 247  | C   | ILE | A | 571 | -1.195 | 24.992 | 16.101 | 1.00 | 21.47 |
| ATOM | 248  | O   | ILE | A | 571 | -0.773 | 23.831 | 16.100 | 1.00 | 21.64 |
| ATOM | 249  | N   | ASP | A | 572 | -1.703 | 25.586 | 15.022 | 1.00 | 18.19 |

FIGURE 3 (Cont.)

|      | A   | B   | C   | D   | E   | F      | G      | H      | I    | J     |
|------|-----|-----|-----|-----|-----|--------|--------|--------|------|-------|
| ATOM | 250 | CA  | ASP | A   | 572 | -1.659 | 24.966 | 13.705 | 1.00 | 18.73 |
| ATOM | 251 | CB  | ASP | A   | 572 | -2.499 | 25.766 | 12.710 | 1.00 | 21.13 |
| ATOM | 252 | CG  | ASP | A   | 572 | -2.697 | 25.046 | 11.384 | 1.00 | 24.70 |
| ATOM | 253 | OD1 | ASP | A   | 572 | -1.966 | 24.071 | 11.093 | 1.00 | 25.36 |
| ATOM | 254 | OD2 | ASP | A   | 572 | -3.571 | 25.398 | 10.560 | 1.00 | 26.39 |
| ATOM | 255 | C   | ASP | A   | 572 | -0.202 | 24.911 | 13.261 | 1.00 | 16.57 |
| ATOM | 256 | O   | ASP | A   | 572 | 0.413  | 25.950 | 13.011 | 1.00 | 16.30 |
| ATOM | 257 | N   | PRO | A   | 573 | 0.354  | 23.704 | 13.176 | 1.00 | 14.26 |
| ATOM | 258 | CA  | PRO | A   | 573 | 1.784  | 23.546 | 12.906 | 1.00 | 15.76 |
| ATOM | 259 | CB  | PRO | A   | 573 | 2.009  | 22.038 | 13.056 | 1.00 | 14.65 |
| ATOM | 260 | CG  | PRO | A   | 573 | 0.670  | 21.426 | 12.783 | 1.00 | 14.61 |
| ATOM | 261 | CD  | PRO | A   | 573 | -0.325 | 22.401 | 13.322 | 1.00 | 16.48 |
| ATOM | 262 | C   | PRO | A   | 573 | 2.197  | 24.040 | 11.521 | 1.00 | 16.02 |
| ATOM | 263 | O   | PRO | A   | 573 | 3.390  | 24.248 | 11.316 | 1.00 | 20.18 |
| ATOM | 264 | N   | THR | A   | 574 | 1.247  | 24.236 | 10.602 | 1.00 | 14.42 |
| ATOM | 265 | CA  | THR | A   | 574 | 1.573  | 24.824 | 9.300  | 1.00 | 14.68 |
| ATOM | 266 | CB  | THR | A   | 574 | 0.363  | 24.805 | 8.319  | 1.00 | 14.50 |
| ATOM | 267 | OG1 | THR | A   | 574 | -0.732 | 25.551 | 8.869  | 1.00 | 13.31 |
| ATOM | 268 | CG2 | THR | A   | 574 | -0.190 | 23.392 | 8.164  | 1.00 | 15.45 |
| ATOM | 269 | C   | THR | A   | 574 | 2.080  | 26.251 | 9.470  | 1.00 | 14.53 |
| ATOM | 270 | O   | THR | A   | 574 | 2.823  | 26.755 | 8.630  | 1.00 | 16.17 |
| ATOM | 271 | N   | GLN | A   | 575 | 1.685  | 26.884 | 10.572 | 1.00 | 12.25 |
| ATOM | 272 | CA  | GLN | A   | 575 | 2.027  | 28.273 | 10.844 | 1.00 | 14.62 |
| ATOM | 273 | CB  | GLN | A   | 575 | 1.069  | 28.845 | 11.881 | 1.00 | 16.34 |
| ATOM | 274 | CG  | GLN | A   | 575 | -0.366 | 28.900 | 11.422 | 1.00 | 21.21 |
| ATOM | 275 | CD  | GLN | A   | 575 | -1.002 | 30.209 | 11.768 | 1.00 | 23.79 |
| ATOM | 276 | OE1 | GLN | A   | 575 | -0.901 | 31.167 | 11.004 | 1.00 | 26.92 |
| ATOM | 277 | NE2 | GLN | A   | 575 | -1.647 | 30.273 | 12.924 | 1.00 | 24.46 |
| ATOM | 278 | C   | GLN | A   | 575 | 3.457  | 28.446 | 11.340 | 1.00 | 12.91 |
| ATOM | 279 | O   | GLN | A   | 575 | 3.979  | 29.564 | 11.371 | 1.00 | 11.86 |
| ATOM | 280 | N   | LEU | A   | 576 | 4.069  | 27.340 | 11.749 | 1.00 | 13.13 |
| ATOM | 281 | CA  | LEU | A   | 576 | 5.435  | 27.343 | 12.261 | 1.00 | 12.98 |
| ATOM | 282 | CB  | LEU | A   | 576 | 5.717  | 26.044 | 13.026 | 1.00 | 13.81 |
| ATOM | 283 | CG  | LEU | A   | 576 | 4.908  | 25.771 | 14.296 | 1.00 | 15.05 |
| ATOM | 284 | CD1 | LEU | A   | 576 | 5.199  | 24.367 | 14.788 | 1.00 | 12.18 |
| ATOM | 285 | CD2 | LEU | A   | 576 | 5.204  | 26.784 | 15.395 | 1.00 | 15.40 |
| ATOM | 286 | C   | LEU | A   | 576 | 6.433  | 27.531 | 11.117 | 1.00 | 14.42 |
| ATOM | 287 | O   | LEU | A   | 576 | 6.149  | 27.157 | 9.977  | 1.00 | 14.10 |
| ATOM | 288 | N   | PRO | A   | 577 | 7.588  | 28.133 | 11.403 | 1.00 | 14.82 |
| ATOM | 289 | CA  | PRO | A   | 577 | 8.582  | 28.355 | 10.356 | 1.00 | 14.42 |
| ATOM | 290 | CB  | PRO | A   | 577 | 9.516  | 29.405 | 10.975 | 1.00 | 16.10 |
| ATOM | 291 | CG  | PRO | A   | 577 | 9.427  | 29.176 | 12.440 | 1.00 | 15.79 |
| ATOM | 292 | CD  | PRO | A   | 577 | 8.049  | 28.628 | 12.714 | 1.00 | 14.94 |
| ATOM | 293 | C   | PRO | A   | 577 | 9.329  | 27.066 | 10.042 | 1.00 | 12.49 |
| ATOM | 294 | O   | PRO | A   | 577 | 9.373  | 26.136 | 10.862 | 1.00 | 10.60 |
| ATOM | 295 | N   | TYR | A   | 578 | 9.885  | 26.993 | 8.840  | 1.00 | 12.70 |
| ATOM | 296 | CA  | TYR | A   | 578 | 10.791 | 25.902 | 8.524  | 1.00 | 15.45 |
| ATOM | 297 | CB  | TYR | A   | 578 | 10.194 | 24.927 | 7.497  | 1.00 | 18.03 |
| ATOM | 298 | CG  | TYR | A   | 578 | 11.207 | 23.912 | 7.019  | 1.00 | 18.79 |
| ATOM | 299 | CD1 | TYR | A   | 578 | 11.554 | 23.830 | 5.675  | 1.00 | 20.34 |
| ATOM | 300 | CE1 | TYR | A   | 578 | 12.507 | 22.915 | 5.237  | 1.00 | 20.18 |
| ATOM | 301 | CZ  | TYR | A   | 578 | 13.120 | 22.081 | 6.146  | 1.00 | 19.10 |

FIGURE 3 (Cont.)

|      | A    | B   | C   | D | E   | F      | G      | H      | I    | J     |
|------|------|-----|-----|---|-----|--------|--------|--------|------|-------|
| ATOM | 302  | OH  | TYR | A | 578 | 14.059 | 21.174 | 5.722  | 1.00 | 18.98 |
| ATOM | 303  | CE2 | TYR | A | 578 | 12.801 | 22.148 | 7.494  | 1.00 | 18.41 |
| ATOM | 304  | CD2 | TYR | A | 578 | 11.849 | 23.062 | 7.922  | 1.00 | 18.92 |
| ATOM | 305  | C   | TYR | A | 578 | 12.110 | 26.493 | 8.048  | 1.00 | 17.36 |
| ATOM | 306  | O   | TYR | A | 578 | 12.166 | 27.163 | 7.017  | 1.00 | 17.98 |
| ATOM | 307  | N   | ASP | A | 579 | 13.157 | 26.263 | 8.834  | 1.00 | 16.89 |
| ATOM | 308  | CA  | ASP | A | 579 | 14.500 | 26.700 | 8.477  | 1.00 | 19.79 |
| ATOM | 309  | CB  | ASP | A | 579 | 15.376 | 26.818 | 9.726  | 1.00 | 21.12 |
| ATOM | 310  | CG  | ASP | A | 579 | 16.663 | 27.598 | 9.478  | 1.00 | 23.88 |
| ATOM | 311  | OD1 | ASP | A | 579 | 17.175 | 27.606 | 8.333  | 1.00 | 24.28 |
| ATOM | 312  | OD2 | ASP | A | 579 | 17.239 | 28.235 | 10.381 | 1.00 | 25.04 |
| ATOM | 313  | C   | ASP | A | 579 | 15.076 | 25.659 | 7.530  | 1.00 | 17.73 |
| ATOM | 314  | O   | ASP | A | 579 | 15.283 | 24.508 | 7.918  | 1.00 | 15.46 |
| ATOM | 315  | N   | HIS | A | 580 | 15.333 | 26.073 | 6.293  | 1.00 | 19.74 |
| ATOM | 316  | CA  | HIS | A | 580 | 15.814 | 25.158 | 5.264  | 1.00 | 20.03 |
| ATOM | 317  | CB  | HIS | A | 580 | 15.636 | 25.767 | 3.875  | 1.00 | 22.13 |
| ATOM | 318  | CG  | HIS | A | 580 | 14.237 | 25.656 | 3.353  | 1.00 | 24.02 |
| ATOM | 319  | ND1 | HIS | A | 580 | 13.210 | 26.459 | 3.802  | 1.00 | 26.54 |
| ATOM | 320  | CE1 | HIS | A | 580 | 12.094 | 26.134 | 3.177  | 1.00 | 25.80 |
| ATOM | 321  | NE2 | HIS | A | 580 | 12.357 | 25.146 | 2.341  | 1.00 | 26.39 |
| ATOM | 322  | CD2 | HIS | A | 580 | 13.689 | 24.822 | 2.438  | 1.00 | 24.66 |
| ATOM | 323  | C   | HIS | A | 580 | 17.246 | 24.670 | 5.495  | 1.00 | 19.97 |
| ATOM | 324  | O   | HIS | A | 580 | 17.757 | 23.867 | 4.718  | 1.00 | 15.37 |
| ATOM | 325  | N   | LYS | A | 581 | 17.873 | 25.126 | 6.582  | 1.00 | 18.20 |
| ATOM | 326  | CA  | LYS | A | 581 | 19.176 | 24.607 | 6.996  | 1.00 | 18.21 |
| ATOM | 327  | CB  | LYS | A | 581 | 19.657 | 25.305 | 8.278  | 1.00 | 21.03 |
| ATOM | 328  | CG  | LYS | A | 581 | 19.158 | 24.670 | 9.578  | 1.00 | 23.61 |
| ATOM | 329  | CD  | LYS | A | 581 | 19.681 | 25.410 | 10.791 | 1.00 | 26.35 |
| ATOM | 330  | CE  | LYS | A | 581 | 18.912 | 25.012 | 12.038 | 1.00 | 29.27 |
| ATOM | 331  | NZ  | LYS | A | 581 | 19.613 | 25.441 | 13.282 | 1.00 | 30.58 |
| ATOM | 332  | C   | LYS | A | 581 | 19.127 | 23.088 | 7.183  | 1.00 | 15.84 |
| ATOM | 333  | O   | LYS | A | 581 | 20.152 | 22.404 | 7.114  | 1.00 | 14.34 |
| ATOM | 334  | N   | TRP | A | 582 | 17.924 | 22.563 | 7.411  | 1.00 | 14.44 |
| ATOM | 335  | CA  | TRP | A | 582 | 17.746 | 21.140 | 7.619  | 1.00 | 13.20 |
| ATOM | 336  | CB  | TRP | A | 582 | 16.416 | 20.858 | 8.330  | 1.00 | 13.37 |
| ATOM | 337  | CG  | TRP | A | 582 | 16.409 | 21.305 | 9.756  | 1.00 | 14.78 |
| ATOM | 338  | CD1 | TRP | A | 582 | 15.680 | 22.329 | 10.291 | 1.00 | 17.64 |
| ATOM | 339  | NE1 | TRP | A | 582 | 15.940 | 22.445 | 11.636 | 1.00 | 17.40 |
| ATOM | 340  | CE2 | TRP | A | 582 | 16.851 | 21.487 | 11.996 | 1.00 | 19.67 |
| ATOM | 341  | CD2 | TRP | A | 582 | 17.172 | 20.753 | 10.830 | 1.00 | 14.70 |
| ATOM | 342  | CE3 | TRP | A | 582 | 18.098 | 19.704 | 10.934 | 1.00 | 17.61 |
| ATOM | 343  | CZ3 | TRP | A | 582 | 18.671 | 19.432 | 12.175 | 1.00 | 20.24 |
| ATOM | 344  | CH2 | TRP | A | 582 | 18.326 | 20.179 | 13.313 | 1.00 | 21.72 |
| ATOM | 345  | CZ2 | TRP | A | 582 | 17.419 | 21.207 | 13.245 | 1.00 | 20.95 |
| ATOM | 346  | C   | TRP | A | 582 | 17.826 | 20.341 | 6.322  | 1.00 | 12.93 |
| ATOM | 347  | O   | TRP | A | 582 | 17.945 | 19.120 | 6.368  | 1.00 | 15.56 |
| ATOM | 348  | N   | GLU | A | 583 | 17.774 | 21.024 | 5.177  | 1.00 | 12.63 |
| ATOM | 349  | CA  | GLU | A | 583 | 17.702 | 20.328 | 3.890  | 1.00 | 12.95 |
| ATOM | 350  | CB  | GLU | A | 583 | 17.457 | 21.289 | 2.719  | 1.00 | 14.33 |
| ATOM | 351  | CG  | GLU | A | 583 | 16.036 | 21.807 | 2.579  | 1.00 | 17.58 |
| ATOM | 352  | CD  | GLU | A | 583 | 14.981 | 20.719 | 2.473  | 1.00 | 19.01 |
| ATOM | 353  | OE1 | GLU | A | 583 | 15.106 | 19.800 | 1.626  | 1.00 | 17.89 |

FIGURE 3 (Cont.)

|      | A   | B   | C   | D | E   | F      | G      | H      | I    | J     |
|------|-----|-----|-----|---|-----|--------|--------|--------|------|-------|
| ATOM | 354 | OE2 | GLU | A | 583 | 14.009 | 20.794 | 3.244  | 1.00 | 23.25 |
| ATOM | 355 | C   | GLU | A | 583 | 18.959 | 19.514 | 3.631  | 1.00 | 15.24 |
| ATOM | 356 | O   | GLU | A | 583 | 20.085 | 20.020 | 3.735  | 1.00 | 14.12 |
| ATOM | 357 | N   | PHE | A | 584 | 18.744 | 18.249 | 3.297  | 1.00 | 11.26 |
| ATOM | 358 | CA  | PHE | A | 584 | 19.825 | 17.337 | 2.974  | 1.00 | 12.40 |
| ATOM | 359 | CB  | PHE | A | 584 | 19.882 | 16.242 | 4.035  | 1.00 | 11.40 |
| ATOM | 360 | CG  | PHE | A | 584 | 21.063 | 15.334 | 3.907  | 1.00 | 12.94 |
| ATOM | 361 | CD1 | PHE | A | 584 | 20.901 | 14.042 | 3.445  | 1.00 | 13.01 |
| ATOM | 362 | CE1 | PHE | A | 584 | 21.988 | 13.190 | 3.330  | 1.00 | 12.10 |
| ATOM | 363 | CZ  | PHE | A | 584 | 23.255 | 13.638 | 3.662  | 1.00 | 10.89 |
| ATOM | 364 | CE2 | PHE | A | 584 | 23.433 | 14.935 | 4.122  | 1.00 | 15.91 |
| ATOM | 365 | CD2 | PHE | A | 584 | 22.337 | 15.776 | 4.243  | 1.00 | 12.36 |
| ATOM | 366 | C   | PHE | A | 584 | 19.557 | 16.750 | 1.592  | 1.00 | 10.81 |
| ATOM | 367 | O   | PHE | A | 584 | 18.414 | 16.405 | 1.295  | 1.00 | 12.00 |
| ATOM | 368 | N   | PRO | A | 585 | 20.587 | 16.649 | 0.745  | 1.00 | 11.16 |
| ATOM | 369 | CA  | PRO | A | 585 | 20.406 | 16.141 | -0.624 | 1.00 | 12.02 |
| ATOM | 370 | CB  | PRO | A | 585 | 21.792 | 16.314 | -1.269 | 1.00 | 10.68 |
| ATOM | 371 | CG  | PRO | A | 585 | 22.573 | 17.177 | -0.347 | 1.00 | 12.55 |
| ATOM | 372 | CD  | PRO | A | 585 | 21.985 | 17.034 | 1.013  | 1.00 | 12.57 |
| ATOM | 373 | C   | PRO | A | 585 | 20.016 | 14.668 | -0.613 | 1.00 | 11.44 |
| ATOM | 374 | O   | PRO | A | 585 | 20.728 | 13.863 | -0.017 | 1.00 | 10.01 |
| ATOM | 375 | N   | ARG | A | 586 | 18.906 | 14.326 | -1.257 | 1.00 | 11.70 |
| ATOM | 376 | CA  | ARG | A | 586 | 18.424 | 12.942 | -1.225 | 1.00 | 14.09 |
| ATOM | 377 | CB  | ARG | A | 586 | 17.006 | 12.814 | -1.806 | 1.00 | 18.04 |
| ATOM | 378 | CG  | ARG | A | 586 | 16.814 | 13.367 | -3.205 | 1.00 | 19.42 |
| ATOM | 379 | CD  | ARG | A | 586 | 15.356 | 13.401 | -3.655 | 1.00 | 19.61 |
| ATOM | 380 | NE  | ARG | A | 586 | 14.589 | 14.466 | -3.005 | 1.00 | 17.66 |
| ATOM | 381 | CZ  | ARG | A | 586 | 13.585 | 14.271 | -2.155 | 1.00 | 17.91 |
| ATOM | 382 | NH1 | ARG | A | 586 | 12.956 | 15.315 | -1.630 | 1.00 | 17.73 |
| ATOM | 383 | NH2 | ARG | A | 586 | 13.207 | 13.042 | -1.816 | 1.00 | 16.88 |
| ATOM | 384 | C   | ARG | A | 586 | 19.389 | 11.940 | -1.877 | 1.00 | 13.69 |
| ATOM | 385 | O   | ARG | A | 586 | 19.365 | 10.762 | -1.536 | 1.00 | 13.93 |
| ATOM | 386 | N   | ASN | A | 587 | 20.244 | 12.405 | -2.790 | 1.00 | 13.41 |
| ATOM | 387 | CA  | ASN | A | 587 | 21.225 | 11.523 | -3.427 | 1.00 | 11.84 |
| ATOM | 388 | CB  | ASN | A | 587 | 21.825 | 12.163 | -4.684 | 1.00 | 12.42 |
| ATOM | 389 | CG  | ASN | A | 587 | 22.430 | 13.528 | -4.412 | 1.00 | 12.47 |
| ATOM | 390 | OD1 | ASN | A | 587 | 21.732 | 14.457 | -3.993 | 1.00 | 12.03 |
| ATOM | 391 | ND2 | ASN | A | 587 | 23.728 | 13.652 | -4.639 | 1.00 | 10.39 |
| ATOM | 392 | C   | ASN | A | 587 | 22.337 | 11.090 | -2.475 | 1.00 | 13.38 |
| ATOM | 393 | O   | ASN | A | 587 | 23.138 | 10.226 | -2.819 | 1.00 | 15.72 |
| ATOM | 394 | N   | ARG | A | 588 | 22.382 | 11.695 | -1.285 | 1.00 | 11.41 |
| ATOM | 395 | CA  | ARG | A | 588 | 23.362 | 11.325 | -0.263 | 1.00 | 14.44 |
| ATOM | 396 | CB  | ARG | A | 588 | 24.033 | 12.573 | 0.316  | 1.00 | 15.66 |
| ATOM | 397 | CG  | ARG | A | 588 | 25.128 | 13.116 | -0.588 | 1.00 | 21.50 |
| ATOM | 398 | CD  | ARG | A | 588 | 25.358 | 14.606 | -0.484 | 1.00 | 28.34 |
| ATOM | 399 | NE  | ARG | A | 588 | 26.030 | 14.972 | 0.758  | 1.00 | 34.14 |
| ATOM | 400 | CZ  | ARG | A | 588 | 27.347 | 15.064 | 0.911  | 1.00 | 37.34 |
| ATOM | 401 | NH1 | ARG | A | 588 | 28.168 | 14.816 | -0.104 | 1.00 | 39.01 |
| ATOM | 402 | NH2 | ARG | A | 588 | 27.847 | 15.411 | 2.089  | 1.00 | 39.81 |
| ATOM | 403 | C   | ARG | A | 588 | 22.746 | 10.450 | 0.834  | 1.00 | 12.55 |
| ATOM | 404 | O   | ARG | A | 588 | 23.337 | 10.249 | 1.900  | 1.00 | 14.39 |
| ATOM | 405 | N   | LEU | A | 589 | 21.565 | 9.920  | 0.537  | 1.00 | 10.25 |

FIGURE 3 (Cont.)

|      | A    | B   | C   | D | E   | F      | G      | H      | I    | J     |
|------|------|-----|-----|---|-----|--------|--------|--------|------|-------|
| ATOM | 406  | CA  | LEU | A | 589 | 20.837 | 9.012  | 1.415  | 1.00 | 14.85 |
| ATOM | 407  | CB  | LEU | A | 589 | 19.416 | 9.548  | 1.609  | 1.00 | 16.14 |
| ATOM | 408  | CG  | LEU | A | 589 | 18.675 | 9.521  | 2.939  | 1.00 | 20.46 |
| ATOM | 409  | CD1 | LEU | A | 589 | 19.525 | 10.029 | 4.106  | 1.00 | 18.12 |
| ATOM | 410  | CD2 | LEU | A | 589 | 17.392 | 10.353 | 2.801  | 1.00 | 16.75 |
| ATOM | 411  | C   | LEU | A | 589 | 20.785 | 7.629  | 0.765  | 1.00 | 18.07 |
| ATOM | 412  | O   | LEU | A | 589 | 20.454 | 7.504  | -0.417 | 1.00 | 18.11 |
| ATOM | 413  | N   | SER | A | 590 | 21.128 | 6.596  | 1.529  | 1.00 | 15.91 |
| ATOM | 414  | CA  | SER | A | 590 | 21.045 | 5.219  | 1.052  | 1.00 | 16.63 |
| ATOM | 415  | CB  | SER | A | 590 | 22.435 | 4.578  | 1.060  | 1.00 | 19.00 |
| ATOM | 416  | OG  | SER | A | 590 | 22.373 | 3.171  | 0.885  | 1.00 | 21.93 |
| ATOM | 417  | C   | SER | A | 590 | 20.084 | 4.454  | 1.964  | 1.00 | 16.53 |
| ATOM | 418  | O   | SER | A | 590 | 20.367 | 4.291  | 3.142  | 1.00 | 14.62 |
| ATOM | 419  | N   | PHE | A | 591 | 18.956 | 4.002  | 1.420  | 1.00 | 14.58 |
| ATOM | 420  | CA  | PHE | A | 591 | 17.935 | 3.301  | 2.207  | 1.00 | 16.49 |
| ATOM | 421  | CB  | PHE | A | 591 | 16.573 | 3.337  | 1.505  | 1.00 | 18.56 |
| ATOM | 422  | CG  | PHE | A | 591 | 15.961 | 4.710  | 1.416  | 1.00 | 22.73 |
| ATOM | 423  | CD1 | PHE | A | 591 | 15.197 | 5.064  | 0.307  | 1.00 | 26.68 |
| ATOM | 424  | CE1 | PHE | A | 591 | 14.617 | 6.326  | 0.212  | 1.00 | 27.89 |
| ATOM | 425  | CZ  | PHE | A | 591 | 14.801 | 7.250  | 1.239  | 1.00 | 27.09 |
| ATOM | 426  | CE2 | PHE | A | 591 | 15.553 | 6.907  | 2.351  | 1.00 | 24.53 |
| ATOM | 427  | CD2 | PHE | A | 591 | 16.124 | 5.639  | 2.439  | 1.00 | 24.10 |
| ATOM | 428  | C   | PHE | A | 591 | 18.294 | 1.857  | 2.507  | 1.00 | 15.28 |
| ATOM | 429  | O   | PHE | A | 591 | 18.783 | 1.130  | 1.640  | 1.00 | 16.73 |
| ATOM | 430  | N   | GLY | A | 592 | 18.036 | 1.448  | 3.746  | 1.00 | 14.04 |
| ATOM | 431  | CA  | GLY | A | 592 | 18.230 | 0.077  | 4.174  | 1.00 | 14.13 |
| ATOM | 432  | C   | GLY | A | 592 | 16.886 | -0.532 | 4.524  | 1.00 | 15.38 |
| ATOM | 433  | O   | GLY | A | 592 | 15.890 | -0.286 | 3.839  | 1.00 | 14.75 |
| ATOM | 434  | N   | LYS | A | 593 | 16.857 | -1.304 | 5.606  | 1.00 | 14.49 |
| ATOM | 435  | CA  | LYS | A | 593 | 15.676 | -2.077 | 5.977  | 1.00 | 14.96 |
| ATOM | 436  | CB  | LYS | A | 593 | 16.027 | -3.131 | 7.036  | 1.00 | 18.95 |
| ATOM | 437  | CG  | LYS | A | 593 | 16.448 | -2.583 | 8.394  | 1.00 | 22.79 |
| ATOM | 438  | CD  | LYS | A | 593 | 16.978 | -3.704 | 9.292  | 1.00 | 26.31 |
| ATOM | 439  | CE  | LYS | A | 593 | 16.592 | -3.474 | 10.748 | 1.00 | 28.47 |
| ATOM | 440  | NZ  | LYS | A | 593 | 17.753 | -3.673 | 11.664 | 1.00 | 29.92 |
| ATOM | 441  | C   | LYS | A | 593 | 14.518 | -1.206 | 6.453  | 1.00 | 13.56 |
| ATOM | 442  | O   | LYS | A | 593 | 14.722 | -0.164 | 7.067  | 1.00 | 10.56 |
| ATOM | 443  | N   | THR | A | 594 | 13.303 | -1.647 | 6.155  | 1.00 | 12.12 |
| ATOM | 444  | CA  | THR | A | 594 | 12.105 | -1.005 | 6.670  | 1.00 | 15.71 |
| ATOM | 445  | CB  | THR | A | 594 | 10.897 | -1.434 | 5.830  | 1.00 | 15.18 |
| ATOM | 446  | OG1 | THR | A | 594 | 11.016 | -0.855 | 4.520  | 1.00 | 15.20 |
| ATOM | 447  | CG2 | THR | A | 594 | 9.596  | -0.840 | 6.385  | 1.00 | 15.77 |
| ATOM | 448  | C   | THR | A | 594 | 11.929 | -1.364 | 8.149  | 1.00 | 15.91 |
| ATOM | 449  | O   | THR | A | 594 | 11.923 | -2.539 | 8.511  | 1.00 | 17.76 |
| ATOM | 450  | N   | LEU | A | 595 | 11.824 | -0.345 | 9.000  | 1.00 | 13.20 |
| ATOM | 451  | CA  | LEU | A | 595 | 11.669 | -0.564 | 10.443 | 1.00 | 15.22 |
| ATOM | 452  | CB  | LEU | A | 595 | 12.204 | 0.631  | 11.232 | 1.00 | 15.86 |
| ATOM | 453  | CG  | LEU | A | 595 | 13.667 | 0.989  | 10.947 | 1.00 | 18.02 |
| ATOM | 454  | CD1 | LEU | A | 595 | 14.069 | 2.295  | 11.629 | 1.00 | 20.02 |
| ATOM | 455  | CD2 | LEU | A | 595 | 14.605 | -0.151 | 11.347 | 1.00 | 17.00 |
| ATOM | 456  | C   | LEU | A | 595 | 10.212 | -0.858 | 10.795 | 1.00 | 16.91 |
| ATOM | 457  | O   | LEU | A | 595 | 9.915  | -1.675 | 11.662 | 1.00 | 19.18 |

FIGURE 3 (Cont.)

| | A | B | C | D | E | F | G | H | I | J |
|---|---|---|---|---|---|---|---|---|---|---|
| ATOM | 458 | N | GLY | A | 596 | 9.303 | -0.189 | 10.101 | 1.00 | 15.86 |
| ATOM | 459 | CA | GLY | A | 596 | 7.898 | -0.521 | 10.188 | 1.00 | 16.70 |
| ATOM | 460 | C | GLY | A | 596 | 7.170 | 0.205 | 9.088 | 1.00 | 16.05 |
| ATOM | 461 | O | GLY | A | 596 | 7.611 | 1.266 | 8.654 | 1.00 | 13.12 |
| ATOM | 462 | N | ALA | A | 597 | 6.079 | -0.391 | 8.621 | 1.00 | 16.45 |
| ATOM | 463 | CA | ALA | A | 597 | 5.199 | 0.252 | 7.662 | 1.00 | 15.53 |
| ATOM | 464 | CB | ALA | A | 597 | 5.236 | -0.474 | 6.332 | 1.00 | 17.05 |
| ATOM | 465 | C | ALA | A | 597 | 3.785 | 0.279 | 8.224 | 1.00 | 16.39 |
| ATOM | 466 | O | ALA | A | 597 | 3.271 | -0.740 | 8.703 | 1.00 | 16.22 |
| ATOM | 467 | N | GLY | A | 598 | 3.168 | 1.450 | 8.177 | 1.00 | 14.52 |
| ATOM | 468 | CA | GLY | A | 598 | 1.801 | 1.609 | 8.630 | 1.00 | 16.51 |
| ATOM | 469 | C | GLY | A | 598 | 0.853 | 1.936 | 7.500 | 1.00 | 16.66 |
| ATOM | 470 | O | GLY | A | 598 | 1.175 | 1.744 | 6.323 | 1.00 | 13.26 |
| ATOM | 471 | N | ALA | A | 599 | -0.319 | 2.450 | 7.862 | 1.00 | 17.31 |
| ATOM | 472 | CA | ALA | A | 599 | -1.361 | 2.752 | 6.887 | 1.00 | 17.30 |
| ATOM | 473 | CB | ALA | A | 599 | -2.687 | 3.017 | 7.586 | 1.00 | 19.57 |
| ATOM | 474 | C | ALA | A | 599 | -1.005 | 3.927 | 5.983 | 1.00 | 15.93 |
| ATOM | 475 | O | ALA | A | 599 | -1.583 | 4.070 | 4.910 | 1.00 | 15.01 |
| ATOM | 476 | N | PHE | A | 600 | -0.062 | 4.760 | 6.423 | 1.00 | 13.25 |
| ATOM | 477 | CA | PHE | A | 600 | 0.230 | 6.025 | 5.746 | 1.00 | 14.29 |
| ATOM | 478 | CB | PHE | A | 600 | 0.011 | 7.211 | 6.693 | 1.00 | 13.65 |
| ATOM | 479 | CG | PHE | A | 600 | -1.283 | 7.158 | 7.441 | 1.00 | 14.30 |
| ATOM | 480 | CD1 | PHE | A | 600 | -2.495 | 7.184 | 6.766 | 1.00 | 16.16 |
| ATOM | 481 | CE1 | PHE | A | 600 | -3.707 | 7.132 | 7.463 | 1.00 | 17.01 |
| ATOM | 482 | CZ | PHE | A | 600 | -3.700 | 7.055 | 8.850 | 1.00 | 17.17 |
| ATOM | 483 | CE2 | PHE | A | 600 | -2.493 | 7.029 | 9.535 | 1.00 | 16.97 |
| ATOM | 484 | CD2 | PHE | A | 600 | -1.287 | 7.081 | 8.828 | 1.00 | 16.18 |
| ATOM | 485 | C | PHE | A | 600 | 1.628 | 6.138 | 5.165 | 1.00 | 12.99 |
| ATOM | 486 | O | PHE | A | 600 | 1.903 | 7.052 | 4.389 | 1.00 | 12.87 |
| ATOM | 487 | N | GLY | A | 601 | 2.510 | 5.225 | 5.546 | 1.00 | 10.77 |
| ATOM | 488 | CA | GLY | A | 601 | 3.899 | 5.306 | 5.140 | 1.00 | 11.53 |
| ATOM | 489 | C | GLY | A | 601 | 4.756 | 4.351 | 5.940 | 1.00 | 11.31 |
| ATOM | 490 | O | GLY | A | 601 | 4.274 | 3.319 | 6.423 | 1.00 | 10.81 |
| ATOM | 491 | N | LYS | A | 602 | 6.034 | 4.689 | 6.068 | 1.00 | 11.68 |
| ATOM | 492 | CA | LYS | A | 602 | 6.973 | 3.825 | 6.756 | 1.00 | 12.51 |
| ATOM | 493 | CB | LYS | A | 602 | 7.481 | 2.714 | 5.821 | 1.00 | 15.57 |
| ATOM | 494 | CG | LYS | A | 602 | 8.254 | 3.179 | 4.597 | 1.00 | 19.86 |
| ATOM | 495 | CD | LYS | A | 602 | 8.486 | 2.004 | 3.650 | 1.00 | 23.35 |
| ATOM | 496 | CE | LYS | A | 602 | 9.342 | 2.405 | 2.463 | 1.00 | 28.39 |
| ATOM | 497 | NZ | LYS | A | 602 | 8.535 | 2.955 | 1.335 | 1.00 | 32.95 |
| ATOM | 498 | C | LYS | A | 602 | 8.133 | 4.605 | 7.341 | 1.00 | 12.18 |
| ATOM | 499 | O | LYS | A | 602 | 8.329 | 5.779 | 7.038 | 1.00 | 10.81 |
| ATOM | 500 | N | VAL | A | 603 | 8.884 | 3.937 | 8.202 | 1.00 | 12.29 |
| ATOM | 501 | CA | VAL | A | 603 | 10.152 | 4.462 | 8.666 | 1.00 | 10.78 |
| ATOM | 502 | CB | VAL | A | 603 | 10.153 | 4.712 | 10.184 | 1.00 | 12.56 |
| ATOM | 503 | CG1 | VAL | A | 603 | 11.507 | 5.264 | 10.637 | 1.00 | 13.13 |
| ATOM | 504 | CG2 | VAL | A | 603 | 9.028 | 5.696 | 10.566 | 1.00 | 9.96 |
| ATOM | 505 | C | VAL | A | 603 | 11.203 | 3.442 | 8.259 | 1.00 | 11.67 |
| ATOM | 506 | O | VAL | A | 603 | 11.020 | 2.246 | 8.454 | 1.00 | 13.61 |
| ATOM | 507 | N | VAL | A | 604 | 12.273 | 3.929 | 7.640 | 1.00 | 11.28 |
| ATOM | 508 | CA | VAL | A | 604 | 13.340 | 3.066 | 7.133 | 1.00 | 13.40 |
| ATOM | 509 | CB | BVAL | A | 604 | 13.454 | 3.230 | 5.588 | 0.35 | 13.52 |

FIGURE 3 (Cont.)

|      | A    | B    | C    | D | E   | F      | G      | H      | I    | J     |
|------|------|------|------|---|-----|--------|--------|--------|------|-------|
| ATOM | 510  | CB   | AVAL | A | 604 | 13.458 | 3.050  | 5.578  | 0.65 | 15.91 |
| ATOM | 511  | CG1  | BVAL | A | 604 | 14.247 | 2.112  | 4.964  | 0.35 | 12.16 |
| ATOM | 512  | CG1  | AVAL | A | 604 | 12.159 | 2.593  | 4.931  | 0.65 | 15.38 |
| ATOM | 513  | CG2  | BVAL | A | 604 | 12.079 | 3.323  | 4.941  | 0.35 | 12.45 |
| ATOM | 514  | CG2  | AVAL | A | 604 | 13.906 | 4.402  | 5.041  | 0.65 | 17.70 |
| ATOM | 515  | C    | VAL  | A | 604 | 14.682 | 3.453  | 7.756  | 1.00 | 13.62 |
| ATOM | 516  | O    | VAL  | A | 604 | 14.935 | 4.632  | 8.026  | 1.00 | 13.97 |
| ATOM | 517  | N    | GLU  | A | 605 | 15.534 | 2.454  | 7.976  | 1.00 | 12.39 |
| ATOM | 518  | CA   | GLU  | A | 605 | 16.934 | 2.689  | 8.296  | 1.00 | 11.74 |
| ATOM | 519  | CB   | GLU  | A | 605 | 17.599 | 1.380  | 8.737  | 1.00 | 15.76 |
| ATOM | 520  | CG   | GLU  | A | 605 | 18.993 | 1.511  | 9.340  | 1.00 | 20.66 |
| ATOM | 521  | CD   | GLU  | A | 605 | 19.622 | 0.168  | 9.706  | 1.00 | 25.13 |
| ATOM | 522  | OE1  | GLU  | A | 605 | 18.950 | -0.879 | 9.573  | 1.00 | 28.14 |
| ATOM | 523  | OE2  | GLU  | A | 605 | 20.799 | 0.152  | 10.132 | 1.00 | 28.18 |
| ATOM | 524  | C    | GLU  | A | 605 | 17.596 | 3.236  | 7.033  | 1.00 | 13.16 |
| ATOM | 525  | O    | GLU  | A | 605 | 17.260 | 2.824  | 5.917  | 1.00 | 13.76 |
| ATOM | 526  | N    | ALA  | A | 606 | 18.509 | 4.185  | 7.198  | 1.00 | 11.95 |
| ATOM | 527  | CA   | ALA  | A | 606 | 19.262 | 4.704  | 6.066  | 1.00 | 10.78 |
| ATOM | 528  | CB   | ALA  | A | 606 | 18.550 | 5.905  | 5.434  | 1.00 | 13.36 |
| ATOM | 529  | C    | ALA  | A | 606 | 20.662 | 5.089  | 6.492  | 1.00 | 11.03 |
| ATOM | 530  | O    | ALA  | A | 606 | 20.940 | 5.247  | 7.680  | 1.00 | 11.30 |
| ATOM | 531  | N    | THR  | A | 607 | 21.547 | 5.214  | 5.512  | 1.00 | 10.36 |
| ATOM | 532  | CA   | THR  | A | 607 | 22.850 | 5.819  | 5.732  | 1.00 | 10.19 |
| ATOM | 533  | CB   | THR  | A | 607 | 23.963 | 4.923  | 5.174  | 1.00 | 11.84 |
| ATOM | 534  | OG1  | THR  | A | 607 | 23.868 | 3.628  | 5.777  | 1.00 | 15.02 |
| ATOM | 535  | CG2  | THR  | A | 607 | 25.331 | 5.411  | 5.635  | 1.00 | 11.74 |
| ATOM | 536  | C    | THR  | A | 607 | 22.860 | 7.179  | 5.054  | 1.00 | 12.46 |
| ATOM | 537  | O    | THR  | A | 607 | 22.529 | 7.297  | 3.870  | 1.00 | 11.08 |
| ATOM | 538  | N    | ALA  | A | 608 | 23.214 | 8.199  | 5.827  | 1.00 | 10.45 |
| ATOM | 539  | CA   | ALA  | A | 608 | 23.342 | 9.549  | 5.307  | 1.00 | 11.08 |
| ATOM | 540  | CB   | ALA  | A | 608 | 22.564 | 10.544 | 6.171  | 1.00 | 9.90  |
| ATOM | 541  | C    | ALA  | A | 608 | 24.816 | 9.885  | 5.277  | 1.00 | 11.11 |
| ATOM | 542  | O    | ALA  | A | 608 | 25.515 | 9.777  | 6.289  | 1.00 | 11.82 |
| ATOM | 543  | N    | TYR  | A | 609 | 25.292 | 10.255 | 4.095  | 1.00 | 11.28 |
| ATOM | 544  | CA   | TYR  | A | 609 | 26.709 | 10.528 | 3.896  | 1.00 | 14.16 |
| ATOM | 545  | CB   | TYR  | A | 609 | 27.162 | 9.973  | 2.550  | 1.00 | 15.93 |
| ATOM | 546  | CG   | TYR  | A | 609 | 27.109 | 8.466  | 2.481  | 1.00 | 19.71 |
| ATOM | 547  | CD1  | TYR  | A | 609 | 28.237 | 7.701  | 2.759  | 1.00 | 21.50 |
| ATOM | 548  | CE1  | TYR  | A | 609 | 28.190 | 6.313  | 2.705  | 1.00 | 23.58 |
| ATOM | 549  | CZ   | TYR  | A | 609 | 27.004 | 5.685  | 2.369  | 1.00 | 23.39 |
| ATOM | 550  | OH   | TYR  | A | 609 | 26.950 | 4.315  | 2.313  | 1.00 | 25.62 |
| ATOM | 551  | CE2  | TYR  | A | 609 | 25.870 | 6.424  | 2.092  | 1.00 | 23.08 |
| ATOM | 552  | CD2  | TYR  | A | 609 | 25.925 | 7.804  | 2.150  | 1.00 | 20.98 |
| ATOM | 553  | C    | TYR  | A | 609 | 26.962 | 12.018 | 3.970  | 1.00 | 14.47 |
| ATOM | 554  | O    | TYR  | A | 609 | 26.412 | 12.782 | 3.175  | 1.00 | 13.47 |
| ATOM | 555  | N    | GLY  | A | 610 | 27.781 | 12.424 | 4.937  | 1.00 | 16.71 |
| ATOM | 556  | CA   | GLY  | A | 610 | 28.145 | 13.821 | 5.111  | 1.00 | 18.88 |
| ATOM | 557  | C    | GLY  | A | 610 | 27.068 | 14.686 | 5.747  | 1.00 | 21.82 |
| ATOM | 558  | O    | GLY  | A | 610 | 26.999 | 15.878 | 5.460  | 1.00 | 21.63 |
| ATOM | 559  | N    | LEU  | A | 611 | 26.234 | 14.094 | 6.603  | 1.00 | 24.37 |
| ATOM | 560  | CA   | LEU  | A | 611 | 25.162 | 14.827 | 7.290  | 1.00 | 27.25 |
| ATOM | 561  | CB   | LEU  | A | 611 | 24.314 | 13.882 | 8.151  | 1.00 | 28.27 |

FIGURE 3 (Cont.)

| | A | B | C | D | E | F | G | H | I | J |
|---|---|---|---|---|---|---|---|---|---|---|
| ATOM | 562 | CG | LEU | A | 611 | 22.788 | 13.902 | 8.016 | 1.00 | 29.11 |
| ATOM | 563 | CD1 | LEU | A | 611 | 22.167 | 12.991 | 9.067 | 1.00 | 28.00 |
| ATOM | 564 | CD2 | LEU | A | 611 | 22.197 | 15.300 | 8.105 | 1.00 | 28.59 |
| ATOM | 565 | C | LEU | A | 611 | 25.688 | 15.994 | 8.139 | 1.00 | 31.10 |
| ATOM | 566 | O | LEU | A | 611 | 25.261 | 17.140 | 7.958 | 1.00 | 32.01 |
| ATOM | 567 | N | ILE | A | 612 | 26.606 | 15.697 | 9.059 | 1.00 | 32.03 |
| ATOM | 568 | CA | ILE | A | 612 | 27.286 | 16.735 | 9.841 | 1.00 | 34.61 |
| ATOM | 569 | CB | ILE | A | 612 | 27.146 | 16.509 | 11.372 | 1.00 | 37.01 |
| ATOM | 570 | CG1 | ILE | A | 612 | 27.012 | 15.014 | 11.714 | 1.00 | 37.80 |
| ATOM | 571 | CD1 | ILE | A | 612 | 25.615 | 14.565 | 12.115 | 1.00 | 37.97 |
| ATOM | 572 | CG2 | ILE | A | 612 | 26.024 | 17.391 | 11.944 | 1.00 | 38.97 |
| ATOM | 573 | C | ILE | A | 612 | 28.756 | 16.865 | 9.444 | 1.00 | 32.94 |
| ATOM | 574 | O | ILE | A | 612 | 29.211 | 17.955 | 9.093 | 1.00 | 36.03 |
| ATOM | 575 | N | LYS | A | 613 | 29.490 | 15.754 | 9.498 | 1.00 | 30.09 |
| ATOM | 576 | CA | LYS | A | 613 | 30.878 | 15.716 | 9.043 | 1.00 | 27.63 |
| ATOM | 577 | CB | LYS | A | 613 | 31.733 | 14.854 | 9.978 | 1.00 | 29.14 |
| ATOM | 578 | CG | LYS | A | 613 | 32.316 | 15.604 | 11.166 | 1.00 | 31.95 |
| ATOM | 579 | CD | LYS | A | 613 | 33.727 | 16.103 | 10.877 | 1.00 | 33.54 |
| ATOM | 580 | CE | LYS | A | 613 | 34.461 | 16.474 | 12.160 | 1.00 | 35.10 |
| ATOM | 581 | NZ | LYS | A | 613 | 35.858 | 15.961 | 12.167 | 1.00 | 35.07 |
| ATOM | 582 | C | LYS | A | 613 | 30.936 | 15.176 | 7.617 | 1.00 | 25.03 |
| ATOM | 583 | O | LYS | A | 613 | 30.442 | 14.079 | 7.343 | 1.00 | 21.88 |
| ATOM | 584 | N | SER | A | 614 | 31.548 | 15.942 | 6.714 | 1.00 | 24.05 |
| ATOM | 585 | CA | SER | A | 614 | 31.529 | 15.613 | 5.283 | 1.00 | 22.29 |
| ATOM | 586 | CB | SER | A | 614 | 32.117 | 16.747 | 4.431 | 1.00 | 23.91 |
| ATOM | 587 | OG | SER | A | 614 | 32.907 | 17.633 | 5.199 | 1.00 | 23.56 |
| ATOM | 588 | C | SER | A | 614 | 32.190 | 14.273 | 4.931 | 1.00 | 21.16 |
| ATOM | 589 | O | SER | A | 614 | 31.820 | 13.647 | 3.936 | 1.00 | 22.63 |
| ATOM | 590 | N | ASP | A | 615 | 33.149 | 13.837 | 5.748 | 1.00 | 17.44 |
| ATOM | 591 | CA | ASP | A | 615 | 33.862 | 12.578 | 5.510 | 1.00 | 16.96 |
| ATOM | 592 | CB | ASP | A | 615 | 35.372 | 12.760 | 5.737 | 1.00 | 17.02 |
| ATOM | 593 | CG | ASP | A | 615 | 35.750 | 12.812 | 7.213 | 1.00 | 18.56 |
| ATOM | 594 | OD1 | ASP | A | 615 | 34.974 | 13.372 | 8.024 | 1.00 | 18.28 |
| ATOM | 595 | OD2 | ASP | A | 615 | 36.814 | 12.318 | 7.652 | 1.00 | 17.70 |
| ATOM | 596 | C | ASP | A | 615 | 33.318 | 11.418 | 6.359 | 1.00 | 18.01 |
| ATOM | 597 | O | ASP | A | 615 | 33.977 | 10.386 | 6.518 | 1.00 | 16.61 |
| ATOM | 598 | N | ALA | A | 616 | 32.114 | 11.594 | 6.897 | 1.00 | 17.58 |
| ATOM | 599 | CA | ALA | A | 616 | 31.533 | 10.610 | 7.796 | 1.00 | 19.05 |
| ATOM | 600 | CB | ALA | A | 616 | 31.532 | 11.137 | 9.224 | 1.00 | 20.52 |
| ATOM | 601 | C | ALA | A | 616 | 30.122 | 10.216 | 7.369 | 1.00 | 19.65 |
| ATOM | 602 | O | ALA | A | 616 | 29.292 | 11.072 | 7.041 | 1.00 | 22.48 |
| ATOM | 603 | N | ALA | A | 617 | 29.870 | 8.911 | 7.364 | 1.00 | 18.26 |
| ATOM | 604 | CA | ALA | A | 617 | 28.541 | 8.369 | 7.126 | 1.00 | 17.07 |
| ATOM | 605 | CB | ALA | A | 617 | 28.627 | 7.098 | 6.310 | 1.00 | 17.89 |
| ATOM | 606 | C | ALA | A | 617 | 27.889 | 8.093 | 8.471 | 1.00 | 18.81 |
| ATOM | 607 | O | ALA | A | 617 | 28.573 | 7.799 | 9.458 | 1.00 | 18.21 |
| ATOM | 608 | N | MET | A | 618 | 26.567 | 8.189 | 8.507 | 1.00 | 17.05 |
| ATOM | 609 | CA | MET | A | 618 | 25.823 | 8.046 | 9.745 | 1.00 | 18.72 |
| ATOM | 610 | CB | MET | A | 618 | 25.518 | 9.439 | 10.285 | 1.00 | 23.45 |
| ATOM | 611 | CG | MET | A | 618 | 24.530 | 9.534 | 11.415 | 1.00 | 27.50 |
| ATOM | 612 | SD | MET | A | 618 | 24.316 | 11.279 | 11.785 | 1.00 | 31.84 |
| ATOM | 613 | CE | MET | A | 618 | 24.321 | 11.220 | 13.579 | 1.00 | 32.21 |

FIGURE 3 (Cont.)

| | A | B | C | D | E | F | G | H | I | J |
|---|---|---|---|---|---|---|---|---|---|---|
| ATOM | 614 | C | MET | A | 618 | 24.543 | 7.272 | 9.472 | 1.00 | 13.64 |
| ATOM | 615 | O | MET | A | 618 | 23.878 | 7.514 | 8.470 | 1.00 | 13.70 |
| ATOM | 616 | N | THR | A | 619 | 24.222 | 6.324 | 10.347 | 1.00 | 12.33 |
| ATOM | 617 | CA | THR | A | 619 | 22.939 | 5.638 | 10.284 | 1.00 | 12.32 |
| ATOM | 618 | CB | THR | A | 619 | 22.967 | 4.322 | 11.063 | 1.00 | 14.99 |
| ATOM | 619 | OG1 | THR | A | 619 | 24.059 | 3.518 | 10.599 | 1.00 | 16.20 |
| ATOM | 620 | CG2 | THR | A | 619 | 21.731 | 3.486 | 10.737 | 1.00 | 15.79 |
| ATOM | 621 | C | THR | A | 619 | 21.861 | 6.558 | 10.840 | 1.00 | 12.12 |
| ATOM | 622 | O | THR | A | 619 | 22.032 | 7.177 | 11.893 | 1.00 | 13.79 |
| ATOM | 623 | N | VAL | A | 620 | 20.765 | 6.654 | 10.102 | 1.00 | 9.92 |
| ATOM | 624 | CA | VAL | A | 620 | 19.650 | 7.519 | 10.454 | 1.00 | 8.81 |
| ATOM | 625 | CB | VAL | A | 620 | 19.647 | 8.822 | 9.601 | 1.00 | 9.60 |
| ATOM | 626 | CG1 | VAL | A | 620 | 20.892 | 9.655 | 9.864 | 1.00 | 12.76 |
| ATOM | 627 | CG2 | VAL | A | 620 | 19.528 | 8.513 | 8.110 | 1.00 | 10.91 |
| ATOM | 628 | C | VAL | A | 620 | 18.338 | 6.766 | 10.253 | 1.00 | 9.65 |
| ATOM | 629 | O | VAL | A | 620 | 18.322 | 5.680 | 9.667 | 1.00 | 11.25 |
| ATOM | 630 | N | ALA | A | 621 | 17.248 | 7.332 | 10.763 | 1.00 | 10.54 |
| ATOM | 631 | CA | ALA | A | 621 | 15.917 | 6.818 | 10.469 | 1.00 | 12.96 |
| ATOM | 632 | CB | ALA | A | 621 | 15.104 | 6.641 | 11.744 | 1.00 | 13.39 |
| ATOM | 633 | C | ALA | A | 621 | 15.260 | 7.827 | 9.549 | 1.00 | 13.27 |
| ATOM | 634 | O | ALA | A | 621 | 15.457 | 9.037 | 9.705 | 1.00 | 14.72 |
| ATOM | 635 | N | VAL | A | 622 | 14.522 | 7.338 | 8.563 | 1.00 | 10.33 |
| ATOM | 636 | CA | VAL | A | 622 | 13.889 | 8.224 | 7.596 | 1.00 | 11.31 |
| ATOM | 637 | CB | VAL | A | 622 | 14.484 | 8.077 | 6.175 | 1.00 | 12.26 |
| ATOM | 638 | CG1 | VAL | A | 622 | 13.801 | 9.032 | 5.194 | 1.00 | 14.49 |
| ATOM | 639 | CG2 | VAL | A | 622 | 15.997 | 8.343 | 6.179 | 1.00 | 14.23 |
| ATOM | 640 | C | VAL | A | 622 | 12.404 | 7.939 | 7.567 | 1.00 | 12.24 |
| ATOM | 641 | O | VAL | A | 622 | 11.990 | 6.802 | 7.334 | 1.00 | 11.64 |
| ATOM | 642 | N | LYS | A | 623 | 11.623 | 8.984 | 7.830 | 1.00 | 12.25 |
| ATOM | 643 | CA | LYS | A | 623 | 10.169 | 8.925 | 7.757 | 1.00 | 13.27 |
| ATOM | 644 | CB | LYS | A | 623 | 9.533 | 9.864 | 8.781 | 1.00 | 17.42 |
| ATOM | 645 | CG | LYS | A | 623 | 10.005 | 9.665 | 10.216 | 1.00 | 22.77 |
| ATOM | 646 | CD | LYS | A | 623 | 9.242 | 10.586 | 11.157 | 1.00 | 25.76 |
| ATOM | 647 | CE | LYS | A | 623 | 8.071 | 9.862 | 11.810 | 1.00 | 28.79 |
| ATOM | 648 | NZ | LYS | A | 623 | 7.952 | 10.199 | 13.262 | 1.00 | 30.66 |
| ATOM | 649 | C | LYS | A | 623 | 9.714 | 9.345 | 6.373 | 1.00 | 12.80 |
| ATOM | 650 | O | LYS | A | 623 | 10.217 | 10.316 | 5.816 | 1.00 | 13.52 |
| ATOM | 651 | N | MET | A | 624 | 8.740 | 8.619 | 5.840 | 1.00 | 10.68 |
| ATOM | 652 | CA | MET | A | 624 | 8.187 | 8.908 | 4.518 | 1.00 | 12.35 |
| ATOM | 653 | CB | MET | A | 624 | 9.013 | 8.227 | 3.422 | 1.00 | 12.92 |
| ATOM | 654 | CG | MET | A | 624 | 8.927 | 6.705 | 3.410 | 1.00 | 14.40 |
| ATOM | 655 | SD | MET | A | 624 | 10.261 | 5.937 | 2.479 | 1.00 | 18.01 |
| ATOM | 656 | CE | MET | A | 624 | 11.659 | 6.583 | 3.315 | 1.00 | 20.11 |
| ATOM | 657 | C | MET | A | 624 | 6.767 | 8.415 | 4.431 | 1.00 | 11.79 |
| ATOM | 658 | O | MET | A | 624 | 6.399 | 7.439 | 5.084 | 1.00 | 10.97 |
| ATOM | 659 | N | LEU | A | 625 | 5.973 | 9.090 | 3.607 | 1.00 | 12.45 |
| ATOM | 660 | CA | LEU | A | 625 | 4.637 | 8.614 | 3.300 | 1.00 | 11.47 |
| ATOM | 661 | CB | LEU | A | 625 | 3.718 | 9.787 | 2.954 | 1.00 | 11.58 |
| ATOM | 662 | CG | LEU | A | 625 | 3.579 | 10.853 | 4.045 | 1.00 | 11.94 |
| ATOM | 663 | CD1 | LEU | A | 625 | 2.500 | 11.818 | 3.651 | 1.00 | 14.53 |
| ATOM | 664 | CD2 | LEU | A | 625 | 3.259 | 10.247 | 5.403 | 1.00 | 16.54 |
| ATOM | 665 | C | LEU | A | 625 | 4.696 | 7.622 | 2.151 | 1.00 | 10.62 |

FIGURE 3 (Cont.)

|      | A    | B   | C   | D | E   | F      | G      | H      | I    | J     |
|------|------|-----|-----|---|-----|--------|--------|--------|------|-------|
| ATOM | 666  | O   | LEU | A | 625 | 5.761  | 7.376  | 1.577  | 1.00 | 10.97 |
| ATOM | 667  | N   | LYS | A | 626 | 3.547  | 7.049  | 1.825  | 1.00 | 11.58 |
| ATOM | 668  | CA  | LYS | A | 626 | 3.409  | 6.178  | 0.668  | 1.00 | 13.47 |
| ATOM | 669  | CB  | LYS | A | 626 | 1.951  | 5.759  | 0.518  | 1.00 | 15.02 |
| ATOM | 670  | CG  | LYS | A | 626 | 1.458  | 4.805  | 1.585  | 1.00 | 20.79 |
| ATOM | 671  | CD  | LYS | A | 626 | 0.076  | 4.301  | 1.210  | 1.00 | 23.62 |
| ATOM | 672  | CE  | LYS | A | 626 | -0.380 | 3.209  | 2.147  | 1.00 | 26.88 |
| ATOM | 673  | NZ  | LYS | A | 626 | -1.805 | 2.855  | 1.906  | 1.00 | 29.25 |
| ATOM | 674  | C   | LYS | A | 626 | 3.850  | 6.920  | -0.592 | 1.00 | 14.65 |
| ATOM | 675  | O   | LYS | A | 626 | 3.647  | 8.131  | -0.690 | 1.00 | 15.09 |
| ATOM | 676  | N   | PRO | A | 627 | 4.438  | 6.205  | -1.553 | 1.00 | 14.78 |
| ATOM | 677  | CA  | PRO | A | 627 | 4.893  | 6.819  | -2.811 | 1.00 | 15.64 |
| ATOM | 678  | CB  | PRO | A | 627 | 5.292  | 5.610  | -3.659 | 1.00 | 17.07 |
| ATOM | 679  | CG  | PRO | A | 627 | 5.680  | 4.576  | -2.660 | 1.00 | 18.28 |
| ATOM | 680  | CD  | PRO | A | 627 | 4.725  | 4.756  | -1.516 | 1.00 | 16.32 |
| ATOM | 681  | C   | PRO | A | 627 | 3.798  | 7.629  | -3.518 | 1.00 | 15.60 |
| ATOM | 682  | O   | PRO | A | 627 | 4.108  | 8.620  | -4.184 | 1.00 | 17.25 |
| ATOM | 683  | N   | SER | A | 628 | 2.543  | 7.210  | -3.353 | 1.00 | 12.78 |
| ATOM | 684  | CA  | SER | A | 628 | 1.403  | 7.843  | -4.004 | 1.00 | 15.33 |
| ATOM | 685  | CB  | SER | A | 628 | 0.281  | 6.818  | -4.215 | 1.00 | 16.60 |
| ATOM | 686  | OG  | SER | A | 628 | -0.098 | 6.217  | -2.987 | 1.00 | 18.76 |
| ATOM | 687  | C   | SER | A | 628 | 0.850  | 9.069  | -3.263 | 1.00 | 13.99 |
| ATOM | 688  | O   | SER | A | 628 | -0.087 | 9.713  | -3.752 | 1.00 | 14.17 |
| ATOM | 689  | N   | ALA | A | 629 | 1.421  | 9.399  | -2.102 | 1.00 | 12.12 |
| ATOM | 690  | CA  | ALA | A | 629 | 0.873  | 10.485 | -1.282 | 1.00 | 12.03 |
| ATOM | 691  | CB  | ALA | A | 629 | 1.645  | 10.621 | 0.039  | 1.00 | 11.77 |
| ATOM | 692  | C   | ALA | A | 629 | 0.846  | 11.815 | -2.034 | 1.00 | 12.54 |
| ATOM | 693  | O   | ALA | A | 629 | 1.830  | 12.198 | -2.676 | 1.00 | 13.18 |
| ATOM | 694  | N   | HIS | A | 630 | -0.292 | 12.503 | -1.970 | 1.00 | 9.67  |
| ATOM | 695  | CA  | HIS | A | 630 | -0.429 | 13.808 | -2.621 | 1.00 | 9.06  |
| ATOM | 696  | CB  | HIS | A | 630 | -1.890 | 14.084 | -3.018 | 1.00 | 7.37  |
| ATOM | 697  | CG  | HIS | A | 630 | -2.833 | 14.173 | -1.861 | 1.00 | 9.42  |
| ATOM | 698  | ND1 | HIS | A | 630 | -3.942 | 13.364 | -1.743 | 1.00 | 10.99 |
| ATOM | 699  | CE1 | HIS | A | 630 | -4.591 | 13.670 | -0.634 | 1.00 | 7.59  |
| ATOM | 700  | NE2 | HIS | A | 630 | -3.943 | 14.649 | -0.029 | 1.00 | 13.53 |
| ATOM | 701  | CD2 | HIS | A | 630 | -2.841 | 14.984 | -0.776 | 1.00 | 7.34  |
| ATOM | 702  | C   | HIS | A | 630 | 0.162  | 14.916 | -1.744 | 1.00 | 9.57  |
| ATOM | 703  | O   | HIS | A | 630 | 0.564  | 14.671 | -0.602 | 1.00 | 9.97  |
| ATOM | 704  | N   | LEU | A | 631 | 0.228  | 16.130 | -2.280 | 1.00 | 8.04  |
| ATOM | 705  | CA  | LEU | A | 631 | 0.970  | 17.194 | -1.611 | 1.00 | 8.77  |
| ATOM | 706  | CB  | LEU | A | 631 | 1.080  | 18.433 | -2.498 | 1.00 | 11.10 |
| ATOM | 707  | CG  | LEU | A | 631 | 2.074  | 18.336 | -3.661 | 1.00 | 14.58 |
| ATOM | 708  | CD1 | LEU | A | 631 | 1.908  | 19.532 | -4.582 | 1.00 | 14.85 |
| ATOM | 709  | CD2 | LEU | A | 631 | 3.513  | 18.226 | -3.162 | 1.00 | 17.93 |
| ATOM | 710  | C   | LEU | A | 631 | 0.411  | 17.563 | -0.242 | 1.00 | 9.05  |
| ATOM | 711  | O   | LEU | A | 631 | 1.171  | 17.883 | 0.664  | 1.00 | 9.62  |
| ATOM | 712  | N   | THR | A | 632 | -0.908 | 17.499 | -0.089 | 1.00 | 9.83  |
| ATOM | 713  | CA  | THR | A | 632 | -1.533 | 17.824 | 1.199  | 1.00 | 10.38 |
| ATOM | 714  | CB  | THR | A | 632 | -3.025 | 18.080 | 1.021  | 1.00 | 9.22  |
| ATOM | 715  | OG1 | THR | A | 632 | -3.182 | 19.236 | 0.196  | 1.00 | 7.51  |
| ATOM | 716  | CG2 | THR | A | 632 | -3.682 | 18.495 | 2.353  | 1.00 | 9.65  |
| ATOM | 717  | C   | THR | A | 632 | -1.258 | 16.756 | 2.256  | 1.00 | 9.21  |

FIGURE 3 (Cont.)

|      | A   | B   | C   | D | E   | F      | G      | H      | I    | J     |
|------|-----|-----|-----|---|-----|--------|--------|--------|------|-------|
| ATOM | 718 | O   | THR | A | 632 | -1.055 | 17.079 | 3.434  | 1.00 | 9.99  |
| ATOM | 719 | N   | GLU | A | 633 | -1.226 | 15.494 | 1.832  | 1.00 | 8.08  |
| ATOM | 720 | CA  | GLU | A | 633 | -0.762 | 14.411 | 2.694  | 1.00 | 10.11 |
| ATOM | 721 | CB  | GLU | A | 633 | -0.892 | 13.051 | 1.989  | 1.00 | 11.27 |
| ATOM | 722 | CG  | GLU | A | 633 | -2.296 | 12.457 | 2.063  | 1.00 | 10.94 |
| ATOM | 723 | CD  | GLU | A | 633 | -2.624 | 11.445 | 0.975  | 1.00 | 15.15 |
| ATOM | 724 | OE1 | GLU | A | 633 | -3.716 | 10.839 | 1.060  | 1.00 | 19.01 |
| ATOM | 725 | OE2 | GLU | A | 633 | -1.833 | 11.260 | 0.021  | 1.00 | 13.01 |
| ATOM | 726 | C   | GLU | A | 633 | 0.678  | 14.679 | 3.123  | 1.00 | 12.56 |
| ATOM | 727 | O   | GLU | A | 633 | 1.012  | 14.613 | 4.308  | 1.00 | 12.75 |
| ATOM | 728 | N   | ARG | A | 634 | 1.519  | 15.018 | 2.150  | 1.00 | 10.86 |
| ATOM | 729 | CA  | ARG | A | 634 | 2.925  | 15.318 | 2.402  | 1.00 | 13.21 |
| ATOM | 730 | CB  | ARG | A | 634 | 3.671  | 15.518 | 1.085  | 1.00 | 14.43 |
| ATOM | 731 | CG  | ARG | A | 634 | 4.009  | 14.211 | 0.401  | 1.00 | 20.03 |
| ATOM | 732 | CD  | ARG | A | 634 | 4.233  | 14.318 | -1.104 | 1.00 | 24.76 |
| ATOM | 733 | NE  | ARG | A | 634 | 5.343  | 13.478 | -1.572 | 1.00 | 37.21 |
| ATOM | 734 | CZ  | ARG | A | 634 | 5.628  | 12.242 | -1.136 | 1.00 | 40.26 |
| ATOM | 735 | NH1 | ARG | A | 634 | 4.893  | 11.644 | -0.205 | 1.00 | 42.88 |
| ATOM | 736 | NH2 | ARG | A | 634 | 6.659  | 11.591 | -1.644 | 1.00 | 42.65 |
| ATOM | 737 | C   | ARG | A | 634 | 3.135  | 16.525 | 3.318  | 1.00 | 10.86 |
| ATOM | 738 | O   | ARG | A | 634 | 4.138  | 16.599 | 4.033  | 1.00 | 11.88 |
| ATOM | 739 | N   | GLU | A | 635 | 2.191  | 17.461 | 3.308  | 1.00 | 11.09 |
| ATOM | 740 | CA  | GLU | A | 635 | 2.298  | 18.641 | 4.166  | 1.00 | 10.87 |
| ATOM | 741 | CB  | GLU | A | 635 | 1.202  | 19.664 | 3.844  | 1.00 | 10.87 |
| ATOM | 742 | CG  | GLU | A | 635 | 1.463  | 21.050 | 4.414  | 1.00 | 13.21 |
| ATOM | 743 | CD  | GLU | A | 635 | 2.678  | 21.734 | 3.807  | 1.00 | 14.41 |
| ATOM | 744 | OE1 | GLU | A | 635 | 3.053  | 21.422 | 2.653  | 1.00 | 14.66 |
| ATOM | 745 | OE2 | GLU | A | 635 | 3.253  | 22.601 | 4.488  | 1.00 | 15.61 |
| ATOM | 746 | C   | GLU | A | 635 | 2.285  | 18.275 | 5.652  | 1.00 | 14.09 |
| ATOM | 747 | O   | GLU | A | 635 | 2.839  | 19.000 | 6.477  | 1.00 | 12.45 |
| ATOM | 748 | N   | ALA | A | 636 | 1.668  | 17.142 | 5.984  | 1.00 | 13.64 |
| ATOM | 749 | CA  | ALA | A | 636 | 1.704  | 16.611 | 7.347  | 1.00 | 14.30 |
| ATOM | 750 | CB  | ALA | A | 636 | 0.825  | 15.361 | 7.469  | 1.00 | 13.49 |
| ATOM | 751 | C   | ALA | A | 636 | 3.131  | 16.312 | 7.804  | 1.00 | 14.81 |
| ATOM | 752 | O   | ALA | A | 636 | 3.492  | 16.596 | 8.949  | 1.00 | 15.73 |
| ATOM | 753 | N   | LEU | A | 637 | 3.941  | 15.742 | 6.915  | 1.00 | 14.60 |
| ATOM | 754 | CA  | LEU | A | 637 | 5.355  | 15.517 | 7.221  | 1.00 | 16.46 |
| ATOM | 755 | CB  | LEU | A | 637 | 6.022  | 14.618 | 6.178  | 1.00 | 17.27 |
| ATOM | 756 | CG  | LEU | A | 637 | 5.995  | 13.114 | 6.420  | 1.00 | 19.51 |
| ATOM | 757 | CD1 | LEU | A | 637 | 6.825  | 12.414 | 5.343  | 1.00 | 18.06 |
| ATOM | 758 | CD2 | LEU | A | 637 | 6.465  | 12.735 | 7.826  | 1.00 | 18.60 |
| ATOM | 759 | C   | LEU | A | 637 | 6.120  | 16.828 | 7.334  | 1.00 | 15.97 |
| ATOM | 760 | O   | LEU | A | 637 | 7.032  | 16.941 | 8.154  | 1.00 | 17.81 |
| ATOM | 761 | N   | MET | A | 638 | 5.752  | 17.810 | 6.512  | 1.00 | 12.48 |
| ATOM | 762 | CA  | MET | A | 638 | 6.314  | 19.161 | 6.628  | 1.00 | 13.06 |
| ATOM | 763 | CB  | BMET| A | 638 | 5.831  | 20.076 | 5.494  | 0.35 | 14.15 |
| ATOM | 764 | CB  | AMET| A | 638 | 5.733  | 20.080 | 5.546  | 0.65 | 13.48 |
| ATOM | 765 | CG  | BMET| A | 638 | 6.353  | 21.520 | 5.556  | 0.35 | 16.16 |
| ATOM | 766 | CG  | AMET| A | 638 | 6.203  | 19.803 | 4.129  | 0.65 | 17.41 |
| ATOM | 767 | SD  | BMET| A | 638 | 8.160  | 21.691 | 5.655  | 0.35 | 21.65 |
| ATOM | 768 | SD  | AMET| A | 638 | 7.994  | 19.697 | 4.011  | 0.65 | 20.02 |
| ATOM | 769 | CE  | BMET| A | 638 | 8.600  | 21.569 | 3.927  | 0.35 | 20.20 |

FIGURE 3 (Cont.)

|   | A | B | C | D | E | F | G | H | I | J |
|---|---|---|---|---|---|---|---|---|---|---|
| ATOM | 770 | CE | AMET | A | 638 | 8.481 | 21.392 | 4.219 | 0.65 | 18.53 |
| ATOM | 771 | C | MET | A | 638 | 5.997 | 19.758 | 7.994 | 1.00 | 12.91 |
| ATOM | 772 | O | MET | A | 638 | 6.844 | 20.403 | 8.606 | 1.00 | 12.31 |
| ATOM | 773 | N | SER | A | 639 | 4.766 | 19.560 | 8.461 | 1.00 | 12.17 |
| ATOM | 774 | CA | SER | A | 639 | 4.358 | 20.089 | 9.757 | 1.00 | 11.12 |
| ATOM | 775 | CB | SER | A | 639 | 2.839 | 20.004 | 9.920 | 1.00 | 11.68 |
| ATOM | 776 | OG | SER | A | 639 | 2.208 | 20.916 | 9.033 | 1.00 | 11.86 |
| ATOM | 777 | C | SER | A | 639 | 5.092 | 19.372 | 10.890 | 1.00 | 13.53 |
| ATOM | 778 | O | SER | A | 639 | 5.479 | 19.996 | 11.877 | 1.00 | 14.62 |
| ATOM | 779 | N | GLU | A | 640 | 5.304 | 18.069 | 10.732 | 1.00 | 12.09 |
| ATOM | 780 | CA | GLU | A | 640 | 6.078 | 17.313 | 11.710 | 1.00 | 16.19 |
| ATOM | 781 | CB | GLU | A | 640 | 6.104 | 15.830 | 11.355 | 1.00 | 19.34 |
| ATOM | 782 | CG | GLU | A | 640 | 6.906 | 14.995 | 12.340 | 1.00 | 21.20 |
| ATOM | 783 | CD | GLU | A | 640 | 6.595 | 13.516 | 12.267 | 1.00 | 25.74 |
| ATOM | 784 | OE1 | GLU | A | 640 | 7.237 | 12.760 | 13.020 | 1.00 | 27.04 |
| ATOM | 785 | OE2 | GLU | A | 640 | 5.727 | 13.109 | 11.461 | 1.00 | 27.38 |
| ATOM | 786 | C | GLU | A | 640 | 7.501 | 17.870 | 11.815 | 1.00 | 14.98 |
| ATOM | 787 | O | GLU | A | 640 | 8.022 | 18.065 | 12.908 | 1.00 | 13.54 |
| ATOM | 788 | N | LEU | A | 641 | 8.100 | 18.132 | 10.656 | 1.00 | 14.33 |
| ATOM | 789 | CA | LEU | A | 641 | 9.408 | 18.761 | 10.540 | 1.00 | 17.35 |
| ATOM | 790 | CB | LEU | A | 641 | 9.695 | 18.980 | 9.059 | 1.00 | 21.31 |
| ATOM | 791 | CG | LEU | A | 641 | 11.092 | 19.159 | 8.510 | 1.00 | 26.24 |
| ATOM | 792 | CD1 | LEU | A | 641 | 12.015 | 18.087 | 9.040 | 1.00 | 25.82 |
| ATOM | 793 | CD2 | LEU | A | 641 | 10.967 | 19.066 | 7.007 | 1.00 | 23.99 |
| ATOM | 794 | C | LEU | A | 641 | 9.455 | 20.101 | 11.266 | 1.00 | 16.93 |
| ATOM | 795 | O | LEU | A | 641 | 10.427 | 20.415 | 11.961 | 1.00 | 16.01 |
| ATOM | 796 | N | LYS | A | 642 | 8.397 | 20.889 | 11.091 | 1.00 | 12.78 |
| ATOM | 797 | CA | LYS | A | 642 | 8.285 | 22.192 | 11.728 | 1.00 | 10.64 |
| ATOM | 798 | CB | LYS | A | 642 | 7.069 | 22.937 | 11.179 | 1.00 | 11.03 |
| ATOM | 799 | CG | LYS | A | 642 | 7.274 | 23.515 | 9.781 | 1.00 | 11.28 |
| ATOM | 800 | CD | LYS | A | 642 | 5.958 | 24.007 | 9.211 | 1.00 | 10.61 |
| ATOM | 801 | CE | LYS | A | 642 | 6.141 | 24.627 | 7.844 | 1.00 | 12.22 |
| ATOM | 802 | NZ | LYS | A | 642 | 4.872 | 25.260 | 7.399 | 1.00 | 14.73 |
| ATOM | 803 | C | LYS | A | 642 | 8.190 | 22.089 | 13.249 | 1.00 | 10.50 |
| ATOM | 804 | O | LYS | A | 642 | 8.768 | 22.901 | 13.974 | 1.00 | 11.10 |
| ATOM | 805 | N | VAL | A | 643 | 7.448 | 21.093 | 13.723 | 1.00 | 8.81 |
| ATOM | 806 | CA | VAL | A | 643 | 7.287 | 20.869 | 15.157 | 1.00 | 9.65 |
| ATOM | 807 | CB | VAL | A | 643 | 6.162 | 19.852 | 15.462 | 1.00 | 9.17 |
| ATOM | 808 | CG1 | VAL | A | 643 | 6.186 | 19.451 | 16.926 | 1.00 | 10.81 |
| ATOM | 809 | CG2 | VAL | A | 643 | 4.792 | 20.453 | 15.104 | 1.00 | 10.75 |
| ATOM | 810 | C | VAL | A | 643 | 8.610 | 20.414 | 15.770 | 1.00 | 10.06 |
| ATOM | 811 | O | VAL | A | 643 | 9.014 | 20.926 | 16.811 | 1.00 | 11.50 |
| ATOM | 812 | N | LEU | A | 644 | 9.289 | 19.476 | 15.113 | 1.00 | 9.28 |
| ATOM | 813 | CA | LEU | A | 644 | 10.577 | 18.995 | 15.616 | 1.00 | 12.38 |
| ATOM | 814 | CB | LEU | A | 644 | 11.117 | 17.846 | 14.757 | 1.00 | 13.62 |
| ATOM | 815 | CG | LEU | A | 644 | 10.408 | 16.494 | 14.894 | 1.00 | 17.20 |
| ATOM | 816 | CD1 | LEU | A | 644 | 10.919 | 15.530 | 13.836 | 1.00 | 21.17 |
| ATOM | 817 | CD2 | LEU | A | 644 | 10.591 | 15.915 | 16.293 | 1.00 | 18.34 |
| ATOM | 818 | C | LEU | A | 644 | 11.600 | 20.123 | 15.664 | 1.00 | 13.12 |
| ATOM | 819 | O | LEU | A | 644 | 12.369 | 20.243 | 16.627 | 1.00 | 14.33 |
| ATOM | 820 | N | SER | A | 645 | 11.613 | 20.943 | 14.622 | 1.00 | 14.37 |
| ATOM | 821 | CA | SER | A | 645 | 12.582 | 22.034 | 14.554 | 1.00 | 15.40 |

FIGURE 3 (Cont.)

|      | A    | B   | C    | D | E   | F      | G      | H      | I    | J     |
|------|------|-----|------|---|-----|--------|--------|--------|------|-------|
| ATOM | 822  | CB  | SER  | A | 645 | 12.647 | 22.635 | 13.144 | 1.00 | 18.99 |
| ATOM | 823  | OG  | SER  | A | 645 | 11.386 | 23.106 | 12.722 | 1.00 | 25.84 |
| ATOM | 824  | C   | SER  | A | 645 | 12.292 | 23.090 | 15.611 | 1.00 | 15.51 |
| ATOM | 825  | O   | SER  | A | 645 | 13.223 | 23.654 | 16.201 | 1.00 | 17.77 |
| ATOM | 826  | N   | TYR  | A | 646 | 11.004 | 23.339 | 15.859 | 1.00 | 11.78 |
| ATOM | 827  | CA  | TYR  | A | 646 | 10.557 | 24.256 | 16.900 | 1.00 | 13.16 |
| ATOM | 828  | CB  | TYR  | A | 646 | 9.026  | 24.404 | 16.877 | 1.00 | 14.79 |
| ATOM | 829  | CG  | TYR  | A | 646 | 8.425  | 24.855 | 18.196 | 1.00 | 14.87 |
| ATOM | 830  | CD1 | TYR  | A | 646 | 7.862  | 23.930 | 19.081 | 1.00 | 15.42 |
| ATOM | 831  | CE1 | TYR  | A | 646 | 7.318  | 24.337 | 20.292 | 1.00 | 16.76 |
| ATOM | 832  | CZ  | TYR  | A | 646 | 7.332  | 25.682 | 20.632 | 1.00 | 17.41 |
| ATOM | 833  | OH  | TYR  | A | 646 | 6.796  | 26.080 | 21.833 | 1.00 | 17.83 |
| ATOM | 834  | CE2 | TYR  | A | 646 | 7.885  | 26.621 | 19.776 | 1.00 | 17.93 |
| ATOM | 835  | CD2 | TYR  | A | 646 | 8.433  | 26.201 | 18.564 | 1.00 | 15.78 |
| ATOM | 836  | C   | TYR  | A | 646 | 11.009 | 23.797 | 18.284 | 1.00 | 13.05 |
| ATOM | 837  | O   | TYR  | A | 646 | 11.440 | 24.609 | 19.102 | 1.00 | 11.85 |
| ATOM | 838  | N   | LEU  | A | 647 | 10.893 | 22.496 | 18.542 | 1.00 | 11.06 |
| ATOM | 839  | CA  | LEU  | A | 647 | 11.199 | 21.948 | 19.864 | 1.00 | 13.06 |
| ATOM | 840  | CB  | LEU  | A | 647 | 10.766 | 20.485 | 19.956 | 1.00 | 14.00 |
| ATOM | 841  | CG  | LEU  | A | 647 | 9.252  | 20.281 | 19.916 | 1.00 | 16.62 |
| ATOM | 842  | CD1 | LEU  | A | 647 | 8.937  | 18.804 | 19.752 | 1.00 | 17.57 |
| ATOM | 843  | CD2 | LEU  | A | 647 | 8.594  | 20.842 | 21.163 | 1.00 | 15.23 |
| ATOM | 844  | C   | LEU  | A | 647 | 12.667 | 22.066 | 20.218 | 1.00 | 14.55 |
| ATOM | 845  | O   | LEU  | A | 647 | 13.013 | 22.359 | 21.366 | 1.00 | 13.34 |
| ATOM | 846  | N   | GLY  | A | 648 | 13.524 | 21.850 | 19.229 | 1.00 | 14.68 |
| ATOM | 847  | CA  | GLY  | A | 648 | 14.953 | 21.844 | 19.458 | 1.00 | 16.21 |
| ATOM | 848  | C   | GLY  | A | 648 | 15.423 | 20.505 | 19.991 | 1.00 | 16.60 |
| ATOM | 849  | O   | GLY  | A | 648 | 14.658 | 19.544 | 20.076 | 1.00 | 18.45 |
| ATOM | 850  | N   | ASN  | A | 649 | 16.693 | 20.451 | 20.361 | 1.00 | 14.53 |
| ATOM | 851  | CA  | ASN  | A | 649 | 17.358 | 19.187 | 20.648 | 1.00 | 14.91 |
| ATOM | 852  | CB  | ASN  | A | 649 | 18.814 | 19.274 | 20.167 | 1.00 | 17.61 |
| ATOM | 853  | CG  | ASN  | A | 649 | 19.486 | 17.921 | 20.068 | 1.00 | 18.34 |
| ATOM | 854  | OD1 | ASN  | A | 649 | 19.610 | 17.349 | 18.980 | 1.00 | 22.27 |
| ATOM | 855  | ND2 | ASN  | A | 649 | 19.939 | 17.409 | 21.198 | 1.00 | 17.79 |
| ATOM | 856  | C   | ASN  | A | 649 | 17.304 | 18.815 | 22.126 | 1.00 | 13.38 |
| ATOM | 857  | O   | ASN  | A | 649 | 17.482 | 19.663 | 22.997 | 1.00 | 12.69 |
| ATOM | 858  | N   | HIS  | A | 650 | 17.043 | 17.543 | 22.407 | 1.00 | 9.42  |
| ATOM | 859  | CA  | HIS  | A | 650 | 17.194 | 17.019 | 23.761 | 1.00 | 10.56 |
| ATOM | 860  | CB  | HIS  | A | 650 | 15.877 | 17.117 | 24.544 | 1.00 | 11.03 |
| ATOM | 861  | CG  | HIS  | A | 650 | 16.022 | 16.852 | 26.013 | 1.00 | 10.82 |
| ATOM | 862  | ND1 | HIS  | A | 650 | 15.978 | 15.582 | 26.548 | 1.00 | 10.93 |
| ATOM | 863  | CE1 | HIS  | A | 650 | 16.126 | 15.651 | 27.858 | 1.00 | 9.88  |
| ATOM | 864  | NE2 | HIS  | A | 650 | 16.248 | 16.922 | 28.197 | 1.00 | 11.46 |
| ATOM | 865  | CD2 | HIS  | A | 650 | 16.191 | 17.694 | 27.061 | 1.00 | 9.57  |
| ATOM | 866  | C   | HIS  | A | 650 | 17.666 | 15.579 | 23.679 | 1.00 | 9.34  |
| ATOM | 867  | O   | HIS  | A | 650 | 17.278 | 14.850 | 22.767 | 1.00 | 11.17 |
| ATOM | 868  | N   | MET  | A | 651 | 18.489 | 15.167 | 24.643 | 1.00 | 10.45 |
| ATOM | 869  | CA  | MET  | A | 651 | 19.044 | 13.817 | 24.657 | 1.00 | 12.31 |
| ATOM | 870  | CB  | MET  | A | 651 | 19.990 | 13.644 | 25.850 | 1.00 | 14.93 |
| ATOM | 871  | CG  | BMET | A | 651 | 21.046 | 12.571 | 25.658 | 0.35 | 18.25 |
| ATOM | 872  | CG  | AMET | A | 651 | 20.709 | 12.291 | 25.928 | 0.65 | 16.29 |
| ATOM | 873  | SD  | BMET | A | 651 | 21.806 | 12.116 | 27.217 | 0.35 | 21.56 |

FIGURE 3 (Cont.)

|      | A    | B   | C    | D    | E   | F      | G      | H      | I    | J     |
|------|------|-----|------|------|-----|--------|--------|--------|------|-------|
| ATOM | 874  | SD  | AMET | A    | 651 | 21.565 | 11.833 | 24.402 | 0.65 | 18.80 |
| ATOM | 875  | CE  | BMET | A    | 651 | 23.461 | 11.680 | 26.680 | 0.35 | 22.06 |
| ATOM | 876  | CE  | AMET | A    | 651 | 23.269 | 12.005 | 24.921 | 0.65 | 19.55 |
| ATOM | 877  | C   | MET  | A    | 651 | 17.953 | 12.741 | 24.695 | 1.00 | 11.21 |
| ATOM | 878  | O   | MET  | A    | 651 | 18.118 | 11.673 | 24.116 | 1.00 | 10.18 |
| ATOM | 879  | N   | ASN  | A    | 652 | 16.842 | 13.035 | 25.368 | 1.00 | 9.32  |
| ATOM | 880  | CA  | ASN  | A    | 652 | 15.809 | 12.024 | 25.584 | 1.00 | 7.68  |
| ATOM | 881  | CB  | ASN  | A    | 652 | 15.414 | 11.989 | 27.060 | 1.00 | 7.90  |
| ATOM | 882  | CG  | ASN  | A    | 652 | 16.575 | 11.600 | 27.952 | 1.00 | 8.44  |
| ATOM | 883  | OD1 | ASN  | A    | 652 | 16.968 | 12.356 | 28.835 | 1.00 | 9.55  |
| ATOM | 884  | ND2 | ASN  | A    | 652 | 17.142 | 10.415 | 27.713 | 1.00 | 8.13  |
| ATOM | 885  | C   | ASN  | A    | 652 | 14.608 | 12.115 | 24.653 | 1.00 | 9.92  |
| ATOM | 886  | O   | ASN  | A    | 652 | 13.529 | 11.599 | 24.947 | 1.00 | 10.16 |
| ATOM | 887  | N   | ILE  | A    | 653 | 14.813 | 12.770 | 23.519 | 1.00 | 8.89  |
| ATOM | 888  | CA  | ILE  | A    | 653 | 13.876 | 12.685 | 22.412 | 1.00 | 11.99 |
| ATOM | 889  | CB  | ILE  | A    | 653 | 13.089 | 14.017 | 22.199 | 1.00 | 14.73 |
| ATOM | 890  | CG1 | ILE  | A    | 653 | 13.971 | 15.119 | 21.602 | 1.00 | 15.91 |
| ATOM | 891  | CD1 | ILE  | A    | 653 | 13.175 | 16.164 | 20.831 | 1.00 | 16.96 |
| ATOM | 892  | CG2 | ILE  | A    | 653 | 12.443 | 14.497 | 23.505 | 1.00 | 13.49 |
| ATOM | 893  | C   | ILE  | A    | 653 | 14.617 | 12.227 | 21.154 | 1.00 | 12.05 |
| ATOM | 894  | O   | ILE  | A    | 653 | 15.849 | 12.359 | 21.063 | 1.00 | 11.32 |
| ATOM | 895  | N   | VAL  | A    | 654 | 13.873 | 11.654 | 20.213 | 1.00 | 11.85 |
| ATOM | 896  | CA  | VAL  | A    | 654 | 14.434 | 11.324 | 18.908 | 1.00 | 12.48 |
| ATOM | 897  | CB  | VAL  | A    | 654 | 13.580 | 10.286 | 18.154 | 1.00 | 13.41 |
| ATOM | 898  | CG1 | VAL  | A    | 654 | 14.136 | 10.029 | 16.752 | 1.00 | 15.21 |
| ATOM | 899  | CG2 | VAL  | A    | 654 | 13.542 | 8.979  | 18.935 | 1.00 | 13.61 |
| ATOM | 900  | C   | VAL  | A    | 654 | 14.530 | 12.635 | 18.138 | 1.00 | 13.24 |
| ATOM | 901  | O   | VAL  | A    | 654 | 13.519 | 13.227 | 17.768 | 1.00 | 14.06 |
| ATOM | 902  | N   | ASN  | A    | 655 | 15.757 | 13.082 | 17.915 | 1.00 | 13.54 |
| ATOM | 903  | CA  | ASN  | A    | 655 | 15.977 | 14.387 | 17.317 | 1.00 | 12.81 |
| ATOM | 904  | CB  | ASN  | A    | 655 | 17.292 | 14.983 | 17.801 | 1.00 | 11.07 |
| ATOM | 905  | CG  | ASN  | A    | 655 | 17.274 | 15.244 | 19.272 | 1.00 | 12.12 |
| ATOM | 906  | OD1 | ASN  | A    | 655 | 16.553 | 16.122 | 19.744 | 1.00 | 13.07 |
| ATOM | 907  | ND2 | ASN  | A    | 655 | 18.034 | 14.467 | 20.014 | 1.00 | 9.75  |
| ATOM | 908  | C   | ASN  | A    | 655 | 15.952 | 14.399 | 15.814 | 1.00 | 12.98 |
| ATOM | 909  | O   | ASN  | A    | 655 | 16.297 | 13.417 | 15.158 | 1.00 | 12.81 |
| ATOM | 910  | N   | LEU  | A    | 656 | 15.547 | 15.546 | 15.291 | 1.00 | 12.16 |
| ATOM | 911  | CA  | LEU  | A    | 656 | 15.627 | 15.839 | 13.875 | 1.00 | 13.58 |
| ATOM | 912  | CB  | LEU  | A    | 656 | 14.886 | 17.148 | 13.592 | 1.00 | 13.17 |
| ATOM | 913  | CG  | LEU  | A    | 656 | 14.881 | 17.678 | 12.157 | 1.00 | 13.80 |
| ATOM | 914  | CD1 | LEU  | A    | 656 | 14.086 | 16.735 | 11.263 | 1.00 | 16.39 |
| ATOM | 915  | CD2 | LEU  | A    | 656 | 14.289 | 19.071 | 12.127 | 1.00 | 14.30 |
| ATOM | 916  | C   | LEU  | A    | 656 | 17.085 | 15.974 | 13.463 | 1.00 | 10.57 |
| ATOM | 917  | O   | LEU  | A    | 656 | 17.881 | 16.609 | 14.161 | 1.00 | 10.92 |
| ATOM | 918  | N   | LEU  | A    | 657 | 17.440 | 15.354 | 12.340 | 1.00 | 10.57 |
| ATOM | 919  | CA  | LEU  | A    | 657 | 18.790 | 15.503 | 11.790 | 1.00 | 13.21 |
| ATOM | 920  | CB  | LEU  | A    | 657 | 19.479 | 14.144 | 11.679 | 1.00 | 12.96 |
| ATOM | 921  | CG  | LEU  | A    | 657 | 19.815 | 13.412 | 12.985 | 1.00 | 11.73 |
| ATOM | 922  | CD1 | LEU  | A    | 657 | 20.440 | 12.057 | 12.690 | 1.00 | 13.27 |
| ATOM | 923  | CD2 | LEU  | A    | 657 | 20.727 | 14.241 | 13.880 | 1.00 | 16.22 |
| ATOM | 924  | C   | LEU  | A    | 657 | 18.805 | 16.192 | 10.432 | 1.00 | 13.60 |
| ATOM | 925  | O   | LEU  | A    | 657 | 19.813 | 16.785 | 10.035 | 1.00 | 12.46 |

FIGURE 3 (Cont.)

|  | A | B | C | D | E | F | G | H | I | J |
|---|---|---|---|---|---|---|---|---|---|---|
| ATOM | 926 | N | GLY | A | 658 | 17.691 | 16.094 | 9.714 | 1.00 | 12.93 |
| ATOM | 927 | CA | GLY | A | 658 | 17.607 | 16.632 | 8.373 | 1.00 | 11.02 |
| ATOM | 928 | C | GLY | A | 658 | 16.292 | 16.345 | 7.685 | 1.00 | 11.60 |
| ATOM | 929 | O | GLY | A | 658 | 15.410 | 15.691 | 8.243 | 1.00 | 10.86 |
| ATOM | 930 | N | ALA | A | 659 | 16.167 | 16.839 | 6.459 | 1.00 | 12.83 |
| ATOM | 931 | CA | ALA | A | 659 | 14.954 | 16.649 | 5.674 | 1.00 | 13.62 |
| ATOM | 932 | CB | ALA | A | 659 | 13.945 | 17.739 | 6.003 | 1.00 | 13.17 |
| ATOM | 933 | C | ALA | A | 659 | 15.269 | 16.695 | 4.197 | 1.00 | 13.30 |
| ATOM | 934 | O | ALA | A | 659 | 16.245 | 17.317 | 3.781 | 1.00 | 12.85 |
| ATOM | 935 | N | CYS | A | 660 | 14.432 | 16.033 | 3.409 | 1.00 | 13.01 |
| ATOM | 936 | CA | CYS | A | 660 | 14.462 | 16.183 | 1.967 | 1.00 | 11.97 |
| ATOM | 937 | CB | CYS | A | 660 | 14.822 | 14.873 | 1.279 | 1.00 | 12.91 |
| ATOM | 938 | SG | CYS | A | 660 | 16.264 | 14.043 | 1.966 | 1.00 | 15.59 |
| ATOM | 939 | C | CYS | A | 660 | 13.057 | 16.591 | 1.593 | 1.00 | 15.02 |
| ATOM | 940 | O | CYS | A | 660 | 12.147 | 15.756 | 1.579 | 1.00 | 14.97 |
| ATOM | 941 | N | THR | A | 661 | 12.872 | 17.883 | 1.332 | 1.00 | 14.65 |
| ATOM | 942 | CA | THR | A | 661 | 11.538 | 18.400 | 1.024 | 1.00 | 17.26 |
| ATOM | 943 | CB | THR | A | 661 | 11.058 | 19.416 | 2.094 | 1.00 | 17.96 |
| ATOM | 944 | OG1 | THR | A | 661 | 11.800 | 20.636 | 1.977 | 1.00 | 17.29 |
| ATOM | 945 | CG2 | THR | A | 661 | 11.366 | 18.928 | 3.505 | 1.00 | 21.43 |
| ATOM | 946 | C | THR | A | 661 | 11.439 | 19.011 | -0.369 | 1.00 | 19.55 |
| ATOM | 947 | O | THR | A | 661 | 10.340 | 19.341 | -0.821 | 1.00 | 21.35 |
| ATOM | 948 | N | ILE | A | 662 | 12.582 | 19.164 | -1.035 | 1.00 | 18.86 |
| ATOM | 949 | CA | ILE | A | 662 | 12.639 | 19.751 | -2.375 | 1.00 | 21.13 |
| ATOM | 950 | CB | ILE | A | 662 | 13.711 | 20.881 | -2.455 | 1.00 | 23.24 |
| ATOM | 951 | CG1 | ILE | A | 662 | 13.621 | 21.847 | -1.274 | 1.00 | 24.34 |
| ATOM | 952 | CD1 | ILE | A | 662 | 14.974 | 22.421 | -0.900 | 1.00 | 24.33 |
| ATOM | 953 | CG2 | ILE | A | 662 | 13.611 | 21.651 | -3.781 | 1.00 | 26.19 |
| ATOM | 954 | C | ILE | A | 662 | 12.979 | 18.689 | -3.418 | 1.00 | 21.67 |
| ATOM | 955 | O | ILE | A | 662 | 13.825 | 17.820 | -3.181 | 1.00 | 21.95 |
| ATOM | 956 | N | GLY | A | 663 | 12.319 | 18.777 | -4.570 | 1.00 | 21.56 |
| ATOM | 957 | CA | GLY | A | 663 | 12.697 | 18.021 | -5.751 | 1.00 | 24.03 |
| ATOM | 958 | C | GLY | A | 663 | 12.418 | 16.534 | -5.686 | 1.00 | 25.65 |
| ATOM | 959 | O | GLY | A | 663 | 13.141 | 15.735 | -6.290 | 1.00 | 26.41 |
| ATOM | 960 | N | GLY | A | 664 | 11.367 | 16.162 | -4.962 | 1.00 | 23.01 |
| ATOM | 961 | CA | GLY | A | 664 | 10.984 | 14.771 | -4.849 | 1.00 | 23.28 |
| ATOM | 962 | C | GLY | A | 664 | 10.268 | 14.444 | -3.555 | 1.00 | 22.36 |
| ATOM | 963 | O | GLY | A | 664 | 9.782 | 15.340 | -2.863 | 1.00 | 22.20 |
| ATOM | 964 | N | PRO | A | 665 | 10.209 | 13.154 | -3.227 | 1.00 | 24.22 |
| ATOM | 965 | CA | PRO | A | 665 | 9.491 | 12.677 | -2.042 | 1.00 | 24.62 |
| ATOM | 966 | CB | PRO | A | 665 | 9.882 | 11.197 | -1.973 | 1.00 | 26.77 |
| ATOM | 967 | CG | PRO | A | 665 | 10.147 | 10.831 | -3.397 | 1.00 | 28.90 |
| ATOM | 968 | CD | PRO | A | 665 | 10.819 | 12.043 | -3.984 | 1.00 | 25.36 |
| ATOM | 969 | C | PRO | A | 665 | 9.885 | 13.401 | -0.754 | 1.00 | 20.81 |
| ATOM | 970 | O | PRO | A | 665 | 11.045 | 13.721 | -0.536 | 1.00 | 24.79 |
| ATOM | 971 | N | THR | A | 666 | 8.892 | 13.664 | 0.078 | 1.00 | 17.06 |
| ATOM | 972 | CA | THR | A | 666 | 9.091 | 14.355 | 1.338 | 1.00 | 16.83 |
| ATOM | 973 | CB | THR | A | 666 | 7.754 | 14.935 | 1.803 | 1.00 | 18.29 |
| ATOM | 974 | OG1 | THR | A | 666 | 7.167 | 15.658 | 0.713 | 1.00 | 17.93 |
| ATOM | 975 | CG2 | THR | A | 666 | 7.968 | 15.989 | 2.877 | 1.00 | 19.68 |
| ATOM | 976 | C | THR | A | 666 | 9.649 | 13.370 | 2.353 | 1.00 | 12.73 |
| ATOM | 977 | O | THR | A | 666 | 9.010 | 12.361 | 2.660 | 1.00 | 12.64 |

FIGURE 3 (Cont.)

| | A | B | C | D | E | F | G | H | I | J |
|---|---|---|---|---|---|---|---|---|---|---|
| ATOM | 978 | N | LEU | A | 667 | 10.853 | 13.657 | 2.844 | 1.00 | 12.96 |
| ATOM | 979 | CA | LEU | A | 667 | 11.535 | 12.776 | 3.800 | 1.00 | 11.40 |
| ATOM | 980 | CB | LEU | A | 667 | 12.793 | 12.138 | 3.171 | 1.00 | 9.23 |
| ATOM | 981 | CG | LEU | A | 667 | 12.641 | 11.466 | 1.798 | 1.00 | 10.77 |
| ATOM | 982 | CD1 | LEU | A | 667 | 13.972 | 10.967 | 1.279 | 1.00 | 12.57 |
| ATOM | 983 | CD2 | LEU | A | 667 | 11.627 | 10.311 | 1.861 | 1.00 | 12.51 |
| ATOM | 984 | C | LEU | A | 667 | 11.930 | 13.560 | 5.043 | 1.00 | 10.45 |
| ATOM | 985 | O | LEU | A | 667 | 12.428 | 14.680 | 4.946 | 1.00 | 14.51 |
| ATOM | 986 | N | VAL | A | 668 | 11.699 | 12.960 | 6.205 | 1.00 | 11.56 |
| ATOM | 987 | CA | VAL | A | 668 | 12.166 | 13.513 | 7.465 | 1.00 | 13.10 |
| ATOM | 988 | CB | VAL | A | 668 | 11.017 | 13.685 | 8.477 | 1.00 | 14.82 |
| ATOM | 989 | CG1 | VAL | A | 668 | 11.551 | 14.198 | 9.806 | 1.00 | 15.65 |
| ATOM | 990 | CG2 | VAL | A | 668 | 9.946 | 14.622 | 7.917 | 1.00 | 15.81 |
| ATOM | 991 | C | VAL | A | 668 | 13.222 | 12.581 | 8.043 | 1.00 | 10.49 |
| ATOM | 992 | O | VAL | A | 668 | 12.965 | 11.399 | 8.285 | 1.00 | 13.45 |
| ATOM | 993 | N | ILE | A | 669 | 14.407 | 13.124 | 8.274 | 1.00 | 10.61 |
| ATOM | 994 | CA | ILE | A | 669 | 15.524 | 12.311 | 8.743 | 1.00 | 11.07 |
| ATOM | 995 | CB | ILE | A | 669 | 16.819 | 12.685 | 7.987 | 1.00 | 11.97 |
| ATOM | 996 | CG1 | ILE | A | 669 | 16.601 | 12.632 | 6.471 | 1.00 | 12.28 |
| ATOM | 997 | CD1 | ILE | A | 669 | 17.699 | 13.343 | 5.686 | 1.00 | 12.92 |
| ATOM | 998 | CG2 | ILE | A | 669 | 17.964 | 11.774 | 8.426 | 1.00 | 10.17 |
| ATOM | 999 | C | ILE | A | 669 | 15.709 | 12.551 | 10.226 | 1.00 | 10.91 |
| ATOM | 1000 | O | ILE | A | 669 | 15.901 | 13.692 | 10.656 | 1.00 | 12.65 |
| ATOM | 1001 | N | THR | A | 670 | 15.654 | 11.479 | 11.004 | 1.00 | 11.68 |
| ATOM | 1002 | CA | THR | A | 670 | 15.823 | 11.584 | 12.453 | 1.00 | 12.39 |
| ATOM | 1003 | CB | THR | A | 670 | 14.509 | 11.273 | 13.224 | 1.00 | 13.44 |
| ATOM | 1004 | OG1 | THR | A | 670 | 14.235 | 9.862 | 13.194 | 1.00 | 16.94 |
| ATOM | 1005 | CG2 | THR | A | 670 | 13.291 | 11.894 | 12.551 | 1.00 | 12.45 |
| ATOM | 1006 | C | THR | A | 670 | 16.926 | 10.666 | 12.933 | 1.00 | 13.69 |
| ATOM | 1007 | O | THR | A | 670 | 17.450 | 9.852 | 12.172 | 1.00 | 14.41 |
| ATOM | 1008 | N | GLU | A | 671 | 17.268 | 10.801 | 14.209 | 1.00 | 14.83 |
| ATOM | 1009 | CA | GLU | A | 671 | 18.233 | 9.920 | 14.842 | 1.00 | 13.08 |
| ATOM | 1010 | CB | GLU | A | 671 | 18.480 | 10.331 | 16.291 | 1.00 | 15.12 |
| ATOM | 1011 | CG | GLU | A | 671 | 19.071 | 11.721 | 16.449 | 1.00 | 15.95 |
| ATOM | 1012 | CD | GLU | A | 671 | 19.281 | 12.101 | 17.901 | 1.00 | 17.90 |
| ATOM | 1013 | OE1 | GLU | A | 671 | 18.355 | 11.897 | 18.714 | 1.00 | 17.24 |
| ATOM | 1014 | OE2 | GLU | A | 671 | 20.374 | 12.609 | 18.229 | 1.00 | 17.83 |
| ATOM | 1015 | C | GLU | A | 671 | 17.730 | 8.493 | 14.788 | 1.00 | 15.43 |
| ATOM | 1016 | O | GLU | A | 671 | 16.531 | 8.236 | 14.909 | 1.00 | 15.19 |
| ATOM | 1017 | N | TYR | A | 672 | 18.666 | 7.575 | 14.586 | 1.00 | 13.69 |
| ATOM | 1018 | CA | TYR | A | 672 | 18.375 | 6.164 | 14.538 | 1.00 | 14.97 |
| ATOM | 1019 | CB | TYR | A | 672 | 19.276 | 5.494 | 13.503 | 1.00 | 15.54 |
| ATOM | 1020 | CG | TYR | A | 672 | 19.136 | 3.999 | 13.438 | 1.00 | 16.12 |
| ATOM | 1021 | CD1 | TYR | A | 672 | 20.139 | 3.169 | 13.934 | 1.00 | 18.47 |
| ATOM | 1022 | CE1 | TYR | A | 672 | 20.023 | 1.789 | 13.866 | 1.00 | 21.79 |
| ATOM | 1023 | CZ | TYR | A | 672 | 18.891 | 1.223 | 13.307 | 1.00 | 21.55 |
| ATOM | 1024 | OH | TYR | A | 672 | 18.782 | -0.148 | 13.250 | 1.00 | 25.75 |
| ATOM | 1025 | CE2 | TYR | A | 672 | 17.877 | 2.020 | 12.809 | 1.00 | 20.78 |
| ATOM | 1026 | CD2 | TYR | A | 672 | 18.005 | 3.406 | 12.873 | 1.00 | 18.73 |
| ATOM | 1027 | C | TYR | A | 672 | 18.640 | 5.570 | 15.908 | 1.00 | 16.16 |
| ATOM | 1028 | O | TYR | A | 672 | 19.684 | 5.833 | 16.512 | 1.00 | 12.89 |
| ATOM | 1029 | N | CYS | A | 673 | 17.701 | 4.759 | 16.384 | 1.00 | 15.55 |

FIGURE 3 (Cont.)

|  | A | B | C | D | E | F | G | H | I | J |
|---|---|---|---|---|---|---|---|---|---|---|
| ATOM | 1030 | CA | CYS | A | 673 | 17.823 | 4.140 | 17.695 | 1.00 | 15.88 |
| ATOM | 1031 | CB | CYS | A | 673 | 16.602 | 4.475 | 18.547 | 1.00 | 16.60 |
| ATOM | 1032 | SG | CYS | A | 673 | 16.404 | 6.249 | 18.830 | 1.00 | 18.76 |
| ATOM | 1033 | C | CYS | A | 673 | 17.992 | 2.639 | 17.514 | 1.00 | 15.30 |
| ATOM | 1034 | O | CYS | A | 673 | 17.031 | 1.930 | 17.201 | 1.00 | 16.59 |
| ATOM | 1035 | N | CYS | A | 674 | 19.222 | 2.170 | 17.712 | 1.00 | 15.44 |
| ATOM | 1036 | CA | CYS | A | 674 | 19.629 | 0.831 | 17.288 | 1.00 | 17.50 |
| ATOM | 1037 | CB | CYS | A | 674 | 21.146 | 0.664 | 17.431 | 1.00 | 21.10 |
| ATOM | 1038 | SG | CYS | A | 674 | 21.791 | 1.070 | 19.068 | 1.00 | 25.41 |
| ATOM | 1039 | C | CYS | A | 674 | 18.909 | -0.321 | 17.987 | 1.00 | 18.35 |
| ATOM | 1040 | O | CYS | A | 674 | 18.817 | -1.421 | 17.435 | 1.00 | 20.44 |
| ATOM | 1041 | N | TYR | A | 675 | 18.401 | -0.079 | 19.190 | 1.00 | 14.36 |
| ATOM | 1042 | CA | TYR | A | 675 | 17.800 | -1.154 | 19.972 | 1.00 | 15.40 |
| ATOM | 1043 | CB | TYR | A | 675 | 18.193 | -1.038 | 21.450 | 1.00 | 15.54 |
| ATOM | 1044 | CG | TYR | A | 675 | 19.689 | -1.069 | 21.654 | 1.00 | 18.45 |
| ATOM | 1045 | CD1 | TYR | A | 675 | 20.467 | -2.088 | 21.097 | 1.00 | 17.77 |
| ATOM | 1046 | CE1 | TYR | A | 675 | 21.838 | -2.111 | 21.259 | 1.00 | 18.13 |
| ATOM | 1047 | CZ | TYR | A | 675 | 22.457 | -1.113 | 21.994 | 1.00 | 20.20 |
| ATOM | 1048 | OH | TYR | A | 675 | 23.820 | -1.144 | 22.164 | 1.00 | 23.13 |
| ATOM | 1049 | CE2 | TYR | A | 675 | 21.714 | -0.092 | 22.560 | 1.00 | 20.64 |
| ATOM | 1050 | CD2 | TYR | A | 675 | 20.334 | -0.071 | 22.382 | 1.00 | 19.13 |
| ATOM | 1051 | C | TYR | A | 675 | 16.288 | -1.272 | 19.787 | 1.00 | 15.41 |
| ATOM | 1052 | O | TYR | A | 675 | 15.670 | -2.196 | 20.318 | 1.00 | 13.56 |
| ATOM | 1053 | N | GLY | A | 676 | 15.712 | -0.349 | 19.019 | 1.00 | 14.21 |
| ATOM | 1054 | CA | GLY | A | 676 | 14.289 | -0.367 | 18.717 | 1.00 | 14.10 |
| ATOM | 1055 | C | GLY | A | 676 | 13.435 | 0.177 | 19.843 | 1.00 | 15.04 |
| ATOM | 1056 | O | GLY | A | 676 | 13.915 | 0.884 | 20.739 | 1.00 | 10.75 |
| ATOM | 1057 | N | ASP | A | 677 | 12.149 | -0.151 | 19.808 | 1.00 | 12.81 |
| ATOM | 1058 | CA | ASP | A | 677 | 11.231 | 0.394 | 20.796 | 1.00 | 15.91 |
| ATOM | 1059 | CB | ASP | A | 677 | 9.782 | 0.381 | 20.289 | 1.00 | 18.54 |
| ATOM | 1060 | CG | ASP | A | 677 | 9.209 | -1.012 | 20.186 | 1.00 | 22.78 |
| ATOM | 1061 | OD1 | ASP | A | 677 | 9.350 | -1.634 | 19.113 | 1.00 | 24.49 |
| ATOM | 1062 | OD2 | ASP | A | 677 | 8.595 | -1.559 | 21.129 | 1.00 | 23.20 |
| ATOM | 1063 | C | ASP | A | 677 | 11.387 | -0.303 | 22.147 | 1.00 | 13.23 |
| ATOM | 1064 | O | ASP | A | 677 | 11.761 | -1.477 | 22.221 | 1.00 | 11.86 |
| ATOM | 1065 | N | LEU | A | 678 | 11.112 | 0.445 | 23.203 | 1.00 | 12.26 |
| ATOM | 1066 | CA | LEU | A | 678 | 11.317 | -0.010 | 24.569 | 1.00 | 13.86 |
| ATOM | 1067 | CB | LEU | A | 678 | 11.129 | 1.162 | 25.537 | 1.00 | 16.12 |
| ATOM | 1068 | CG | LEU | A | 678 | 11.453 | 0.967 | 27.017 | 1.00 | 17.20 |
| ATOM | 1069 | CD1 | LEU | A | 678 | 12.875 | 0.419 | 27.213 | 1.00 | 17.58 |
| ATOM | 1070 | CD2 | LEU | A | 678 | 11.268 | 2.293 | 27.743 | 1.00 | 18.58 |
| ATOM | 1071 | C | LEU | A | 678 | 10.385 | -1.155 | 24.932 | 1.00 | 15.31 |
| ATOM | 1072 | O | LEU | A | 678 | 10.773 | -2.061 | 25.670 | 1.00 | 13.12 |
| ATOM | 1073 | N | LEU | A | 679 | 9.162 | -1.116 | 24.414 | 1.00 | 12.29 |
| ATOM | 1074 | CA | LEU | A | 679 | 8.220 | -2.206 | 24.664 | 1.00 | 13.96 |
| ATOM | 1075 | CB | LEU | A | 679 | 6.879 | -1.947 | 23.980 | 1.00 | 15.13 |
| ATOM | 1076 | CG | LEU | A | 679 | 5.812 | -3.006 | 24.295 | 1.00 | 15.89 |
| ATOM | 1077 | CD1 | LEU | A | 679 | 5.528 | -3.095 | 25.801 | 1.00 | 16.50 |
| ATOM | 1078 | CD2 | LEU | A | 679 | 4.544 | -2.735 | 23.513 | 1.00 | 17.78 |
| ATOM | 1079 | C | LEU | A | 679 | 8.790 | -3.557 | 24.228 | 1.00 | 12.52 |
| ATOM | 1080 | O | LEU | A | 679 | 8.794 | -4.515 | 25.004 | 1.00 | 10.88 |
| ATOM | 1081 | N | ASN | A | 680 | 9.267 | -3.623 | 22.987 | 1.00 | 11.76 |

FIGURE 3 (Cont.)

| | A | B | C | D | E | F | G | H | I | J |
|---|---|---|---|---|---|---|---|---|---|---|
| ATOM | 1082 | CA | ASN | A | 680 | 9.883 | -4.834 | 22.457 | 1.00 | 11.44 |
| ATOM | 1083 | CB | ASN | A | 680 | 10.240 | -4.642 | 20.982 | 1.00 | 12.70 |
| ATOM | 1084 | CG | ASN | A | 680 | 10.978 | -5.829 | 20.403 | 1.00 | 17.04 |
| ATOM | 1085 | OD1 | ASN | A | 680 | 10.400 | -6.896 | 20.210 | 1.00 | 18.85 |
| ATOM | 1086 | ND2 | ASN | A | 680 | 12.268 | -5.650 | 20.125 | 1.00 | 16.71 |
| ATOM | 1087 | C | ASN | A | 680 | 11.122 | -5.219 | 23.256 | 1.00 | 11.88 |
| ATOM | 1088 | O | ASN | A | 680 | 11.356 | -6.398 | 23.535 | 1.00 | 10.10 |
| ATOM | 1089 | N | PHE | A | 681 | 11.914 | -4.215 | 23.621 | 1.00 | 10.62 |
| ATOM | 1090 | CA | PHE | A | 681 | 13.122 | -4.437 | 24.405 | 1.00 | 12.46 |
| ATOM | 1091 | CB | PHE | A | 681 | 13.873 | -3.114 | 24.589 | 1.00 | 13.75 |
| ATOM | 1092 | CG | PHE | A | 681 | 15.183 | -3.247 | 25.305 | 1.00 | 16.36 |
| ATOM | 1093 | CD1 | PHE | A | 681 | 15.263 | -3.039 | 26.682 | 1.00 | 17.21 |
| ATOM | 1094 | CE1 | PHE | A | 681 | 16.484 | -3.153 | 27.351 | 1.00 | 18.59 |
| ATOM | 1095 | CZ | PHE | A | 681 | 17.631 | -3.466 | 26.643 | 1.00 | 17.88 |
| ATOM | 1096 | CE2 | PHE | A | 681 | 17.565 | -3.672 | 25.267 | 1.00 | 18.62 |
| ATOM | 1097 | CD2 | PHE | A | 681 | 16.342 | -3.561 | 24.605 | 1.00 | 17.61 |
| ATOM | 1098 | C | PHE | A | 681 | 12.791 | -5.081 | 25.756 | 1.00 | 11.89 |
| ATOM | 1099 | O | PHE | A | 681 | 13.418 | -6.066 | 26.151 | 1.00 | 12.11 |
| ATOM | 1100 | N | LEU | A | 682 | 11.810 | -4.518 | 26.458 | 1.00 | 11.54 |
| ATOM | 1101 | CA | LEU | A | 682 | 11.408 | -5.032 | 27.767 | 1.00 | 12.79 |
| ATOM | 1102 | CB | LEU | A | 682 | 10.319 | -4.148 | 28.383 | 1.00 | 13.68 |
| ATOM | 1103 | CG | LEU | A | 682 | 10.708 | -2.726 | 28.794 | 1.00 | 15.16 |
| ATOM | 1104 | CD1 | LEU | A | 682 | 9.447 | -1.901 | 29.077 | 1.00 | 13.35 |
| ATOM | 1105 | CD2 | LEU | A | 682 | 11.632 | -2.754 | 30.005 | 1.00 | 16.80 |
| ATOM | 1106 | C | LEU | A | 682 | 10.904 | -6.457 | 27.655 | 1.00 | 12.21 |
| ATOM | 1107 | O | LEU | A | 682 | 11.229 | -7.312 | 28.479 | 1.00 | 12.21 |
| ATOM | 1108 | N | ARG | A | 683 | 10.117 | -6.720 | 26.620 | 1.00 | 12.53 |
| ATOM | 1109 | CA | ARG | A | 683 | 9.562 | -8.059 | 26.436 | 1.00 | 10.92 |
| ATOM | 1110 | CB | ARG | A | 683 | 8.456 | -8.045 | 25.380 | 1.00 | 13.95 |
| ATOM | 1111 | CG | ARG | A | 683 | 7.227 | -7.305 | 25.849 | 1.00 | 14.25 |
| ATOM | 1112 | CD | ARG | A | 683 | 6.125 | -7.204 | 24.824 | 1.00 | 14.84 |
| ATOM | 1113 | NE | ARG | A | 683 | 4.942 | -6.588 | 25.418 | 1.00 | 16.36 |
| ATOM | 1114 | CZ | ARG | A | 683 | 3.828 | -6.287 | 24.760 | 1.00 | 17.30 |
| ATOM | 1115 | NH1 | ARG | A | 683 | 2.817 | -5.732 | 25.406 | 1.00 | 15.01 |
| ATOM | 1116 | NH2 | ARG | A | 683 | 3.723 | -6.532 | 23.460 | 1.00 | 19.98 |
| ATOM | 1117 | C | ARG | A | 683 | 10.634 | -9.088 | 26.104 | 1.00 | 13.44 |
| ATOM | 1118 | O | ARG | A | 683 | 10.604 | -10.202 | 26.620 | 1.00 | 12.85 |
| ATOM | 1119 | N | ARG | A | 684 | 11.599 | -8.711 | 25.266 | 1.00 | 11.37 |
| ATOM | 1120 | CA | ARG | A | 684 | 12.655 | -9.651 | 24.876 | 1.00 | 13.86 |
| ATOM | 1121 | CB | ARG | A | 684 | 13.385 | -9.160 | 23.625 | 1.00 | 16.39 |
| ATOM | 1122 | CG | ARG | A | 684 | 12.515 | -9.195 | 22.376 | 1.00 | 19.95 |
| ATOM | 1123 | CD | ARG | A | 684 | 13.282 | -9.242 | 21.079 | 1.00 | 24.12 |
| ATOM | 1124 | NE | ARG | A | 684 | 14.066 | -10.468 | 20.951 | 1.00 | 26.24 |
| ATOM | 1125 | CZ | ARG | A | 684 | 15.123 | -10.603 | 20.160 | 1.00 | 27.82 |
| ATOM | 1126 | NH1 | ARG | A | 684 | 15.773 | -11.758 | 20.115 | 1.00 | 26.91 |
| ATOM | 1127 | NH2 | ARG | A | 684 | 15.530 | -9.588 | 19.409 | 1.00 | 28.87 |
| ATOM | 1128 | C | ARG | A | 684 | 13.648 | -9.910 | 26.007 | 1.00 | 12.11 |
| ATOM | 1129 | O | ARG | A | 684 | 14.176 | -11.021 | 26.140 | 1.00 | 10.02 |
| ATOM | 1130 | N | LYS | A | 685 | 13.888 | -8.882 | 26.818 | 1.00 | 13.60 |
| ATOM | 1131 | CA | LYS | A | 685 | 14.862 | -8.958 | 27.908 | 1.00 | 15.52 |
| ATOM | 1132 | CB | LYS | A | 685 | 15.558 | -7.602 | 28.111 | 1.00 | 13.73 |
| ATOM | 1133 | CG | LYS | A | 685 | 16.392 | -7.127 | 26.925 | 1.00 | 13.82 |

FIGURE 3 (Cont.)

|  | A | B | C | D | E | F | G | H | I | J |
|---|---|---|---|---|---|---|---|---|---|---|
| ATOM | 1134 | CD | LYS | A | 685 | 17.755 | -7.780 | 26.881 | 1.00 | 11.62 |
| ATOM | 1135 | CE | LYS | A | 685 | 18.686 | -7.054 | 25.923 | 1.00 | 12.86 |
| ATOM | 1136 | NZ | LYS | A | 685 | 20.007 | -7.739 | 25.854 | 1.00 | 11.09 |
| ATOM | 1137 | C | LYS | A | 685 | 14.224 | -9.415 | 29.220 | 1.00 | 16.18 |
| ATOM | 1138 | O | LYS | A | 685 | 14.922 | -9.635 | 30.218 | 1.00 | 16.18 |
| ATOM | 1139 | N | ARG | A | 686 | 12.901 | -9.570 | 29.201 | 1.00 | 13.94 |
| ATOM | 1140 | CA | ARG | A | 686 | 12.128 | -9.926 | 30.389 | 1.00 | 17.26 |
| ATOM | 1141 | CB | ARG | A | 686 | 10.675 | -10.220 | 30.002 | 1.00 | 17.10 |
| ATOM | 1142 | CG | ARG | A | 686 | 9.786 | -10.609 | 31.168 | 1.00 | 17.75 |
| ATOM | 1143 | CD | ARG | A | 686 | 8.407 | -11.064 | 30.752 | 1.00 | 19.01 |
| ATOM | 1144 | NE | ARG | A | 686 | 7.607 | -9.945 | 30.270 | 1.00 | 17.08 |
| ATOM | 1145 | CZ | ARG | A | 686 | 6.374 | -10.048 | 29.789 | 1.00 | 16.89 |
| ATOM | 1146 | NH1 | ARG | A | 686 | 5.736 | -8.960 | 29.382 | 1.00 | 14.85 |
| ATOM | 1147 | NH2 | ARG | A | 686 | 5.781 | -11.237 | 29.710 | 1.00 | 16.43 |
| ATOM | 1148 | C | ARG | A | 686 | 12.725 | -11.107 | 31.148 | 1.00 | 16.06 |
| ATOM | 1149 | O | ARG | A | 686 | 12.940 | -11.031 | 32.360 | 1.00 | 16.93 |
| ATOM | 1150 | N | ASP | A | 687 | 12.996 | -12.193 | 30.432 | 1.00 | 17.76 |
| ATOM | 1151 | CA | ASP | A | 687 | 13.546 | -13.399 | 31.040 | 1.00 | 17.40 |
| ATOM | 1152 | CB | ASP | A | 687 | 13.701 | -14.501 | 29.989 | 1.00 | 21.45 |
| ATOM | 1153 | CG | ASP | A | 687 | 12.374 | -15.167 | 29.638 | 1.00 | 24.63 |
| ATOM | 1154 | OD1 | ASP | A | 687 | 11.325 | -14.773 | 30.203 | 1.00 | 26.54 |
| ATOM | 1155 | OD2 | ASP | A | 687 | 12.284 | -16.093 | 28.806 | 1.00 | 27.82 |
| ATOM | 1156 | C | ASP | A | 687 | 14.864 | -13.157 | 31.787 | 1.00 | 17.69 |
| ATOM | 1157 | O | ASP | A | 687 | 15.102 | -13.762 | 32.840 | 1.00 | 16.75 |
| ATOM | 1158 | N | SER | A | 688 | 15.698 | -12.264 | 31.252 | 1.00 | 15.75 |
| ATOM | 1159 | CA | SER | A | 688 | 16.988 | -11.926 | 31.867 | 1.00 | 18.80 |
| ATOM | 1160 | CB | SER | A | 688 | 17.889 | -11.169 | 30.880 | 1.00 | 18.10 |
| ATOM | 1161 | OG | SER | A | 688 | 17.569 | -9.785 | 30.822 | 1.00 | 19.55 |
| ATOM | 1162 | C | SER | A | 688 | 16.823 | -11.130 | 33.168 | 1.00 | 17.97 |
| ATOM | 1163 | O | SER | A | 688 | 17.718 | -11.126 | 34.020 | 1.00 | 17.26 |
| ATOM | 1164 | N | PHE | A | 689 | 15.682 | -10.457 | 33.305 | 1.00 | 17.77 |
| ATOM | 1165 | CA | PHE | A | 689 | 15.328 | -9.765 | 34.540 | 1.00 | 17.37 |
| ATOM | 1166 | CB | PHE | A | 689 | 14.187 | -8.769 | 34.300 | 1.00 | 16.58 |
| ATOM | 1167 | CG | PHE | A | 689 | 13.884 | -7.901 | 35.483 | 1.00 | 18.01 |
| ATOM | 1168 | CD1 | PHE | A | 689 | 13.087 | -8.370 | 36.527 | 1.00 | 18.26 |
| ATOM | 1169 | CE1 | PHE | A | 689 | 12.812 | -7.569 | 37.627 | 1.00 | 20.07 |
| ATOM | 1170 | CZ | PHE | A | 689 | 13.325 | -6.274 | 37.689 | 1.00 | 20.98 |
| ATOM | 1171 | CE2 | PHE | A | 689 | 14.117 | -5.793 | 36.650 | 1.00 | 21.14 |
| ATOM | 1172 | CD2 | PHE | A | 689 | 14.393 | -6.607 | 35.555 | 1.00 | 20.22 |
| ATOM | 1173 | C | PHE | A | 689 | 14.921 | -10.757 | 35.626 | 1.00 | 16.66 |
| ATOM | 1174 | O | PHE | A | 689 | 15.330 | -10.619 | 36.777 | 1.00 | 16.64 |
| ATOM | 1175 | N | ILE | A | 690 | 14.099 | -11.734 | 35.251 | 1.00 | 18.68 |
| ATOM | 1176 | CA | ILE | A | 690 | 13.584 | -12.747 | 36.179 | 1.00 | 21.04 |
| ATOM | 1177 | CB | ILE | A | 690 | 12.406 | -13.528 | 35.521 | 1.00 | 23.20 |
| ATOM | 1178 | CG1 | ILE | A | 690 | 11.254 | -12.565 | 35.194 | 1.00 | 24.58 |
| ATOM | 1179 | CD1 | ILE | A | 690 | 10.320 | -13.040 | 34.081 | 1.00 | 26.68 |
| ATOM | 1180 | CG2 | ILE | A | 690 | 11.924 | -14.675 | 36.420 | 1.00 | 23.62 |
| ATOM | 1181 | C | ILE | A | 690 | 14.689 | -13.690 | 36.676 | 1.00 | 21.48 |
| ATOM | 1182 | O | ILE | A | 690 | 14.721 | -14.067 | 37.853 | 1.00 | 18.55 |
| ATOM | 1183 | N | CYS | A | 691 | 15.596 | -14.063 | 35.780 | 1.00 | 22.18 |
| ATOM | 1184 | CA | CYS | A | 691 | 16.764 | -14.842 | 36.165 | 1.00 | 20.13 |
| ATOM | 1185 | CB | CYS | A | 691 | 16.555 | -16.327 | 35.866 | 1.00 | 23.45 |

FIGURE 3 (Cont.)

|      | A    | B    | C   | D | E    | F      | G       | H      | I    | J     |
|------|------|------|-----|---|------|--------|---------|--------|------|-------|
| ATOM | 1186 | SG   | CYS | A | 691  | 17.956 | -17.363 | 36.347 | 1.00 | 27.11 |
| ATOM | 1187 | C    | CYS | A | 691  | 18.017 | -14.312 | 35.477 | 1.00 | 20.48 |
| ATOM | 1188 | O    | CYS | A | 691  | 18.137 | -14.372 | 34.252 | 1.00 | 17.95 |
| ATOM | 1189 | N    | SER | A | 692  | 18.944 | -13.799 | 36.284 | 1.00 | 21.42 |
| ATOM | 1190 | CA   | SER | A | 692  | 20.167 | -13.158 | 35.795 | 1.00 | 23.44 |
| ATOM | 1191 | CB   | SER | A | 692  | 20.879 | -12.433 | 36.942 | 1.00 | 23.16 |
| ATOM | 1192 | OG   | SER | A | 692  | 21.297 | -13.351 | 37.939 | 1.00 | 23.94 |
| ATOM | 1193 | C    | SER | A | 692  | 21.137 | -14.123 | 35.106 | 1.00 | 23.83 |
| ATOM | 1194 | O    | SER | A | 692  | 21.996 | -13.695 | 34.330 | 1.00 | 24.80 |
| ATOM | 1195 | N    | LYS | A | 693  | 21.002 | -15.416 | 35.399 | 1.00 | 24.48 |
| ATOM | 1196 | CA   | LYS | A | 693  | 21.868 | -16.440 | 34.815 | 1.00 | 24.89 |
| ATOM | 1197 | CB   | LYS | A | 693  | 22.061 | -17.608 | 35.786 | 1.00 | 24.62 |
| ATOM | 1198 | CG   | LYS | A | 693  | 22.955 | -17.282 | 36.973 | 1.00 | 25.89 |
| ATOM | 1199 | CD   | LYS | A | 693  | 23.033 | -18.442 | 37.949 | 1.00 | 25.80 |
| ATOM | 1200 | CE   | LYS | A | 693  | 21.952 | -18.344 | 39.015 | 1.00 | 26.96 |
| ATOM | 1201 | NZ   | LYS | A | 693  | 21.550 | -19.689 | 39.512 | 1.00 | 29.04 |
| ATOM | 1202 | C    | LYS | A | 693  | 21.346 | -16.951 | 33.473 | 1.00 | 25.84 |
| ATOM | 1203 | O    | LYS | A | 693  | 22.060 | -17.652 | 32.750 | 1.00 | 25.41 |
| ATOM | 1204 | N    | THR | A | 753  | 20.102 | -16.596 | 33.147 | 1.00 | 26.98 |
| ATOM | 1205 | CA   | THR | A | 753  | 19.499 | -16.952 | 31.864 | 1.00 | 29.19 |
| ATOM | 1206 | CB   | THR | A | 753  | 17.976 | -16.687 | 31.885 | 1.00 | 31.74 |
| ATOM | 1207 | OG1  | THR | A | 753  | 17.356 | -17.529 | 32.864 | 1.00 | 33.28 |
| ATOM | 1208 | CG2  | THR | A | 753  | 17.320 | -17.132 | 30.579 | 1.00 | 32.31 |
| ATOM | 1209 | C    | THR | A | 753  | 20.159 | -16.166 | 30.737 | 1.00 | 29.29 |
| ATOM | 1210 | O    | THR | A | 753  | 20.856 | -15.177 | 30.973 | 1.00 | 29.23 |
| ATOM | 1211 | N    | SER | A | 753b | 21.199 | -17.236 | 28.110 | 1.00 | 30.85 |
| ATOM | 1212 | CA   | SER | A | 753b | 21.692 | -15.883 | 27.872 | 1.00 | 27.77 |
| ATOM | 1213 | CB   | SER | A | 753b | 22.632 | -15.871 | 26.667 | 1.00 | 29.13 |
| ATOM | 1214 | OG   | SER | A | 753b | 23.800 | -16.624 | 26.939 | 1.00 | 29.18 |
| ATOM | 1215 | C    | SER | A | 753b | 20.541 | -14.898 | 27.660 | 1.00 | 26.33 |
| ATOM | 1216 | O    | SER | A | 753b | 19.440 | -15.306 | 27.273 | 1.00 | 24.29 |
| ATOM | 1217 | N    | PRO | A | 754  | 20.777 | -13.610 | 27.929 | 1.00 | 23.91 |
| ATOM | 1218 | CA   | PRO | A | 754  | 19.803 | -12.573 | 27.571 | 1.00 | 22.57 |
| ATOM | 1219 | CB   | PRO | A | 754  | 20.486 | -11.277 | 28.015 | 1.00 | 22.43 |
| ATOM | 1220 | CG   | PRO | A | 754  | 21.464 | -11.696 | 29.042 | 1.00 | 22.46 |
| ATOM | 1221 | CD   | PRO | A | 754  | 21.963 | -13.039 | 28.599 | 1.00 | 23.13 |
| ATOM | 1222 | C    | PRO | A | 754  | 19.601 | -12.559 | 26.063 | 1.00 | 23.25 |
| ATOM | 1223 | O    | PRO | A | 754  | 20.520 | -12.944 | 25.324 | 1.00 | 19.98 |
| ATOM | 1224 | N    | ALA | A | 755  | 18.416 | -12.146 | 25.620 | 1.00 | 23.19 |
| ATOM | 1225 | CA   | ALA | A | 755  | 18.145 | -11.989 | 24.198 | 1.00 | 25.54 |
| ATOM | 1226 | CB   | ALA | A | 755  | 16.720 | -11.504 | 23.973 | 1.00 | 25.12 |
| ATOM | 1227 | C    | ALA | A | 755  | 19.142 | -10.992 | 23.628 | 1.00 | 26.55 |
| ATOM | 1228 | O    | ALA | A | 755  | 19.283 | -9.881  | 24.145 | 1.00 | 28.13 |
| ATOM | 1229 | N    | ILE | A | 756  | 19.855 | -11.408 | 22.586 | 1.00 | 25.69 |
| ATOM | 1230 | CA   | ILE | A | 756  | 20.801 | -10.530 | 21.913 | 1.00 | 25.69 |
| ATOM | 1231 | CB   | ILE | A | 756  | 21.881 | -11.338 | 21.159 | 1.00 | 26.12 |
| ATOM | 1232 | CG1  | ILE | A | 756  | 22.701 | -12.190 | 22.135 | 1.00 | 26.25 |
| ATOM | 1233 | CD1  | ILE | A | 756  | 23.073 | -13.555 | 21.593 | 1.00 | 26.14 |
| ATOM | 1234 | CG2  | ILE | A | 756  | 22.796 | -10.406 | 20.362 | 1.00 | 26.91 |
| ATOM | 1235 | C    | ILE | A | 756  | 20.049 | -9.608  | 20.959 | 1.00 | 26.24 |
| ATOM | 1236 | O    | ILE | A | 756  | 19.366 | -10.065 | 20.038 | 1.00 | 25.49 |
| ATOM | 1237 | N    | MET | A | 757  | 20.179 | -8.309  | 21.199 | 1.00 | 25.23 |

FIGURE 3 (Cont.)

|      | A    | B   | C   | D | E   | F      | G       | H      | I    | J     |
|------|------|-----|-----|---|-----|--------|---------|--------|------|-------|
| ATOM | 1238 | CA  | MET | A | 757 | 19.552 | -7.300  | 20.361 | 1.00 | 25.17 |
| ATOM | 1239 | CB  | MET | A | 757 | 18.486 | -6.553  | 21.154 | 1.00 | 25.99 |
| ATOM | 1240 | CG  | MET | A | 757 | 17.281 | -7.415  | 21.471 | 1.00 | 27.80 |
| ATOM | 1241 | SD  | MET | A | 757 | 16.156 | -6.639  | 22.607 | 1.00 | 30.79 |
| ATOM | 1242 | CE  | MET | A | 757 | 15.396 | -5.431  | 21.534 | 1.00 | 29.40 |
| ATOM | 1243 | C   | MET | A | 757 | 20.620 | -6.356  | 19.828 | 1.00 | 24.55 |
| ATOM | 1244 | O   | MET | A | 757 | 21.169 | -5.541  | 20.571 | 1.00 | 22.90 |
| ATOM | 1245 | N   | GLU | A | 758 | 20.908 | -6.486  | 18.533 | 1.00 | 25.24 |
| ATOM | 1246 | CA  | GLU | A | 758 | 22.065 | -5.849  | 17.905 | 1.00 | 26.69 |
| ATOM | 1247 | CB  | GLU | A | 758 | 21.889 | -4.326  | 17.790 | 1.00 | 29.37 |
| ATOM | 1248 | CG  | GLU | A | 758 | 20.984 | -3.883  | 16.647 | 1.00 | 32.46 |
| ATOM | 1249 | CD  | GLU | A | 758 | 21.563 | -4.188  | 15.274 | 1.00 | 34.30 |
| ATOM | 1250 | OE1 | GLU | A | 758 | 22.607 | -3.599  | 14.916 | 1.00 | 35.29 |
| ATOM | 1251 | OE2 | GLU | A | 758 | 20.975 | -5.021  | 14.551 | 1.00 | 35.63 |
| ATOM | 1252 | C   | GLU | A | 758 | 23.336 | -6.237  | 18.669 | 1.00 | 25.77 |
| ATOM | 1253 | O   | GLU | A | 758 | 23.693 | -7.416  | 18.710 | 1.00 | 26.75 |
| ATOM | 1254 | N   | ASP | A | 759 | 24.003 | -5.262  | 19.283 | 1.00 | 24.10 |
| ATOM | 1255 | CA  | ASP | A | 759 | 25.194 | -5.548  | 20.080 | 1.00 | 24.46 |
| ATOM | 1256 | CB  | ASP | A | 759 | 26.314 | -4.542  | 19.773 | 1.00 | 26.14 |
| ATOM | 1257 | CG  | ASP | A | 759 | 25.996 | -3.134  | 20.250 | 1.00 | 28.02 |
| ATOM | 1258 | OD1 | ASP | A | 759 | 24.807 | -2.743  | 20.256 | 1.00 | 28.66 |
| ATOM | 1259 | OD2 | ASP | A | 759 | 26.881 | -2.342  | 20.635 | 1.00 | 30.06 |
| ATOM | 1260 | C   | ASP | A | 759 | 24.904 | -5.629  | 21.588 | 1.00 | 23.42 |
| ATOM | 1261 | O   | ASP | A | 759 | 25.823 | -5.818  | 22.394 | 1.00 | 23.74 |
| ATOM | 1262 | N   | ASP | A | 760 | 23.629 | -5.506  | 21.958 | 1.00 | 19.84 |
| ATOM | 1263 | CA  | ASP | A | 760 | 23.221 | -5.559  | 23.365 | 1.00 | 20.05 |
| ATOM | 1264 | CB  | ASP | A | 760 | 22.041 | -4.617  | 23.634 | 1.00 | 20.61 |
| ATOM | 1265 | CG  | ASP | A | 760 | 21.744 | -4.445  | 25.121 | 1.00 | 23.29 |
| ATOM | 1266 | OD1 | ASP | A | 760 | 21.669 | -5.460  | 25.854 | 1.00 | 21.78 |
| ATOM | 1267 | OD2 | ASP | A | 760 | 21.561 | -3.324  | 25.643 | 1.00 | 22.36 |
| ATOM | 1268 | C   | ASP | A | 760 | 22.866 | -6.973  | 23.805 | 1.00 | 18.51 |
| ATOM | 1269 | O   | ASP | A | 760 | 21.753 | -7.448  | 23.563 | 1.00 | 17.70 |
| ATOM | 1270 | N   | GLU | A | 761 | 23.814 | -7.631  | 24.468 | 1.00 | 18.14 |
| ATOM | 1271 | CA  | GLU | A | 761 | 23.597 | -8.975  | 25.008 | 1.00 | 19.37 |
| ATOM | 1272 | CB  | GLU | A | 761 | 24.674 | -9.949  | 24.501 | 1.00 | 19.98 |
| ATOM | 1273 | CG  | GLU | A | 761 | 26.107 | -9.491  | 24.712 | 1.00 | 22.95 |
| ATOM | 1274 | CD  | GLU | A | 761 | 27.119 | -10.543 | 24.294 | 1.00 | 25.30 |
| ATOM | 1275 | OE1 | GLU | A | 761 | 27.392 | -11.462 | 25.097 | 1.00 | 25.07 |
| ATOM | 1276 | OE2 | GLU | A | 761 | 27.640 | -10.451 | 23.162 | 1.00 | 26.91 |
| ATOM | 1277 | C   | GLU | A | 761 | 23.532 | -8.971  | 26.543 | 1.00 | 17.60 |
| ATOM | 1278 | O   | GLU | A | 761 | 23.642 | -10.016 | 27.185 | 1.00 | 18.14 |
| ATOM | 1279 | N   | LEU | A | 762 | 23.338 | -7.783  | 27.108 | 1.00 | 17.02 |
| ATOM | 1280 | CA  | LEU | A | 762 | 23.325 | -7.575  | 28.551 | 1.00 | 17.83 |
| ATOM | 1281 | CB  | LEU | A | 762 | 23.742 | -6.132  | 28.851 | 1.00 | 23.26 |
| ATOM | 1282 | CG  | LEU | A | 762 | 24.416 | -5.766  | 30.173 | 1.00 | 26.22 |
| ATOM | 1283 | CD1 | LEU | A | 762 | 25.910 | -6.041  | 30.118 | 1.00 | 26.42 |
| ATOM | 1284 | CD2 | LEU | A | 762 | 24.145 | -4.294  | 30.483 | 1.00 | 28.50 |
| ATOM | 1285 | C   | LEU | A | 762 | 21.945 | -7.839  | 29.141 | 1.00 | 17.89 |
| ATOM | 1286 | O   | LEU | A | 762 | 20.929 | -7.658  | 28.473 | 1.00 | 14.14 |
| ATOM | 1287 | N   | ALA | A | 763 | 21.913 | -8.255  | 30.402 | 1.00 | 15.57 |
| ATOM | 1288 | CA  | ALA | A | 763 | 20.651 | -8.452  | 31.101 | 1.00 | 15.49 |
| ATOM | 1289 | CB  | ALA | A | 763 | 20.874 | -9.228  | 32.395 | 1.00 | 16.97 |

FIGURE 3 (Cont.)

|      | A    | B    | C   | D | E   | F      | G      | H      | I    | J     |
|------|------|------|-----|---|-----|--------|--------|--------|------|-------|
| ATOM | 1290 | C    | ALA | A | 763 | 19.938 | -7.126 | 31.379 | 1.00 | 15.90 |
| ATOM | 1291 | O    | ALA | A | 763 | 20.534 | -6.048 | 31.300 | 1.00 | 16.29 |
| ATOM | 1292 | N    | LEU | A | 764 | 18.650 | -7.226 | 31.680 | 1.00 | 15.23 |
| ATOM | 1293 | CA   | LEU | A | 764 | 17.864 | -6.103 | 32.162 | 1.00 | 15.22 |
| ATOM | 1294 | CB   | LEU | A | 764 | 16.481 | -6.136 | 31.508 | 1.00 | 16.61 |
| ATOM | 1295 | CG   | LEU | A | 764 | 15.473 | -5.034 | 31.828 | 1.00 | 17.56 |
| ATOM | 1296 | CD1  | LEU | A | 764 | 15.748 | -3.794 | 30.988 | 1.00 | 19.75 |
| ATOM | 1297 | CD2  | LEU | A | 764 | 14.064 | -5.547 | 31.576 | 1.00 | 17.57 |
| ATOM | 1298 | C    | LEU | A | 764 | 17.740 | -6.242 | 33.675 | 1.00 | 15.99 |
| ATOM | 1299 | O    | LEU | A | 764 | 17.484 | -7.341 | 34.178 | 1.00 | 16.82 |
| ATOM | 1300 | N    | ASP | A | 765 | 17.944 | -5.144 | 34.401 | 1.00 | 15.02 |
| ATOM | 1301 | CA   | ASP | A | 765 | 17.783 | -5.157 | 35.859 | 1.00 | 14.77 |
| ATOM | 1302 | CB   | ASP | A | 765 | 19.115 | -5.404 | 36.589 | 1.00 | 16.61 |
| ATOM | 1303 | CG   | ASP | A | 765 | 20.126 | -4.272 | 36.415 | 1.00 | 17.74 |
| ATOM | 1304 | OD1  | ASP | A | 765 | 19.761 | -3.162 | 35.969 | 1.00 | 18.87 |
| ATOM | 1305 | OD2  | ASP | A | 765 | 21.328 | -4.411 | 36.723 | 1.00 | 20.46 |
| ATOM | 1306 | C    | ASP | A | 765 | 17.053 | -3.922 | 36.379 | 1.00 | 14.83 |
| ATOM | 1307 | O    | ASP | A | 765 | 16.689 | -3.036 | 35.595 | 1.00 | 12.90 |
| ATOM | 1308 | N    | LEU | A | 766 | 16.835 | -3.868 | 37.694 | 1.00 | 11.80 |
| ATOM | 1309 | CA   | LEU | A | 766 | 16.070 | -2.780 | 38.303 | 1.00 | 13.95 |
| ATOM | 1310 | CB   | LEU | A | 766 | 15.898 | -2.996 | 39.815 | 1.00 | 14.48 |
| ATOM | 1311 | CG   | LEU | A | 766 | 15.010 | -1.976 | 40.545 | 1.00 | 17.06 |
| ATOM | 1312 | CD1  | LEU | A | 766 | 13.568 | -2.010 | 40.034 | 1.00 | 16.69 |
| ATOM | 1313 | CD2  | LEU | A | 766 | 15.049 | -2.158 | 42.055 | 1.00 | 15.56 |
| ATOM | 1314 | C    | LEU | A | 766 | 16.681 | -1.408 | 38.028 | 1.00 | 14.13 |
| ATOM | 1315 | O    | LEU | A | 766 | 15.952 | -0.438 | 37.785 | 1.00 | 13.72 |
| ATOM | 1316 | N    | GLU | A | 767 | 18.012 | -1.333 | 38.062 | 1.00 | 13.51 |
| ATOM | 1317 | CA   | GLU | A | 767 | 18.707 | -0.084 | 37.764 | 1.00 | 17.13 |
| ATOM | 1318 | CB   | GLU | A | 767 | 20.218 | -0.232 | 37.943 | 1.00 | 18.79 |
| ATOM | 1319 | CG   | GLU | A | 767 | 20.659 | -0.098 | 39.391 | 1.00 | 25.37 |
| ATOM | 1320 | CD   | GLU | A | 767 | 22.141 | -0.344 | 39.577 | 1.00 | 28.94 |
| ATOM | 1321 | OE1  | GLU | A | 767 | 22.535 | -1.520 | 39.738 | 1.00 | 32.28 |
| ATOM | 1322 | OE2  | GLU | A | 767 | 22.912 |  0.640 | 39.563 | 1.00 | 31.60 |
| ATOM | 1323 | C    | GLU | A | 767 | 18.361 |  0.454 | 36.372 | 1.00 | 15.30 |
| ATOM | 1324 | O    | GLU | A | 767 | 18.154 |  1.656 | 36.217 | 1.00 | 12.38 |
| ATOM | 1325 | N    | ASP | A | 768 | 18.265 | -0.437 | 35.379 | 1.00 | 14.26 |
| ATOM | 1326 | CA   | ASP | A | 768 | 17.827 | -0.047 | 34.031 | 1.00 | 13.18 |
| ATOM | 1327 | CB   | ASP | A | 768 | 17.829 | -1.246 | 33.071 | 1.00 | 16.47 |
| ATOM | 1328 | CG   | ASP | A | 768 | 19.230 | -1.751 | 32.751 | 1.00 | 22.60 |
| ATOM | 1329 | OD1  | ASP | A | 768 | 19.519 | -2.928 | 33.053 | 1.00 | 24.96 |
| ATOM | 1330 | OD2  | ASP | A | 768 | 20.105 | -1.061 | 32.183 | 1.00 | 23.92 |
| ATOM | 1331 | C    | ASP | A | 768 | 16.430 |  0.581 | 34.049 | 1.00 | 13.02 |
| ATOM | 1332 | O    | ASP | A | 768 | 16.197 |  1.612 | 33.421 | 1.00 | 12.75 |
| ATOM | 1333 | N    | LEU | A | 769 | 15.500 | -0.053 | 34.760 | 1.00 | 11.67 |
| ATOM | 1334 | CA   | LEU | A | 769 | 14.114 |  0.419 | 34.812 | 1.00 | 10.94 |
| ATOM | 1335 | CB   | LEU | A | 769 | 13.229 | -0.583 | 35.550 | 1.00 | 10.89 |
| ATOM | 1336 | CG   | LEU | A | 769 | 13.211 | -2.027 | 35.048 | 1.00 | 15.34 |
| ATOM | 1337 | CD1  | LEU | A | 769 | 12.206 | -2.832 | 35.851 | 1.00 | 13.45 |
| ATOM | 1338 | CD2  | LEU | A | 769 | 12.896 | -2.092 | 33.563 | 1.00 | 12.15 |
| ATOM | 1339 | C    | LEU | A | 769 | 13.997 |  1.781 | 35.465 | 1.00 | 11.85 |
| ATOM | 1340 | O    | LEU | A | 769 | 13.233 |  2.632 | 35.001 | 1.00 | 11.62 |
| ATOM | 1341 | N    | LEU | A | 770 | 14.768 |  1.988 | 36.529 | 1.00 | 11.66 |

FIGURE 3 (Cont.)

| | A | B | C | D | E | F | G | H | I | J |
|---|---|---|---|---|---|---|---|---|---|---|
| ATOM | 1342 | CA | LEU | A | 770 | 14.832 | 3.284 | 37.195 | 1.00 | 13.76 |
| ATOM | 1343 | CB | LEU | A | 770 | 15.694 | 3.194 | 38.454 | 1.00 | 15.00 |
| ATOM | 1344 | CG | LEU | A | 770 | 15.069 | 2.406 | 39.608 | 1.00 | 17.61 |
| ATOM | 1345 | CD1 | LEU | A | 770 | 16.052 | 2.317 | 40.774 | 1.00 | 19.00 |
| ATOM | 1346 | CD2 | LEU | A | 770 | 13.759 | 3.041 | 40.052 | 1.00 | 18.30 |
| ATOM | 1347 | C | LEU | A | 770 | 15.378 | 4.357 | 36.261 | 1.00 | 13.58 |
| ATOM | 1348 | O | LEU | A | 770 | 14.846 | 5.468 | 36.198 | 1.00 | 11.50 |
| ATOM | 1349 | N | SER | A | 771 | 16.438 | 4.007 | 35.537 | 1.00 | 12.36 |
| ATOM | 1350 | CA | SER | A | 771 | 17.031 | 4.897 | 34.545 | 1.00 | 14.51 |
| ATOM | 1351 | CB | SER | A | 771 | 18.281 | 4.270 | 33.929 | 1.00 | 15.00 |
| ATOM | 1352 | OG | SER | A | 771 | 18.826 | 5.125 | 32.935 | 1.00 | 15.47 |
| ATOM | 1353 | C | SER | A | 771 | 16.034 | 5.260 | 33.446 | 1.00 | 13.51 |
| ATOM | 1354 | O | SER | A | 771 | 15.903 | 6.430 | 33.090 | 1.00 | 14.22 |
| ATOM | 1355 | N | PHE | A | 772 | 15.337 | 4.262 | 32.911 | 1.00 | 10.74 |
| ATOM | 1356 | CA | PHE | A | 772 | 14.337 | 4.513 | 31.870 | 1.00 | 13.55 |
| ATOM | 1357 | CB | PHE | A | 772 | 13.717 | 3.206 | 31.350 | 1.00 | 11.86 |
| ATOM | 1358 | CG | PHE | A | 772 | 14.710 | 2.257 | 30.707 | 1.00 | 13.88 |
| ATOM | 1359 | CD1 | PHE | A | 772 | 14.390 | 0.914 | 30.551 | 1.00 | 15.11 |
| ATOM | 1360 | CE1 | PHE | A | 772 | 15.292 | 0.021 | 29.967 | 1.00 | 15.17 |
| ATOM | 1361 | CZ | PHE | A | 772 | 16.522 | 0.472 | 29.528 | 1.00 | 15.67 |
| ATOM | 1362 | CE2 | PHE | A | 772 | 16.864 | 1.813 | 29.678 | 1.00 | 16.44 |
| ATOM | 1363 | CD2 | PHE | A | 772 | 15.956 | 2.698 | 30.265 | 1.00 | 14.09 |
| ATOM | 1364 | C | PHE | A | 772 | 13.240 | 5.445 | 32.385 | 1.00 | 14.06 |
| ATOM | 1365 | O | PHE | A | 772 | 12.819 | 6.354 | 31.679 | 1.00 | 12.52 |
| ATOM | 1366 | N | SER | A | 773 | 12.798 | 5.226 | 33.623 | 1.00 | 13.22 |
| ATOM | 1367 | CA | SER | A | 773 | 11.771 | 6.079 | 34.232 | 1.00 | 13.21 |
| ATOM | 1368 | CB | BSER | A | 773 | 11.353 | 5.543 | 35.608 | 0.35 | 12.27 |
| ATOM | 1369 | CB | ASER | A | 773 | 11.495 | 5.625 | 35.672 | 0.65 | 13.84 |
| ATOM | 1370 | OG | BSER | A | 773 | 12.238 | 5.954 | 36.626 | 0.35 | 8.77 |
| ATOM | 1371 | OG | ASER | A | 773 | 11.118 | 4.267 | 35.733 | 0.65 | 15.06 |
| ATOM | 1372 | C | SER | A | 773 | 12.224 | 7.528 | 34.295 | 1.00 | 13.90 |
| ATOM | 1373 | O | SER | A | 773 | 11.460 | 8.455 | 34.005 | 1.00 | 13.14 |
| ATOM | 1374 | N | TYR | A | 774 | 13.478 | 7.704 | 34.690 | 1.00 | 11.28 |
| ATOM | 1375 | CA | TYR | A | 774 | 14.073 | 9.016 | 34.861 | 1.00 | 11.13 |
| ATOM | 1376 | CB | TYR | A | 774 | 15.430 | 8.846 | 35.530 | 1.00 | 12.24 |
| ATOM | 1377 | CG | TYR | A | 774 | 16.184 | 10.121 | 35.786 | 1.00 | 14.46 |
| ATOM | 1378 | CD1 | TYR | A | 774 | 17.527 | 10.219 | 35.452 | 1.00 | 18.16 |
| ATOM | 1379 | CE1 | TYR | A | 774 | 18.246 | 11.384 | 35.692 | 1.00 | 20.77 |
| ATOM | 1380 | CZ | TYR | A | 774 | 17.613 | 12.472 | 36.265 | 1.00 | 20.30 |
| ATOM | 1381 | OH | TYR | A | 774 | 18.338 | 13.622 | 36.497 | 1.00 | 21.42 |
| ATOM | 1382 | CE2 | TYR | A | 774 | 16.276 | 12.404 | 36.610 | 1.00 | 17.59 |
| ATOM | 1383 | CD2 | TYR | A | 774 | 15.564 | 11.227 | 36.372 | 1.00 | 15.57 |
| ATOM | 1384 | C | TYR | A | 774 | 14.238 | 9.719 | 33.515 | 1.00 | 12.13 |
| ATOM | 1385 | O | TYR | A | 774 | 13.881 | 10.887 | 33.369 | 1.00 | 10.90 |
| ATOM | 1386 | N | GLN | A | 775 | 14.772 | 8.992 | 32.539 | 1.00 | 12.04 |
| ATOM | 1387 | CA | GLN | A | 775 | 15.060 | 9.554 | 31.220 | 1.00 | 11.86 |
| ATOM | 1388 | CB | GLN | A | 775 | 15.792 | 8.532 | 30.371 | 1.00 | 12.70 |
| ATOM | 1389 | CG | GLN | A | 775 | 17.236 | 8.312 | 30.751 | 1.00 | 13.95 |
| ATOM | 1390 | CD | GLN | A | 775 | 17.915 | 7.367 | 29.801 | 1.00 | 16.57 |
| ATOM | 1391 | OE1 | GLN | A | 775 | 18.206 | 7.733 | 28.662 | 1.00 | 17.83 |
| ATOM | 1392 | NE2 | GLN | A | 775 | 18.170 | 6.147 | 30.255 | 1.00 | 16.32 |
| ATOM | 1393 | C | GLN | A | 775 | 13.788 | 9.982 | 30.493 | 1.00 | 12.47 |

FIGURE 3 (Cont.)

|      | A    | B    | C    | D | E   | F      | G      | H      | I    | J     |
|------|------|------|------|---|-----|--------|--------|--------|------|-------|
| ATOM | 1394 | O    | GLN  | A | 775 | 13.748 | 11.040 | 29.862 | 1.00 | 12.04 |
| ATOM | 1395 | N    | VAL  | A | 776 | 12.757 | 9.144  | 30.571 | 1.00 | 11.99 |
| ATOM | 1396 | CA   | VAL  | A | 776 | 11.467 | 9.462  | 29.956 | 1.00 | 13.69 |
| ATOM | 1397 | CB   | VAL  | A | 776 | 10.523 | 8.231  | 29.931 | 1.00 | 13.42 |
| ATOM | 1398 | CG1  | VAL  | A | 776 | 9.105  | 8.603  | 29.467 | 1.00 | 14.90 |
| ATOM | 1399 | CG2  | VAL  | A | 776 | 11.105 | 7.150  | 29.016 | 1.00 | 16.02 |
| ATOM | 1400 | C    | VAL  | A | 776 | 10.841 | 10.673 | 30.645 | 1.00 | 13.74 |
| ATOM | 1401 | O    | VAL  | A | 776 | 10.311 | 11.565 | 29.980 | 1.00 | 13.57 |
| ATOM | 1402 | N    | ALA  | A | 777 | 10.922 | 10.725 | 31.974 | 1.00 | 13.01 |
| ATOM | 1403 | CA   | ALA  | A | 777 | 10.451 | 11.915 | 32.690 | 1.00 | 12.78 |
| ATOM | 1404 | CB   | ALA  | A | 777 | 10.598 | 11.747 | 34.200 | 1.00 | 12.05 |
| ATOM | 1405 | C    | ALA  | A | 777 | 11.166 | 13.187 | 32.228 | 1.00 | 13.14 |
| ATOM | 1406 | O    | ALA  | A | 777 | 10.529 | 14.227 | 32.056 | 1.00 | 13.33 |
| ATOM | 1407 | N    | LYS  | A | 778 | 12.483 | 13.107 | 32.046 | 1.00 | 12.39 |
| ATOM | 1408 | CA   | LYS  | A | 778 | 13.267 | 14.258 | 31.592 | 1.00 | 12.06 |
| ATOM | 1409 | CB   | LYS  | A | 778 | 14.764 | 13.938 | 31.628 | 1.00 | 14.24 |
| ATOM | 1410 | CG   | LYS  | A | 778 | 15.359 | 13.972 | 33.029 | 1.00 | 15.23 |
| ATOM | 1411 | CD   | LYS  | A | 778 | 16.881 | 13.916 | 32.984 | 1.00 | 18.24 |
| ATOM | 1412 | CE   | LYS  | A | 778 | 17.378 | 12.547 | 32.536 | 1.00 | 17.29 |
| ATOM | 1413 | NZ   | LYS  | A | 778 | 18.864 | 12.477 | 32.545 | 1.00 | 18.61 |
| ATOM | 1414 | C    | LYS  | A | 778 | 12.863 | 14.706 | 30.187 | 1.00 | 12.72 |
| ATOM | 1415 | O    | LYS  | A | 778 | 12.731 | 15.898 | 29.929 | 1.00 | 12.89 |
| ATOM | 1416 | N    | GLY  | A | 779 | 12.660 | 13.744 | 29.289 | 1.00 | 13.02 |
| ATOM | 1417 | CA   | GLY  | A | 779 | 12.246 | 14.048 | 27.930 | 1.00 | 13.14 |
| ATOM | 1418 | C    | GLY  | A | 779 | 10.855 | 14.667 | 27.890 | 1.00 | 12.69 |
| ATOM | 1419 | O    | GLY  | A | 779 | 10.598 | 15.568 | 27.097 | 1.00 | 12.91 |
| ATOM | 1420 | N    | MET  | A | 780 | 9.956  | 14.162 | 28.732 | 1.00 | 13.99 |
| ATOM | 1421 | CA   | MET  | A | 780 | 8.606  | 14.698 | 28.819 | 1.00 | 12.92 |
| ATOM | 1422 | CB   | MET  | A | 780 | 7.680  | 13.741 | 29.570 | 1.00 | 13.49 |
| ATOM | 1423 | CG   | MET  | A | 780 | 7.267  | 12.497 | 28.779 | 1.00 | 14.65 |
| ATOM | 1424 | SD   | MET  | A | 780 | 6.642  | 12.835 | 27.110 | 1.00 | 16.48 |
| ATOM | 1425 | CE   | MET  | A | 780 | 5.175  | 13.819 | 27.470 | 1.00 | 14.14 |
| ATOM | 1426 | C    | MET  | A | 780 | 8.589  | 16.077 | 29.462 | 1.00 | 14.81 |
| ATOM | 1427 | O    | MET  | A | 780 | 7.829  | 16.945 | 29.034 | 1.00 | 13.62 |
| ATOM | 1428 | N    | ALA  | A | 781 | 9.421  | 16.273 | 30.489 | 1.00 | 12.52 |
| ATOM | 1429 | CA   | ALA  | A | 781 | 9.627  | 17.603 | 31.072 | 1.00 | 13.04 |
| ATOM | 1430 | CB   | ALA  | A | 781 | 10.640 | 17.545 | 32.209 | 1.00 | 13.55 |
| ATOM | 1431 | C    | ALA  | A | 781 | 10.085 | 18.592 | 30.002 | 1.00 | 13.06 |
| ATOM | 1432 | O    | ALA  | A | 781 | 9.612  | 19.727 | 29.951 | 1.00 | 11.41 |
| ATOM | 1433 | N    | PHE  | A | 782 | 10.999 | 18.151 | 29.138 | 1.00 | 13.67 |
| ATOM | 1434 | CA   | PHE  | A | 782 | 11.483 | 18.990 | 28.048 | 1.00 | 11.93 |
| ATOM | 1435 | CB   | PHE  | A | 782 | 12.613 | 18.289 | 27.287 | 1.00 | 12.09 |
| ATOM | 1436 | CG   | PHE  | A | 782 | 13.054 | 19.012 | 26.047 | 1.00 | 13.77 |
| ATOM | 1437 | CD1  | PHE  | A | 782 | 12.625 | 18.591 | 24.789 | 1.00 | 14.29 |
| ATOM | 1438 | CE1  | PHE  | A | 782 | 13.037 | 19.261 | 23.638 | 1.00 | 10.81 |
| ATOM | 1439 | CZ   | PHE  | A | 782 | 13.880 | 20.353 | 23.735 | 1.00 | 13.99 |
| ATOM | 1440 | CE2  | PHE  | A | 782 | 14.309 | 20.787 | 24.979 | 1.00 | 15.40 |
| ATOM | 1441 | CD2  | PHE  | A | 782 | 13.894 | 20.114 | 26.131 | 1.00 | 14.58 |
| ATOM | 1442 | C    | PHE  | A | 782 | 10.333 | 19.335 | 27.098 | 1.00 | 10.58 |
| ATOM | 1443 | O    | PHE  | A | 782 | 10.158 | 20.493 | 26.724 | 1.00 | 10.37 |
| ATOM | 1444 | N    | LEU  | A | 783 | 9.556  | 18.330 | 26.712 | 1.00 | 10.53 |
| ATOM | 1445 | CA   | LEU  | A | 783 | 8.429  | 18.576 | 25.822 | 1.00 | 12.65 |

FIGURE 3 (Cont.)

| | A | B | C | D | E | F | G | H | I | J |
|---|---|---|---|---|---|---|---|---|---|---|
| ATOM | 1446 | CB | LEU | A | 783 | 7.737 | 17.274 | 25.417 | 1.00 | 12.65 |
| ATOM | 1447 | CG | LEU | A | 783 | 8.540 | 16.383 | 24.460 | 1.00 | 14.00 |
| ATOM | 1448 | CD1 | LEU | A | 783 | 7.852 | 15.029 | 24.266 | 1.00 | 16.82 |
| ATOM | 1449 | CD2 | LEU | A | 783 | 8.786 | 17.063 | 23.121 | 1.00 | 16.94 |
| ATOM | 1450 | C | LEU | A | 783 | 7.452 | 19.567 | 26.447 | 1.00 | 11.96 |
| ATOM | 1451 | O | LEU | A | 783 | 7.075 | 20.547 | 25.811 | 1.00 | 10.16 |
| ATOM | 1452 | N | ALA | A | 784 | 7.085 | 19.334 | 27.706 | 1.00 | 12.79 |
| ATOM | 1453 | CA | ALA | A | 784 | 6.157 | 20.217 | 28.410 | 1.00 | 12.82 |
| ATOM | 1454 | CB | ALA | A | 784 | 5.778 | 19.624 | 29.781 | 1.00 | 14.07 |
| ATOM | 1455 | C | ALA | A | 784 | 6.698 | 21.642 | 28.546 | 1.00 | 13.91 |
| ATOM | 1456 | O | ALA | A | 784 | 5.940 | 22.609 | 28.443 | 1.00 | 12.30 |
| ATOM | 1457 | N | SER | A | 785 | 8.012 | 21.771 | 28.732 | 1.00 | 13.11 |
| ATOM | 1458 | CA | SER | A | 785 | 8.666 | 23.080 | 28.795 | 1.00 | 14.09 |
| ATOM | 1459 | CB | SER | A | 785 | 10.149 | 22.931 | 29.166 | 1.00 | 15.68 |
| ATOM | 1460 | OG | SER | A | 785 | 10.932 | 22.563 | 28.040 | 1.00 | 13.51 |
| ATOM | 1461 | C | SER | A | 785 | 8.525 | 23.880 | 27.491 | 1.00 | 11.41 |
| ATOM | 1462 | O | SER | A | 785 | 8.657 | 25.100 | 27.493 | 1.00 | 11.06 |
| ATOM | 1463 | N | LYS | A | 786 | 8.269 | 23.176 | 26.387 | 1.00 | 11.70 |
| ATOM | 1464 | CA | LYS | A | 786 | 8.060 | 23.807 | 25.087 | 1.00 | 14.24 |
| ATOM | 1465 | CB | LYS | A | 786 | 8.826 | 23.059 | 23.989 | 1.00 | 13.18 |
| ATOM | 1466 | CG | LYS | A | 786 | 10.319 | 22.864 | 24.245 | 1.00 | 15.90 |
| ATOM | 1467 | CD | LYS | A | 786 | 11.045 | 24.180 | 24.463 | 1.00 | 18.73 |
| ATOM | 1468 | CE | LYS | A | 786 | 12.544 | 24.006 | 24.302 | 1.00 | 20.82 |
| ATOM | 1469 | NZ | LYS | A | 786 | 13.204 | 25.308 | 24.072 | 1.00 | 22.13 |
| ATOM | 1470 | C | LYS | A | 786 | 6.577 | 23.886 | 24.721 | 1.00 | 13.35 |
| ATOM | 1471 | O | LYS | A | 786 | 6.234 | 24.142 | 23.568 | 1.00 | 12.42 |
| ATOM | 1472 | N | ASN | A | 787 | 5.709 | 23.669 | 25.707 | 1.00 | 12.99 |
| ATOM | 1473 | CA | ASN | A | 787 | 4.258 | 23.671 | 25.504 | 1.00 | 12.93 |
| ATOM | 1474 | CB | ASN | A | 787 | 3.759 | 25.062 | 25.096 | 1.00 | 14.77 |
| ATOM | 1475 | CG | ASN | A | 787 | 3.825 | 26.054 | 26.235 | 1.00 | 18.56 |
| ATOM | 1476 | OD1 | ASN | A | 787 | 3.509 | 25.722 | 27.379 | 1.00 | 18.99 |
| ATOM | 1477 | ND2 | ASN | A | 787 | 4.244 | 27.276 | 25.933 | 1.00 | 20.48 |
| ATOM | 1478 | C | ASN | A | 787 | 3.822 | 22.606 | 24.505 | 1.00 | 10.94 |
| ATOM | 1479 | O | ASN | A | 787 | 2.912 | 22.808 | 23.701 | 1.00 | 11.19 |
| ATOM | 1480 | N | CYS | A | 788 | 4.501 | 21.471 | 24.569 | 1.00 | 10.23 |
| ATOM | 1481 | CA | CYS | A | 788 | 4.217 | 20.361 | 23.679 | 1.00 | 12.39 |
| ATOM | 1482 | CB | CYS | A | 788 | 5.503 | 19.860 | 23.035 | 1.00 | 15.15 |
| ATOM | 1483 | SG | CYS | A | 788 | 5.226 | 18.534 | 21.847 | 1.00 | 20.44 |
| ATOM | 1484 | C | CYS | A | 788 | 3.539 | 19.236 | 24.437 | 1.00 | 13.76 |
| ATOM | 1485 | O | CYS | A | 788 | 3.952 | 18.881 | 25.541 | 1.00 | 12.95 |
| ATOM | 1486 | N | ILE | A | 789 | 2.481 | 18.697 | 23.842 | 1.00 | 12.50 |
| ATOM | 1487 | CA | ILE | A | 789 | 1.809 | 17.519 | 24.377 | 1.00 | 13.87 |
| ATOM | 1488 | CB | ILE | A | 789 | 0.309 | 17.796 | 24.631 | 1.00 | 18.20 |
| ATOM | 1489 | CG1 | ILE | A | 789 | 0.152 | 18.856 | 25.723 | 1.00 | 20.46 |
| ATOM | 1490 | CD1 | ILE | A | 789 | -1.045 | 19.759 | 25.527 | 1.00 | 25.05 |
| ATOM | 1491 | CG2 | ILE | A | 789 | -0.417 | 16.525 | 25.072 | 1.00 | 21.62 |
| ATOM | 1492 | C | ILE | A | 789 | 2.000 | 16.374 | 23.392 | 1.00 | 13.14 |
| ATOM | 1493 | O | ILE | A | 789 | 1.882 | 16.561 | 22.181 | 1.00 | 13.38 |
| ATOM | 1494 | N | HIS | A | 790 | 2.299 | 15.197 | 23.931 | 1.00 | 11.91 |
| ATOM | 1495 | CA | HIS | A | 790 | 2.643 | 14.024 | 23.144 | 1.00 | 12.33 |
| ATOM | 1496 | CB | HIS | A | 790 | 3.476 | 13.074 | 24.004 | 1.00 | 13.98 |
| ATOM | 1497 | CG | HIS | A | 790 | 4.063 | 11.924 | 23.251 | 1.00 | 15.19 |

FIGURE 3 (Cont.)

|  | A | B | C | D | E | F | G | H | I | J |
|---|---|---|---|---|---|---|---|---|---|---|
| ATOM | 1498 | ND1 | HIS | A | 790 | 3.294 | 11.006 | 22.570 | 1.00 | 16.02 |
| ATOM | 1499 | CE1 | HIS | A | 790 | 4.082 | 10.105 | 22.009 | 1.00 | 17.59 |
| ATOM | 1500 | NE2 | HIS | A | 790 | 5.333 | 10.406 | 22.306 | 1.00 | 19.43 |
| ATOM | 1501 | CD2 | HIS | A | 790 | 5.348 | 11.536 | 23.086 | 1.00 | 17.98 |
| ATOM | 1502 | C | HIS | A | 790 | 1.374 | 13.331 | 22.643 | 1.00 | 12.67 |
| ATOM | 1503 | O | HIS | A | 790 | 1.230 | 13.061 | 21.442 | 1.00 | 11.56 |
| ATOM | 1504 | N | ARG | A | 791 | 0.461 | 13.065 | 23.577 | 1.00 | 12.12 |
| ATOM | 1505 | CA | ARG | A | 791 | -0.862 | 12.483 | 23.303 | 1.00 | 11.82 |
| ATOM | 1506 | CB | ARG | A | 791 | -1.579 | 13.179 | 22.134 | 1.00 | 13.33 |
| ATOM | 1507 | CG | ARG | A | 791 | -1.785 | 14.682 | 22.300 | 1.00 | 15.83 |
| ATOM | 1508 | CD | ARG | A | 791 | -2.669 | 15.288 | 21.222 | 1.00 | 16.98 |
| ATOM | 1509 | NE | ARG | A | 791 | -2.369 | 14.724 | 19.905 | 1.00 | 21.86 |
| ATOM | 1510 | CZ | ARG | A | 791 | -3.258 | 14.526 | 18.939 | 1.00 | 24.58 |
| ATOM | 1511 | NH1 | ARG | A | 791 | -4.535 | 14.857 | 19.108 | 1.00 | 24.45 |
| ATOM | 1512 | NH2 | ARG | A | 791 | -2.862 | 14.003 | 17.788 | 1.00 | 26.47 |
| ATOM | 1513 | C | ARG | A | 791 | -0.854 | 10.971 | 23.077 | 1.00 | 13.15 |
| ATOM | 1514 | O | ARG | A | 791 | -1.915 | 10.347 | 23.082 | 1.00 | 14.01 |
| ATOM | 1515 | N | ASP | A | 792 | 0.324 | 10.385 | 22.883 | 1.00 | 12.35 |
| ATOM | 1516 | CA | ASP | A | 792 | 0.422 | 8.933 | 22.723 | 1.00 | 13.89 |
| ATOM | 1517 | CB | ASP | A | 792 | 0.364 | 8.521 | 21.241 | 1.00 | 15.07 |
| ATOM | 1518 | CG | ASP | A | 792 | 0.100 | 7.024 | 21.062 | 1.00 | 17.15 |
| ATOM | 1519 | OD1 | ASP | A | 792 | 0.232 | 6.508 | 19.935 | 1.00 | 16.54 |
| ATOM | 1520 | OD2 | ASP | A | 792 | -0.234 | 6.286 | 22.008 | 1.00 | 15.39 |
| ATOM | 1521 | C | ASP | A | 792 | 1.662 | 8.374 | 23.422 | 1.00 | 13.36 |
| ATOM | 1522 | O | ASP | A | 792 | 2.372 | 7.520 | 22.880 | 1.00 | 13.73 |
| ATOM | 1523 | N | LEU | A | 793 | 1.920 | 8.861 | 24.628 | 1.00 | 13.68 |
| ATOM | 1524 | CA | LEU | A | 793 | 3.051 | 8.363 | 25.410 | 1.00 | 14.70 |
| ATOM | 1525 | CB | LEU | A | 793 | 3.355 | 9.280 | 26.601 | 1.00 | 16.47 |
| ATOM | 1526 | CG | LEU | A | 793 | 4.554 | 8.872 | 27.466 | 1.00 | 18.01 |
| ATOM | 1527 | CD1 | LEU | A | 793 | 5.853 | 8.880 | 26.648 | 1.00 | 17.55 |
| ATOM | 1528 | CD2 | LEU | A | 793 | 4.666 | 9.798 | 28.686 | 1.00 | 16.05 |
| ATOM | 1529 | C | LEU | A | 793 | 2.785 | 6.937 | 25.883 | 1.00 | 14.15 |
| ATOM | 1530 | O | LEU | A | 793 | 1.765 | 6.661 | 26.504 | 1.00 | 15.14 |
| ATOM | 1531 | N | ALA | A | 794 | 3.718 | 6.044 | 25.569 | 1.00 | 11.63 |
| ATOM | 1532 | CA | ALA | A | 794 | 3.590 | 4.613 | 25.834 | 1.00 | 14.78 |
| ATOM | 1533 | CB | ALA | A | 794 | 2.530 | 3.989 | 24.937 | 1.00 | 14.36 |
| ATOM | 1534 | C | ALA | A | 794 | 4.947 | 4.014 | 25.537 | 1.00 | 12.71 |
| ATOM | 1535 | O | ALA | A | 794 | 5.732 | 4.619 | 24.805 | 1.00 | 14.64 |
| ATOM | 1536 | N | ALA | A | 795 | 5.239 | 2.841 | 26.100 | 1.00 | 13.03 |
| ATOM | 1537 | CA | ALA | A | 795 | 6.537 | 2.213 | 25.861 | 1.00 | 11.30 |
| ATOM | 1538 | CB | ALA | A | 795 | 6.698 | 0.950 | 26.671 | 1.00 | 12.03 |
| ATOM | 1539 | C | ALA | A | 795 | 6.811 | 1.952 | 24.373 | 1.00 | 14.59 |
| ATOM | 1540 | O | ALA | A | 795 | 7.962 | 1.986 | 23.940 | 1.00 | 14.60 |
| ATOM | 1541 | N | ARG | A | 796 | 5.751 | 1.716 | 23.598 | 1.00 | 13.94 |
| ATOM | 1542 | CA | ARG | A | 796 | 5.876 | 1.525 | 22.151 | 1.00 | 13.62 |
| ATOM | 1543 | CB | ARG | A | 796 | 4.553 | 1.034 | 21.554 | 1.00 | 13.67 |
| ATOM | 1544 | CG | ARG | A | 796 | 3.445 | 2.087 | 21.614 | 1.00 | 11.94 |
| ATOM | 1545 | CD | ARG | A | 796 | 2.094 | 1.633 | 21.087 | 1.00 | 12.69 |
| ATOM | 1546 | NE | ARG | A | 796 | 1.097 | 2.627 | 21.472 | 1.00 | 11.21 |
| ATOM | 1547 | CZ | ARG | A | 796 | 0.386 | 2.572 | 22.592 | 1.00 | 14.68 |
| ATOM | 1548 | NH1 | ARG | A | 796 | -0.476 | 3.538 | 22.876 | 1.00 | 14.83 |
| ATOM | 1549 | NH2 | ARG | A | 796 | 0.517 | 1.541 | 23.420 | 1.00 | 14.71 |

FIGURE 3 (Cont.)

|  | A | B | C | D | E | F | G | H | I | J |
|---|---|---|---|---|---|---|---|---|---|---|
| ATOM | 1550 | C | ARG | A | 796 | 6.359 | 2.782 | 21.405 | 1.00 | 13.76 |
| ATOM | 1551 | O | ARG | A | 796 | 6.806 | 2.687 | 20.265 | 1.00 | 12.78 |
| ATOM | 1552 | N | ASN | A | 797 | 6.258 | 3.945 | 22.052 | 1.00 | 13.08 |
| ATOM | 1553 | CA | ASN | A | 797 | 6.683 | 5.223 | 21.466 | 1.00 | 14.41 |
| ATOM | 1554 | CB | ASN | A | 797 | 5.532 | 6.243 | 21.486 | 1.00 | 15.61 |
| ATOM | 1555 | CG | ASN | A | 797 | 4.571 | 6.057 | 20.322 | 1.00 | 16.11 |
| ATOM | 1556 | OD1 | ASN | A | 797 | 4.976 | 5.662 | 19.232 | 1.00 | 18.27 |
| ATOM | 1557 | ND2 | ASN | A | 797 | 3.292 | 6.330 | 20.553 | 1.00 | 16.93 |
| ATOM | 1558 | C | ASN | A | 797 | 7.921 | 5.799 | 22.142 | 1.00 | 16.10 |
| ATOM | 1559 | O | ASN | A | 797 | 8.201 | 6.998 | 22.059 | 1.00 | 17.34 |
| ATOM | 1560 | N | ILE | A | 798 | 8.650 | 4.931 | 22.832 | 1.00 | 13.75 |
| ATOM | 1561 | CA | ILE | A | 798 | 9.942 | 5.293 | 23.393 | 1.00 | 14.41 |
| ATOM | 1562 | CB | ILE | A | 798 | 9.912 | 5.237 | 24.930 | 1.00 | 15.04 |
| ATOM | 1563 | CG1 | ILE | A | 798 | 8.895 | 6.257 | 25.467 | 1.00 | 16.71 |
| ATOM | 1564 | CD1 | ILE | A | 798 | 8.300 | 5.893 | 26.802 | 1.00 | 18.62 |
| ATOM | 1565 | CG2 | ILE | A | 798 | 11.301 | 5.561 | 25.514 | 1.00 | 15.66 |
| ATOM | 1566 | C | ILE | A | 798 | 10.957 | 4.332 | 22.779 | 1.00 | 12.61 |
| ATOM | 1567 | O | ILE | A | 798 | 10.732 | 3.124 | 22.726 | 1.00 | 14.70 |
| ATOM | 1568 | N | LEU | A | 799 | 12.049 | 4.878 | 22.264 | 1.00 | 11.98 |
| ATOM | 1569 | CA | LEU | A | 799 | 13.049 | 4.062 | 21.588 | 1.00 | 12.32 |
| ATOM | 1570 | CB | LEU | A | 799 | 13.350 | 4.612 | 20.189 | 1.00 | 15.30 |
| ATOM | 1571 | CG | LEU | A | 799 | 12.203 | 4.823 | 19.196 | 1.00 | 14.97 |
| ATOM | 1572 | CD1 | LEU | A | 799 | 12.742 | 5.365 | 17.882 | 1.00 | 16.15 |
| ATOM | 1573 | CD2 | LEU | A | 799 | 11.409 | 3.541 | 18.951 | 1.00 | 16.61 |
| ATOM | 1574 | C | LEU | A | 799 | 14.318 | 4.026 | 22.413 | 1.00 | 13.84 |
| ATOM | 1575 | O | LEU | A | 799 | 14.546 | 4.890 | 23.252 | 1.00 | 15.78 |
| ATOM | 1576 | N | LEU | A | 800 | 15.138 | 3.016 | 22.161 | 1.00 | 14.00 |
| ATOM | 1577 | CA | LEU | A | 800 | 16.342 | 2.799 | 22.941 | 1.00 | 15.67 |
| ATOM | 1578 | CB | LEU | A | 800 | 16.270 | 1.439 | 23.639 | 1.00 | 18.95 |
| ATOM | 1579 | CG | LEU | A | 800 | 16.173 | 1.355 | 25.163 | 1.00 | 24.38 |
| ATOM | 1580 | CD1 | LEU | A | 800 | 16.473 | -0.066 | 25.578 | 1.00 | 24.95 |
| ATOM | 1581 | CD2 | LEU | A | 800 | 17.122 | 2.295 | 25.869 | 1.00 | 22.04 |
| ATOM | 1582 | C | LEU | A | 800 | 17.541 | 2.846 | 22.024 | 1.00 | 12.84 |
| ATOM | 1583 | O | LEU | A | 800 | 17.549 | 2.223 | 20.964 | 1.00 | 11.92 |
| ATOM | 1584 | N | THR | A | 801 | 18.563 | 3.586 | 22.435 | 1.00 | 11.71 |
| ATOM | 1585 | CA | THR | A | 801 | 19.758 | 3.729 | 21.623 | 1.00 | 13.67 |
| ATOM | 1586 | CB | THR | A | 801 | 19.794 | 5.144 | 20.962 | 1.00 | 14.16 |
| ATOM | 1587 | OG1 | THR | A | 801 | 20.865 | 5.212 | 20.015 | 1.00 | 17.24 |
| ATOM | 1588 | CG2 | THR | A | 801 | 20.116 | 6.248 | 21.983 | 1.00 | 14.58 |
| ATOM | 1589 | C | THR | A | 801 | 21.011 | 3.411 | 22.443 | 1.00 | 14.78 |
| ATOM | 1590 | O | THR | A | 801 | 20.904 | 2.970 | 23.590 | 1.00 | 13.96 |
| ATOM | 1591 | N | HIS | A | 802 | 22.179 | 3.622 | 21.840 | 1.00 | 14.77 |
| ATOM | 1592 | CA | HIS | A | 802 | 23.480 | 3.390 | 22.470 | 1.00 | 16.75 |
| ATOM | 1593 | CB | HIS | A | 802 | 24.576 | 4.090 | 21.668 | 1.00 | 20.66 |
| ATOM | 1594 | CG | HIS | A | 802 | 24.567 | 3.749 | 20.210 | 1.00 | 23.63 |
| ATOM | 1595 | ND1 | HIS | A | 802 | 24.970 | 2.521 | 19.731 | 1.00 | 23.91 |
| ATOM | 1596 | CE1 | HIS | A | 802 | 24.855 | 2.506 | 18.415 | 1.00 | 26.33 |
| ATOM | 1597 | NE2 | HIS | A | 802 | 24.384 | 3.677 | 18.024 | 1.00 | 26.28 |
| ATOM | 1598 | CD2 | HIS | A | 802 | 24.194 | 4.473 | 19.128 | 1.00 | 24.50 |
| ATOM | 1599 | C | HIS | A | 802 | 23.542 | 3.848 | 23.926 | 1.00 | 16.23 |
| ATOM | 1600 | O | HIS | A | 802 | 23.020 | 4.911 | 24.279 | 1.00 | 14.09 |
| ATOM | 1601 | N | GLY | A | 803 | 24.181 | 3.031 | 24.761 | 1.00 | 15.67 |

FIGURE 3 (Cont.)

|  | A | B | C | D | E | F | G | H | I | J |
|---|---|---|---|---|---|---|---|---|---|---|
| ATOM | 1602 | CA | GLY | A | 803 | 24.291 | 3.303 | 26.186 | 1.00 | 15.82 |
| ATOM | 1603 | C | GLY | A | 803 | 22.985 | 3.170 | 26.946 | 1.00 | 15.63 |
| ATOM | 1604 | O | GLY | A | 803 | 22.872 | 3.648 | 28.074 | 1.00 | 16.39 |
| ATOM | 1605 | N | ARG | A | 804 | 22.000 | 2.517 | 26.324 | 1.00 | 14.47 |
| ATOM | 1606 | CA | ARG | A | 804 | 20.650 | 2.382 | 26.870 | 1.00 | 15.54 |
| ATOM | 1607 | CB | ARG | A | 804 | 20.605 | 1.394 | 28.042 | 1.00 | 16.74 |
| ATOM | 1608 | CG | ARG | A | 804 | 20.742 | -0.053 | 27.593 | 1.00 | 15.88 |
| ATOM | 1609 | CD | ARG | A | 804 | 20.736 | -1.054 | 28.721 | 1.00 | 16.01 |
| ATOM | 1610 | NE | ARG | A | 804 | 20.812 | -2.426 | 28.222 | 1.00 | 15.03 |
| ATOM | 1611 | CZ | ARG | A | 804 | 20.582 | -3.505 | 28.961 | 1.00 | 16.11 |
| ATOM | 1612 | NH1 | ARG | A | 804 | 20.674 | -4.714 | 28.418 | 1.00 | 14.70 |
| ATOM | 1613 | NH2 | ARG | A | 804 | 20.260 | -3.383 | 30.245 | 1.00 | 14.20 |
| ATOM | 1614 | C | ARG | A | 804 | 20.026 | 3.730 | 27.221 | 1.00 | 15.64 |
| ATOM | 1615 | O | ARG | A | 804 | 19.442 | 3.913 | 28.298 | 1.00 | 15.85 |
| ATOM | 1616 | N | ILE | A | 805 | 20.169 | 4.669 | 26.289 | 1.00 | 12.79 |
| ATOM | 1617 | CA | ILE | A | 805 | 19.515 | 5.967 | 26.378 | 1.00 | 12.79 |
| ATOM | 1618 | CB | ILE | A | 805 | 20.394 | 7.071 | 25.738 | 1.00 | 13.73 |
| ATOM | 1619 | CG1 | ILE | A | 805 | 21.587 | 7.393 | 26.647 | 1.00 | 16.38 |
| ATOM | 1620 | CD1 | ILE | A | 805 | 22.758 | 8.003 | 25.931 | 1.00 | 17.77 |
| ATOM | 1621 | CG2 | ILE | A | 805 | 19.588 | 8.338 | 25.484 | 1.00 | 13.74 |
| ATOM | 1622 | C | ILE | A | 805 | 18.144 | 5.864 | 25.711 | 1.00 | 12.05 |
| ATOM | 1623 | O | ILE | A | 805 | 18.026 | 5.346 | 24.602 | 1.00 | 13.03 |
| ATOM | 1624 | N | THR | A | 806 | 17.111 | 6.320 | 26.410 | 1.00 | 14.84 |
| ATOM | 1625 | CA | THR | A | 806 | 15.750 | 6.279 | 25.881 | 1.00 | 15.34 |
| ATOM | 1626 | CB | THR | A | 806 | 14.694 | 5.997 | 26.967 | 1.00 | 20.15 |
| ATOM | 1627 | OG1 | THR | A | 806 | 14.825 | 6.952 | 28.028 | 1.00 | 19.76 |
| ATOM | 1628 | CG2 | THR | A | 806 | 14.927 | 4.653 | 27.631 | 1.00 | 22.78 |
| ATOM | 1629 | C | THR | A | 806 | 15.422 | 7.595 | 25.223 | 1.00 | 14.32 |
| ATOM | 1630 | O | THR | A | 806 | 15.822 | 8.657 | 25.696 | 1.00 | 12.80 |
| ATOM | 1631 | N | LYS | A | 807 | 14.674 | 7.512 | 24.134 | 1.00 | 13.09 |
| ATOM | 1632 | CA | LYS | A | 807 | 14.305 | 8.689 | 23.384 | 1.00 | 13.71 |
| ATOM | 1633 | CB | LYS | A | 807 | 15.135 | 8.788 | 22.112 | 1.00 | 11.90 |
| ATOM | 1634 | CG | LYS | A | 807 | 16.616 | 9.125 | 22.355 | 1.00 | 9.39 |
| ATOM | 1635 | CD | LYS | A | 807 | 17.397 | 9.116 | 21.057 | 1.00 | 10.65 |
| ATOM | 1636 | CE | LYS | A | 807 | 18.754 | 9.806 | 21.210 | 1.00 | 12.04 |
| ATOM | 1637 | NZ | LYS | A | 807 | 18.628 | 11.262 | 21.488 | 1.00 | 9.18 |
| ATOM | 1638 | C | LYS | A | 807 | 12.823 | 8.604 | 23.072 | 1.00 | 11.99 |
| ATOM | 1639 | O | LYS | A | 807 | 12.355 | 7.638 | 22.468 | 1.00 | 15.02 |
| ATOM | 1640 | N | ILE | A | 808 | 12.092 | 9.614 | 23.517 | 1.00 | 11.63 |
| ATOM | 1641 | CA | ILE | A | 808 | 10.675 | 9.726 | 23.207 | 1.00 | 14.34 |
| ATOM | 1642 | CB | ILE | A | 808 | 10.012 | 10.785 | 24.103 | 1.00 | 15.35 |
| ATOM | 1643 | CG1 | ILE | A | 808 | 10.152 | 10.381 | 25.573 | 1.00 | 17.98 |
| ATOM | 1644 | CD1 | ILE | A | 808 | 10.053 | 11.533 | 26.517 | 1.00 | 18.05 |
| ATOM | 1645 | CG2 | ILE | A | 808 | 8.535 | 10.947 | 23.753 | 1.00 | 16.51 |
| ATOM | 1646 | C | ILE | A | 808 | 10.505 | 10.089 | 21.736 | 1.00 | 13.56 |
| ATOM | 1647 | O | ILE | A | 808 | 11.237 | 10.916 | 21.193 | 1.00 | 13.34 |
| ATOM | 1648 | N | CYS | A | 809 | 9.525 | 9.464 | 21.097 | 1.00 | 16.59 |
| ATOM | 1649 | CA | CYS | A | 809 | 9.254 | 9.718 | 19.694 | 1.00 | 18.56 |
| ATOM | 1650 | CB | BCYS | A | 809 | 10.034 | 8.674 | 18.883 | 0.35 | 20.65 |
| ATOM | 1651 | CB | ACYS | A | 809 | 10.079 | 8.805 | 18.789 | 0.65 | 19.50 |
| ATOM | 1652 | SG | BCYS | A | 809 | 9.824 | 8.680 | 17.093 | 0.35 | 23.96 |
| ATOM | 1653 | SG | ACYS | A | 809 | 9.500 | 7.111 | 18.727 | 0.65 | 18.49 |

FIGURE 3 (Cont.)

| | A | B | C | D | E | F | G | H | I | J |
|---|---|---|---|---|---|---|---|---|---|---|
| ATOM | 1654 | C | CYS | A | 809 | 7.762 | 9.564 | 19.436 | 1.00 | 21.29 |
| ATOM | 1655 | O | CYS | A | 809 | 6.990 | 9.337 | 20.367 | 1.00 | 22.15 |
| ATOM | 1656 | N | ASP | A | 810 | 7.354 | 9.739 | 18.184 | 1.00 | 24.00 |
| ATOM | 1657 | CA | ASP | A | 810 | 6.101 | 9.166 | 17.717 | 1.00 | 24.17 |
| ATOM | 1658 | CB | ASP | A | 810 | 5.126 | 10.222 | 17.212 | 1.00 | 26.77 |
| ATOM | 1659 | CG | ASP | A | 810 | 3.941 | 9.603 | 16.486 | 1.00 | 29.64 |
| ATOM | 1660 | OD1 | ASP | A | 810 | 3.295 | 8.710 | 17.077 | 1.00 | 30.82 |
| ATOM | 1661 | OD2 | ASP | A | 810 | 3.594 | 9.926 | 15.332 | 1.00 | 29.21 |
| ATOM | 1662 | C | ASP | A | 810 | 6.441 | 8.213 | 16.593 | 1.00 | 21.99 |
| ATOM | 1663 | O | ASP | A | 810 | 6.901 | 8.641 | 15.528 | 1.00 | 21.61 |
| ATOM | 1664 | N | PHE | A | 811 | 6.227 | 6.922 | 16.835 | 1.00 | 19.09 |
| ATOM | 1665 | CA | PHE | A | 811 | 6.556 | 5.903 | 15.846 | 1.00 | 17.73 |
| ATOM | 1666 | CB | PHE | A | 811 | 7.327 | 4.744 | 16.495 | 1.00 | 20.34 |
| ATOM | 1667 | CG | PHE | A | 811 | 8.430 | 4.196 | 15.629 | 1.00 | 23.44 |
| ATOM | 1668 | CD1 | PHE | A | 811 | 9.454 | 5.027 | 15.171 | 1.00 | 24.34 |
| ATOM | 1669 | CE1 | PHE | A | 811 | 10.475 | 4.528 | 14.363 | 1.00 | 26.45 |
| ATOM | 1670 | CZ | PHE | A | 811 | 10.476 | 3.186 | 14.003 | 1.00 | 25.90 |
| ATOM | 1671 | CE2 | PHE | A | 811 | 9.459 | 2.345 | 14.452 | 1.00 | 26.57 |
| ATOM | 1672 | CD2 | PHE | A | 811 | 8.440 | 2.856 | 15.260 | 1.00 | 25.88 |
| ATOM | 1673 | C | PHE | A | 811 | 5.319 | 5.400 | 15.102 | 1.00 | 16.41 |
| ATOM | 1674 | O | PHE | A | 811 | 5.367 | 4.367 | 14.429 | 1.00 | 15.25 |
| ATOM | 1675 | N | GLY | A | 812 | 4.227 | 6.156 | 15.213 | 1.00 | 15.02 |
| ATOM | 1676 | CA | GLY | A | 812 | 2.951 | 5.808 | 14.605 | 1.00 | 14.31 |
| ATOM | 1677 | C | GLY | A | 812 | 2.972 | 5.624 | 13.100 | 1.00 | 11.60 |
| ATOM | 1678 | O | GLY | A | 812 | 2.247 | 4.780 | 12.567 | 1.00 | 13.26 |
| ATOM | 1679 | N | LEU | A | 813 | 3.798 | 6.406 | 12.405 | 1.00 | 10.32 |
| ATOM | 1680 | CA | LEU | A | 813 | 3.937 | 6.250 | 10.961 | 1.00 | 10.31 |
| ATOM | 1681 | CB | LEU | A | 813 | 4.885 | 7.308 | 10.380 | 1.00 | 10.29 |
| ATOM | 1682 | CG | LEU | A | 813 | 5.076 | 7.329 | 8.864 | 1.00 | 10.58 |
| ATOM | 1683 | CD1 | LEU | A | 813 | 3.795 | 7.729 | 8.128 | 1.00 | 9.50 |
| ATOM | 1684 | CD2 | LEU | A | 813 | 6.219 | 8.252 | 8.487 | 1.00 | 10.77 |
| ATOM | 1685 | C | LEU | A | 813 | 4.409 | 4.844 | 10.578 | 1.00 | 8.58 |
| ATOM | 1686 | O | LEU | A | 813 | 4.072 | 4.348 | 9.510 | 1.00 | 10.36 |
| ATOM | 1687 | N | ALA | A | 814 | 5.187 | 4.214 | 11.454 | 1.00 | 8.94 |
| ATOM | 1688 | CA | ALA | A | 814 | 5.720 | 2.883 | 11.171 | 1.00 | 13.07 |
| ATOM | 1689 | CB | ALA | A | 814 | 7.098 | 2.725 | 11.799 | 1.00 | 13.87 |
| ATOM | 1690 | C | ALA | A | 814 | 4.782 | 1.773 | 11.656 | 1.00 | 15.59 |
| ATOM | 1691 | O | ALA | A | 814 | 5.084 | 0.592 | 11.511 | 1.00 | 18.85 |
| ATOM | 1692 | N | ARG | A | 815 | 3.645 | 2.162 | 12.223 | 1.00 | 16.00 |
| ATOM | 1693 | CA | ARG | A | 815 | 2.740 | 1.225 | 12.876 | 1.00 | 21.03 |
| ATOM | 1694 | CB | ARG | A | 815 | 2.462 | 1.704 | 14.304 | 1.00 | 25.18 |
| ATOM | 1695 | CG | ARG | A | 815 | 1.953 | 0.634 | 15.255 | 1.00 | 31.11 |
| ATOM | 1696 | CD | ARG | A | 815 | 2.795 | 0.454 | 16.511 | 1.00 | 33.53 |
| ATOM | 1697 | NE | ARG | A | 815 | 3.132 | 1.722 | 17.158 | 1.00 | 33.75 |
| ATOM | 1698 | CZ | ARG | A | 815 | 4.351 | 2.050 | 17.586 | 1.00 | 34.05 |
| ATOM | 1699 | NH1 | ARG | A | 815 | 5.373 | 1.212 | 17.440 | 1.00 | 35.66 |
| ATOM | 1700 | NH2 | ARG | A | 815 | 4.552 | 3.226 | 18.155 | 1.00 | 30.10 |
| ATOM | 1701 | C | ARG | A | 815 | 1.437 | 1.109 | 12.100 | 1.00 | 19.44 |
| ATOM | 1702 | O | ARG | A | 815 | 0.866 | 2.118 | 11.683 | 1.00 | 19.04 |
| ATOM | 1703 | N | ASP | A | 816 | 0.977 | -0.118 | 11.880 | 1.00 | 23.54 |
| ATOM | 1704 | CA | ASP | A | 816 | -0.364 | -0.307 | 11.344 | 1.00 | 24.90 |
| ATOM | 1705 | CB | ASP | A | 816 | -0.466 | -1.521 | 10.419 | 1.00 | 29.33 |

FIGURE 3 (Cont.)

|      | A    | B    | C   | D | E   | F      | G      | H      | I    | J     |
|------|------|------|-----|---|-----|--------|--------|--------|------|-------|
| ATOM | 1706 | CG   | ASP | A | 816 | -1.567 | -1.360 |  9.373 | 1.00 | 32.14 |
| ATOM | 1707 | OD1  | ASP | A | 816 | -2.574 | -0.664 |  9.655 | 1.00 | 32.77 |
| ATOM | 1708 | OD2  | ASP | A | 816 | -1.511 | -1.883 |  8.238 | 1.00 | 34.22 |
| ATOM | 1709 | C    | ASP | A | 816 | -1.331 | -0.417 | 12.511 | 1.00 | 23.48 |
| ATOM | 1710 | O    | ASP | A | 816 | -1.486 | -1.483 | 13.113 | 1.00 | 21.23 |
| ATOM | 1711 | N    | ILE | A | 817 | -1.967 |  0.709 | 12.815 | 1.00 | 20.65 |
| ATOM | 1712 | CA   | ILE | A | 817 | -2.805 |  0.869 | 14.000 | 1.00 | 21.62 |
| ATOM | 1713 | CB   | ILE | A | 817 | -3.271 |  2.347 | 14.105 | 1.00 | 23.96 |
| ATOM | 1714 | CG1  | ILE | A | 817 | -2.065 |  3.302 | 14.212 | 1.00 | 26.04 |
| ATOM | 1715 | CD1  | ILE | A | 817 | -1.061 |  2.967 | 15.307 | 1.00 | 27.40 |
| ATOM | 1716 | CG2  | ILE | A | 817 | -4.234 |  2.554 | 15.265 | 1.00 | 24.84 |
| ATOM | 1717 | C    | ILE | A | 817 | -3.991 | -0.099 | 14.009 | 1.00 | 20.32 |
| ATOM | 1718 | O    | ILE | A | 817 | -4.385 | -0.597 | 15.066 | 1.00 | 18.64 |
| ATOM | 1719 | N    | LYS | A | 818 | -4.529 | -0.370 | 12.821 | 1.00 | 18.30 |
| ATOM | 1720 | CA   | LYS | A | 818 | -5.640 | -1.305 | 12.634 | 1.00 | 20.88 |
| ATOM | 1721 | CB   | LYS | A | 818 | -5.995 | -1.411 | 11.149 | 1.00 | 22.29 |
| ATOM | 1722 | CG   | LYS | A | 818 | -6.770 | -0.224 | 10.599 | 1.00 | 25.56 |
| ATOM | 1723 | CD   | LYS | A | 818 | -7.749 | -0.662 |  9.517 | 1.00 | 27.12 |
| ATOM | 1724 | CE   | LYS | A | 818 | -7.207 | -0.372 |  8.125 | 1.00 | 30.11 |
| ATOM | 1725 | NZ   | LYS | A | 818 | -7.607 |  0.981 |  7.640 | 1.00 | 31.13 |
| ATOM | 1726 | C    | LYS | A | 818 | -5.344 | -2.702 | 13.178 | 1.00 | 20.49 |
| ATOM | 1727 | O    | LYS | A | 818 | -6.258 | -3.426 | 13.573 | 1.00 | 20.87 |
| ATOM | 1728 | N    | ASN | A | 819 | -4.068 | -3.077 | 13.182 | 1.00 | 21.47 |
| ATOM | 1729 | CA   | ASN | A | 819 | -3.658 | -4.398 | 13.651 | 1.00 | 22.15 |
| ATOM | 1730 | CB   | ASN | A | 819 | -2.793 | -5.099 | 12.592 | 1.00 | 23.66 |
| ATOM | 1731 | CG   | ASN | A | 819 | -3.624 | -5.847 | 11.553 | 1.00 | 25.25 |
| ATOM | 1732 | OD1  | ASN | A | 819 | -4.674 | -5.374 | 11.113 | 1.00 | 25.24 |
| ATOM | 1733 | ND2  | ASN | A | 819 | -3.150 | -7.023 | 11.154 | 1.00 | 26.74 |
| ATOM | 1734 | C    | ASN | A | 819 | -2.966 | -4.370 | 15.021 | 1.00 | 21.83 |
| ATOM | 1735 | O    | ASN | A | 819 | -2.357 | -5.358 | 15.438 | 1.00 | 23.27 |
| ATOM | 1736 | N    | ASP | A | 820 | -3.079 | -3.236 | 15.713 | 1.00 | 20.18 |
| ATOM | 1737 | CA   | ASP | A | 820 | -2.563 | -3.079 | 17.072 | 1.00 | 20.49 |
| ATOM | 1738 | CB   | ASP | A | 820 | -1.675 | -1.833 | 17.168 | 1.00 | 20.58 |
| ATOM | 1739 | CG   | ASP | A | 820 | -0.816 | -1.816 | 18.426 | 1.00 | 22.07 |
| ATOM | 1740 | OD1  | ASP | A | 820 | -1.237 | -2.379 | 19.459 | 1.00 | 21.82 |
| ATOM | 1741 | OD2  | ASP | A | 820 |  0.300 | -1.256 | 18.476 | 1.00 | 24.31 |
| ATOM | 1742 | C    | ASP | A | 820 | -3.714 | -2.981 | 18.079 | 1.00 | 21.13 |
| ATOM | 1743 | O    | ASP | A | 820 | -4.370 | -1.942 | 18.181 | 1.00 | 20.65 |
| ATOM | 1744 | N    | SER | A | 821 | -3.939 | -4.059 | 18.829 | 1.00 | 20.69 |
| ATOM | 1745 | CA   | SER | A | 821 | -5.060 | -4.146 | 19.775 | 1.00 | 21.71 |
| ATOM | 1746 | CB   | SER | A | 821 | -5.217 | -5.581 | 20.295 | 1.00 | 23.80 |
| ATOM | 1747 | OG   | SER | A | 821 | -4.161 | -5.920 | 21.179 | 1.00 | 25.27 |
| ATOM | 1748 | C    | SER | A | 821 | -4.954 | -3.157 | 20.947 | 1.00 | 20.23 |
| ATOM | 1749 | O    | SER | A | 821 | -5.908 | -2.972 | 21.702 | 1.00 | 21.85 |
| ATOM | 1750 | N    | ASN | A | 822 | -3.797 | -2.519 | 21.081 | 1.00 | 17.12 |
| ATOM | 1751 | CA   | ASN | A | 822 | -3.612 | -1.454 | 22.067 | 1.00 | 17.33 |
| ATOM | 1752 | CB   | ASN | A | 822 | -2.122 | -1.214 | 22.315 | 1.00 | 17.30 |
| ATOM | 1753 | CG   | ASN | A | 822 | -1.450 | -2.409 | 22.964 | 1.00 | 19.41 |
| ATOM | 1754 | OD1  | ASN | A | 822 | -1.745 | -2.748 | 24.107 | 1.00 | 19.35 |
| ATOM | 1755 | ND2  | ASN | A | 822 | -0.567 | -3.074 | 22.224 | 1.00 | 20.10 |
| ATOM | 1756 | C    | ASN | A | 822 | -4.340 | -0.164 | 21.675 | 1.00 | 17.76 |
| ATOM | 1757 | O    | ASN | A | 822 | -4.506 |  0.745 | 22.497 | 1.00 | 17.64 |

FIGURE 3 (Cont.)

|      | A    | B    | C   | D   | E   | F       | G      | H      | I    | J     |
|------|------|------|-----|-----|-----|---------|--------|--------|------|-------|
| ATOM | 1758 | N    | TYR | A   | 823 | -4.768  | -0.095 | 20.415 | 1.00 | 15.79 |
| ATOM | 1759 | CA   | TYR | A   | 823 | -5.622  | 0.987  | 19.934 | 1.00 | 14.06 |
| ATOM | 1760 | CB   | TYR | A   | 823 | -5.076  | 1.589  | 18.638 | 1.00 | 13.51 |
| ATOM | 1761 | CG   | TYR | A   | 823 | -3.738  | 2.276  | 18.834 | 1.00 | 11.34 |
| ATOM | 1762 | CD1  | TYR | A   | 823 | -3.665  | 3.651  | 19.060 | 1.00 | 12.19 |
| ATOM | 1763 | CE1  | TYR | A   | 823 | -2.433  | 4.290  | 19.252 | 1.00 | 13.16 |
| ATOM | 1764 | CZ   | TYR | A   | 823 | -1.265  | 3.537  | 19.222 | 1.00 | 12.23 |
| ATOM | 1765 | OH   | TYR | A   | 823 | -0.046  | 4.147  | 19.403 | 1.00 | 11.70 |
| ATOM | 1766 | CE2  | TYR | A   | 823 | -1.315  | 2.170  | 19.005 | 1.00 | 13.00 |
| ATOM | 1767 | CD2  | TYR | A   | 823 | -2.548  | 1.545  | 18.810 | 1.00 | 12.91 |
| ATOM | 1768 | C    | TYR | A   | 823 | -7.027  | 0.456  | 19.738 | 1.00 | 14.71 |
| ATOM | 1769 | O    | TYR | A   | 823 | -7.232  | -0.548 | 19.053 | 1.00 | 15.94 |
| ATOM | 1770 | N    | VAL | A   | 824 | -7.991  | 1.129  | 20.359 | 1.00 | 14.88 |
| ATOM | 1771 | CA   | VAL | A   | 824 | -9.371  | 0.651  | 20.391 | 1.00 | 17.28 |
| ATOM | 1772 | CB   | VAL | A   | 824 | -9.887  | 0.500  | 21.851 | 1.00 | 18.38 |
| ATOM | 1773 | CG1  | VAL | A   | 824 | -11.249 | -0.193 | 21.897 | 1.00 | 22.26 |
| ATOM | 1774 | CG2  | VAL | A   | 824 | -8.885  | -0.276 | 22.695 | 1.00 | 21.64 |
| ATOM | 1775 | C    | VAL | A   | 824 | -10.243 | 1.624  | 19.616 | 1.00 | 19.33 |
| ATOM | 1776 | O    | VAL | A   | 824 | -9.997  | 2.832  | 19.624 | 1.00 | 17.58 |
| ATOM | 1777 | N    | VAL | A   | 825 | -11.250 | 1.093  | 18.935 | 1.00 | 21.15 |
| ATOM | 1778 | CA   | VAL | A   | 825 | -12.202 | 1.936  | 18.227 | 1.00 | 24.30 |
| ATOM | 1779 | CB   | VAL | A   | 825 | -13.087 | 1.123  | 17.256 | 1.00 | 24.14 |
| ATOM | 1780 | CG1  | VAL | A   | 825 | -14.123 | 2.020  | 16.590 | 1.00 | 25.45 |
| ATOM | 1781 | CG2  | VAL | A   | 825 | -12.228 | 0.438  | 16.207 | 1.00 | 23.09 |
| ATOM | 1782 | C    | VAL | A   | 825 | -13.051 | 2.696  | 19.247 | 1.00 | 26.81 |
| ATOM | 1783 | O    | VAL | A   | 825 | -13.813 | 2.100  | 20.011 | 1.00 | 29.04 |
| ATOM | 1784 | N    | LYS | A   | 826 | -12.874 | 4.011  | 19.270 | 1.00 | 29.63 |
| ATOM | 1785 | CA   | LYS | A   | 826 | -13.672 | 4.893  | 20.107 | 1.00 | 33.49 |
| ATOM | 1786 | CB   | LYS | A   | 826 | -12.838 | 5.445  | 21.265 | 1.00 | 35.78 |
| ATOM | 1787 | CG   | LYS | A   | 826 | -13.603 | 5.585  | 22.579 | 1.00 | 36.55 |
| ATOM | 1788 | CD   | LYS | A   | 826 | -14.196 | 6.975  | 22.751 | 1.00 | 37.22 |
| ATOM | 1789 | CE   | LYS | A   | 826 | -13.174 | 7.957  | 23.295 | 1.00 | 37.35 |
| ATOM | 1790 | NZ   | LYS | A   | 826 | -13.233 | 9.243  | 22.548 | 1.00 | 38.58 |
| ATOM | 1791 | C    | LYS | A   | 826 | -14.199 | 6.024  | 19.240 | 1.00 | 35.04 |
| ATOM | 1792 | O    | LYS | A   | 826 | -13.436 | 6.892  | 18.803 | 1.00 | 36.76 |
| ATOM | 1793 | N    | GLY | A   | 827 | -15.504 | 5.995  | 18.981 | 1.00 | 36.44 |
| ATOM | 1794 | CA   | GLY | A   | 827 | -16.143 | 6.963  | 18.108 | 1.00 | 36.52 |
| ATOM | 1795 | C    | GLY | A   | 827 | -15.811 | 6.690  | 16.655 | 1.00 | 36.47 |
| ATOM | 1796 | O    | GLY | A   | 827 | -16.304 | 5.724  | 16.065 | 1.00 | 36.07 |
| ATOM | 1797 | N    | ASN | A   | 828 | -14.958 | 7.538  | 16.088 | 1.00 | 36.25 |
| ATOM | 1798 | CA   | ASN | A   | 828 | -14.561 | 7.424  | 14.688 | 1.00 | 36.26 |
| ATOM | 1799 | CB   | ASN | A   | 828 | -14.776 | 8.759  | 13.969 | 1.00 | 37.33 |
| ATOM | 1800 | CG   | ASN | A   | 828 | -15.109 | 8.585  | 12.501 | 1.00 | 38.57 |
| ATOM | 1801 | OD1  | ASN | A   | 828 | -14.429 | 9.133  | 11.632 | 1.00 | 39.53 |
| ATOM | 1802 | ND2  | ASN | A   | 828 | -16.163 | 7.826  | 12.216 | 1.00 | 38.64 |
| ATOM | 1803 | C    | ASN | A   | 828 | -13.121 | 6.950  | 14.492 | 1.00 | 34.39 |
| ATOM | 1804 | O    | ASN | A   | 828 | -12.783 | 6.391  | 13.446 | 1.00 | 34.30 |
| ATOM | 1805 | N    | ALA | A   | 829 | -12.283 | 7.173  | 15.502 | 1.00 | 33.13 |
| ATOM | 1806 | CA   | ALA | A   | 829 | -10.861 | 6.859  | 15.417 | 1.00 | 29.05 |
| ATOM | 1807 | CB   | ALA | A   | 829 | -10.025 | 8.069  | 15.841 | 1.00 | 29.96 |
| ATOM | 1808 | C    | ALA | A   | 829 | -10.485 | 5.628  | 16.242 | 1.00 | 27.95 |
| ATOM | 1809 | O    | ALA | A   | 829 | -11.333 | 5.025  | 16.904 | 1.00 | 27.42 |

FIGURE 3 (Cont.)

|      | A    | B   | C   | D | E   | F       | G      | H      | I    | J     |
|------|------|-----|-----|---|-----|---------|--------|--------|------|-------|
| ATOM | 1810 | N   | ARG | A | 830 | -9.209  | 5.255  | 16.169 | 1.00 | 24.35 |
| ATOM | 1811 | CA  | ARG | A | 830 | -8.649  | 4.185  | 16.987 | 1.00 | 23.02 |
| ATOM | 1812 | CB  | ARG | A | 830 | -7.961  | 3.135  | 16.113 | 1.00 | 24.09 |
| ATOM | 1813 | CG  | ARG | A | 830 | -8.907  | 2.417  | 15.163 | 1.00 | 24.66 |
| ATOM | 1814 | CD  | ARG | A | 830 | -8.224  | 1.443  | 14.221 | 1.00 | 26.24 |
| ATOM | 1815 | NE  | ARG | A | 830 | -9.196  | 0.634  | 13.488 | 1.00 | 26.43 |
| ATOM | 1816 | CZ  | ARG | A | 830 | -9.608  | -0.574 | 13.863 | 1.00 | 27.33 |
| ATOM | 1817 | NH1 | ARG | A | 830 | -9.135  | -1.134 | 14.971 | 1.00 | 26.98 |
| ATOM | 1818 | NH2 | ARG | A | 830 | -10.497 | -1.227 | 13.127 | 1.00 | 26.62 |
| ATOM | 1819 | C   | ARG | A | 830 | -7.666  | 4.815  | 17.962 | 1.00 | 20.44 |
| ATOM | 1820 | O   | ARG | A | 830 | -6.672  | 5.410  | 17.549 | 1.00 | 21.73 |
| ATOM | 1821 | N   | LEU | A | 831 | -7.955  | 4.687  | 19.254 | 1.00 | 17.81 |
| ATOM | 1822 | CA  | LEU | A | 831 | -7.244  | 5.447  | 20.282 | 1.00 | 15.41 |
| ATOM | 1823 | CB  | LEU | A | 831 | -8.190  | 6.468  | 20.931 | 1.00 | 17.06 |
| ATOM | 1824 | CG  | LEU | A | 831 | -8.756  | 7.576  | 20.027 | 1.00 | 18.11 |
| ATOM | 1825 | CD1 | LEU | A | 831 | -9.902  | 8.284  | 20.720 | 1.00 | 20.10 |
| ATOM | 1826 | CD2 | LEU | A | 831 | -7.672  | 8.580  | 19.615 | 1.00 | 21.39 |
| ATOM | 1827 | C   | LEU | A | 831 | -6.617  | 4.552  | 21.350 | 1.00 | 13.55 |
| ATOM | 1828 | O   | LEU | A | 831 | -7.152  | 3.484  | 21.654 | 1.00 | 14.27 |
| ATOM | 1829 | N   | PRO | A | 832 | -5.491  | 4.985  | 21.918 | 1.00 | 12.55 |
| ATOM | 1830 | CA  | PRO | A | 832 | -4.790  | 4.196  | 22.947 | 1.00 | 12.76 |
| ATOM | 1831 | CB  | PRO | A | 832 | -3.402  | 4.829  | 22.957 | 1.00 | 10.97 |
| ATOM | 1832 | CG  | PRO | A | 832 | -3.681  | 6.291  | 22.640 | 1.00 | 11.32 |
| ATOM | 1833 | CD  | PRO | A | 832 | -4.793  | 6.256  | 21.639 | 1.00 | 11.89 |
| ATOM | 1834 | C   | PRO | A | 832 | -5.474  | 4.351  | 24.311 | 1.00 | 11.51 |
| ATOM | 1835 | O   | PRO | A | 832 | -4.886  | 4.891  | 25.259 | 1.00 | 11.32 |
| ATOM | 1836 | N   | VAL | A | 833 | -6.715  | 3.878  | 24.391 | 1.00 | 12.11 |
| ATOM | 1837 | CA  | VAL | A | 833 | -7.596  | 4.157  | 25.530 | 1.00 | 14.17 |
| ATOM | 1838 | CB  | VAL | A | 833 | -8.997  | 3.509  | 25.343 | 1.00 | 14.16 |
| ATOM | 1839 | CG1 | VAL | A | 833 | -9.835  | 3.658  | 26.601 | 1.00 | 12.98 |
| ATOM | 1840 | CG2 | VAL | A | 833 | -9.716  | 4.129  | 24.141 | 1.00 | 14.08 |
| ATOM | 1841 | C   | VAL | A | 833 | -6.993  | 3.785  | 26.888 | 1.00 | 13.00 |
| ATOM | 1842 | O   | VAL | A | 833 | -7.133  | 4.533  | 27.859 | 1.00 | 12.99 |
| ATOM | 1843 | N   | LYS | A | 834 | -6.290  | 2.656  | 26.945 | 1.00 | 11.18 |
| ATOM | 1844 | CA  | LYS | A | 834 | -5.687  | 2.202  | 28.199 | 1.00 | 11.32 |
| ATOM | 1845 | CB  | LYS | A | 834 | -5.186  | 0.764  | 28.064 | 1.00 | 11.76 |
| ATOM | 1846 | CG  | LYS | A | 834 | -6.326  | -0.240 | 28.006 | 1.00 | 10.56 |
| ATOM | 1847 | CD  | LYS | A | 834 | -5.832  | -1.660 | 28.226 | 1.00 | 10.37 |
| ATOM | 1848 | CE  | LYS | A | 834 | -6.996  | -2.630 | 28.194 | 1.00 | 13.72 |
| ATOM | 1849 | NZ  | LYS | A | 834 | -6.538  | -4.027 | 28.454 | 1.00 | 13.49 |
| ATOM | 1850 | C   | LYS | A | 834 | -4.578  | 3.108  | 28.717 | 1.00 | 12.29 |
| ATOM | 1851 | O   | LYS | A | 834 | -4.184  | 2.999  | 29.877 | 1.00 | 11.86 |
| ATOM | 1852 | N   | TRP | A | 835 | -4.089  | 4.006  | 27.859 | 1.00 | 11.21 |
| ATOM | 1853 | CA  | TRP | A | 835 | -3.091  | 5.007  | 28.249 | 1.00 | 12.86 |
| ATOM | 1854 | CB  | TRP | A | 835 | -2.018  | 5.124  | 27.163 | 1.00 | 12.51 |
| ATOM | 1855 | CG  | TRP | A | 835 | -1.035  | 3.996  | 27.189 | 1.00 | 12.61 |
| ATOM | 1856 | CD1 | TRP | A | 835 | 0.212   | 4.013  | 27.746 | 1.00 | 13.14 |
| ATOM | 1857 | NE1 | TRP | A | 835 | 0.823   | 2.792  | 27.583 | 1.00 | 11.39 |
| ATOM | 1858 | CE2 | TRP | A | 835 | -0.024  | 1.956  | 26.903 | 1.00 | 11.35 |
| ATOM | 1859 | CD2 | TRP | A | 835 | -1.211  | 2.681  | 26.642 | 1.00 | 11.82 |
| ATOM | 1860 | CE3 | TRP | A | 835 | -2.247  | 2.043  | 25.946 | 1.00 | 11.89 |
| ATOM | 1861 | CZ3 | TRP | A | 835 | -2.076  | 0.719  | 25.545 | 1.00 | 13.02 |

FIGURE 3 (Cont.)

|  | A | B | C | D | E | F | G | H | I | J |
|---|---|---|---|---|---|---|---|---|---|---|
| ATOM | 1862 | CH2 | TRP | A | 835 | -0.879 | 0.024 | 25.827 | 1.00 | 12.31 |
| ATOM | 1863 | CZ2 | TRP | A | 835 | 0.151 | 0.625 | 26.506 | 1.00 | 13.58 |
| ATOM | 1864 | C | TRP | A | 835 | -3.694 | 6.390 | 28.504 | 1.00 | 13.18 |
| ATOM | 1865 | O | TRP | A | 835 | -2.997 | 7.304 | 28.950 | 1.00 | 13.72 |
| ATOM | 1866 | N | MET | A | 836 | -4.983 | 6.536 | 28.219 | 1.00 | 11.88 |
| ATOM | 1867 | CA | MET | A | 836 | -5.632 | 7.842 | 28.218 | 1.00 | 12.92 |
| ATOM | 1868 | CB | MET | A | 836 | -6.668 | 7.919 | 27.095 | 1.00 | 12.90 |
| ATOM | 1869 | CG | MET | A | 836 | -6.057 | 8.033 | 25.710 | 1.00 | 16.85 |
| ATOM | 1870 | SD | MET | A | 836 | -7.281 | 7.726 | 24.434 | 1.00 | 18.24 |
| ATOM | 1871 | CE | MET | A | 836 | -8.321 | 9.219 | 24.583 | 1.00 | 15.95 |
| ATOM | 1872 | C | MET | A | 836 | -6.275 | 8.188 | 29.550 | 1.00 | 13.10 |
| ATOM | 1873 | O | MET | A | 836 | -6.845 | 7.330 | 30.227 | 1.00 | 14.17 |
| ATOM | 1874 | N | ALA | A | 837 | -6.161 | 9.457 | 29.918 | 1.00 | 14.23 |
| ATOM | 1875 | CA | ALA | A | 837 | -6.793 | 9.988 | 31.116 | 1.00 | 14.38 |
| ATOM | 1876 | CB | ALA | A | 837 | -6.289 | 11.391 | 31.377 | 1.00 | 13.53 |
| ATOM | 1877 | C | ALA | A | 837 | -8.317 | 9.984 | 30.938 | 1.00 | 15.10 |
| ATOM | 1878 | O | ALA | A | 837 | -8.801 | 10.130 | 29.819 | 1.00 | 14.17 |
| ATOM | 1879 | N | PRO | A | 838 | -9.076 | 9.808 | 32.021 | 1.00 | 17.25 |
| ATOM | 1880 | CA | PRO | A | 838 | -10.542 | 9.796 | 31.929 | 1.00 | 18.73 |
| ATOM | 1881 | CB | PRO | A | 838 | -10.989 | 9.756 | 33.393 | 1.00 | 20.01 |
| ATOM | 1882 | CG | PRO | A | 838 | -9.853 | 9.178 | 34.124 | 1.00 | 17.30 |
| ATOM | 1883 | CD | PRO | A | 838 | -8.617 | 9.610 | 33.405 | 1.00 | 16.62 |
| ATOM | 1884 | C | PRO | A | 838 | -11.085 | 11.049 | 31.243 | 1.00 | 19.48 |
| ATOM | 1885 | O | PRO | A | 838 | -12.063 | 10.952 | 30.497 | 1.00 | 19.79 |
| ATOM | 1886 | N | GLU | A | 839 | -10.446 | 12.197 | 31.468 | 1.00 | 19.10 |
| ATOM | 1887 | CA | GLU | A | 839 | -10.904 | 13.453 | 30.869 | 1.00 | 20.29 |
| ATOM | 1888 | CB | GLU | A | 839 | -10.331 | 14.667 | 31.616 | 1.00 | 20.25 |
| ATOM | 1889 | CG | GLU | A | 839 | -8.850 | 14.920 | 31.394 | 1.00 | 19.93 |
| ATOM | 1890 | CD | GLU | A | 839 | -7.953 | 14.248 | 32.426 | 1.00 | 17.90 |
| ATOM | 1891 | OE1 | GLU | A | 839 | -8.437 | 13.430 | 33.245 | 1.00 | 18.58 |
| ATOM | 1892 | OE2 | GLU | A | 839 | -6.741 | 14.536 | 32.407 | 1.00 | 18.31 |
| ATOM | 1893 | C | GLU | A | 839 | -10.650 | 13.539 | 29.355 | 1.00 | 20.00 |
| ATOM | 1894 | O | GLU | A | 839 | -11.350 | 14.266 | 28.648 | 1.00 | 23.22 |
| ATOM | 1895 | N | SER | A | 840 | -9.661 | 12.796 | 28.864 | 1.00 | 18.07 |
| ATOM | 1896 | CA | SER | A | 840 | -9.402 | 12.703 | 27.429 | 1.00 | 17.44 |
| ATOM | 1897 | CB | SER | A | 840 | -7.982 | 12.209 | 27.159 | 1.00 | 18.29 |
| ATOM | 1898 | OG | SER | A | 840 | -7.028 | 12.992 | 27.848 | 1.00 | 19.64 |
| ATOM | 1899 | C | SER | A | 840 | -10.390 | 11.755 | 26.767 | 1.00 | 17.26 |
| ATOM | 1900 | O | SER | A | 840 | -10.847 | 12.004 | 25.652 | 1.00 | 18.74 |
| ATOM | 1901 | N | ILE | A | 841 | -10.700 | 10.661 | 27.457 | 1.00 | 16.43 |
| ATOM | 1902 | CA | ILE | A | 841 | -11.666 | 9.683 | 26.967 | 1.00 | 18.69 |
| ATOM | 1903 | CB | ILE | A | 841 | -11.691 | 8.443 | 27.893 | 1.00 | 18.34 |
| ATOM | 1904 | CG1 | ILE | A | 841 | -10.399 | 7.631 | 27.742 | 1.00 | 19.27 |
| ATOM | 1905 | CD1 | ILE | A | 841 | -10.081 | 6.755 | 28.939 | 1.00 | 19.73 |
| ATOM | 1906 | CG2 | ILE | A | 841 | -12.913 | 7.576 | 27.608 | 1.00 | 16.97 |
| ATOM | 1907 | C | ILE | A | 841 | -13.059 | 10.304 | 26.863 | 1.00 | 21.31 |
| ATOM | 1908 | O | ILE | A | 841 | -13.758 | 10.129 | 25.860 | 1.00 | 22.20 |
| ATOM | 1909 | N | PHE | A | 842 | -13.445 | 11.049 | 27.895 | 1.00 | 21.93 |
| ATOM | 1910 | CA | PHE | A | 842 | -14.821 | 11.520 | 28.025 | 1.00 | 24.77 |
| ATOM | 1911 | CB | PHE | A | 842 | -15.284 | 11.396 | 29.483 | 1.00 | 26.49 |
| ATOM | 1912 | CG | PHE | A | 842 | -15.368 | 9.966 | 29.970 | 1.00 | 28.92 |
| ATOM | 1913 | CD1 | PHE | A | 842 | -14.431 | 9.464 | 30.868 | 1.00 | 29.83 |

FIGURE 3 (Cont.)

|   | A | B | C | D | E | F | G | H | I | J |
|---|---|---|---|---|---|---|---|---|---|---|
| ATOM | 1914 | CE1 | PHE | A | 842 | -14.498 | 8.147 | 31.314 | 1.00 | 29.96 |
| ATOM | 1915 | CZ | PHE | A | 842 | -15.514 | 7.314 | 30.862 | 1.00 | 30.63 |
| ATOM | 1916 | CE2 | PHE | A | 842 | -16.458 | 7.800 | 29.964 | 1.00 | 31.27 |
| ATOM | 1917 | CD2 | PHE | A | 842 | -16.379 | 9.120 | 29.521 | 1.00 | 30.69 |
| ATOM | 1918 | C | PHE | A | 842 | -15.081 | 12.924 | 27.464 | 1.00 | 25.31 |
| ATOM | 1919 | O | PHE | A | 842 | -16.217 | 13.245 | 27.120 | 1.00 | 26.31 |
| ATOM | 1920 | N | ASN | A | 843 | -14.036 | 13.744 | 27.362 | 1.00 | 25.37 |
| ATOM | 1921 | CA | ASN | A | 843 | -14.171 | 15.109 | 26.844 | 1.00 | 27.40 |
| ATOM | 1922 | CB | ASN | A | 843 | -13.870 | 16.139 | 27.943 | 1.00 | 29.83 |
| ATOM | 1923 | CG | ASN | A | 843 | -14.641 | 15.871 | 29.227 | 1.00 | 31.75 |
| ATOM | 1924 | OD1 | ASN | A | 843 | -15.874 | 15.857 | 29.238 | 1.00 | 32.07 |
| ATOM | 1925 | ND2 | ASN | A | 843 | -13.913 | 15.656 | 30.319 | 1.00 | 32.29 |
| ATOM | 1926 | C | ASN | A | 843 | -13.336 | 15.400 | 25.587 | 1.00 | 27.46 |
| ATOM | 1927 | O | ASN | A | 843 | -13.434 | 16.490 | 25.010 | 1.00 | 26.09 |
| ATOM | 1928 | N | CYS | A | 844 | -12.531 | 14.419 | 25.175 | 1.00 | 25.83 |
| ATOM | 1929 | CA | CYS | A | 844 | -11.681 | 14.497 | 23.976 | 1.00 | 28.07 |
| ATOM | 1930 | CB | CYS | A | 844 | -12.517 | 14.698 | 22.707 | 1.00 | 31.48 |
| ATOM | 1931 | SG | CYS | A | 844 | -13.704 | 13.376 | 22.407 | 1.00 | 35.89 |
| ATOM | 1932 | C | CYS | A | 844 | -10.557 | 15.533 | 24.055 | 1.00 | 27.69 |
| ATOM | 1933 | O | CYS | A | 844 | -10.029 | 15.965 | 23.027 | 1.00 | 29.84 |
| ATOM | 1934 | N | VAL | A | 845 | -10.184 | 15.915 | 25.273 | 1.00 | 24.39 |
| ATOM | 1935 | CA | VAL | A | 845 | -9.146 | 16.924 | 25.471 | 1.00 | 22.89 |
| ATOM | 1936 | CB | VAL | A | 845 | -9.568 | 18.022 | 26.490 | 1.00 | 23.15 |
| ATOM | 1937 | CG1 | VAL | A | 845 | -10.629 | 18.938 | 25.888 | 1.00 | 24.80 |
| ATOM | 1938 | CG2 | VAL | A | 845 | -10.055 | 17.407 | 27.804 | 1.00 | 24.49 |
| ATOM | 1939 | C | VAL | A | 845 | -7.820 | 16.301 | 25.894 | 1.00 | 20.34 |
| ATOM | 1940 | O | VAL | A | 845 | -7.778 | 15.409 | 26.737 | 1.00 | 21.39 |
| ATOM | 1941 | N | TYR | A | 846 | -6.740 | 16.778 | 25.292 | 1.00 | 17.70 |
| ATOM | 1942 | CA | TYR | A | 846 | -5.401 | 16.336 | 25.656 | 1.00 | 16.41 |
| ATOM | 1943 | CB | TYR | A | 846 | -4.650 | 15.821 | 24.435 | 1.00 | 18.31 |
| ATOM | 1944 | CG | TYR | A | 846 | -5.249 | 14.567 | 23.829 | 1.00 | 21.36 |
| ATOM | 1945 | CD1 | TYR | A | 846 | -6.270 | 14.648 | 22.882 | 1.00 | 22.92 |
| ATOM | 1946 | CE1 | TYR | A | 846 | -6.823 | 13.505 | 22.320 | 1.00 | 24.90 |
| ATOM | 1947 | CZ | TYR | A | 846 | -6.351 | 12.259 | 22.698 | 1.00 | 25.03 |
| ATOM | 1948 | OH | TYR | A | 846 | -6.908 | 11.131 | 22.135 | 1.00 | 26.30 |
| ATOM | 1949 | CE2 | TYR | A | 846 | -5.335 | 12.147 | 23.637 | 1.00 | 22.95 |
| ATOM | 1950 | CD2 | TYR | A | 846 | -4.791 | 13.303 | 24.198 | 1.00 | 21.96 |
| ATOM | 1951 | C | TYR | A | 846 | -4.675 | 17.511 | 26.280 | 1.00 | 15.46 |
| ATOM | 1952 | O | TYR | A | 846 | -4.708 | 18.624 | 25.756 | 1.00 | 13.06 |
| ATOM | 1953 | N | THR | A | 847 | -4.040 | 17.254 | 27.415 | 1.00 | 15.54 |
| ATOM | 1954 | CA | THR | A | 847 | -3.426 | 18.297 | 28.222 | 1.00 | 14.02 |
| ATOM | 1955 | CB | THR | A | 847 | -4.302 | 18.587 | 29.452 | 1.00 | 14.95 |
| ATOM | 1956 | OG1 | THR | A | 847 | -4.400 | 17.399 | 30.246 | 1.00 | 14.62 |
| ATOM | 1957 | CG2 | THR | A | 847 | -5.748 | 18.886 | 29.055 | 1.00 | 14.40 |
| ATOM | 1958 | C | THR | A | 847 | -2.064 | 17.827 | 28.707 | 1.00 | 13.31 |
| ATOM | 1959 | O | THR | A | 847 | -1.702 | 16.671 | 28.519 | 1.00 | 13.25 |
| ATOM | 1960 | N | PHE | A | 848 | -1.323 | 18.728 | 29.346 | 1.00 | 14.54 |
| ATOM | 1961 | CA | PHE | A | 848 | -0.092 | 18.355 | 30.033 | 1.00 | 14.66 |
| ATOM | 1962 | CB | PHE | A | 848 | 0.539 | 19.583 | 30.697 | 1.00 | 15.48 |
| ATOM | 1963 | CG | PHE | A | 848 | 0.966 | 20.647 | 29.727 | 1.00 | 15.97 |
| ATOM | 1964 | CD1 | PHE | A | 848 | 1.761 | 20.331 | 28.627 | 1.00 | 15.38 |
| ATOM | 1965 | CE1 | PHE | A | 848 | 2.155 | 21.313 | 27.727 | 1.00 | 15.91 |

FIGURE 3 (Cont.)

|  | A | B | C | D | E | F | G | H | I | J |
|---|---|---|---|---|---|---|---|---|---|---|
| ATOM | 1966 | CZ | PHE | A | 848 | 1.766 | 22.633 | 27.930 | 1.00 | 16.66 |
| ATOM | 1967 | CE2 | PHE | A | 848 | 0.982 | 22.964 | 29.028 | 1.00 | 18.91 |
| ATOM | 1968 | CD2 | PHE | A | 848 | 0.587 | 21.973 | 29.921 | 1.00 | 16.95 |
| ATOM | 1969 | C | PHE | A | 848 | -0.379 | 17.283 | 31.078 | 1.00 | 15.74 |
| ATOM | 1970 | O | PHE | A | 848 | 0.412 | 16.356 | 31.266 | 1.00 | 16.45 |
| ATOM | 1971 | N | GLU | A | 849 | -1.531 | 17.416 | 31.736 | 1.00 | 13.89 |
| ATOM | 1972 | CA | GLU | A | 849 | -1.947 | 16.521 | 32.811 | 1.00 | 13.80 |
| ATOM | 1973 | CB | GLU | A | 849 | -3.109 | 17.137 | 33.593 | 1.00 | 14.18 |
| ATOM | 1974 | CG | GLU | A | 849 | -2.735 | 18.391 | 34.370 | 1.00 | 16.22 |
| ATOM | 1975 | CD | GLU | A | 849 | -2.988 | 19.675 | 33.592 | 1.00 | 20.47 |
| ATOM | 1976 | OE1 | GLU | A | 849 | -2.865 | 20.766 | 34.187 | 1.00 | 23.53 |
| ATOM | 1977 | OE2 | GLU | A | 849 | -3.307 | 19.603 | 32.389 | 1.00 | 19.79 |
| ATOM | 1978 | C | GLU | A | 849 | -2.335 | 15.138 | 32.306 | 1.00 | 11.93 |
| ATOM | 1979 | O | GLU | A | 849 | -2.130 | 14.144 | 33.004 | 1.00 | 12.90 |
| ATOM | 1980 | N | SER | A | 850 | -2.907 | 15.071 | 31.106 | 1.00 | 11.76 |
| ATOM | 1981 | CA | SER | A | 850 | -3.229 | 13.778 | 30.510 | 1.00 | 12.35 |
| ATOM | 1982 | CB | SER | A | 850 | -4.280 | 13.903 | 29.393 | 1.00 | 12.41 |
| ATOM | 1983 | OG | SER | A | 850 | -3.778 | 14.577 | 28.254 | 1.00 | 17.03 |
| ATOM | 1984 | C | SER | A | 850 | -1.964 | 13.042 | 30.047 | 1.00 | 11.64 |
| ATOM | 1985 | O | SER | A | 850 | -1.920 | 11.820 | 30.082 | 1.00 | 10.47 |
| ATOM | 1986 | N | ASP | A | 851 | -0.934 | 13.788 | 29.641 | 1.00 | 11.59 |
| ATOM | 1987 | CA | ASP | A | 851 | 0.377 | 13.196 | 29.339 | 1.00 | 11.31 |
| ATOM | 1988 | CB | ASP | A | 851 | 1.343 | 14.251 | 28.793 | 1.00 | 11.88 |
| ATOM | 1989 | CG | ASP | A | 851 | 1.381 | 14.290 | 27.268 | 1.00 | 14.49 |
| ATOM | 1990 | OD1 | ASP | A | 851 | 2.176 | 15.093 | 26.731 | 1.00 | 14.73 |
| ATOM | 1991 | OD2 | ASP | A | 851 | 0.663 | 13.574 | 26.524 | 1.00 | 13.90 |
| ATOM | 1992 | C | ASP | A | 851 | 0.981 | 12.547 | 30.585 | 1.00 | 11.26 |
| ATOM | 1993 | O | ASP | A | 851 | 1.590 | 11.479 | 30.510 | 1.00 | 12.18 |
| ATOM | 1994 | N | VAL | A | 852 | 0.790 | 13.195 | 31.733 | 1.00 | 12.03 |
| ATOM | 1995 | CA | VAL | A | 852 | 1.256 | 12.658 | 33.010 | 1.00 | 11.20 |
| ATOM | 1996 | CB | VAL | A | 852 | 1.139 | 13.705 | 34.146 | 1.00 | 9.14 |
| ATOM | 1997 | CG1 | VAL | A | 852 | 1.365 | 13.071 | 35.509 | 1.00 | 12.13 |
| ATOM | 1998 | CG2 | VAL | A | 852 | 2.146 | 14.830 | 33.922 | 1.00 | 12.68 |
| ATOM | 1999 | C | VAL | A | 852 | 0.513 | 11.358 | 33.341 | 1.00 | 12.75 |
| ATOM | 2000 | O | VAL | A | 852 | 1.135 | 10.381 | 33.752 | 1.00 | 11.99 |
| ATOM | 2001 | N | TRP | A | 853 | -0.806 | 11.341 | 33.152 | 1.00 | 10.65 |
| ATOM | 2002 | CA | TRP | A | 853 | -1.554 | 10.085 | 33.282 | 1.00 | 10.39 |
| ATOM | 2003 | CB | TRP | A | 853 | -3.015 | 10.261 | 32.850 | 1.00 | 10.58 |
| ATOM | 2004 | CG | TRP | A | 853 | -3.824 | 8.989 | 32.981 | 1.00 | 11.26 |
| ATOM | 2005 | CD1 | TRP | A | 853 | -3.755 | 7.882 | 32.179 | 1.00 | 12.17 |
| ATOM | 2006 | NE1 | TRP | A | 853 | -4.632 | 6.919 | 32.621 | 1.00 | 11.38 |
| ATOM | 2007 | CE2 | TRP | A | 853 | -5.296 | 7.394 | 33.719 | 1.00 | 12.43 |
| ATOM | 2008 | CD2 | TRP | A | 853 | -4.806 | 8.694 | 33.979 | 1.00 | 11.96 |
| ATOM | 2009 | CE3 | TRP | A | 853 | -5.340 | 9.406 | 35.064 | 1.00 | 12.71 |
| ATOM | 2010 | CZ3 | TRP | A | 853 | -6.317 | 8.807 | 35.843 | 1.00 | 13.89 |
| ATOM | 2011 | CH2 | TRP | A | 853 | -6.777 | 7.512 | 35.564 | 1.00 | 13.47 |
| ATOM | 2012 | CZ2 | TRP | A | 853 | -6.281 | 6.789 | 34.509 | 1.00 | 14.53 |
| ATOM | 2013 | C | TRP | A | 853 | -0.875 | 8.976 | 32.465 | 1.00 | 11.92 |
| ATOM | 2014 | O | TRP | A | 853 | -0.573 | 7.902 | 32.997 | 1.00 | 13.29 |
| ATOM | 2015 | N | SER | A | 854 | -0.622 | 9.247 | 31.184 | 1.00 | 10.83 |
| ATOM | 2016 | CA | SER | A | 854 | -0.024 | 8.252 | 30.289 | 1.00 | 10.46 |
| ATOM | 2017 | CB | SER | A | 854 | 0.109 | 8.789 | 28.864 | 1.00 | 10.79 |

FIGURE 3 (Cont.)

| | A | B | C | D | E | F | G | H | I | J |
|---|---|---|---|---|---|---|---|---|---|---|
| ATOM | 2018 | OG | SER | A | 854 | -1.161 | 9.068 | 28.302 | 1.00 | 15.38 |
| ATOM | 2019 | C | SER | A | 854 | 1.340 | 7.808 | 30.794 | 1.00 | 12.10 |
| ATOM | 2020 | O | SER | A | 854 | 1.687 | 6.637 | 30.691 | 1.00 | 12.06 |
| ATOM | 2021 | N | TYR | A | 855 | 2.100 | 8.747 | 31.351 | 1.00 | 13.23 |
| ATOM | 2022 | CA | TYR | A | 855 | 3.410 | 8.423 | 31.899 | 1.00 | 14.48 |
| ATOM | 2023 | CB | TYR | A | 855 | 4.135 | 9.697 | 32.340 | 1.00 | 11.94 |
| ATOM | 2024 | CG | TYR | A | 855 | 5.428 | 9.420 | 33.050 | 1.00 | 14.43 |
| ATOM | 2025 | CD1 | TYR | A | 855 | 6.592 | 9.133 | 32.333 | 1.00 | 13.77 |
| ATOM | 2026 | CE1 | TYR | A | 855 | 7.792 | 8.863 | 32.993 | 1.00 | 14.30 |
| ATOM | 2027 | CZ | TYR | A | 855 | 7.820 | 8.874 | 34.377 | 1.00 | 15.64 |
| ATOM | 2028 | OH | TYR | A | 855 | 8.993 | 8.614 | 35.041 | 1.00 | 13.27 |
| ATOM | 2029 | CE2 | TYR | A | 855 | 6.671 | 9.144 | 35.111 | 1.00 | 16.35 |
| ATOM | 2030 | CD2 | TYR | A | 855 | 5.488 | 9.419 | 34.450 | 1.00 | 14.87 |
| ATOM | 2031 | C | TYR | A | 855 | 3.274 | 7.431 | 33.056 | 1.00 | 12.60 |
| ATOM | 2032 | O | TYR | A | 855 | 4.075 | 6.512 | 33.191 | 1.00 | 13.69 |
| ATOM | 2033 | N | GLY | A | 856 | 2.251 | 7.620 | 33.886 | 1.00 | 12.78 |
| ATOM | 2034 | CA | GLY | A | 856 | 1.922 | 6.655 | 34.926 | 1.00 | 12.63 |
| ATOM | 2035 | C | GLY | A | 856 | 1.633 | 5.268 | 34.363 | 1.00 | 12.45 |
| ATOM | 2036 | O | GLY | A | 856 | 2.090 | 4.272 | 34.918 | 1.00 | 13.16 |
| ATOM | 2037 | N | ILE | A | 857 | 0.865 | 5.199 | 33.276 | 1.00 | 13.56 |
| ATOM | 2038 | CA | ILE | A | 857 | 0.620 | 3.919 | 32.596 | 1.00 | 12.65 |
| ATOM | 2039 | CB | ILE | A | 857 | -0.448 | 4.051 | 31.460 | 1.00 | 11.56 |
| ATOM | 2040 | CG1 | ILE | A | 857 | -1.776 | 4.615 | 32.001 | 1.00 | 10.33 |
| ATOM | 2041 | CD1 | ILE | A | 857 | -2.477 | 3.742 | 33.059 | 1.00 | 12.66 |
| ATOM | 2042 | CG2 | ILE | A | 857 | -0.677 | 2.697 | 30.764 | 1.00 | 10.72 |
| ATOM | 2043 | C | ILE | A | 857 | 1.929 | 3.357 | 32.045 | 1.00 | 12.90 |
| ATOM | 2044 | O | ILE | A | 857 | 2.180 | 2.153 | 32.131 | 1.00 | 13.23 |
| ATOM | 2045 | N | PHE | A | 858 | 2.756 | 4.232 | 31.476 | 1.00 | 13.92 |
| ATOM | 2046 | CA | PHE | A | 858 | 4.075 | 3.821 | 30.994 | 1.00 | 15.09 |
| ATOM | 2047 | CB | PHE | A | 858 | 4.824 | 4.995 | 30.339 | 1.00 | 14.75 |
| ATOM | 2048 | CG | PHE | A | 858 | 6.298 | 4.759 | 30.227 | 1.00 | 12.92 |
| ATOM | 2049 | CD1 | PHE | A | 858 | 6.785 | 3.786 | 29.353 | 1.00 | 16.59 |
| ATOM | 2050 | CE1 | PHE | A | 858 | 8.137 | 3.529 | 29.261 | 1.00 | 18.13 |
| ATOM | 2051 | CZ | PHE | A | 858 | 9.033 | 4.247 | 30.049 | 1.00 | 15.82 |
| ATOM | 2052 | CE2 | PHE | A | 858 | 8.562 | 5.214 | 30.930 | 1.00 | 15.49 |
| ATOM | 2053 | CD2 | PHE | A | 858 | 7.194 | 5.466 | 31.017 | 1.00 | 15.06 |
| ATOM | 2054 | C | PHE | A | 858 | 4.932 | 3.219 | 32.119 | 1.00 | 15.34 |
| ATOM | 2055 | O | PHE | A | 858 | 5.594 | 2.195 | 31.918 | 1.00 | 13.14 |
| ATOM | 2056 | N | LEU | A | 859 | 4.923 | 3.855 | 33.295 | 1.00 | 13.53 |
| ATOM | 2057 | CA | LEU | A | 859 | 5.657 | 3.322 | 34.447 | 1.00 | 14.48 |
| ATOM | 2058 | CB | LEU | A | 859 | 5.524 | 4.231 | 35.670 | 1.00 | 13.99 |
| ATOM | 2059 | CG | LEU | A | 859 | 6.308 | 5.552 | 35.678 | 1.00 | 16.48 |
| ATOM | 2060 | CD1 | LEU | A | 859 | 6.199 | 6.180 | 37.042 | 1.00 | 17.47 |
| ATOM | 2061 | CD2 | LEU | A | 859 | 7.770 | 5.365 | 35.285 | 1.00 | 15.71 |
| ATOM | 2062 | C | LEU | A | 859 | 5.170 | 1.918 | 34.785 | 1.00 | 13.42 |
| ATOM | 2063 | O | LEU | A | 859 | 5.957 | 1.036 | 35.125 | 1.00 | 13.20 |
| ATOM | 2064 | N | TRP | A | 860 | 3.865 | 1.711 | 34.668 | 1.00 | 13.41 |
| ATOM | 2065 | CA | TRP | A | 860 | 3.299 | 0.395 | 34.890 | 1.00 | 12.92 |
| ATOM | 2066 | CB | TRP | A | 860 | 1.764 | 0.431 | 34.925 | 1.00 | 11.31 |
| ATOM | 2067 | CG | TRP | A | 860 | 1.193 | -0.831 | 35.468 | 1.00 | 14.90 |
| ATOM | 2068 | CD1 | TRP | A | 860 | 0.825 | -1.082 | 36.763 | 1.00 | 12.82 |
| ATOM | 2069 | NE1 | TRP | A | 860 | 0.367 | -2.375 | 36.881 | 1.00 | 11.17 |

FIGURE 3 (Cont.)

| | A | B | C | D | E | F | G | H | I | J |
|---|---|---|---|---|---|---|---|---|---|---|
| ATOM | 2070 | CE2 | TRP | A | 860 | 0.434 | -2.983 | 35.655 | 1.00 | 14.00 |
| ATOM | 2071 | CD2 | TRP | A | 860 | 0.953 | -2.040 | 34.743 | 1.00 | 12.31 |
| ATOM | 2072 | CE3 | TRP | A | 860 | 1.111 | -2.420 | 33.402 | 1.00 | 14.77 |
| ATOM | 2073 | CZ3 | TRP | A | 860 | 0.757 | -3.701 | 33.024 | 1.00 | 13.35 |
| ATOM | 2074 | CH2 | TRP | A | 860 | 0.250 | -4.619 | 33.956 | 1.00 | 13.01 |
| ATOM | 2075 | CZ2 | TRP | A | 860 | 0.071 | -4.278 | 35.271 | 1.00 | 12.79 |
| ATOM | 2076 | C | TRP | A | 860 | 3.817 | -0.602 | 33.851 | 1.00 | 11.49 |
| ATOM | 2077 | O | TRP | A | 860 | 4.229 | -1.686 | 34.229 | 1.00 | 13.89 |
| ATOM | 2078 | N | GLU | A | 861 | 3.795 | -0.239 | 32.562 | 1.00 | 12.28 |
| ATOM | 2079 | CA | GLU | A | 861 | 4.371 | -1.090 | 31.499 | 1.00 | 14.03 |
| ATOM | 2080 | CB | GLU | A | 861 | 4.395 | -0.362 | 30.152 | 1.00 | 16.36 |
| ATOM | 2081 | CG | GLU | A | 861 | 3.071 | 0.040 | 29.546 | 1.00 | 16.74 |
| ATOM | 2082 | CD | GLU | A | 861 | 3.302 | 0.627 | 28.168 | 1.00 | 16.61 |
| ATOM | 2083 | OE1 | GLU | A | 861 | 3.382 | -0.157 | 27.205 | 1.00 | 16.12 |
| ATOM | 2084 | OE2 | GLU | A | 861 | 3.475 | 1.863 | 28.060 | 1.00 | 17.07 |
| ATOM | 2085 | C | GLU | A | 861 | 5.820 | -1.436 | 31.805 | 1.00 | 15.52 |
| ATOM | 2086 | O | GLU | A | 861 | 6.261 | -2.571 | 31.623 | 1.00 | 11.84 |
| ATOM | 2087 | N | LEU | A | 862 | 6.557 | -0.425 | 32.246 | 1.00 | 13.90 |
| ATOM | 2088 | CA | LEU | A | 862 | 7.985 | -0.546 | 32.499 | 1.00 | 16.17 |
| ATOM | 2089 | CB | LEU | A | 862 | 8.545 | 0.831 | 32.873 | 1.00 | 18.96 |
| ATOM | 2090 | CG | LEU | A | 862 | 10.036 | 1.022 | 33.134 | 1.00 | 19.96 |
| ATOM | 2091 | CD1 | LEU | A | 862 | 10.866 | 0.604 | 31.927 | 1.00 | 19.49 |
| ATOM | 2092 | CD2 | LEU | A | 862 | 10.270 | 2.486 | 33.457 | 1.00 | 18.76 |
| ATOM | 2093 | C | LEU | A | 862 | 8.285 | -1.566 | 33.584 | 1.00 | 13.90 |
| ATOM | 2094 | O | LEU | A | 862 | 9.048 | -2.516 | 33.372 | 1.00 | 14.07 |
| ATOM | 2095 | N | PHE | A | 863 | 7.660 | -1.384 | 34.743 | 1.00 | 11.19 |
| ATOM | 2096 | CA | PHE | A | 863 | 7.946 | -2.241 | 35.886 | 1.00 | 13.30 |
| ATOM | 2097 | CB | PHE | A | 863 | 7.691 | -1.488 | 37.191 | 1.00 | 13.16 |
| ATOM | 2098 | CG | PHE | A | 863 | 8.714 | -0.427 | 37.464 | 1.00 | 15.45 |
| ATOM | 2099 | CD1 | PHE | A | 863 | 8.465 | 0.899 | 37.128 | 1.00 | 15.11 |
| ATOM | 2100 | CE1 | PHE | A | 863 | 9.422 | 1.883 | 37.361 | 1.00 | 17.13 |
| ATOM | 2101 | CZ | PHE | A | 863 | 10.654 | 1.538 | 37.915 | 1.00 | 15.95 |
| ATOM | 2102 | CE2 | PHE | A | 863 | 10.916 | 0.214 | 38.244 | 1.00 | 16.04 |
| ATOM | 2103 | CD2 | PHE | A | 863 | 9.950 | -0.761 | 38.007 | 1.00 | 13.52 |
| ATOM | 2104 | C | PHE | A | 863 | 7.233 | -3.588 | 35.829 | 1.00 | 13.03 |
| ATOM | 2105 | O | PHE | A | 863 | 7.505 | -4.468 | 36.645 | 1.00 | 14.20 |
| ATOM | 2106 | N | SER | A | 864 | 6.342 | -3.752 | 34.850 | 1.00 | 12.23 |
| ATOM | 2107 | CA | SER | A | 864 | 5.727 | -5.052 | 34.576 | 1.00 | 12.80 |
| ATOM | 2108 | CB | BSER | A | 864 | 4.246 | -4.898 | 34.215 | 0.35 | 11.86 |
| ATOM | 2109 | CB | ASER | A | 864 | 4.265 | -4.877 | 34.181 | 0.65 | 13.62 |
| ATOM | 2110 | OG | BSER | A | 864 | 3.539 | -4.199 | 35.224 | 0.35 | 8.26 |
| ATOM | 2111 | OG | ASER | A | 864 | 4.188 | -4.266 | 32.907 | 0.65 | 12.31 |
| ATOM | 2112 | C | SER | A | 864 | 6.470 | -5.745 | 33.438 | 1.00 | 13.54 |
| ATOM | 2113 | O | SER | A | 864 | 6.004 | -6.754 | 32.903 | 1.00 | 14.23 |
| ATOM | 2114 | N | LEU | A | 865 | 7.615 | -5.179 | 33.060 | 1.00 | 13.08 |
| ATOM | 2115 | CA | LEU | A | 865 | 8.482 | -5.752 | 32.026 | 1.00 | 12.73 |
| ATOM | 2116 | CB | LEU | A | 865 | 9.083 | -7.088 | 32.493 | 1.00 | 13.77 |
| ATOM | 2117 | CG | LEU | A | 865 | 9.759 | -7.051 | 33.869 | 1.00 | 16.86 |
| ATOM | 2118 | CD1 | LEU | A | 865 | 10.065 | -8.457 | 34.368 | 1.00 | 15.73 |
| ATOM | 2119 | CD2 | LEU | A | 865 | 11.023 | -6.192 | 33.849 | 1.00 | 17.82 |
| ATOM | 2120 | C | LEU | A | 865 | 7.752 | -5.903 | 30.696 | 1.00 | 13.60 |
| ATOM | 2121 | O | LEU | A | 865 | 7.846 | -6.939 | 30.022 | 1.00 | 14.87 |

FIGURE 3 (Cont.)

|      | A    | B    | C    | D    | E   | F      | G      | H      | I    | J     |
|------|------|------|------|------|-----|--------|--------|--------|------|-------|
| ATOM | 2122 | N    | GLY  | A    | 866 | 7.006  | -4.865 | 30.338 | 1.00 | 13.32 |
| ATOM | 2123 | CA   | GLY  | A    | 866 | 6.384  | -4.789 | 29.032 | 1.00 | 14.96 |
| ATOM | 2124 | C    | GLY  | A    | 866 | 5.033  | -5.459 | 28.911 | 1.00 | 13.99 |
| ATOM | 2125 | O    | GLY  | A    | 866 | 4.587  | -5.736 | 27.802 | 1.00 | 16.04 |
| ATOM | 2126 | N    | SER  | A    | 867 | 4.372  | -5.715 | 30.037 | 1.00 | 14.03 |
| ATOM | 2127 | CA   | SER  | A    | 867 | 3.008  | -6.229 | 30.001 | 1.00 | 14.59 |
| ATOM | 2128 | CB   | BSER | A    | 867 | 2.561  | -6.644 | 31.402 | 0.35 | 13.18 |
| ATOM | 2129 | CB   | ASER | A    | 867 | 2.551  | -6.660 | 31.395 | 0.65 | 16.96 |
| ATOM | 2130 | OG   | BSER | A    | 867 | 3.325  | -7.740 | 31.876 | 0.35 | 11.59 |
| ATOM | 2131 | OG   | ASER | A    | 867 | 1.185  | -7.045 | 31.391 | 0.65 | 22.39 |
| ATOM | 2132 | C    | SER  | A    | 867 | 2.084  | -5.149 | 29.454 | 1.00 | 13.56 |
| ATOM | 2133 | O    | SER  | A    | 867 | 2.314  | -3.959 | 29.677 | 1.00 | 13.53 |
| ATOM | 2134 | N    | SER  | A    | 868 | 1.053  | -5.554 | 28.718 | 1.00 | 14.46 |
| ATOM | 2135 | CA   | SER  | A    | 868 | 0.012  | -4.615 | 28.323 | 1.00 | 15.46 |
| ATOM | 2136 | CB   | SER  | A    | 868 | -0.886 | -5.222 | 27.238 | 1.00 | 19.64 |
| ATOM | 2137 | OG   | SER  | A    | 868 | -1.416 | -6.460 | 27.665 | 1.00 | 22.46 |
| ATOM | 2138 | C    | SER  | A    | 868 | -0.800 | -4.253 | 29.570 | 1.00 | 14.62 |
| ATOM | 2139 | O    | SER  | A    | 868 | -1.038 | -5.115 | 30.423 | 1.00 | 15.29 |
| ATOM | 2140 | N    | PRO  | A    | 869 | -1.196 | -2.985 | 29.699 | 1.00 | 15.98 |
| ATOM | 2141 | CA   | PRO  | A    | 869 | -1.914 | -2.512 | 30.889 | 1.00 | 14.15 |
| ATOM | 2142 | CB   | PRO  | A    | 869 | -1.972 | -0.994 | 30.683 | 1.00 | 14.64 |
| ATOM | 2143 | CG   | PRO  | A    | 869 | -1.888 | -0.812 | 29.225 | 1.00 | 16.02 |
| ATOM | 2144 | CD   | PRO  | A    | 869 | -0.976 | -1.899 | 28.727 | 1.00 | 15.10 |
| ATOM | 2145 | C    | PRO  | A    | 869 | -3.318 | -3.086 | 30.992 | 1.00 | 13.57 |
| ATOM | 2146 | O    | PRO  | A    | 869 | -3.853 | -3.574 | 29.996 | 1.00 | 12.86 |
| ATOM | 2147 | N    | TYR  | A    | 870 | -3.890 | -3.027 | 32.197 | 1.00 | 12.72 |
| ATOM | 2148 | CA   | TYR  | A    | 870 | -5.175 | -3.654 | 32.513 | 1.00 | 11.23 |
| ATOM | 2149 | CB   | TYR  | A    | 870 | -6.343 | -2.739 | 32.104 | 1.00 | 12.04 |
| ATOM | 2150 | CG   | TYR  | A    | 870 | -6.204 | -1.327 | 32.605 | 1.00 | 10.74 |
| ATOM | 2151 | CD1  | TYR  | A    | 870 | -5.594 | -0.342 | 31.814 | 1.00 | 9.95  |
| ATOM | 2152 | CE1  | TYR  | A    | 870 | -5.460 | 0.973  | 32.269 | 1.00 | 10.91 |
| ATOM | 2153 | CZ   | TYR  | A    | 870 | -5.946 | 1.313  | 33.523 | 1.00 | 10.87 |
| ATOM | 2154 | OH   | TYR  | A    | 870 | -5.806 | 2.605  | 33.976 | 1.00 | 11.30 |
| ATOM | 2155 | CE2  | TYR  | A    | 870 | -6.551 | 0.356  | 34.330 | 1.00 | 10.96 |
| ATOM | 2156 | CD2  | TYR  | A    | 870 | -6.681 | -0.963 | 33.865 | 1.00 | 10.99 |
| ATOM | 2157 | C    | TYR  | A    | 870 | -5.275 | -5.024 | 31.845 | 1.00 | 10.66 |
| ATOM | 2158 | O    | TYR  | A    | 870 | -6.189 | -5.266 | 31.056 | 1.00 | 10.79 |
| ATOM | 2159 | N    | PRO  | A    | 871 | -4.317 | -5.908 | 32.146 | 1.00 | 12.37 |
| ATOM | 2160 | CA   | PRO  | A    | 871 | -4.223 | -7.205 | 31.468 | 1.00 | 13.07 |
| ATOM | 2161 | CB   | PRO  | A    | 871 | -3.109 | -7.949 | 32.227 | 1.00 | 13.18 |
| ATOM | 2162 | CG   | PRO  | A    | 871 | -2.468 | -6.975 | 33.128 | 1.00 | 13.44 |
| ATOM | 2163 | CD   | PRO  | A    | 871 | -3.273 | -5.735 | 33.174 | 1.00 | 12.90 |
| ATOM | 2164 | C    | PRO  | A    | 871 | -5.526 | -7.979 | 31.586 | 1.00 | 12.23 |
| ATOM | 2165 | O    | PRO  | A    | 871 | -6.075 | -8.098 | 32.688 | 1.00 | 11.77 |
| ATOM | 2166 | N    | GLY  | A    | 872 | -6.021 | -8.469 | 30.453 | 1.00 | 11.96 |
| ATOM | 2167 | CA   | GLY  | A    | 872 | -7.224 | -9.279 | 30.416 | 1.00 | 12.49 |
| ATOM | 2168 | C    | GLY  | A    | 872 | -8.515 | -8.516 | 30.647 | 1.00 | 14.29 |
| ATOM | 2169 | O    | GLY  | A    | 872 | -9.559 | -9.122 | 30.870 | 1.00 | 13.00 |
| ATOM | 2170 | N    | MET  | A    | 873 | -8.444 | -7.187 | 30.603 | 1.00 | 12.88 |
| ATOM | 2171 | CA   | MET  | A    | 873 | -9.635 | -6.358 | 30.720 | 1.00 | 15.74 |
| ATOM | 2172 | CB   | MET  | A    | 873 | -9.467 | -5.306 | 31.816 | 1.00 | 17.38 |
| ATOM | 2173 | CG   | MET  | A    | 873 | -9.274 | -5.867 | 33.210 | 1.00 | 22.01 |

FIGURE 3 (Cont.)

|      | A    | B   | C   | D | E   | F       | G      | H      | I    | J     |
|------|------|-----|-----|---|-----|---------|--------|--------|------|-------|
| ATOM | 2174 | SD  | MET | A | 873 | -9.151  | -4.565 | 34.446 | 1.00 | 23.90 |
| ATOM | 2175 | CE  | MET | A | 873 | -9.709  | -5.456 | 35.912 | 1.00 | 24.43 |
| ATOM | 2176 | C   | MET | A | 873 | -9.855  | -5.672 | 29.383 | 1.00 | 16.22 |
| ATOM | 2177 | O   | MET | A | 873 | -9.116  | -4.757 | 29.040 | 1.00 | 15.77 |
| ATOM | 2178 | N   | PRO | A | 874 | -10.850 | -6.115 | 28.616 | 1.00 | 18.39 |
| ATOM | 2179 | CA  | PRO | A | 874 | -11.142 | -5.480 | 27.325 | 1.00 | 19.00 |
| ATOM | 2180 | CB  | PRO | A | 874 | -12.267 | -6.342 | 26.747 | 1.00 | 19.19 |
| ATOM | 2181 | CG  | PRO | A | 874 | -12.856 | -7.063 | 27.912 | 1.00 | 20.66 |
| ATOM | 2182 | CD  | PRO | A | 874 | -11.759 | -7.238 | 28.908 | 1.00 | 17.88 |
| ATOM | 2183 | C   | PRO | A | 874 | -11.619 | -4.041 | 27.516 | 1.00 | 16.92 |
| ATOM | 2184 | O   | PRO | A | 874 | -12.216 | -3.727 | 28.550 | 1.00 | 17.09 |
| ATOM | 2185 | N   | VAL | A | 875 | -11.345 | -3.180 | 26.542 | 1.00 | 16.24 |
| ATOM | 2186 | CA  | VAL | A | 875 | -11.887 | -1.827 | 26.577 | 1.00 | 16.54 |
| ATOM | 2187 | CB  | VAL | A | 875 | -11.067 | -0.837 | 25.735 | 1.00 | 17.99 |
| ATOM | 2188 | CG1 | VAL | A | 875 | -11.719 |  0.538 | 25.756 | 1.00 | 17.93 |
| ATOM | 2189 | CG2 | VAL | A | 875 | -9.641  | -0.743 | 26.266 | 1.00 | 17.26 |
| ATOM | 2190 | C   | VAL | A | 875 | -13.351 | -1.857 | 26.132 | 1.00 | 17.67 |
| ATOM | 2191 | O   | VAL | A | 875 | -13.661 | -1.971 | 24.941 | 1.00 | 16.88 |
| ATOM | 2192 | N   | ASP | A | 876 | -14.242 | -1.784 | 27.115 | 1.00 | 17.54 |
| ATOM | 2193 | CA  | ASP | A | 876 | -15.681 | -1.784 | 26.871 | 1.00 | 17.40 |
| ATOM | 2194 | CB  | ASP | A | 876 | -16.255 | -3.203 | 27.018 | 1.00 | 19.76 |
| ATOM | 2195 | CG  | ASP | A | 876 | -15.857 | -3.867 | 28.329 | 1.00 | 21.66 |
| ATOM | 2196 | OD1 | ASP | A | 876 | -15.775 | -5.113 | 28.361 | 1.00 | 23.27 |
| ATOM | 2197 | OD2 | ASP | A | 876 | -15.606 | -3.233 | 29.378 | 1.00 | 21.50 |
| ATOM | 2198 | C   | ASP | A | 876 | -16.365 | -0.807 | 27.829 | 1.00 | 15.84 |
| ATOM | 2199 | O   | ASP | A | 876 | -15.688 | -0.105 | 28.578 | 1.00 | 15.75 |
| ATOM | 2200 | N   | SER | A | 877 | -17.699 | -0.772 | 27.813 | 1.00 | 17.26 |
| ATOM | 2201 | CA  | SER | A | 877 | -18.467 |  0.147 | 28.663 | 1.00 | 18.24 |
| ATOM | 2202 | CB  | SER | A | 877 | -19.971 | -0.023 | 28.432 | 1.00 | 17.72 |
| ATOM | 2203 | OG  | SER | A | 877 | -20.396 | -1.333 | 28.768 | 1.00 | 19.73 |
| ATOM | 2204 | C   | SER | A | 877 | -18.132 |  0.018 | 30.157 | 1.00 | 18.30 |
| ATOM | 2205 | O   | SER | A | 877 | -18.075 |  1.025 | 30.877 | 1.00 | 16.88 |
| ATOM | 2206 | N   | LYS | A | 878 | -17.898 | -1.219 | 30.600 | 1.00 | 18.10 |
| ATOM | 2207 | CA  | LYS | A | 878 | -17.475 | -1.518 | 31.969 | 1.00 | 20.20 |
| ATOM | 2208 | CB  | LYS | A | 878 | -17.371 | -3.035 | 32.176 | 1.00 | 24.06 |
| ATOM | 2209 | CG  | LYS | A | 878 | -17.018 | -3.476 | 33.596 | 1.00 | 26.22 |
| ATOM | 2210 | CD  | LYS | A | 878 | -17.663 | -4.815 | 33.943 | 1.00 | 27.62 |
| ATOM | 2211 | CE  | LYS | A | 878 | -16.627 | -5.817 | 34.437 | 1.00 | 28.87 |
| ATOM | 2212 | NZ  | LYS | A | 878 | -16.946 | -7.207 | 34.010 | 1.00 | 29.19 |
| ATOM | 2213 | C   | LYS | A | 878 | -16.140 | -0.850 | 32.302 | 1.00 | 19.39 |
| ATOM | 2214 | O   | LYS | A | 878 | -16.005 | -0.223 | 33.353 | 1.00 | 19.05 |
| ATOM | 2215 | N   | PHE | A | 879 | -15.167 | -0.991 | 31.402 | 1.00 | 17.76 |
| ATOM | 2216 | CA  | PHE | A | 879 | -13.844 | -0.395 | 31.571 | 1.00 | 18.17 |
| ATOM | 2217 | CB  | PHE | A | 879 | -12.962 | -0.686 | 30.351 | 1.00 | 17.70 |
| ATOM | 2218 | CG  | PHE | A | 879 | -11.578 | -0.115 | 30.454 | 1.00 | 16.97 |
| ATOM | 2219 | CD1 | PHE | A | 879 | -11.281 |  1.128 | 29.905 | 1.00 | 15.86 |
| ATOM | 2220 | CE1 | PHE | A | 879 | -10.006 |  1.664 | 30.010 | 1.00 | 17.45 |
| ATOM | 2221 | CZ  | PHE | A | 879 | -9.007  |  0.951 | 30.659 | 1.00 | 16.80 |
| ATOM | 2222 | CE2 | PHE | A | 879 | -9.288  | -0.287 | 31.208 | 1.00 | 18.02 |
| ATOM | 2223 | CD2 | PHE | A | 879 | -10.573 | -0.816 | 31.108 | 1.00 | 18.09 |
| ATOM | 2224 | C   | PHE | A | 879 | -13.936 |  1.111 | 31.816 | 1.00 | 17.54 |
| ATOM | 2225 | O   | PHE | A | 879 | -13.389 |  1.621 | 32.793 | 1.00 | 13.17 |

FIGURE 3 (Cont.)

|      | A    | B    | C   | D | E   | F       | G      | H      | I    | J     |
|------|------|------|-----|---|-----|---------|--------|--------|------|-------|
| ATOM | 2226 | N    | TYR | A | 880 | -14.656 | 1.806  | 30.936 | 1.00 | 21.23 |
| ATOM | 2227 | CA   | TYR | A | 880 | -14.840 | 3.254  | 31.034 | 1.00 | 22.41 |
| ATOM | 2228 | CB   | TYR | A | 880 | -15.744 | 3.748  | 29.902 | 1.00 | 24.19 |
| ATOM | 2229 | CG   | TYR | A | 880 | -15.111 | 3.620  | 28.539 | 1.00 | 25.29 |
| ATOM | 2230 | CD1  | TYR | A | 880 | -15.725 | 2.884  | 27.527 | 1.00 | 25.90 |
| ATOM | 2231 | CE1  | TYR | A | 880 | -15.133 | 2.763  | 26.272 | 1.00 | 26.07 |
| ATOM | 2232 | CZ   | TYR | A | 880 | -13.921 | 3.384  | 26.030 | 1.00 | 25.39 |
| ATOM | 2233 | OH   | TYR | A | 880 | -13.312 | 3.280  | 24.803 | 1.00 | 26.76 |
| ATOM | 2234 | CE2  | TYR | A | 880 | -13.297 | 4.113  | 27.022 | 1.00 | 26.84 |
| ATOM | 2235 | CD2  | TYR | A | 880 | -13.889 | 4.226  | 28.264 | 1.00 | 25.81 |
| ATOM | 2236 | C    | TYR | A | 880 | -15.406 | 3.668  | 32.387 | 1.00 | 22.36 |
| ATOM | 2237 | O    | TYR | A | 880 | -14.892 | 4.590  | 33.032 | 1.00 | 22.22 |
| ATOM | 2238 | N    | LYS | A | 881 | -16.445 | 2.955  | 32.813 | 1.00 | 22.25 |
| ATOM | 2239 | CA   | LYS | A | 881 | -17.130 | 3.216  | 34.072 | 1.00 | 22.88 |
| ATOM | 2240 | CB   | LYS | A | 881 | -18.386 | 2.347  | 34.192 | 1.00 | 24.13 |
| ATOM | 2241 | CG   | LYS | A | 881 | -19.652 | 3.017  | 33.657 | 1.00 | 26.69 |
| ATOM | 2242 | CD   | LYS | A | 881 | -20.913 | 2.268  | 34.077 | 1.00 | 27.28 |
| ATOM | 2243 | CE   | LYS | A | 881 | -22.007 | 3.228  | 34.526 | 1.00 | 27.66 |
| ATOM | 2244 | NZ   | LYS | A | 881 | -22.890 | 2.626  | 35.567 | 1.00 | 27.48 |
| ATOM | 2245 | C    | LYS | A | 881 | -16.221 | 3.023  | 35.285 | 1.00 | 21.93 |
| ATOM | 2246 | O    | LYS | A | 881 | -16.170 | 3.888  | 36.159 | 1.00 | 19.31 |
| ATOM | 2247 | N    | MET | A | 882 | -15.492 | 1.909  | 35.345 | 1.00 | 21.78 |
| ATOM | 2248 | CA   | MET | A | 882 | -14.646 | 1.681  | 36.516 | 1.00 | 22.17 |
| ATOM | 2249 | CB   | MET | A | 882 | -14.240 | 0.215  | 36.725 | 1.00 | 26.82 |
| ATOM | 2250 | CG   | MET | A | 882 | -13.730 | -0.546 | 35.527 | 1.00 | 31.06 |
| ATOM | 2251 | SD   | MET | A | 882 | -14.212 | -2.282 | 35.739 | 1.00 | 35.07 |
| ATOM | 2252 | CE   | MET | A | 882 | -12.721 | -2.966 | 36.485 | 1.00 | 34.90 |
| ATOM | 2253 | C    | MET | A | 882 | -13.454 | 2.616  | 36.601 | 1.00 | 17.93 |
| ATOM | 2254 | O    | MET | A | 882 | -13.042 | 2.969  | 37.699 | 1.00 | 17.66 |
| ATOM | 2255 | N    | ILE | A | 883 | -12.935 | 3.053  | 35.454 | 1.00 | 15.93 |
| ATOM | 2256 | CA   | ILE | A | 883 | -11.896 | 4.081  | 35.443 | 1.00 | 18.89 |
| ATOM | 2257 | CB   | ILE | A | 883 | -11.341 | 4.314  | 34.007 | 1.00 | 19.60 |
| ATOM | 2258 | CG1  | ILE | A | 883 | -10.578 | 3.073  | 33.509 | 1.00 | 20.95 |
| ATOM | 2259 | CD1  | ILE | A | 883 | -9.389  | 2.655  | 34.377 | 1.00 | 20.67 |
| ATOM | 2260 | CG2  | ILE | A | 883 | -10.425 | 5.535  | 33.956 | 1.00 | 22.56 |
| ATOM | 2261 | C    | ILE | A | 883 | -12.459 | 5.368  | 36.052 | 1.00 | 18.45 |
| ATOM | 2262 | O    | ILE | A | 883 | -11.825 | 5.989  | 36.904 | 1.00 | 16.78 |
| ATOM | 2263 | N    | LYS | A | 884 | -13.664 | 5.738  | 35.630 | 1.00 | 20.81 |
| ATOM | 2264 | CA   | LYS | A | 884 | -14.342 | 6.918  | 36.165 | 1.00 | 24.36 |
| ATOM | 2265 | CB   | LYS | A | 884 | -15.613 | 7.229  | 35.362 | 1.00 | 27.04 |
| ATOM | 2266 | CG   | LYS | A | 884 | -16.232 | 8.627  | 35.599 | 1.00 | 30.39 |
| ATOM | 2267 | CD   | LYS | A | 884 | -15.188 | 9.744  | 35.802 | 1.00 | 32.78 |
| ATOM | 2268 | CE   | LYS | A | 884 | -14.619 | 10.268 | 34.482 | 1.00 | 33.43 |
| ATOM | 2269 | NZ   | LYS | A | 884 | -15.596 | 11.100 | 33.726 | 1.00 | 34.96 |
| ATOM | 2270 | C    | LYS | A | 884 | -14.658 | 6.781  | 37.656 | 1.00 | 24.55 |
| ATOM | 2271 | O    | LYS | A | 884 | -14.529 | 7.748  | 38.408 | 1.00 | 28.33 |
| ATOM | 2272 | N    | GLU | A | 885 | -15.058 | 5.583  | 38.078 | 1.00 | 23.01 |
| ATOM | 2273 | CA   | GLU | A | 885 | -15.392 | 5.338  | 39.482 | 1.00 | 23.30 |
| ATOM | 2274 | CB   | GLU | A | 885 | -16.415 | 4.196  | 39.625 | 1.00 | 25.59 |
| ATOM | 2275 | CG   | GLU | A | 885 | -15.837 | 2.790  | 39.729 | 1.00 | 29.02 |
| ATOM | 2276 | CD   | GLU | A | 885 | -16.855 | 1.699  | 39.423 | 1.00 | 31.36 |
| ATOM | 2277 | OE1  | GLU | A | 885 | -16.447 | 0.520  | 39.326 | 1.00 | 33.28 |

FIGURE 3 (Cont.)

| | A | B | C | D | E | F | G | H | I | J |
|---|---|---|---|---|---|---|---|---|---|---|
| ATOM | 2278 | OE2 | GLU | A | 885 | -18.058 | 2.009 | 39.277 | 1.00 | 31.04 |
| ATOM | 2279 | C | GLU | A | 885 | -14.157 | 5.136 | 40.372 | 1.00 | 21.75 |
| ATOM | 2280 | O | GLU | A | 885 | -14.274 | 5.006 | 41.591 | 1.00 | 22.56 |
| ATOM | 2281 | N | GLY | A | 886 | -12.977 | 5.117 | 39.757 | 1.00 | 19.26 |
| ATOM | 2282 | CA | GLY | A | 886 | -11.733 | 5.141 | 40.501 | 1.00 | 17.46 |
| ATOM | 2283 | C | GLY | A | 886 | -10.893 | 3.875 | 40.498 | 1.00 | 16.92 |
| ATOM | 2284 | O | GLY | A | 886 | -9.930 | 3.795 | 41.259 | 1.00 | 15.13 |
| ATOM | 2285 | N | PHE | A | 887 | -11.238 | 2.892 | 39.664 | 1.00 | 16.25 |
| ATOM | 2286 | CA | PHE | A | 887 | -10.393 | 1.701 | 39.533 | 1.00 | 15.63 |
| ATOM | 2287 | CB | PHE | A | 887 | -10.996 | 0.643 | 38.602 | 1.00 | 16.52 |
| ATOM | 2288 | CG | PHE | A | 887 | -10.071 | -0.526 | 38.342 | 1.00 | 19.86 |
| ATOM | 2289 | CD1 | PHE | A | 887 | -9.169 | -0.503 | 37.275 | 1.00 | 22.47 |
| ATOM | 2290 | CE1 | PHE | A | 887 | -8.305 | -1.575 | 37.048 | 1.00 | 23.02 |
| ATOM | 2291 | CZ | PHE | A | 887 | -8.336 | -2.679 | 37.894 | 1.00 | 22.37 |
| ATOM | 2292 | CE2 | PHE | A | 887 | -9.223 | -2.708 | 38.961 | 1.00 | 21.79 |
| ATOM | 2293 | CD2 | PHE | A | 887 | -10.081 | -1.633 | 39.181 | 1.00 | 21.56 |
| ATOM | 2294 | C | PHE | A | 887 | -9.015 | 2.085 | 39.010 | 1.00 | 13.22 |
| ATOM | 2295 | O | PHE | A | 887 | -8.895 | 2.857 | 38.058 | 1.00 | 12.58 |
| ATOM | 2296 | N | ARG | A | 888 | -7.985 | 1.525 | 39.634 | 1.00 | 12.23 |
| ATOM | 2297 | CA | ARG | A | 888 | -6.615 | 1.716 | 39.193 | 1.00 | 12.50 |
| ATOM | 2298 | CB | ARG | A | 888 | -5.889 | 2.731 | 40.084 | 1.00 | 14.15 |
| ATOM | 2299 | CG | ARG | A | 888 | -6.489 | 4.136 | 40.078 | 1.00 | 14.37 |
| ATOM | 2300 | CD | ARG | A | 888 | -6.397 | 4.871 | 38.745 | 1.00 | 11.99 |
| ATOM | 2301 | NE | ARG | A | 888 | -6.949 | 6.225 | 38.845 | 1.00 | 13.68 |
| ATOM | 2302 | CZ | ARG | A | 888 | -8.207 | 6.553 | 38.573 | 1.00 | 14.74 |
| ATOM | 2303 | NH1 | ARG | A | 888 | -9.080 | 5.633 | 38.174 | 1.00 | 13.75 |
| ATOM | 2304 | NH2 | ARG | A | 888 | -8.597 | 7.816 | 38.701 | 1.00 | 14.31 |
| ATOM | 2305 | C | ARG | A | 888 | -5.887 | 0.381 | 39.225 | 1.00 | 10.33 |
| ATOM | 2306 | O | ARG | A | 888 | -6.207 | -0.496 | 40.030 | 1.00 | 13.21 |
| ATOM | 2307 | N | MET | A | 889 | -4.911 | 0.225 | 38.339 | 1.00 | 10.68 |
| ATOM | 2308 | CA | MET | A | 889 | -4.115 | -0.996 | 38.313 | 1.00 | 13.08 |
| ATOM | 2309 | CB | MET | A | 889 | -3.117 | -0.949 | 37.168 | 1.00 | 14.60 |
| ATOM | 2310 | CG | MET | A | 889 | -3.701 | -1.373 | 35.843 | 1.00 | 16.43 |
| ATOM | 2311 | SD | MET | A | 889 | -2.431 | -1.443 | 34.600 | 1.00 | 14.28 |
| ATOM | 2312 | CE | MET | A | 889 | -2.125 | 0.301 | 34.329 | 1.00 | 14.68 |
| ATOM | 2313 | C | MET | A | 889 | -3.366 | -1.175 | 39.623 | 1.00 | 12.18 |
| ATOM | 2314 | O | MET | A | 889 | -2.943 | -0.194 | 40.244 | 1.00 | 12.43 |
| ATOM | 2315 | N | LEU | A | 890 | -3.218 | -2.431 | 40.037 | 1.00 | 10.30 |
| ATOM | 2316 | CA | LEU | A | 890 | -2.366 | -2.776 | 41.163 | 1.00 | 13.89 |
| ATOM | 2317 | CB | LEU | A | 890 | -2.581 | -4.233 | 41.570 | 1.00 | 14.02 |
| ATOM | 2318 | CG | LEU | A | 890 | -3.957 | -4.668 | 42.076 | 1.00 | 16.72 |
| ATOM | 2319 | CD1 | LEU | A | 890 | -3.929 | -6.157 | 42.377 | 1.00 | 16.45 |
| ATOM | 2320 | CD2 | LEU | A | 890 | -4.388 | -3.880 | 43.312 | 1.00 | 18.97 |
| ATOM | 2321 | C | LEU | A | 890 | -0.905 | -2.563 | 40.784 | 1.00 | 13.90 |
| ATOM | 2322 | O | LEU | A | 890 | -0.573 | -2.426 | 39.604 | 1.00 | 14.96 |
| ATOM | 2323 | N | SER | A | 891 | -0.035 | -2.537 | 41.789 | 1.00 | 14.26 |
| ATOM | 2324 | CA | SER | A | 891 | 1.391 | -2.407 | 41.543 | 1.00 | 13.99 |
| ATOM | 2325 | CB | SER | A | 891 | 2.174 | -2.327 | 42.856 | 1.00 | 16.54 |
| ATOM | 2326 | OG | SER | A | 891 | 3.560 | -2.157 | 42.581 | 1.00 | 16.30 |
| ATOM | 2327 | C | SER | A | 891 | 1.918 | -3.581 | 40.727 | 1.00 | 14.59 |
| ATOM | 2328 | O | SER | A | 891 | 1.498 | -4.721 | 40.935 | 1.00 | 13.07 |
| ATOM | 2329 | N | PRO | A | 892 | 2.842 | -3.298 | 39.811 | 1.00 | 14.07 |

FIGURE 3 (Cont.)

|  | A | B | C | D | E | F | G | H | I | J |
|---|---|---|---|---|---|---|---|---|---|---|
| ATOM | 2330 | CA | PRO | A | 892 | 3.659 | -4.347 | 39.200 | 1.00 | 16.16 |
| ATOM | 2331 | CB | PRO | A | 892 | 4.596 | -3.560 | 38.273 | 1.00 | 15.77 |
| ATOM | 2332 | CG | PRO | A | 892 | 3.894 | -2.287 | 38.010 | 1.00 | 16.73 |
| ATOM | 2333 | CD | PRO | A | 892 | 3.186 | -1.958 | 39.298 | 1.00 | 13.60 |
| ATOM | 2334 | C | PRO | A | 892 | 4.470 | -5.026 | 40.295 | 1.00 | 14.22 |
| ATOM | 2335 | O | PRO | A | 892 | 4.850 | -4.365 | 41.265 | 1.00 | 14.76 |
| ATOM | 2336 | N | GLU | A | 893 | 4.730 | -6.321 | 40.147 | 1.00 | 15.64 |
| ATOM | 2337 | CA | GLU | A | 893 | 5.508 | -7.060 | 41.133 | 1.00 | 17.59 |
| ATOM | 2338 | CB | GLU | A | 893 | 5.708 | -8.510 | 40.675 | 1.00 | 18.93 |
| ATOM | 2339 | CG | GLU | A | 893 | 6.387 | -9.406 | 41.699 | 1.00 | 24.92 |
| ATOM | 2340 | CD | GLU | A | 893 | 6.938 | -10.684 | 41.092 | 1.00 | 27.14 |
| ATOM | 2341 | OE1 | GLU | A | 893 | 6.350 | -11.179 | 40.106 | 1.00 | 29.48 |
| ATOM | 2342 | OE2 | GLU | A | 893 | 7.960 | -11.195 | 41.601 | 1.00 | 29.16 |
| ATOM | 2343 | C | GLU | A | 893 | 6.856 | -6.395 | 41.411 | 1.00 | 15.31 |
| ATOM | 2344 | O | GLU | A | 893 | 7.299 | -6.328 | 42.557 | 1.00 | 16.60 |
| ATOM | 2345 | N | HIS | A | 894 | 7.483 | -5.876 | 40.360 | 1.00 | 17.10 |
| ATOM | 2346 | CA | HIS | A | 894 | 8.859 | -5.400 | 40.440 | 1.00 | 17.17 |
| ATOM | 2347 | CB | HIS | A | 894 | 9.630 | -5.865 | 39.204 | 1.00 | 22.20 |
| ATOM | 2348 | CG | HIS | A | 894 | 9.689 | -7.353 | 39.069 | 1.00 | 25.34 |
| ATOM | 2349 | ND1 | HIS | A | 894 | 10.376 | -8.150 | 39.958 | 1.00 | 27.53 |
| ATOM | 2350 | CE1 | HIS | A | 894 | 10.247 | -9.416 | 39.601 | 1.00 | 27.68 |
| ATOM | 2351 | NE2 | HIS | A | 894 | 9.494 | -9.468 | 38.518 | 1.00 | 27.56 |
| ATOM | 2352 | CD2 | HIS | A | 894 | 9.129 | -8.191 | 38.165 | 1.00 | 27.26 |
| ATOM | 2353 | C | HIS | A | 894 | 9.001 | -3.893 | 40.637 | 1.00 | 16.64 |
| ATOM | 2354 | O | HIS | A | 894 | 10.116 | -3.371 | 40.651 | 1.00 | 15.70 |
| ATOM | 2355 | N | ALA | A | 895 | 7.877 | -3.200 | 40.796 | 1.00 | 12.26 |
| ATOM | 2356 | CA | ALA | A | 895 | 7.898 | -1.767 | 41.048 | 1.00 | 13.16 |
| ATOM | 2357 | CB | ALA | A | 895 | 6.546 | -1.135 | 40.698 | 1.00 | 13.87 |
| ATOM | 2358 | C | ALA | A | 895 | 8.243 | -1.502 | 42.508 | 1.00 | 14.00 |
| ATOM | 2359 | O | ALA | A | 895 | 7.597 | -2.052 | 43.399 | 1.00 | 13.28 |
| ATOM | 2360 | N | PRO | A | 896 | 9.263 | -0.678 | 42.762 | 1.00 | 15.05 |
| ATOM | 2361 | CA | PRO | A | 896 | 9.502 | -0.167 | 44.118 | 1.00 | 16.22 |
| ATOM | 2362 | CB | PRO | A | 896 | 10.654 | 0.820 | 43.923 | 1.00 | 18.48 |
| ATOM | 2363 | CG | PRO | A | 896 | 11.330 | 0.382 | 42.671 | 1.00 | 16.99 |
| ATOM | 2364 | CD | PRO | A | 896 | 10.249 | -0.164 | 41.794 | 1.00 | 16.87 |
| ATOM | 2365 | C | PRO | A | 896 | 8.253 | 0.578 | 44.581 | 1.00 | 14.65 |
| ATOM | 2366 | O | PRO | A | 896 | 7.600 | 1.200 | 43.741 | 1.00 | 14.10 |
| ATOM | 2367 | N | ALA | A | 897 | 7.922 | 0.510 | 45.869 | 1.00 | 14.95 |
| ATOM | 2368 | CA | ALA | A | 897 | 6.724 | 1.178 | 46.392 | 1.00 | 15.27 |
| ATOM | 2369 | CB | ALA | A | 897 | 6.614 | 0.989 | 47.895 | 1.00 | 14.44 |
| ATOM | 2370 | C | ALA | A | 897 | 6.661 | 2.666 | 46.031 | 1.00 | 16.75 |
| ATOM | 2371 | O | ALA | A | 897 | 5.587 | 3.187 | 45.711 | 1.00 | 14.94 |
| ATOM | 2372 | N | GLU | A | 898 | 7.810 | 3.339 | 46.083 | 1.00 | 17.29 |
| ATOM | 2373 | CA | GLU | A | 898 | 7.892 | 4.760 | 45.748 | 1.00 | 19.20 |
| ATOM | 2374 | CB | GLU | A | 898 | 9.258 | 5.334 | 46.137 | 1.00 | 24.99 |
| ATOM | 2375 | CG | GLU | A | 898 | 9.185 | 6.429 | 47.198 | 1.00 | 31.09 |
| ATOM | 2376 | CD | GLU | A | 898 | 10.353 | 6.419 | 48.177 | 1.00 | 35.60 |
| ATOM | 2377 | OE1 | GLU | A | 898 | 10.214 | 7.020 | 49.268 | 1.00 | 36.84 |
| ATOM | 2378 | OE2 | GLU | A | 898 | 11.413 | 5.825 | 47.867 | 1.00 | 37.87 |
| ATOM | 2379 | C | GLU | A | 898 | 7.568 | 5.049 | 44.271 | 1.00 | 17.43 |
| ATOM | 2380 | O | GLU | A | 898 | 7.019 | 6.102 | 43.954 | 1.00 | 16.88 |
| ATOM | 2381 | N | MET | A | 899 | 7.903 | 4.115 | 43.381 | 1.00 | 16.72 |

FIGURE 3 (Cont.)

| | A | B | C | D | E | F | G | H | I | J |
|---|---|---|---|---|---|---|---|---|---|---|
| ATOM | 2382 | CA | MET | A | 899 | 7.551 | 4.235 | 41.964 | 1.00 | 15.07 |
| ATOM | 2383 | CB | MET | A | 899 | 8.330 | 3.227 | 41.112 | 1.00 | 18.86 |
| ATOM | 2384 | CG | MET | A | 899 | 9.820 | 3.537 | 40.940 | 1.00 | 23.64 |
| ATOM | 2385 | SD | MET | A | 899 | 10.196 | 5.232 | 40.410 | 1.00 | 28.22 |
| ATOM | 2386 | CE | MET | A | 899 | 9.397 | 5.309 | 38.869 | 1.00 | 23.01 |
| ATOM | 2387 | C | MET | A | 899 | 6.050 | 4.035 | 41.763 | 1.00 | 17.09 |
| ATOM | 2388 | O | MET | A | 899 | 5.412 | 4.760 | 40.986 | 1.00 | 16.02 |
| ATOM | 2389 | N | TYR | A | 900 | 5.485 | 3.054 | 42.461 | 1.00 | 16.03 |
| ATOM | 2390 | CA | TYR | A | 900 | 4.044 | 2.845 | 42.412 | 1.00 | 13.97 |
| ATOM | 2391 | CB | TYR | A | 900 | 3.630 | 1.554 | 43.118 | 1.00 | 14.90 |
| ATOM | 2392 | CG | TYR | A | 900 | 2.154 | 1.252 | 42.984 | 1.00 | 13.81 |
| ATOM | 2393 | CD1 | TYR | A | 900 | 1.545 | 1.166 | 41.725 | 1.00 | 13.62 |
| ATOM | 2394 | CE1 | TYR | A | 900 | 0.171 | 0.890 | 41.606 | 1.00 | 10.58 |
| ATOM | 2395 | CZ | TYR | A | 900 | -0.591 | 0.722 | 42.750 | 1.00 | 13.97 |
| ATOM | 2396 | OH | TYR | A | 900 | -1.943 | 0.449 | 42.651 | 1.00 | 14.21 |
| ATOM | 2397 | CE2 | TYR | A | 900 | -0.006 | 0.814 | 44.005 | 1.00 | 13.01 |
| ATOM | 2398 | CD2 | TYR | A | 900 | 1.358 | 1.080 | 44.113 | 1.00 | 14.72 |
| ATOM | 2399 | C | TYR | A | 900 | 3.312 | 4.061 | 42.985 | 1.00 | 14.06 |
| ATOM | 2400 | O | TYR | A | 900 | 2.258 | 4.444 | 42.478 | 1.00 | 13.93 |
| ATOM | 2401 | N | ASP | A | 901 | 3.892 | 4.682 | 44.014 | 1.00 | 13.38 |
| ATOM | 2402 | CA | ASP | A | 901 | 3.363 | 5.932 | 44.568 | 1.00 | 14.42 |
| ATOM | 2403 | CB | ASP | A | 901 | 4.263 | 6.460 | 45.692 | 1.00 | 15.59 |
| ATOM | 2404 | CG | ASP | A | 901 | 3.967 | 5.833 | 47.047 | 1.00 | 19.50 |
| ATOM | 2405 | OD1 | ASP | A | 901 | 3.048 | 4.994 | 47.170 | 1.00 | 20.38 |
| ATOM | 2406 | OD2 | ASP | A | 901 | 4.623 | 6.135 | 48.066 | 1.00 | 22.55 |
| ATOM | 2407 | C | ASP | A | 901 | 3.242 | 6.999 | 43.474 | 1.00 | 16.20 |
| ATOM | 2408 | O | ASP | A | 901 | 2.224 | 7.689 | 43.381 | 1.00 | 16.04 |
| ATOM | 2409 | N | ILE | A | 902 | 4.286 | 7.132 | 42.656 | 1.00 | 15.15 |
| ATOM | 2410 | CA | ILE | A | 902 | 4.278 | 8.084 | 41.542 | 1.00 | 17.16 |
| ATOM | 2411 | CB | ILE | A | 902 | 5.672 | 8.180 | 40.847 | 1.00 | 16.47 |
| ATOM | 2412 | CG1 | ILE | A | 902 | 6.691 | 8.836 | 41.789 | 1.00 | 18.83 |
| ATOM | 2413 | CD1 | ILE | A | 902 | 8.120 | 8.778 | 41.296 | 1.00 | 17.55 |
| ATOM | 2414 | CG2 | ILE | A | 902 | 5.582 | 8.969 | 39.525 | 1.00 | 17.74 |
| ATOM | 2415 | C | ILE | A | 902 | 3.169 | 7.736 | 40.547 | 1.00 | 15.70 |
| ATOM | 2416 | O | ILE | A | 902 | 2.415 | 8.619 | 40.126 | 1.00 | 17.77 |
| ATOM | 2417 | N | MET | A | 903 | 3.065 | 6.453 | 40.199 | 1.00 | 14.70 |
| ATOM | 2418 | CA | MET | A | 903 | 2.001 | 5.968 | 39.322 | 1.00 | 15.98 |
| ATOM | 2419 | CB | MET | A | 903 | 2.024 | 4.438 | 39.204 | 1.00 | 15.13 |
| ATOM | 2420 | CG | MET | A | 903 | 3.165 | 3.865 | 38.402 | 1.00 | 18.22 |
| ATOM | 2421 | SD | MET | A | 903 | 3.027 | 2.058 | 38.381 | 1.00 | 19.77 |
| ATOM | 2422 | CE | MET | A | 903 | 4.711 | 1.615 | 38.626 | 1.00 | 17.50 |
| ATOM | 2423 | C | MET | A | 903 | 0.639 | 6.405 | 39.840 | 1.00 | 14.60 |
| ATOM | 2424 | O | MET | A | 903 | -0.142 | 7.002 | 39.102 | 1.00 | 14.45 |
| ATOM | 2425 | N | LYS | A | 904 | 0.360 | 6.111 | 41.113 | 1.00 | 12.08 |
| ATOM | 2426 | CA | LYS | A | 904 | -0.920 | 6.471 | 41.718 | 1.00 | 13.15 |
| ATOM | 2427 | CB | LYS | A | 904 | -0.986 | 6.023 | 43.183 | 1.00 | 13.44 |
| ATOM | 2428 | CG | LYS | A | 904 | -1.005 | 4.510 | 43.369 | 1.00 | 15.90 |
| ATOM | 2429 | CD | LYS | A | 904 | -1.277 | 4.136 | 44.816 | 1.00 | 16.32 |
| ATOM | 2430 | CE | LYS | A | 904 | -0.005 | 4.154 | 45.645 | 1.00 | 18.18 |
| ATOM | 2431 | NZ | LYS | A | 904 | -0.258 | 3.662 | 47.028 | 1.00 | 20.19 |
| ATOM | 2432 | C | LYS | A | 904 | -1.219 | 7.967 | 41.608 | 1.00 | 13.15 |
| ATOM | 2433 | O | LYS | A | 904 | -2.356 | 8.349 | 41.330 | 1.00 | 12.40 |

FIGURE 3 (Cont.)

|  | A | B | C | D | E | F | G | H | I | J |
|---|---|---|---|---|---|---|---|---|---|---|
| ATOM | 2434 | N | THR | A | 905 | -0.204 | 8.809 | 41.816 | 1.00 | 13.18 |
| ATOM | 2435 | CA | THR | A | 905 | -0.410 | 10.258 | 41.719 | 1.00 | 13.91 |
| ATOM | 2436 | CB | THR | A | 905 | 0.732 | 11.071 | 42.372 | 1.00 | 16.29 |
| ATOM | 2437 | OG1 | THR | A | 905 | 1.978 | 10.784 | 41.724 | 1.00 | 17.64 |
| ATOM | 2438 | CG2 | THR | A | 905 | 0.950 | 10.643 | 43.828 | 1.00 | 18.40 |
| ATOM | 2439 | C | THR | A | 905 | -0.620 | 10.702 | 40.275 | 1.00 | 13.47 |
| ATOM | 2440 | O | THR | A | 905 | -1.378 | 11.640 | 40.020 | 1.00 | 13.38 |
| ATOM | 2441 | N | CYS | A | 906 | 0.056 | 10.035 | 39.338 | 1.00 | 12.88 |
| ATOM | 2442 | CA | CYS | A | 906 | -0.156 | 10.286 | 37.912 | 1.00 | 13.39 |
| ATOM | 2443 | CB | CYS | A | 906 | 0.792 | 9.451 | 37.050 | 1.00 | 11.99 |
| ATOM | 2444 | SG | CYS | A | 906 | 2.515 | 9.963 | 37.156 | 1.00 | 17.46 |
| ATOM | 2445 | C | CYS | A | 906 | -1.596 | 9.967 | 37.530 | 1.00 | 13.97 |
| ATOM | 2446 | O | CYS | A | 906 | -2.136 | 10.556 | 36.602 | 1.00 | 13.71 |
| ATOM | 2447 | N | TRP | A | 907 | -2.213 | 9.038 | 38.256 | 1.00 | 14.44 |
| ATOM | 2448 | CA | TRP | A | 907 | -3.577 | 8.615 | 37.952 | 1.00 | 13.70 |
| ATOM | 2449 | CB | TRP | A | 907 | -3.719 | 7.098 | 38.053 | 1.00 | 13.32 |
| ATOM | 2450 | CG | TRP | A | 907 | -2.762 | 6.315 | 37.233 | 1.00 | 11.48 |
| ATOM | 2451 | CD1 | TRP | A | 907 | -2.191 | 6.675 | 36.044 | 1.00 | 12.13 |
| ATOM | 2452 | NE1 | TRP | A | 907 | -1.363 | 5.672 | 35.593 | 1.00 | 12.53 |
| ATOM | 2453 | CE2 | TRP | A | 907 | -1.399 | 4.634 | 36.488 | 1.00 | 12.27 |
| ATOM | 2454 | CD2 | TRP | A | 907 | -2.277 | 5.008 | 37.531 | 1.00 | 11.34 |
| ATOM | 2455 | CE3 | TRP | A | 907 | -2.490 | 4.108 | 38.586 | 1.00 | 12.05 |
| ATOM | 2456 | CZ3 | TRP | A | 907 | -1.836 | 2.878 | 38.565 | 1.00 | 10.55 |
| ATOM | 2457 | CH2 | TRP | A | 907 | -0.965 | 2.538 | 37.514 | 1.00 | 12.14 |
| ATOM | 2458 | CZ2 | TRP | A | 907 | -0.735 | 3.400 | 36.467 | 1.00 | 12.59 |
| ATOM | 2459 | C | TRP | A | 907 | -4.638 | 9.273 | 38.827 | 1.00 | 14.46 |
| ATOM | 2460 | O | TRP | A | 907 | -5.768 | 8.783 | 38.918 | 1.00 | 14.39 |
| ATOM | 2461 | N | ASP | A | 908 | -4.297 | 10.381 | 39.474 | 1.00 | 14.82 |
| ATOM | 2462 | CA | ASP | A | 908 | -5.319 | 11.091 | 40.229 | 1.00 | 14.56 |
| ATOM | 2463 | CB | ASP | A | 908 | -4.761 | 12.347 | 40.885 | 1.00 | 15.73 |
| ATOM | 2464 | CG | ASP | A | 908 | -5.571 | 12.766 | 42.088 | 1.00 | 17.26 |
| ATOM | 2465 | OD1 | ASP | A | 908 | -5.095 | 12.571 | 43.221 | 1.00 | 19.21 |
| ATOM | 2466 | OD2 | ASP | A | 908 | -6.706 | 13.274 | 41.995 | 1.00 | 18.28 |
| ATOM | 2467 | C | ASP | A | 908 | -6.500 | 11.450 | 39.325 | 1.00 | 13.77 |
| ATOM | 2468 | O | ASP | A | 908 | -6.306 | 11.887 | 38.191 | 1.00 | 11.86 |
| ATOM | 2469 | N | ALA | A | 909 | -7.716 | 11.240 | 39.829 | 1.00 | 15.64 |
| ATOM | 2470 | CA | ALA | A | 909 | -8.937 | 11.603 | 39.107 | 1.00 | 17.19 |
| ATOM | 2471 | CB | ALA | A | 909 | -10.168 | 11.213 | 39.910 | 1.00 | 18.28 |
| ATOM | 2472 | C | ALA | A | 909 | -8.959 | 13.098 | 38.778 | 1.00 | 18.07 |
| ATOM | 2473 | O | ALA | A | 909 | -9.421 | 13.500 | 37.710 | 1.00 | 20.79 |
| ATOM | 2474 | N | ASP | A | 910 | -8.447 | 13.902 | 39.706 | 1.00 | 16.97 |
| ATOM | 2475 | CA | ASP | A | 910 | -8.314 | 15.342 | 39.530 | 1.00 | 17.29 |
| ATOM | 2476 | CB | ASP | A | 910 | -8.361 | 16.033 | 40.899 | 1.00 | 16.88 |
| ATOM | 2477 | CG | ASP | A | 910 | -8.368 | 17.556 | 40.811 | 1.00 | 17.44 |
| ATOM | 2478 | OD1 | ASP | A | 910 | -8.176 | 18.129 | 39.714 | 1.00 | 16.98 |
| ATOM | 2479 | OD2 | ASP | A | 910 | -8.560 | 18.266 | 41.818 | 1.00 | 18.64 |
| ATOM | 2480 | C | ASP | A | 910 | -6.988 | 15.627 | 38.823 | 1.00 | 16.08 |
| ATOM | 2481 | O | ASP | A | 910 | -5.919 | 15.398 | 39.396 | 1.00 | 16.42 |
| ATOM | 2482 | N | PRO | A | 911 | -7.052 | 16.125 | 37.587 | 1.00 | 16.59 |
| ATOM | 2483 | CA | PRO | A | 911 | -5.836 | 16.376 | 36.800 | 1.00 | 16.23 |
| ATOM | 2484 | CB | PRO | A | 911 | -6.374 | 16.942 | 35.478 | 1.00 | 18.88 |
| ATOM | 2485 | CG | PRO | A | 911 | -7.811 | 16.539 | 35.430 | 1.00 | 18.42 |

FIGURE 3 (Cont.)

|      | A    | B   | C   | D | E   | F      | G      | H      | I    | J     |
|------|------|-----|-----|---|-----|--------|--------|--------|------|-------|
| ATOM | 2486 | CD  | PRO | A | 911 | -8.275 | 16.503 | 36.853 | 1.00 | 17.96 |
| ATOM | 2487 | C   | PRO | A | 911 | -4.906 | 17.382 | 37.477 | 1.00 | 15.69 |
| ATOM | 2488 | O   | PRO | A | 911 | -3.689 | 17.257 | 37.351 | 1.00 | 15.72 |
| ATOM | 2489 | N   | LEU | A | 912 | -5.473 | 18.347 | 38.200 | 1.00 | 15.62 |
| ATOM | 2490 | CA  | LEU | A | 912 | -4.672 | 19.372 | 38.873 | 1.00 | 17.61 |
| ATOM | 2491 | CB  | LEU | A | 912 | -5.541 | 20.574 | 39.268 | 1.00 | 18.34 |
| ATOM | 2492 | CG  | LEU | A | 912 | -6.349 | 21.309 | 38.188 | 1.00 | 20.98 |
| ATOM | 2493 | CD1 | LEU | A | 912 | -7.103 | 22.488 | 38.797 | 1.00 | 21.22 |
| ATOM | 2494 | CD2 | LEU | A | 912 | -5.476 | 21.767 | 37.013 | 1.00 | 22.32 |
| ATOM | 2495 | C   | LEU | A | 912 | -3.909 | 18.834 | 40.092 | 1.00 | 16.82 |
| ATOM | 2496 | O   | LEU | A | 912 | -3.054 | 19.524 | 40.649 | 1.00 | 15.19 |
| ATOM | 2497 | N   | LYS | A | 913 | -4.217 | 17.603 | 40.496 | 1.00 | 14.45 |
| ATOM | 2498 | CA  | LYS | A | 913 | -3.555 | 16.984 | 41.641 | 1.00 | 14.70 |
| ATOM | 2499 | CB  | LYS | A | 913 | -4.551 | 16.179 | 42.477 | 1.00 | 16.23 |
| ATOM | 2500 | CG  | LYS | A | 913 | -5.490 | 17.033 | 43.311 | 1.00 | 18.87 |
| ATOM | 2501 | CD  | LYS | A | 913 | -5.387 | 16.692 | 44.788 | 1.00 | 23.21 |
| ATOM | 2502 | CE  | LYS | A | 913 | -6.698 | 16.960 | 45.508 | 1.00 | 23.71 |
| ATOM | 2503 | NZ  | LYS | A | 913 | -6.593 | 18.129 | 46.425 | 1.00 | 27.00 |
| ATOM | 2504 | C   | LYS | A | 913 | -2.384 | 16.103 | 41.210 | 1.00 | 15.78 |
| ATOM | 2505 | O   | LYS | A | 913 | -1.572 | 15.682 | 42.038 | 1.00 | 14.41 |
| ATOM | 2506 | N   | ARG | A | 914 | -2.299 | 15.833 | 39.910 | 1.00 | 12.98 |
| ATOM | 2507 | CA  | ARG | A | 914 | -1.207 | 15.030 | 39.371 | 1.00 | 13.17 |
| ATOM | 2508 | CB  | ARG | A | 914 | -1.511 | 14.596 | 37.935 | 1.00 | 12.91 |
| ATOM | 2509 | CG  | ARG | A | 914 | -2.772 | 13.756 | 37.814 | 1.00 | 13.89 |
| ATOM | 2510 | CD  | ARG | A | 914 | -3.174 | 13.420 | 36.388 | 1.00 | 14.38 |
| ATOM | 2511 | NE  | ARG | A | 914 | -4.573 | 13.003 | 36.349 | 1.00 | 14.52 |
| ATOM | 2512 | CZ  | ARG | A | 914 | -5.370 | 13.104 | 35.291 | 1.00 | 14.21 |
| ATOM | 2513 | NH1 | ARG | A | 914 | -4.912 | 13.591 | 34.146 | 1.00 | 14.53 |
| ATOM | 2514 | NH2 | ARG | A | 914 | -6.632 | 12.702 | 35.382 | 1.00 | 14.11 |
| ATOM | 2515 | C   | ARG | A | 914 | 0.087  | 15.841 | 39.426 | 1.00 | 13.01 |
| ATOM | 2516 | O   | ARG | A | 914 | 0.050  | 17.073 | 39.376 | 1.00 | 11.39 |
| ATOM | 2517 | N   | PRO | A | 915 | 1.222  | 15.165 | 39.566 | 1.00 | 12.86 |
| ATOM | 2518 | CA  | PRO | A | 915 | 2.513  | 15.855 | 39.518 | 1.00 | 15.12 |
| ATOM | 2519 | CB  | PRO | A | 915 | 3.514  | 14.758 | 39.881 | 1.00 | 12.81 |
| ATOM | 2520 | CG  | PRO | A | 915 | 2.833  | 13.472 | 39.510 | 1.00 | 13.66 |
| ATOM | 2521 | CD  | PRO | A | 915 | 1.373  | 13.711 | 39.766 | 1.00 | 14.23 |
| ATOM | 2522 | C   | PRO | A | 915 | 2.781  | 16.367 | 38.110 | 1.00 | 14.15 |
| ATOM | 2523 | O   | PRO | A | 915 | 2.224  | 15.833 | 37.154 | 1.00 | 13.56 |
| ATOM | 2524 | N   | THR | A | 916 | 3.602  | 17.403 | 37.989 | 1.00 | 14.04 |
| ATOM | 2525 | CA  | THR | A | 916 | 4.112  | 17.801 | 36.682 | 1.00 | 12.68 |
| ATOM | 2526 | CB  | THR | A | 916 | 4.548  | 19.271 | 36.678 | 1.00 | 13.42 |
| ATOM | 2527 | OG1 | THR | A | 916 | 5.646  | 19.437 | 37.585 | 1.00 | 13.01 |
| ATOM | 2528 | CG2 | THR | A | 916 | 3.456  | 20.168 | 37.246 | 1.00 | 15.51 |
| ATOM | 2529 | C   | THR | A | 916 | 5.316  | 16.923 | 36.403 | 1.00 | 12.18 |
| ATOM | 2530 | O   | THR | A | 916 | 5.816  | 16.243 | 37.301 | 1.00 | 12.42 |
| ATOM | 2531 | N   | PHE | A | 917 | 5.788  | 16.938 | 35.163 | 1.00 | 11.72 |
| ATOM | 2532 | CA  | PHE | A | 917 | 6.994  | 16.199 | 34.822 | 1.00 | 11.84 |
| ATOM | 2533 | CB  | PHE | A | 917 | 7.188  | 16.163 | 33.305 | 1.00 | 12.72 |
| ATOM | 2534 | CG  | PHE | A | 917 | 6.295  | 15.167 | 32.621 | 1.00 | 13.56 |
| ATOM | 2535 | CD1 | PHE | A | 917 | 6.392  | 13.813 | 32.928 | 1.00 | 13.05 |
| ATOM | 2536 | CE1 | PHE | A | 917 | 5.566  | 12.886 | 32.309 | 1.00 | 15.31 |
| ATOM | 2537 | CZ  | PHE | A | 917 | 4.613  | 13.310 | 31.381 | 1.00 | 13.32 |

FIGURE 3 (Cont.)

|      | A    | B   | C   | D | E   | F      | G      | H      | I    | J     |
|------|------|-----|-----|---|-----|--------|--------|--------|------|-------|
| ATOM | 2538 | CE2 | PHE | A | 917 | 4.493  | 14.649 | 31.077 | 1.00 | 13.84 |
| ATOM | 2539 | CD2 | PHE | A | 917 | 5.334  | 15.583 | 31.706 | 1.00 | 13.70 |
| ATOM | 2540 | C   | PHE | A | 917 | 8.219  | 16.759 | 35.533 | 1.00 | 12.27 |
| ATOM | 2541 | O   | PHE | A | 917 | 9.107  | 16.006 | 35.924 | 1.00 | 12.07 |
| ATOM | 2542 | N   | LYS | A | 918 | 8.253  | 18.077 | 35.716 | 1.00 | 12.27 |
| ATOM | 2543 | CA  | LYS | A | 918 | 9.318  | 18.703 | 36.492 | 1.00 | 15.28 |
| ATOM | 2544 | CB  | LYS | A | 918 | 9.106  | 20.214 | 36.585 | 1.00 | 18.77 |
| ATOM | 2545 | CG  | LYS | A | 918 | 9.273  | 20.945 | 35.272 | 1.00 | 25.35 |
| ATOM | 2546 | CD  | LYS | A | 918 | 10.281 | 22.085 | 35.384 | 1.00 | 28.46 |
| ATOM | 2547 | CE  | LYS | A | 918 | 10.977 | 22.352 | 34.049 | 1.00 | 30.86 |
| ATOM | 2548 | NZ  | LYS | A | 918 | 11.405 | 21.103 | 33.343 | 1.00 | 29.76 |
| ATOM | 2549 | C   | LYS | A | 918 | 9.383  | 18.095 | 37.895 | 1.00 | 15.23 |
| ATOM | 2550 | O   | LYS | A | 918 | 10.473 | 17.806 | 38.407 | 1.00 | 15.86 |
| ATOM | 2551 | N   | GLN | A | 919 | 8.213  | 17.896 | 38.501 | 1.00 | 12.96 |
| ATOM | 2552 | CA  | GLN | A | 919 | 8.129  | 17.346 | 39.849 | 1.00 | 13.15 |
| ATOM | 2553 | CB  | GLN | A | 919 | 6.725  | 17.524 | 40.429 | 1.00 | 14.94 |
| ATOM | 2554 | CG  | GLN | A | 919 | 6.425  | 18.955 | 40.853 | 1.00 | 15.94 |
| ATOM | 2555 | CD  | GLN | A | 919 | 4.964  | 19.191 | 41.203 | 1.00 | 18.37 |
| ATOM | 2556 | OE1 | GLN | A | 919 | 4.074  | 18.494 | 40.717 | 1.00 | 18.81 |
| ATOM | 2557 | NE2 | GLN | A | 919 | 4.717  | 20.181 | 42.049 | 1.00 | 19.39 |
| ATOM | 2558 | C   | GLN | A | 919 | 8.549  | 15.881 | 39.856 | 1.00 | 14.95 |
| ATOM | 2559 | O   | GLN | A | 919 | 9.299  | 15.462 | 40.743 | 1.00 | 14.53 |
| ATOM | 2560 | N   | ILE | A | 920 | 8.086  | 15.127 | 38.852 | 1.00 | 12.64 |
| ATOM | 2561 | CA  | ILE | A | 920 | 8.421  | 13.709 | 38.702 | 1.00 | 13.76 |
| ATOM | 2562 | CB  | ILE | A | 920 | 7.676  | 13.074 | 37.499 | 1.00 | 15.35 |
| ATOM | 2563 | CG1 | ILE | A | 920 | 6.166  | 13.014 | 37.767 | 1.00 | 15.89 |
| ATOM | 2564 | CD1 | ILE | A | 920 | 5.329  | 12.655 | 36.538 | 1.00 | 15.57 |
| ATOM | 2565 | CG2 | ILE | A | 920 | 8.233  | 11.676 | 37.196 | 1.00 | 14.14 |
| ATOM | 2566 | C   | ILE | A | 920 | 9.928  | 13.515 | 38.560 | 1.00 | 14.14 |
| ATOM | 2567 | O   | ILE | A | 920 | 10.505 | 12.639 | 39.209 | 1.00 | 13.07 |
| ATOM | 2568 | N   | VAL | A | 921 | 10.554 | 14.331 | 37.710 | 1.00 | 13.47 |
| ATOM | 2569 | CA  | VAL | A | 921 | 12.011 | 14.320 | 37.555 | 1.00 | 13.04 |
| ATOM | 2570 | CB  | VAL | A | 921 | 12.487 | 15.389 | 36.542 | 1.00 | 12.27 |
| ATOM | 2571 | CG1 | VAL | A | 921 | 14.005 | 15.595 | 36.607 | 1.00 | 11.84 |
| ATOM | 2572 | CG2 | VAL | A | 921 | 12.077 | 14.993 | 35.136 | 1.00 | 11.24 |
| ATOM | 2573 | C   | VAL | A | 921 | 12.705 | 14.519 | 38.906 | 1.00 | 14.85 |
| ATOM | 2574 | O   | VAL | A | 921 | 13.646 | 13.797 | 39.241 | 1.00 | 15.18 |
| ATOM | 2575 | N   | GLN | A | 922 | 12.229 | 15.493 | 39.676 | 1.00 | 13.46 |
| ATOM | 2576 | CA  | GLN | A | 922 | 12.803 | 15.775 | 40.992 | 1.00 | 18.94 |
| ATOM | 2577 | CB  | GLN | A | 922 | 12.213 | 17.066 | 41.568 | 1.00 | 22.54 |
| ATOM | 2578 | CG  | GLN | A | 922 | 13.234 | 17.983 | 42.240 | 1.00 | 30.27 |
| ATOM | 2579 | CD  | GLN | A | 922 | 13.923 | 18.952 | 41.277 | 1.00 | 33.07 |
| ATOM | 2580 | OE1 | GLN | A | 922 | 14.165 | 20.109 | 41.629 | 1.00 | 35.71 |
| ATOM | 2581 | NE2 | GLN | A | 922 | 14.254 | 18.480 | 40.076 | 1.00 | 34.55 |
| ATOM | 2582 | C   | GLN | A | 922 | 12.617 | 14.595 | 41.950 | 1.00 | 18.45 |
| ATOM | 2583 | O   | GLN | A | 922 | 13.532 | 14.249 | 42.707 | 1.00 | 17.61 |
| ATOM | 2584 | N   | LEU | A | 923 | 11.443 | 13.968 | 41.887 | 1.00 | 16.84 |
| ATOM | 2585 | CA  | LEU | A | 923 | 11.113 | 12.822 | 42.740 | 1.00 | 18.05 |
| ATOM | 2586 | CB  | LEU | A | 923 | 9.620  | 12.488 | 42.658 | 1.00 | 18.59 |
| ATOM | 2587 | CG  | LEU | A | 923 | 8.651  | 13.403 | 43.411 | 1.00 | 21.06 |
| ATOM | 2588 | CD1 | LEU | A | 923 | 7.242  | 13.258 | 42.855 | 1.00 | 21.98 |
| ATOM | 2589 | CD2 | LEU | A | 923 | 8.671  | 13.127 | 44.908 | 1.00 | 20.78 |

FIGURE 3 (Cont.)

| | A | B | C | D | E | F | G | H | I | J |
|---|---|---|---|---|---|---|---|---|---|---|
| ATOM | 2590 | C | LEU | A | 923 | 11.936 | 11.585 | 42.400 | 1.00 | 18.16 |
| ATOM | 2591 | O | LEU | A | 923 | 12.409 | 10.887 | 43.295 | 1.00 | 16.32 |
| ATOM | 2592 | N | ILE | A | 924 | 12.106 | 11.312 | 41.109 | 1.00 | 17.42 |
| ATOM | 2593 | CA | ILE | A | 924 | 12.902 | 10.162 | 40.688 | 1.00 | 17.42 |
| ATOM | 2594 | CB | ILE | A | 924 | 12.648 | 9.809 | 39.206 | 1.00 | 19.23 |
| ATOM | 2595 | CG1 | ILE | A | 924 | 11.195 | 9.368 | 39.012 | 1.00 | 19.74 |
| ATOM | 2596 | CD1 | ILE | A | 924 | 10.828 | 9.058 | 37.570 | 1.00 | 17.84 |
| ATOM | 2597 | CG2 | ILE | A | 924 | 13.584 | 8.689 | 38.747 | 1.00 | 19.15 |
| ATOM | 2598 | C | ILE | A | 924 | 14.386 | 10.392 | 40.979 | 1.00 | 18.42 |
| ATOM | 2599 | O | ILE | A | 924 | 15.103 | 9.456 | 41.339 | 1.00 | 17.22 |
| ATOM | 2600 | N | GLU | A | 925 | 14.833 | 11.640 | 40.848 | 1.00 | 18.58 |
| ATOM | 2601 | CA | GLU | A | 925 | 16.192 | 12.014 | 41.229 | 1.00 | 20.74 |
| ATOM | 2602 | CB | GLU | A | 925 | 16.424 | 13.510 | 41.003 | 1.00 | 23.19 |
| ATOM | 2603 | CG | GLU | A | 925 | 17.186 | 13.824 | 39.727 | 1.00 | 28.22 |
| ATOM | 2604 | CD | GLU | A | 925 | 16.960 | 15.241 | 39.221 | 1.00 | 30.50 |
| ATOM | 2605 | OE1 | GLU | A | 925 | 16.524 | 16.112 | 40.010 | 1.00 | 33.46 |
| ATOM | 2606 | OE2 | GLU | A | 925 | 17.227 | 15.486 | 38.027 | 1.00 | 30.60 |
| ATOM | 2607 | C | GLU | A | 925 | 16.477 | 11.648 | 42.685 | 1.00 | 21.51 |
| ATOM | 2608 | O | GLU | A | 925 | 17.537 | 11.097 | 42.996 | 1.00 | 21.41 |
| ATOM | 2609 | N | LYS | A | 926 | 15.521 | 11.948 | 43.564 | 1.00 | 20.77 |
| ATOM | 2610 | CA | LYS | A | 926 | 15.620 | 11.615 | 44.985 | 1.00 | 23.02 |
| ATOM | 2611 | CB | LYS | A | 926 | 14.459 | 12.252 | 45.759 | 1.00 | 24.95 |
| ATOM | 2612 | CG | LYS | A | 926 | 14.611 | 12.234 | 47.277 | 1.00 | 28.22 |
| ATOM | 2613 | CD | LYS | A | 926 | 13.426 | 12.915 | 47.951 | 1.00 | 30.26 |
| ATOM | 2614 | CE | LYS | A | 926 | 13.373 | 12.604 | 49.442 | 1.00 | 31.85 |
| ATOM | 2615 | NZ | LYS | A | 926 | 12.618 | 11.346 | 49.716 | 1.00 | 32.11 |
| ATOM | 2616 | C | LYS | A | 926 | 15.637 | 10.097 | 45.192 | 1.00 | 22.30 |
| ATOM | 2617 | O | LYS | A | 926 | 16.396 | 9.582 | 46.014 | 1.00 | 20.26 |
| ATOM | 2618 | N | GLN | A | 927 | 14.803 | 9.396 | 44.429 | 1.00 | 22.06 |
| ATOM | 2619 | CA | GLN | A | 927 | 14.707 | 7.941 | 44.488 | 1.00 | 23.53 |
| ATOM | 2620 | CB | GLN | A | 927 | 13.568 | 7.466 | 43.599 | 1.00 | 26.84 |
| ATOM | 2621 | CG | GLN | A | 927 | 12.303 | 7.126 | 44.338 | 1.00 | 30.15 |
| ATOM | 2622 | CD | GLN | A | 927 | 11.413 | 6.229 | 43.518 | 1.00 | 32.30 |
| ATOM | 2623 | OE1 | GLN | A | 927 | 11.767 | 5.081 | 43.245 | 1.00 | 32.67 |
| ATOM | 2624 | NE2 | GLN | A | 927 | 10.263 | 6.750 | 43.103 | 1.00 | 34.12 |
| ATOM | 2625 | C | GLN | A | 927 | 15.999 | 7.241 | 44.069 | 1.00 | 24.62 |
| ATOM | 2626 | O | GLN | A | 927 | 16.449 | 6.315 | 44.746 | 1.00 | 24.36 |
| ATOM | 2627 | N | ILE | A | 928 | 16.579 | 7.680 | 42.951 | 1.00 | 23.48 |
| ATOM | 2628 | CA | ILE | A | 928 | 17.840 | 7.131 | 42.451 | 1.00 | 24.54 |
| ATOM | 2629 | CB | ILE | A | 928 | 18.197 | 7.729 | 41.063 | 1.00 | 25.84 |
| ATOM | 2630 | CG1 | ILE | A | 928 | 17.248 | 7.198 | 39.988 | 1.00 | 26.87 |
| ATOM | 2631 | CD1 | ILE | A | 928 | 17.209 | 8.056 | 38.731 | 1.00 | 28.06 |
| ATOM | 2632 | CG2 | ILE | A | 928 | 19.652 | 7.426 | 40.687 | 1.00 | 28.03 |
| ATOM | 2633 | C | ILE | A | 928 | 18.960 | 7.390 | 43.453 | 1.00 | 24.55 |
| ATOM | 2634 | O | ILE | A | 928 | 19.743 | 6.488 | 43.763 | 1.00 | 23.57 |
| ATOM | 2635 | N | SER | A | 929 | 19.016 | 8.623 | 43.957 | 1.00 | 25.66 |
| ATOM | 2636 | CA | SER | A | 929 | 19.986 | 9.026 | 44.975 | 1.00 | 26.56 |
| ATOM | 2637 | CB | SER | A | 929 | 19.790 | 10.502 | 45.331 | 1.00 | 26.67 |
| ATOM | 2638 | OG | SER | A | 929 | 20.828 | 10.967 | 46.175 | 1.00 | 28.72 |
| ATOM | 2639 | C | SER | A | 929 | 19.893 | 8.162 | 46.236 | 1.00 | 28.11 |
| ATOM | 2640 | O | SER | A | 929 | 20.912 | 7.721 | 46.772 | 1.00 | 27.56 |
| ATOM | 2641 | N | GLU | A | 930 | 18.668 | 7.923 | 46.700 | 1.00 | 29.48 |

FIGURE 3 (Cont.)

| | A | B | C | D | E | F | G | H | I | J |
|---|---|---|---|---|---|---|---|---|---|---|
| ATOM | 2642 | CA | GLU | A | 930 | 18.426 | 7.102 | 47.885 | 1.00 | 31.79 |
| ATOM | 2643 | CB | GLU | A | 930 | 16.995 | 7.304 | 48.388 | 1.00 | 34.00 |
| ATOM | 2644 | CG | GLU | A | 930 | 16.889 | 8.186 | 49.622 | 1.00 | 37.06 |
| ATOM | 2645 | CD | GLU | A | 930 | 15.636 | 9.046 | 49.632 | 1.00 | 38.68 |
| ATOM | 2646 | OE1 | GLU | A | 930 | 14.534 | 8.512 | 49.370 | 1.00 | 39.05 |
| ATOM | 2647 | OE2 | GLU | A | 930 | 15.754 | 10.260 | 49.911 | 1.00 | 39.48 |
| ATOM | 2648 | C | GLU | A | 930 | 18.681 | 5.616 | 47.620 | 1.00 | 32.02 |
| ATOM | 2649 | O | GLU | A | 930 | 18.981 | 4.856 | 48.544 | 1.00 | 31.44 |
| ATOM | 2650 | N | SER | A | 931 | 18.563 | 5.215 | 46.356 | 1.00 | 31.54 |
| ATOM | 2651 | CA | SER | A | 931 | 18.744 | 3.822 | 45.949 | 1.00 | 33.22 |
| ATOM | 2652 | CB | SER | A | 931 | 18.077 | 3.572 | 44.594 | 1.00 | 34.69 |
| ATOM | 2653 | OG | SER | A | 931 | 16.686 | 3.355 | 44.747 | 1.00 | 36.99 |
| ATOM | 2654 | C | SER | A | 931 | 20.206 | 3.385 | 45.885 | 1.00 | 33.12 |
| ATOM | 2655 | O | SER | A | 931 | 20.487 | 2.187 | 45.827 | 1.00 | 32.40 |
| ATOM | 2656 | N | THR | A | 932 | 21.129 | 4.349 | 45.886 | 1.00 | 32.64 |
| ATOM | 2657 | CA | THR | A | 932 | 22.560 | 4.044 | 45.835 | 1.00 | 33.21 |
| ATOM | 2658 | CB | THR | A | 932 | 23.426 | 5.328 | 45.737 | 1.00 | 34.58 |
| ATOM | 2659 | OG1 | THR | A | 932 | 23.148 | 6.193 | 46.846 | 1.00 | 36.24 |
| ATOM | 2660 | CG2 | THR | A | 932 | 23.033 | 6.163 | 44.520 | 1.00 | 34.49 |
| ATOM | 2661 | C | THR | A | 932 | 22.973 | 3.200 | 47.040 | 1.00 | 31.93 |
| ATOM | 2662 | O | THR | A | 932 | 22.680 | 3.551 | 48.187 | 1.00 | 30.67 |
| ATOM | 2663 | N | ASN | A | 933 | 23.642 | 2.083 | 46.756 | 1.00 | 31.72 |
| ATOM | 2664 | CA | ASN | A | 933 | 23.996 | 1.071 | 47.756 | 1.00 | 31.73 |
| ATOM | 2665 | CB | ASN | A | 933 | 24.927 | 1.647 | 48.837 | 1.00 | 31.64 |
| ATOM | 2666 | CG | ASN | A | 933 | 26.354 | 1.813 | 48.352 | 1.00 | 31.87 |
| ATOM | 2667 | OD1 | ASN | A | 933 | 26.609 | 2.488 | 47.354 | 1.00 | 31.22 |
| ATOM | 2668 | ND2 | ASN | A | 933 | 27.295 | 1.197 | 49.060 | 1.00 | 31.27 |
| ATOM | 2669 | C | ASN | A | 933 | 22.778 | 0.380 | 48.385 | 1.00 | 31.44 |
| ATOM | 2670 | O | ASN | A | 933 | 22.843 | -0.086 | 49.525 | 1.00 | 31.65 |
| ATOM | 2671 | N | HIS | A | 934 | 21.678 | 0.318 | 47.635 | 1.00 | 29.95 |
| ATOM | 2672 | CA | HIS | A | 934 | 20.467 | -0.368 | 48.085 | 1.00 | 30.43 |
| ATOM | 2673 | CB | HIS | A | 934 | 19.413 | 0.640 | 48.556 | 1.00 | 31.57 |
| ATOM | 2674 | CG | HIS | A | 934 | 19.664 | 1.183 | 49.928 | 1.00 | 33.08 |
| ATOM | 2675 | ND1 | HIS | A | 934 | 20.239 | 0.434 | 50.933 | 1.00 | 33.17 |
| ATOM | 2676 | CE1 | HIS | A | 934 | 20.336 | 1.169 | 52.026 | 1.00 | 34.56 |
| ATOM | 2677 | CE1 | HIS | A | 934 | 20.415 | 1.198 | 51.997 | 1.00 | 34.56 |
| ATOM | 2678 | NE2 | HIS | A | 934 | 19.842 | 2.366 | 51.768 | 1.00 | 34.54 |
| ATOM | 2679 | CD2 | HIS | A | 934 | 19.413 | 2.401 | 50.463 | 1.00 | 33.53 |
| ATOM | 2680 | C | HIS | A | 934 | 19.876 | -1.286 | 47.015 | 1.00 | 30.26 |
| ATOM | 2681 | O | HIS | A | 934 | 18.863 | -1.946 | 47.251 | 1.00 | 29.70 |
| ATOM | 2682 | N | ILE | A | 935 | 20.509 | -1.325 | 45.846 | 1.00 | 30.07 |
| ATOM | 2683 | CA | ILE | A | 935 | 20.045 | -2.173 | 44.749 | 1.00 | 31.14 |
| ATOM | 2684 | CB | ILE | A | 935 | 20.283 | -1.499 | 43.373 | 1.00 | 32.06 |
| ATOM | 2685 | CG1 | ILE | A | 935 | 19.829 | -0.029 | 43.382 | 1.00 | 33.15 |
| ATOM | 2686 | CD1 | ILE | A | 935 | 18.344 | 0.204 | 43.080 | 1.00 | 33.81 |
| ATOM | 2687 | CG2 | ILE | A | 935 | 19.608 | -2.300 | 42.264 | 1.00 | 33.19 |
| ATOM | 2688 | C | ILE | A | 935 | 20.725 | -3.541 | 44.795 | 1.00 | 30.91 |
| ATOM | 2689 | O | ILE | A | 935 | 21.939 | -3.635 | 44.974 | 1.00 | 31.35 |
| ATOM | 2690 | O | HOH | W | 928 | 4.035 | 18.393 | 33.017 | 1.00 | 26.43 |
| ATOM | 2691 | O | HOH | W | 929 | 1.480 | 18.826 | 33.898 | 1.00 | 29.06 |
| ATOM | 2692 | O | HOH | W | 930 | 0.237 | 17.146 | 35.707 | 1.00 | 24.87 |
| ATOM | 2693 | O | HOH | W | 931 | -1.288 | 18.453 | 37.535 | 1.00 | 26.98 |

FIGURE 3 (Cont.)

|      | A    | B | C   | D | E   | F       | G       | H      | I    | J     |
|------|------|---|-----|---|-----|---------|---------|--------|------|-------|
| ATOM | 2694 | O | HOH | W | 932 | 6.542   | 19.896  | 33.788 | 1.00 | 24.11 |
| ATOM | 2695 | O | HOH | W | 933 | 2.976   | 17.381  | 30.660 | 1.00 | 25.51 |
| ATOM | 2696 | O | HOH | W | 934 | 3.342   | 17.268  | 27.889 | 1.00 | 23.00 |
| ATOM | 2697 | O | HOH | W | 935 | -5.170  | 11.125  | 27.642 | 1.00 | 29.33 |
| ATOM | 2698 | O | HOH | W | 936 | 0.331   | 10.703  | 26.128 | 1.00 | 17.82 |
| ATOM | 2699 | O | HOH | W | 937 | -0.656  | 6.475   | 24.714 | 1.00 | 22.82 |
| ATOM | 2700 | O | HOH | W | 938 | -2.818  | 10.627  | 26.841 | 1.00 | 35.31 |
| ATOM | 2701 | O | HOH | W | 939 | -2.277  | 13.304  | 26.515 | 1.00 | 26.86 |
| ATOM | 2702 | O | HOH | W | 940 | -5.557  | 4.315   | 31.949 | 1.00 | 22.93 |
| ATOM | 2703 | O | HOH | W | 941 | -7.643  | 4.731   | 30.474 | 1.00 | 25.68 |
| ATOM | 2704 | O | HOH | W | 942 | -4.500  | 2.445   | 36.480 | 1.00 | 20.45 |
| ATOM | 2705 | O | HOH | W | 943 | -4.581  | 6.670   | 41.493 | 1.00 | 31.18 |
| ATOM | 2706 | O | HOH | W | 944 | -4.120  | 1.971   | 44.001 | 1.00 | 40.19 |
| ATOM | 2707 | O | HOH | W | 945 | -0.588  | 0.902   | 47.341 | 1.00 | 43.55 |
| ATOM | 2708 | O | HOH | W | 946 | 3.349   | -0.528  | 46.494 | 1.00 | 30.14 |
| ATOM | 2709 | O | HOH | W | 947 | 5.020   | -1.816  | 44.718 | 1.00 | 29.61 |
| ATOM | 2710 | O | HOH | W | 948 | -0.867  | -2.896  | 44.469 | 1.00 | 27.04 |
| ATOM | 2711 | O | HOH | W | 949 | 6.593   | -6.515  | 37.784 | 1.00 | 31.90 |
| ATOM | 2712 | O | HOH | W | 950 | 14.435  | 1.933   | 15.849 | 1.00 | 35.12 |
| ATOM | 2713 | O | HOH | W | 951 | 15.173  | 4.355   | 15.109 | 1.00 | 27.41 |
| ATOM | 2714 | O | HOH | W | 952 | 14.276  | 6.777   | 15.285 | 1.00 | 29.66 |
| ATOM | 2715 | O | HOH | W | 953 | 12.124  | 7.869   | 13.779 | 1.00 | 35.71 |
| ATOM | 2716 | O | HOH | W | 954 | 10.379  | 9.850   | 14.499 | 1.00 | 59.65 |
| ATOM | 2717 | O | HOH | W | 955 | 9.151   | 11.593  | 16.555 | 1.00 | 39.60 |
| ATOM | 2718 | O | HOH | W | 956 | 7.016   | 12.862  | 15.690 | 1.00 | 46.09 |
| ATOM | 2719 | O | HOH | W | 957 | 4.731   | 14.130  | 16.326 | 1.00 | 35.47 |
| ATOM | 2720 | O | HOH | W | 958 | 3.850   | 12.367  | 14.447 | 1.00 | 30.33 |
| ATOM | 2721 | O | HOH | W | 959 | 5.083   | 8.938   | 13.342 | 1.00 | 25.99 |
| ATOM | 2722 | O | HOH | W | 960 | 1.383   | 8.858   | 14.448 | 1.00 | 39.43 |
| ATOM | 2723 | O | HOH | W | 961 | -0.600  | 6.683   | 15.297 | 1.00 | 51.81 |
| ATOM | 2724 | O | HOH | W | 963 | 1.691   | -0.966  | 23.181 | 1.00 | 24.40 |
| ATOM | 2725 | O | HOH | W | 964 | 1.161   | -3.068  | 25.024 | 1.00 | 26.92 |
| ATOM | 2726 | O | HOH | W | 965 | 2.456   | -2.557  | 27.269 | 1.00 | 20.79 |
| ATOM | 2727 | O | HOH | W | 966 | 3.439   | 0.566   | 24.725 | 1.00 | 17.74 |
| ATOM | 2728 | O | HOH | W | 967 | -1.660  | 9.743   | 12.063 | 1.00 | 32.49 |
| ATOM | 2729 | O | HOH | W | 968 | -1.261  | 10.360  | 4.848  | 1.00 | 18.87 |
| ATOM | 2730 | O | HOH | W | 969 | -0.810  | 13.026  | 5.608  | 1.00 | 24.75 |
| ATOM | 2731 | O | HOH | W | 970 | -3.629  | 9.250   | 3.441  | 1.00 | 39.78 |
| ATOM | 2732 | O | HOH | W | 971 | 0.115   | 8.574   | 3.138  | 1.00 | 31.21 |
| ATOM | 2733 | O | HOH | W | 972 | 1.518   | 4.860   | 8.887  | 1.00 | 24.92 |
| ATOM | 2734 | O | HOH | W | 973 | -5.907  | 0.682   | 24.721 | 1.00 | 23.84 |
| ATOM | 2735 | O | HOH | W | 974 | -6.372  | -2.188  | 24.443 | 1.00 | 27.27 |
| ATOM | 2736 | O | HOH | W | 975 | -5.897  | -7.040  | 35.202 | 1.00 | 32.18 |
| ATOM | 2737 | O | HOH | W | 976 | 4.266   | 11.629  | 42.794 | 1.00 | 38.84 |
| ATOM | 2738 | O | HOH | W | 977 | 7.181   | 8.481   | 45.324 | 1.00 | 35.08 |
| ATOM | 2739 | O | HOH | W | 978 | -2.566  | 15.837  | 8.201  | 1.00 | 28.26 |
| ATOM | 2740 | O | HOH | W | 979 | -2.134  | 17.385  | 5.895  | 1.00 | 31.28 |
| ATOM | 2741 | O | HOH | W | 980 | -0.696  | 17.382  | 10.186 | 1.00 | 36.04 |
| ATOM | 2742 | O | HOH | W | 981 | -0.330  | 10.787  | 14.240 | 1.00 | 37.62 |
| ATOM | 2743 | O | HOH | W | 982 | 0.654   | 21.769  | 17.118 | 1.00 | 29.64 |
| ATOM | 2744 | O | HOH | W | 983 | 1.130   | 19.389  | 15.630 | 1.00 | 24.79 |
| ATOM | 2745 | O | HOH | W | 984 | -1.203  | 18.960  | 14.304 | 1.00 | 40.51 |

FIGURE 3 (Cont.)

| | A | B | C | D | E | F | G | H | I | J |
|---|---|---|---|---|---|---|---|---|---|---|
| ATOM | 2746 | O | HOH | W | 985 | 3.230 | 27.861 | 22.916 | 1.00 | 42.41 |
| ATOM | 2747 | O | HOH | W | 987 | -3.054 | 28.846 | 17.861 | 1.00 | 30.49 |
| ATOM | 2748 | O | HOH | W | 988 | -8.147 | 22.157 | 27.494 | 1.00 | 47.61 |
| ATOM | 2749 | O | HOH | W | 989 | -7.817 | 22.840 | 20.075 | 1.00 | 44.48 |
| ATOM | 2750 | O | HOH | W | 990 | -7.021 | 20.249 | 25.033 | 1.00 | 55.27 |
| ATOM | 2751 | O | HOH | W | 991 | -2.662 | 28.174 | 15.296 | 1.00 | 37.85 |
| ATOM | 2752 | O | HOH | W | 992 | -2.202 | 21.533 | 10.231 | 1.00 | 41.54 |
| ATOM | 2753 | O | HOH | W | 993 | -0.388 | 19.844 | 9.076 | 1.00 | 32.06 |
| ATOM | 2754 | O | HOH | W | 994 | -1.365 | 19.876 | 6.530 | 1.00 | 38.40 |
| ATOM | 2755 | O | HOH | W | 995 | -2.172 | 22.166 | 4.730 | 1.00 | 34.76 |
| ATOM | 2756 | O | HOH | W | 996 | 3.412 | 22.729 | 7.150 | 1.00 | 21.20 |
| ATOM | 2757 | O | HOH | W | 997 | -4.176 | 31.082 | 9.630 | 1.00 | 49.20 |
| ATOM | 2758 | O | HOH | W | 998 | 9.294 | 25.563 | 13.530 | 1.00 | 23.26 |
| ATOM | 2759 | O | HOH | W | 999 | 11.070 | 26.856 | 14.853 | 1.00 | 42.41 |
| ATOM | 2760 | O | HOH | W1000 | | 14.045 | 29.013 | 5.592 | 1.00 | 51.97 |
| ATOM | 2761 | O | HOH | W1001 | | 12.554 | 25.142 | 11.372 | 1.00 | 36.07 |
| ATOM | 2762 | O | HOH | W1002 | | 13.473 | 26.911 | 12.928 | 1.00 | 54.57 |
| ATOM | 2763 | O | HOH | W1003 | | 19.642 | 29.065 | 9.401 | 1.00 | 54.83 |
| ATOM | 2764 | O | HOH | W1004 | | 16.678 | 26.516 | 14.094 | 1.00 | 57.84 |
| ATOM | 2765 | O | HOH | W1005 | | 21.518 | 21.950 | 4.875 | 1.00 | 26.83 |
| ATOM | 2766 | O | HOH | W1006 | | 16.789 | 18.216 | 0.254 | 1.00 | 22.19 |
| ATOM | 2767 | O | HOH | W1007 | | 16.837 | 16.507 | -1.959 | 1.00 | 36.07 |
| ATOM | 2768 | O | HOH | W1008 | | 14.095 | 10.474 | -2.683 | 1.00 | 33.28 |
| ATOM | 2769 | O | HOH | W1009 | | 16.955 | 9.287 | -1.677 | 1.00 | 39.52 |
| ATOM | 2770 | O | HOH | W1010 | | 24.686 | 7.717 | -1.869 | 1.00 | 58.48 |
| ATOM | 2771 | O | HOH | W1011 | | 21.766 | 1.681 | 4.019 | 1.00 | 48.79 |
| ATOM | 2772 | O | HOH | W1012 | | 19.354 | -1.676 | 6.944 | 1.00 | 29.21 |
| ATOM | 2773 | O | HOH | W1013 | | 13.015 | -4.062 | 4.684 | 1.00 | 33.33 |
| ATOM | 2774 | O | HOH | W1014 | | 9.411 | -1.730 | 2.858 | 1.00 | 37.16 |
| ATOM | 2775 | O | HOH | W1015 | | 0.010 | 4.892 | 11.153 | 1.00 | 36.21 |
| ATOM | 2776 | O | HOH | W1016 | | -1.461 | 2.697 | 10.549 | 1.00 | 37.63 |
| ATOM | 2777 | O | HOH | W1018 | | 6.563 | 4.679 | 1.807 | 1.00 | 34.66 |
| ATOM | 2778 | O | HOH | W1019 | | 4.775 | 2.837 | 2.055 | 1.00 | 31.23 |
| ATOM | 2779 | O | HOH | W1020 | | 28.292 | 12.883 | 9.234 | 1.00 | 47.83 |
| ATOM | 2780 | O | HOH | W1021 | | 38.288 | 13.630 | 9.340 | 1.00 | 42.92 |
| ATOM | 2781 | O | HOH | W1022 | | 25.925 | 5.828 | 12.374 | 1.00 | 36.55 |
| ATOM | 2782 | O | HOH | W1023 | | 21.173 | 8.524 | 14.013 | 1.00 | 27.85 |
| ATOM | 2783 | O | HOH | W1024 | | 6.792 | 11.186 | 1.762 | 1.00 | 19.22 |
| ATOM | 2784 | O | HOH | W1025 | | -1.106 | 11.703 | -5.400 | 1.00 | 42.41 |
| ATOM | 2785 | O | HOH | W1026 | | 3.420 | 19.478 | 0.807 | 1.00 | 27.44 |
| ATOM | 2786 | O | HOH | W1027 | | 12.826 | 18.252 | 18.289 | 1.00 | 36.01 |
| ATOM | 2787 | O | HOH | W1028 | | 14.952 | 17.593 | 17.217 | 1.00 | 29.57 |
| ATOM | 2788 | O | HOH | W1029 | | 15.760 | 22.942 | 16.053 | 1.00 | 37.45 |
| ATOM | 2789 | O | HOH | W1030 | | 18.221 | 22.655 | 19.977 | 1.00 | 35.43 |
| ATOM | 2790 | O | HOH | W1031 | | 21.151 | 15.187 | 18.012 | 1.00 | 41.98 |
| ATOM | 2791 | O | HOH | W1032 | | 21.025 | 15.172 | 21.756 | 1.00 | 32.22 |
| ATOM | 2792 | O | HOH | W1033 | | 20.869 | 12.732 | 20.832 | 1.00 | 29.73 |
| ATOM | 2793 | O | HOH | W1034 | | 19.692 | 17.103 | 26.369 | 1.00 | 28.10 |
| ATOM | 2794 | O | HOH | W1035 | | 17.191 | 20.092 | 29.973 | 1.00 | 51.01 |
| ATOM | 2795 | O | HOH | W1036 | | 14.073 | 17.917 | 31.013 | 1.00 | 27.72 |
| ATOM | 2796 | O | HOH | W1037 | | 10.958 | 12.690 | 18.234 | 1.00 | 34.05 |
| ATOM | 2797 | O | HOH | W1038 | | 21.377 | 4.040 | 17.413 | 1.00 | 39.60 |

FIGURE 3 (Cont.)

| | A | B | C | D | E | F | G | H | I | J |
|---|---|---|---|---|---|---|---|---|---|---|
| ATOM | 2798 | O | HOH | W1039 | | 13.250 | -3.139 | 20.737 | 1.00 | 26.91 |
| ATOM | 2799 | O | HOH | W1040 | | 6.744 | -3.146 | 20.203 | 1.00 | 38.14 |
| ATOM | 2800 | O | HOH | W1041 | | 16.195 | -12.075 | 27.722 | 1.00 | 35.91 |
| ATOM | 2801 | O | HOH | W1042 | | 12.052 | -12.588 | 27.621 | 1.00 | 33.58 |
| ATOM | 2802 | O | HOH | W1043 | | 19.016 | -9.163 | 35.777 | 1.00 | 32.49 |
| ATOM | 2803 | O | HOH | W1044 | | 26.075 | -6.113 | 25.219 | 1.00 | 35.31 |
| ATOM | 2804 | O | HOH | W1045 | | 23.430 | -1.536 | 25.518 | 1.00 | 42.56 |
| ATOM | 2805 | O | HOH | W1046 | | 24.207 | -9.322 | 31.635 | 1.00 | 39.93 |
| ATOM | 2806 | O | HOH | W1047 | | 17.235 | -6.127 | 39.571 | 1.00 | 34.02 |
| ATOM | 2807 | O | HOH | W1048 | | 19.475 | 7.532 | 34.187 | 1.00 | 41.76 |
| ATOM | 2808 | O | HOH | W1049 | | 20.349 | 3.515 | 31.025 | 1.00 | 47.91 |
| ATOM | 2809 | O | HOH | W1050 | | 19.865 | 9.963 | 32.620 | 1.00 | 35.64 |
| ATOM | 2810 | O | HOH | W1051 | | 19.783 | 10.432 | 29.589 | 1.00 | 37.56 |
| ATOM | 2811 | O | HOH | W1052 | | 20.367 | 13.924 | 34.594 | 1.00 | 43.55 |
| ATOM | 2812 | O | HOH | W1053 | | 8.735 | 20.953 | 32.115 | 1.00 | 28.16 |
| ATOM | 2813 | O | HOH | W1054 | | 8.068 | 23.585 | 32.161 | 1.00 | 47.20 |
| ATOM | 2814 | O | HOH | W1055 | | 13.179 | 24.074 | 28.048 | 1.00 | 42.43 |
| ATOM | 2815 | O | HOH | W1056 | | -2.398 | 8.569 | 25.279 | 1.00 | 27.52 |
| ATOM | 2816 | O | HOH | W1057 | | 2.216 | -1.906 | 20.483 | 1.00 | 32.54 |
| ATOM | 2817 | O | HOH | W1059 | | -6.654 | -1.224 | 16.440 | 1.00 | 32.52 |
| ATOM | 2818 | O | HOH | W1060 | | 0.986 | -5.543 | 22.596 | 1.00 | 38.04 |
| ATOM | 2819 | O | HOH | W1061 | | -6.357 | 17.008 | 31.808 | 1.00 | 38.24 |
| ATOM | 2820 | O | HOH | W1062 | | -4.331 | -7.254 | 27.797 | 1.00 | 42.03 |
| ATOM | 2821 | O | HOH | W1063 | | -11.189 | 8.387 | 38.082 | 1.00 | 38.62 |
| ATOM | 2822 | O | HOH | W1064 | | -8.659 | 0.121 | 42.044 | 1.00 | 34.00 |
| ATOM | 2823 | O | HOH | W1065 | | -2.537 | -6.136 | 37.210 | 1.00 | 41.97 |
| ATOM | 2824 | O | HOH | W1066 | | 9.436 | -1.117 | 47.701 | 1.00 | 39.35 |
| ATOM | 2825 | O | HOH | W1067 | | 3.188 | 2.335 | 47.115 | 1.00 | 40.75 |
| ATOM | 2826 | O | HOH | W1068 | | 0.716 | 7.883 | 45.823 | 1.00 | 42.53 |
| ATOM | 2827 | O | HOH | W1069 | | -8.142 | 9.826 | 42.294 | 1.00 | 31.67 |
| ATOM | 2828 | O | HOH | W1070 | | -6.929 | 7.676 | 42.076 | 1.00 | 36.41 |
| ATOM | 2829 | O | HOH | W1071 | | 6.070 | 22.006 | 38.218 | 1.00 | 37.69 |
| ATOM | 2830 | O | HOH | W1072 | | 12.878 | 18.929 | 37.675 | 1.00 | 33.23 |
| ATOM | 2831 | O | HOH | W1073 | | 14.219 | 17.786 | 33.778 | 1.00 | 39.97 |
| ATOM | 2832 | O | HOH | W1074 | | 8.977 | 16.822 | 43.324 | 1.00 | 44.20 |
| ATOM | 2833 | O | HOH | W1075 | | 11.593 | -7.363 | 42.326 | 1.00 | 59.42 |
| ATOM | 2834 | O | HOH | W1076 | | 13.137 | -7.673 | 45.252 | 1.00 | 50.37 |
| ATOM | 2835 | O | HOH | W1077 | | 9.917 | -8.524 | 45.281 | 1.00 | 56.39 |
| ATOM | 2836 | O | HOH | W1078 | | 7.217 | -13.967 | 29.220 | 1.00 | 51.16 |
| ATOM | 2837 | O | HOH | W1079 | | 21.076 | -12.604 | 32.147 | 1.00 | 42.78 |
| ATOM | 2838 | O | HOH | W1080 | | 20.534 | -15.400 | 39.384 | 1.00 | 62.43 |
| ATOM | 2839 | O | HOH | W1081 | | 23.545 | -16.326 | 23.507 | 1.00 | 63.12 |
| ATOM | 2840 | O | HOH | W1082 | | 16.343 | -1.451 | 14.878 | 1.00 | 45.15 |
| ATOM | 2841 | O | HOH | W1083 | | 9.209 | -0.147 | 16.839 | 1.00 | 41.02 |
| ATOM | 2842 | O | HOH | W1084 | | 11.560 | -3.397 | 12.960 | 1.00 | 41.62 |
| ATOM | 2843 | O | HOH | W1085 | | -7.885 | 16.664 | 20.033 | 1.00 | 58.90 |
| ATOM | 2844 | O | HOH | W1086 | | 21.695 | -1.562 | 34.976 | 1.00 | 46.96 |
| ATOM | 2845 | O | HOH | W1087 | | -1.120 | 0.377 | 4.646 | 1.00 | 56.35 |
| ATOM | 2846 | O | HOH | W1089 | | -9.753 | 12.028 | 21.565 | 1.00 | 51.86 |
| ATOM | 2847 | O | HOH | W1090 | | -3.465 | 9.534 | 20.963 | 1.00 | 49.57 |
| ATOM | 2848 | O | HOH | W1091 | | 1.851 | 6.787 | 17.773 | 1.00 | 37.93 |
| ATOM | 2849 | O | HOH | W1092 | | -0.179 | 7.378 | 12.518 | 1.00 | 44.44 |
| ATOM | 2850 | O | HOH | W1093 | | -4.829 | 3.142 | 10.558 | 1.00 | 51.22 |
| ATOM | 2851 | O | HOH | W1094 | | -6.523 | 4.061 | 8.478 | 1.00 | 56.13 |
| ATOM | 2852 | O | HOH | W1095 | | -5.236 | 5.882 | 4.388 | 1.00 | 44.24 |
| ATOM | 2853 | O | HOH | W1096 | | 14.281 | -7.242 | 18.612 | 1.00 | 50.39 |
| ATOM | 2854 | O | HOH | W1097 | | -2.678 | 21.200 | 15.625 | 1.00 | 44.19 |

FIGURE 3 (Cont.)

|  | A | B | C | D E | F | G | H | I | J |
|---|---|---|---|---|---|---|---|---|---|
| ATOM | 2855 | O | HOH | W1098 | -0.860 | 28.329 | 7.768 | 1.00 | 48.82 |
| ATOM | 2856 | O | HOH | W1099 | -0.337 | 29.264 | 14.797 | 1.00 | 46.76 |
| ATOM | 2857 | O | HOH | W1100 | -2.386 | 32.682 | 10.595 | 1.00 | 45.61 |
| ATOM | 2858 | O | HOH | W1101 | 10.547 | 22.987 | 1.444 | 1.00 | 47.09 |
| ATOM | 2859 | O | HOH | W1102 | 20.484 | 18.057 | 6.996 | 1.00 | 46.94 |
| ATOM | 2860 | O | HOH | W1103 | 25.941 | 11.091 | -4.680 | 1.00 | 44.03 |
| ATOM | 2861 | O | HOH | W1104 | 21.180 | 1.943 | -1.176 | 1.00 | 41.15 |
| ATOM | 2862 | O | HOH | W1105 | 18.527 | 3.971 | -1.434 | 1.00 | 34.61 |
| ATOM | 2863 | O | HOH | W1106 | 13.143 | -0.323 | 2.925 | 1.00 | 37.48 |
| ATOM | 2864 | O | HOH | W1107 | 5.347 | -3.519 | 9.105 | 1.00 | 42.57 |
| ATOM | 2865 | O | HOH | W1108 | 3.237 | 1.982 | 4.021 | 1.00 | 35.20 |
| ATOM | 2866 | O | HOH | W1109 | -3.173 | 4.977 | 2.982 | 1.00 | 53.75 |
| ATOM | 2867 | O | HOH | W1110 | -1.952 | 7.296 | 2.535 | 1.00 | 46.07 |
| ATOM | 2868 | O | HOH | W1111 | 27.213 | 4.430 | 8.838 | 1.00 | 44.44 |
| ATOM | 2869 | O | HOH | W1112 | 22.234 | 17.011 | 11.479 | 1.00 | 33.65 |
| ATOM | 2870 | O | HOH | W1113 | 28.493 | 18.976 | 13.615 | 1.00 | 63.32 |
| ATOM | 2871 | O | HOH | W1114 | 36.123 | 16.781 | 7.304 | 1.00 | 48.30 |
| ATOM | 2872 | O | HOH | W1115 | 26.503 | 11.504 | 7.925 | 1.00 | 55.19 |
| ATOM | 2873 | O | HOH | W1116 | 3.650 | 11.093 | -4.358 | 1.00 | 42.25 |
| ATOM | 2874 | O | HOH | W1117 | 2.510 | 14.591 | -4.169 | 1.00 | 39.71 |
| ATOM | 2875 | O | HOH | W1118 | -2.981 | 9.772 | -1.920 | 1.00 | 40.41 |
| ATOM | 2876 | O | HOH | W1119 | 5.540 | 23.133 | 2.694 | 1.00 | 50.53 |
| ATOM | 2877 | O | HOH | W1120 | 20.995 | 19.028 | 23.041 | 1.00 | 46.71 |
| ATOM | 2878 | O | HOH | W1121 | 18.023 | 19.952 | 25.578 | 1.00 | 43.02 |
| ATOM | 2879 | O | HOH | W1122 | 8.049 | 18.414 | 0.411 | 1.00 | 47.69 |
| ATOM | 2880 | O | HOH | W1123 | 5.892 | 19.573 | -0.522 | 1.00 | 41.98 |
| ATOM | 2881 | O | HOH | W1124 | 19.165 | -13.921 | 21.351 | 1.00 | 41.53 |
| ATOM | 2882 | O | HOH | W1125 | 19.614 | -3.507 | 39.393 | 1.00 | 51.36 |
| ATOM | 2883 | O | HOH | W1126 | 3.920 | 23.416 | 31.323 | 1.00 | 53.96 |
| ATOM | 2884 | O | HOH | W1127 | 11.520 | 26.506 | 21.703 | 1.00 | 50.31 |
| ATOM | 2885 | O | HOH | W1128 | 21.981 | 5.589 | 30.420 | 1.00 | 60.57 |
| ATOM | 2886 | O | HOH | W1129 | -0.398 | -4.925 | 19.583 | 1.00 | 68.66 |
| ATOM | 2887 | O | HOH | W1130 | -7.267 | -4.227 | 16.670 | 1.00 | 44.28 |
| ATOM | 2888 | O | HOH | W1131 | 0.838 | -5.187 | 17.010 | 1.00 | 60.71 |
| ATOM | 2889 | O | HOH | W1132 | -4.202 | -4.686 | 27.495 | 1.00 | 42.60 |
| ATOM | 2890 | O | HOH | W1133 | -11.212 | 10.692 | 23.304 | 1.00 | 53.42 |
| ATOM | 2891 | O | HOH | W1134 | -2.880 | -1.093 | 45.737 | 1.00 | 52.44 |
| ATOM | 2892 | O | HOH | W1135 | -3.033 | 1.757 | 46.556 | 1.00 | 50.55 |
| ATOM | 2893 | O | HOH | W1136 | 2.585 | 10.032 | 46.615 | 1.00 | 51.25 |
| ATOM | 2894 | O | HOH | W1137 | -4.513 | 4.908 | 43.503 | 1.00 | 38.21 |
| ATOM | 2895 | O | HOH | W1138 | -1.066 | 21.111 | 36.774 | 1.00 | 39.14 |
| ATOM | 2896 | O | HOH | W1139 | 1.292 | 19.196 | 40.598 | 1.00 | 47.17 |
| ATOM | 2897 | O | HOH | W1140 | 3.513 | 22.603 | 39.647 | 1.00 | 46.18 |
| END | | | | | | | | | |

SEQUENCE LISTING

```
<160> NUMBER OF SEQ ID NOS: 5

<210> SEQ ID NO 1
<211> LENGTH: 976
<212> TYPE: PRT
<213> ORGANISM: Homo sapiens
<220> FEATURE:
<221> NAME/KEY: Amino acid sequence for full-length human wild type
      c-Kit
<222> LOCATION: (1)..(976)

<400> SEQUENCE: 1

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
                20                  25                  30

Glu Pro Ser Pro Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
        50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
```

-continued

```
                245                 250                 255
Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
    290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
    370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
    450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
        515                 520                 525

Phe Val Ile Val Ala Gly Met Met Cys Ile Ile Val Met Ile Leu Thr
    530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
        595                 600                 605

Tyr Gly Leu Ile Lys Ser Asp Ala Ala Met Thr Val Ala Val Lys Met
    610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
            660                 665                 670
```

-continued

```
Cys Cys Tyr Gly Asp Leu Leu Asn Phe Leu Arg Arg Lys Arg Asp Ser
            675                 680                 685

Phe Ile Cys Ser Lys Gln Glu Asp His Ala Glu Ala Ala Leu Tyr Lys
        690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
        755                 760                 765

Leu Leu Ser Phe Ser Tyr Gln Val Ala Lys Gly Met Ala Phe Leu Ala
        770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
        835                 840                 845

Glu Ser Asp Val Trp Ser Tyr Gly Ile Phe Leu Trp Glu Leu Phe Ser
        850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
        930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975
```

<210> SEQ ID NO 2
<211> LENGTH: 1176
<212> TYPE: DNA
<213> ORGANISM: Homo sapiens
<220> FEATURE:
<221> NAME/KEY: Human cDNA sequence encoding residues 544-935 of c-Kit
<222> LOCATION: (1)..(1176)

<400> SEQUENCE: 2

```
acctacaaat atttacagaa acccatgtat gaagtacagt ggaaggttgt tgaggagata      60
aatggaaaca attatgttta catagaccca acacaacttc cttatgatca caaatgggag    120
tttcccagaa acaggctgag ttttggaaa accctgggtg ctggagcttt cgggaaggtt      180
gttgaggcaa ctgcttatgg cttaattaag tcagatgcgg ccatgactgt cgctgtaaag    240
atgctcaagc cgagtgccca tttgacagaa cgggaagccc tcatgtctga actcaaagtc    300
```

-continued

```
ctgagttacc ttggtaatca catgaatatt gtgaatctac ttggagcctg caccattgga    360
gggcccaccc tggtcattac agaatattgt tgctatggtg atcttttgaa tttttttgaga   420 agaaaacgtg attcatttat ttgttcaaag caggaagatc atgcagaagc tgcactttat    480
aagaatcttc tgcattcaaa ggagtcttcc tgcagcgata gtactaatga gtacatggac    540
atgaaacctg gagtttctta tgttgtccca accaaggccg acaaaaggag atctgtgaga    600
ataggctcat acatagaaag gatgtgact cccgccatca tggaggatga cgagttggcc     660
ctagacttag aagacttgct gagcttttct taccaggtgg caaagggcat ggctttcctc    720
gcctccaaga attgtattca gagacttg gcagccagaa atatcctcct tactcatggt      780
cggatcacaa agatttgtga ttttggtcta gccagagaca tcaagaatga ttctaattat    840
gtggttaaag gaaacgctcg actacctgtg aagtggatgg cacctgaaag cattttcaac    900
tgtgtataca cgtttgaaag tgacgtctgg tcctatggga ttttctttg ggagctgttc     960 tctttaggaa gcagcccta tcctggaatg ccggtcgatt ctaagttcta caagatgatc    1020
aaggaaggct tccggatgct cagccctgaa cacgcacctg ctgaaatgta tgacataatg   1080
aagacttgct gggatgcaga tccctaaaa agaccaacat tcaagcaaat tgttcagcta    1140
attgagaagc agatttcaga gagcaccaat catatt                              1176
```

<210> SEQ ID NO 3
<211> LENGTH: 365
<212> TYPE: PRT
<213> ORGANISM: Homo sapiens
<220> FEATURE:
<221> NAME/KEY: N-terminal 6x-histidine tag, spacer region and rTEV
      protease cleavage site
<222> LOCATION: (1)..(31)
<220> FEATURE:
<221> NAME/KEY: Residues 544-693 and 753-935 of c-kit including an
      inserted serine between residues 753 and 754
<222> LOCATION: (32)..(365)

<400> SEQUENCE: 3

Met Ser Tyr Tyr His His His His His His Asp Tyr Asp Ile Pro Thr
1               5                   10                  15

Thr Glu Asn Leu Tyr Phe Gln Gly Ala Met Glu Pro Gly Gly Ser Thr
            20                  25                  30

Tyr Lys Tyr Leu Gln Lys Pro Met Tyr Glu Val Gln Trp Lys Val Val
        35                  40                  45

Glu Glu Ile Asn Gly Asn Asn Tyr Val Tyr Ile Asp Pro Thr Gln Leu
    50                  55                  60

Pro Tyr Asp His Lys Trp Glu Phe Pro Arg Asn Arg Leu Ser Phe Gly
65                  70                  75                  80

Lys Thr Leu Gly Ala Gly Ala Phe Gly Lys Val Val Glu Ala Thr Ala
                85                  90                  95

Tyr Gly Leu Ile Lys Ser Asp Ala Ala Met Thr Val Ala Val Lys Met
            100                 105                 110

Leu Lys Pro Ser Ala His Leu Thr Glu Arg Glu Ala Leu Met Ser Glu
        115                 120                 125

Leu Lys Val Leu Ser Tyr Leu Gly Asn His Met Asn Ile Val Asn Leu
    130                 135                 140

Leu Gly Ala Cys Thr Ile Gly Gly Pro Thr Leu Val Ile Thr Glu Tyr
145                 150                 155                 160

Cys Cys Tyr Gly Asp Leu Leu Asn Phe Leu Arg Arg Lys Arg Asp Ser
                165                 170                 175

-continued

```
Phe Ile Cys Ser Lys Thr Ser Pro Ala Ile Met Glu Asp Asp Glu Leu
            180                 185                 190

Ala Leu Asp Leu Glu Asp Leu Leu Ser Phe Ser Tyr Gln Val Ala Lys
        195                 200                 205

Gly Met Ala Phe Leu Ala Ser Lys Asn Cys Ile His Arg Asp Leu Ala
    210                 215                 220

Ala Arg Asn Ile Leu Leu Thr His Gly Arg Ile Thr Lys Ile Cys Asp
225                 230                 235                 240

Phe Gly Leu Ala Arg Asp Ile Lys Asn Asp Ser Asn Tyr Val Val Lys
                245                 250                 255

Gly Asn Ala Arg Leu Pro Val Lys Trp Met Ala Pro Glu Ser Ile Phe
            260                 265                 270

Asn Cys Val Tyr Thr Phe Glu Ser Asp Val Trp Ser Tyr Gly Ile Phe
        275                 280                 285

Leu Trp Glu Leu Phe Ser Leu Gly Ser Ser Pro Tyr Pro Gly Met Pro
    290                 295                 300

Val Asp Ser Lys Phe Tyr Lys Met Ile Lys Glu Gly Phe Arg Met Leu
305                 310                 315                 320

Ser Pro Glu His Ala Pro Ala Glu Met Tyr Asp Ile Met Lys Thr Cys
                325                 330                 335

Trp Asp Ala Asp Pro Leu Lys Arg Pro Thr Phe Lys Gln Ile Val Gln
            340                 345                 350

Leu Ile Glu Lys Gln Ile Ser Glu Ser Thr Asn His Ile
        355                 360                 365

<210> SEQ ID NO 4
<211> LENGTH: 1302
<212> TYPE: DNA
<213> ORGANISM: Homo sapiens
<220> FEATURE:
<221> NAME/KEY: Human cDNA sequence encoding residues 544-976 of c-Kit
<222> LOCATION: (1)..(1302)

<400> SEQUENCE: 4
acctacaaat atttacagaa acccatgtat gaagtacagt ggaaggttgt tgaggagata      60
aatggaaaca attatgttta catagaccca acacaacttc cttatgatca caaatgggag    120
tttcccagaa acaggctgag ttttgggaaa accctgggtg ctggagcttt cgggaaggtt    180
gttgaggcaa ctgcttatgg cttaattaag tcagatgcgg ccatgactgt cgctgtaaag    240
atgctcaagc cgagtgccca tttgacagaa cgggaagccc tcatgtctga actcaaagtc    300
ctgagttacc ttggtaatca catgaatatt gtgaatctac ttggagcctg caccattgga    360
gggcccaccc tggtcattac agaatattgt gctatggtga tcttttgaa ttttttgaga    420 agaaaacgtg attcatttat ttgttcaaag caggaagatc atgcagaagc tgcacttat    480 aagaatcttc tgcattcaaa ggagtcttcc tgcagcgata gtactaatga gtacatggac    540
atgaaacctg gagtttctta tgttgtccca accaaggccg acaaaaggag atctgtgaga    600
ataggctcat acatagaaag agatgtgact cccgccatca tggaggatga cgagttggcc    660
ctagacttag aagacttgct gagctttct taccaggtgg caaagggcat ggcttcctc    720 gcctccaaga attgtattca cagagacttg gcagccagaa atatcctcct tactcatggt    780
cggatcacaa agatttgtga ttttggtcta gccagagaca tcaagaatga ttctaattat    840
gtggttaaag gaaacgctcg actacctgtg aagtggatgg cacctgaaag catttcaac    900 tgtgtataca cgtttgaaag tgacgtctgg tcctatggga ttttctttg ggagctgttc    960
```

-continued

```
tctttaggaa gcagcccta tcctggaatg ccggtcgatt ctaagttcta caagatgatc    1020
aaggaaggct tccggatgct cagccctgaa cacgcacctg ctgaaatgta tgacataatg    1080
aagacttgct gggatgcaga tcccctaaaa agaccaacat tcaagcaaat tgttcagcta    1140
attgagaagc agatttcaga gagcaccaat catatttact ccaacttagc aaactgcagc    1200
cccaaccgac agaagcccgt ggtagaccat tctgtgcgga tcaattctgt cggcagcacc    1260
gcttcctcct cccagcctct gcttgtgcac gacgatgtct ga                      1302
```

<210> SEQ ID NO 5
<211> LENGTH: 406
<212> TYPE: PRT
<213> ORGANISM: Homo sapiens
<220> FEATURE:
<221> NAME/KEY: N-terminal 6x-histidine tag, spacer region and rTEV
      protease cleavage site
<222> LOCATION: (1)..(31)
<220> FEATURE:
<221> NAME/KEY: Residues 544-693 and 753-976 of c-kit including an
      inserted serine between residues 753 and 754
<222> LOCATION: (32)..(406)

<400> SEQUENCE: 5

Met Ser Tyr Tyr His His His His His His Asp Tyr Asp Ile Pro Thr
1               5                   10                  15

Thr Glu Asn Leu Tyr Phe Gln Gly Ala Met Glu Pro Gly Gly Ser Thr
            20                  25                  30

Tyr Lys Tyr Leu Gln Lys Pro Met Tyr Glu Val Gln Trp Lys Val Val
        35                  40                  45

Glu Glu Ile Asn Gly Asn Asn Tyr Val Tyr Ile Asp Pro Thr Gln Leu
    50                  55                  60

Pro Tyr Asp His Lys Trp Glu Phe Pro Arg Asn Arg Leu Ser Phe Gly
65                  70                  75                  80

Lys Thr Leu Gly Ala Gly Ala Phe Gly Lys Val Val Glu Ala Thr Ala
                85                  90                  95

Tyr Gly Leu Ile Lys Ser Asp Ala Ala Met Thr Val Ala Val Lys Met
            100                 105                 110

Leu Lys Pro Ser Ala His Leu Thr Glu Arg Glu Ala Leu Met Ser Glu
        115                 120                 125

Leu Lys Val Leu Ser Tyr Leu Gly Asn His Met Asn Ile Val Asn Leu
    130                 135                 140

Leu Gly Ala Cys Thr Ile Gly Gly Pro Thr Leu Val Ile Thr Glu Tyr
145                 150                 155                 160

Cys Cys Tyr Gly Asp Leu Leu Asn Phe Leu Arg Arg Lys Arg Asp Ser
                165                 170                 175

Phe Ile Cys Ser Lys Thr Ser Pro Ala Ile Met Glu Asp Asp Glu Leu
            180                 185                 190

Ala Leu Asp Leu Glu Asp Leu Leu Ser Phe Ser Tyr Gln Val Ala Lys
        195                 200                 205

Gly Met Ala Phe Leu Ala Ser Lys Asn Cys Ile His Arg Asp Leu Ala
    210                 215                 220

Ala Arg Asn Ile Leu Leu Thr His Gly Arg Ile Thr Lys Ile Cys Asp
225                 230                 235                 240

Phe Gly Leu Ala Arg Asp Ile Lys Asn Asp Ser Asn Tyr Val Val Lys
                245                 250                 255

Gly Asn Ala Arg Leu Pro Val Lys Trp Met Ala Pro Glu Ser Ile Phe
            260                 265                 270

```
Asn Cys Val Tyr Thr Phe Glu Ser Asp Val Trp Ser Tyr Gly Ile Phe
        275                 280                 285

Leu Trp Glu Leu Phe Ser Leu Gly Ser Ser Pro Tyr Pro Gly Met Pro
        290                 295                 300

Val Asp Ser Lys Phe Tyr Lys Met Ile Lys Glu Gly Phe Arg Met Leu
305                 310                 315                 320

Ser Pro Glu His Ala Pro Ala Glu Met Tyr Asp Ile Met Lys Thr Cys
                325                 330                 335

Trp Asp Ala Asp Pro Leu Lys Arg Pro Thr Phe Lys Gln Ile Val Gln
                340                 345                 350

Leu Ile Glu Lys Gln Ile Ser Glu Ser Thr Asn His Ile Tyr Ser Asn
        355                 360                 365

Leu Ala Asn Cys Ser Pro Asn Arg Gln Lys Pro Val Val Asp His Ser
        370                 375                 380

Val Arg Ile Asn Ser Val Gly Ser Thr Ala Ser Ser Ser Gln Pro Leu
385                 390                 395                 400
Leu Val His Asp Asp Val
                405
```

CRYSTALLIZATION OF C-KIT TYROSINE KINASE LEADING TO AUTOINHIBITED CRYSTAL STRUCTURE

FIELD OF THE INVENTION

The present invention relates to a member of a family of human receptor tyrosine protein kinases and more specifically to a particular tyrosine protein kinase known as c-KIT tyrosine kinase (c-KIT). Provided is c-KIT in crystalline form, methods of forming crystals comprising c-KIT, methods of using crystals comprising c-KIT, a crystal structure of autoinhibited c-KIT, and methods of using the crystal structure.

BACKGROUND OF THE INVENTION

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three-dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein.

SUMMARY OF THE INVENTION

The present invention is directed to crystals comprising c-KIT and particularly crystals comprising autoinhibited c-KIT that have sufficient size and quality to obtain useful information about the structural properties of c-KIT and molecules or complexes that may associate with c-KIT.

In one embodiment, a composition is provided that comprises a protein in crystalline form wherein the protein has 55%, 65%, 78%, 85%, 90%, 95%, 97%, 99% or greater identity with residues 544-693 and 753-935 of SEQ. ID No. 1.

In one variation, the protein has activity characteristic of c-KIT. For example, the protein may optionally be inhibited by inhibitors of wild type c-KIT.

The protein crystal may also diffract X-rays for a determination of structure coordinates to a resolution of 4 Å, 3.5 Å, 3.0 Å or less.

In one variation, the protein crystal has a crystal lattice in a $P2_12_12_1$ space group. The protein crystal may also have a crystal lattice having unit cell dimensions, +/−5%, of a=44.489 Å b=77.277 Å and c=94.701 Å, $\alpha=\beta=\gamma=90$.

The present invention is also directed to crystallizing c-KIT. The present invention is also directed to the conditions useful for crystallizing c-KIT. It should be recognized that a wide variety of crystallization methods can be used in combination with the crystallization conditions to form crystals comprising c-KIT including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein that has at least 55% identity with residues 544-693 and 753-935 of SEQ. ID No. 1 in a concentration between 1 mg/ml and 50 mg/ml; 5-50% w/v of precipitant wherein the precipitant comprises one or more members of the group consisting of PEG MME having a molecular weight range between 300-10000, and PEG having a molecular weight range between 100-10000; optionally 0.05 to 2.5M additives wherein the additives comprise a monovalent and/or divalent salt (for example, sodium, lithium, magnesium, calcium, and the like); and storing the crystallization volume under conditions suitable for crystal formation. The method also optionally further includes performing the crystallization at a temperature between 1° C.-37° C.

The method may optionally further comprise forming a protein crystal that has a crystal lattice in a $P2_12_12$ space group. The method also optionally further comprises forming a protein crystal that has a crystal lattice having unit cell dimensions, +/−5%, of a=44.489 Å b=77.277 Å and c=94.701 Å, $\alpha=\beta=\gamma=90$. The invention also relates to protein crystals formed by these methods.

The present invention is also directed to structure coordinates for autoinhibited c-KIT as well as structure coordinates that are comparatively similar to these structure coordinates. It is noted that these comparatively similar structure coordinates may encompass proteins with similar sequences and/or structures, such as other protein tyrosine kinases. For example, machine-readable data storage media is provided having data storage material encoded with machine-readable data that comprises structure coordinates that are comparatively similar to the structure coordinates of c-KIT. The present invention is also directed to a machine readable data storage medium having data storage material encoded with machine readable data, which, when read by an appropriate machine, can display a three dimensional representation of all or a portion of a structure of c-KIT or a model that is comparatively similar to the structure of all or a portion of c-KIT.

Various embodiments of machine readable data storage medium are provided that comprise data storage material encoded with machine readable data. The machine readable data comprises: structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1. The amino acids being overlayed and compared need not to be identical when the RMSD calculation is performed on alpha carbons and main chain atoms but the amino acids being overlayed and compared must have identical side chains when the RMSD calculation is performed on all non-hydrogen atoms.

For example, in one embodiment where the comparison is based on the 4 Angstrom set of amino acid residues (Column 1) and is based on superimposing alpha-carbon atoms (Column 2), the structure coordinates may have a root mean square deviation equal to or less than 0.40 Å, 0.27 Å or 0.20 Å when compared to the structure coordinates of FIG. 3.

TABLE 1

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| Table 2 | alpha-carbon atoms[1] | 0.40 | 0.27 | 0.20 |
| (4 Angstrom set) | main-chain atoms[1] | 0.47 | 0.31 | 0.24 |
|  | all non-hydrogen[2] | 0.41 | 0.27 | 0.21 |
| Table 3 | alpha-carbon atoms[1] | 0.96 | 0.64 | 0.48 |
| (7 Angstrom set) | main-chain atoms[1] | 0.97 | 0.65 | 0.49 |
|  | all non-hydrogen[2] | 0.87 | 0.58 | 0.43 |
| Table 4 | alpha-carbon atoms[1] | 2.19 | 1.46 | 1.09 |
| (10 Angstrom set) | main-chain atoms[1] | 2.11 | 1.41 | 1.06 |
|  | all non-hydrogen[2] | 1.34 | 0.89 | 0.67 |
| 544-693 and 753-935 | alpha-carbon atoms[1] | 1.87 | 1.24 | 0.93 |
| of | main-chain atoms[1] | 1.81 | 1.20 | 0.90 |
| SEQ. ID No. 1 | all non-hydrogen[2] | 1.20 | 0.80 | 0.60 |

[1]the RMSD computed between the atoms of all amino acids that are common to both the target and the reference in the aligned and superposed structure. The amino acids need not to be identical.
[2]the RMSD computed only between identical amino acids, which are common to both the target and the reference in the aligned and superposed structure.

The present invention is also directed to a three-dimensional structure of all or a portion of c-KIT. This three-dimensional structure may be used to identify binding sites, to provide mutants having desirable binding properties, and ultimately, to design, characterize, or identify ligands capable of interacting with c-KIT. Ligands that interact with c-KIT may be any type of atom, compound, protein or chemical group that binds to or otherwise associates with the protein. Examples of types of ligands include natural substrates for c-KIT, inhibitors of c-KIT, and heavy atoms. The inhibitors of c-KIT may optionally be used as drugs to treat therapeutic indications by modifying the in vivo activity of c-KIT.

In various embodiments, methods are provided for displaying a three dimensional representation of a structure of a protein comprising:

taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

computing a three dimensional representation of a structure based on the structure coordinates; and displaying the three dimensional representation.

The present invention is also directed to a method for solving a three-dimensional crystal structure of a target protein using the structure of c-KIT.

In various embodiments, computational methods are provided comprising: taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

computing phases based on the structural coordinates;

computing an electron density map based on the computed phases; and determining a three-dimensional crystal structure based on the computed electron density map.

In various embodiments, computational methods are provided comprising: taking an X-ray diffraction pattern of a crystal of the target protein; and computing a three-dimensional electron density map from the X-ray diffraction pattern by molecular replacement, wherein structure coordinates used as a molecular replacement model comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

These methods may optionally further comprise determining a three-dimensional crystal structure based upon the computed three-dimensional electron density map.

The present invention is also directed to using a crystal structure of c-KIT, in particular the structure coordinates of autoinhibited c-KIT and the surface contour defined by them, in methods for screening, designing, or optimizing molecules or other chemical entities that interact with and preferably inhibit c-KIT.

One skilled in the art will appreciate the numerous uses of the inventions described herein, particularly in the areas of drug design, screening and optimization of drug candidates, as well as in determining additional unknown crystal structures. For example, a further aspect of the present invention relates to using a three-dimensional crystal structure of all or a portion of c-KIT and/or its structure coordinates to evaluate the ability of entities to associate with c-KIT. The entities may be any entity that may function as a ligand and thus may be any type of atom, compound, protein (such as antibodies) or chemical group that can bind to or otherwise associate with a protein.

In various embodiments, methods are provided for evaluating a potential of an entity to associate with a protein comprising:

creating a computer model of a protein structure using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

performing a fitting operation between the entity and the computer model; and analyzing results of the fitting operation to quantify an association between the entity and the model.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and employing the three-dimensional structure to design or select an entity that can associate with the protein; and contacting the entity with a protein having at least 55% identity with residues 544-693 and 753-935 of SEQ. ID No. 1.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and employing the three-dimensional structure to design or select an entity that can associate with the protein.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

employing the computer model to design or select an entity that can associate with the protein; and contacting the entity with a protein having at least 55% identity with residues 544-693 and 753-935 of SEQ. ID No. 1.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and employing the computer model to design or select an entity that can associate with the protein.

In other embodiments, methods are provided for evaluating the ability of an entity to associate with a protein, the method comprising:

constructing a computer model defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and selecting an entity to be evaluated by a method selected from the group consisting of (i) assembling molecular fragments into the entity, (ii) selecting an entity from a small molecule database, (iii) de novo ligand design of the entity, and (iv) modifying a known ligand for c-KIT, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In other embodiments, methods are provided for evaluating the ability of an entity to associate with a protein, the method comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and selecting an entity to be evaluated by a method selected from the group consisting of (i) assembling molecular fragments into the entity, (ii) selecting an entity from a small molecule database, (iii) de novo ligand design of the entity, and (iv) modifying a known ligand for c-KIT, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In regard to each of these embodiments, the protein may optionally have activity characteristic of c-KIT. For example, the protein may optionally be inhibited by inhibitors of wild type c-KIT.

In another embodiment, a method is provided for identifying an entity that associates with a protein comprising: taking structure coordinates from diffraction data obtained from a crystal of a protein that has at least 55%, 65%, 78%, 85%, 90%, 95%, 97%, 99% or more identity with the residues 544-693 and 753-935 of SEQ. ID No. 1; and performing rational drug design using a three dimensional structure that is based on the obtained structure coordinates. The protein crystals may optionally have a crystal lattice having unit cell dimensions, +/−5%, of a=44.489 Å b=77.277 Å and c=94.701 Å, α=β=γ=90. The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. 1, 2, and 3 referred to in this application.

FIG. 3 lists a set of atomic structure coordinates for autoinhibited c-KIT (SEQ ID NO:3) as derived by X-ray crystallography from a crystal that comprises the protein. The following abbreviations are used in FIG. 3: "X, Y, Z" crystallographically define the atomic position of the element measured; "B" is a thermal factor that measures movement of the atom around its atomic center; "Occ" is an occupancy factor that refers to the fraction of the molecules in which each atom occupies the position specified by the coordinates (a value of "1" indicates that each atom has the same conformation, i.e., the same position, in all molecules of the crystal).

DETAILED DESCRIPTION OF THE INVENTION

Figure 2:
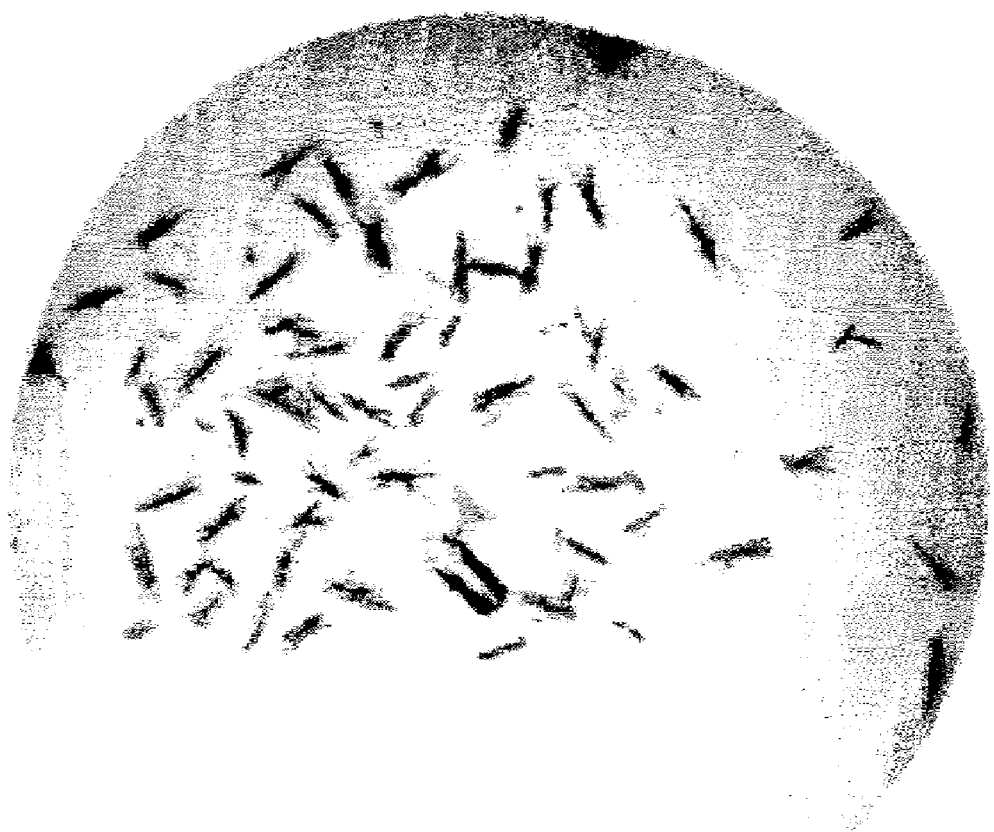
FIG. 2 illustrates crystal of c-KIT corresponding to SEQ. ID No. 3, having a crystal lattice in a $P2_12_12$, space group and unit cell dimensions, +/−5%, of a=44.489 Å b=77.277 Å and c=94.701 Å, α=β=γ=90.

The present invention relates to a member of a family of human receptor tyrosine protein kinases and more specifically to a particular tyrosine protein kinase known as c-KIT tyrosine kinase (c-KIT). Provided is c-KIT in crystalline form, methods of forming crystals comprising c-KIT, methods of using crystals comprising c-KIT, a crystal structure of c-KIT, and methods of using the crystal structure.

In describing protein structure and function herein, reference is made to amino acids comprising the protein. The amino acids may also be referred to by their conventional abbreviations; A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

1. c-KIT

The receptor protein tyrosine kinase c-KIT belongs to the type III receptor tyrosine kinase subfamily. Ligation of c-KIT receptor by its ligand, the Stem Cell Factor (SCF) induces its dimerization, followed by induction of multiple intracellular signaling pathways leading to cell proliferation and activation. C-KIT and SCF are essential for haemopoiesis, melanogenesis and fertility. SCF acts at multiple levels of the haemopoietic hierarchy to promote cell survival, proliferation, differentiation, adhesion and functional activation. It is of particular importance in the mast cell and erythroid lineages, but also acts on multipotential stem and progenitor cells, megakaryocytes, and a subset of lymphoid progenitors. The c-KIT gene also plays a fundamental role during the establishment, the maintenance and the function of germ cells. In the embryonal gonad the c-KIT tyrosine kinase receptor and its ligand are required for the survival and proliferation of primordial germ cells. In the postnatal animal, c-KIT/SCF are required for the production of the mature gametes in response to gonadotropic hormones, i.e. for the survival and/or proliferation of the only proliferating germ cells of the testis, the spermatogonia, and for the growth and maturation of the oocytes. Multiple isoforms of c-KIT also exist as a result of alternate mRNA splicing, proteolytic cleavage and the use of cryptic internal promoters in certain cell types.

Multiple studies have linked the c-KIT receptor kinase to the biological and genetic underpinnings of gastrointestinal stromal tumors (GISTs). The activity of c-KIT is tightly regulated in cells and the constitutive activation of the c-KIT receptor tyrosine kinase is a central pathogenetic event in most GISTs and generally results from oncogenic point mutations, which can involve either extracellular or cytoplasmic domains of the receptor. Oncogenic mutations enable the c-KIT receptor to phosphorylate various substrate proteins, leading to activation of signal transduction cascades, which regulate cell proliferation, apoptosis, chemotaxis, and adhesion. Activating mutations in c-KIT, have also been identified in dysplasias and leukaemias of the mast cell lineage and have been shown to contribute to transformation in model systems.

In one embodiment, c-KIT comprises the wild-type form of full length c-KIT, set forth herein as SEQ. ID No. 1 (GenBank Accession Number NM_000222; Yarden, Y., Kuang, W. J., Yang-Feng, T., Coussens, L., Munemitsu, S., Dull, T. J., Chen, E., Schlessinger, J., Francke, U. and Ullrich, A. "Human proto-oncogene c-kit: a new cell surface receptor tyrosine kinase for an unidentified ligand, *EMBO J.* 6 (1987) 3341-3351".).

In another embodiment, c-KIT comprises residues 544-693 and 753-935 of SEQ. ID No. 1 which comprises the active site domain of wild-type c-KIT that is represented in the set of structural coordinates shown in FIG. 3.

It should be recognized that the invention may be readily extended to various variants of wild-type c-KIT and variants of fragments thereof. In another embodiment, c-KIT comprises a sequence that has at least 55% identity, preferably at least 65%, 78%, 85%, 90%, 95%, 97%, 99% or higher identity with SEQ. ID No. 1.

It is also noted that the above sequences of c-KIT are also intended to encompass isoforms, mutants and fusion proteins of these sequences. An example of a fusion protein is provided by SEQ. ID No. 3, which includes a 6 residue N-terminal tag (6 residues are histidine) and a recombinant tobacco etch virus (rTEV) protease cleavage site that may be used to facilitate purification of the protein.

With the crystal structure provided herein, it is now known where amino acid residues are positioned in the autoinhibited structure of c-KIT. As a result, the impact of different substitutions can be more easily predicted and understood.

For example, based on the crystal structure, applicants have determined that the c-KIT amino acids shown in Table 2 encompass a 4-Angstrom radius around the c-KIT active site and thus likely to interact with any active site inhibitor of c-KIT. Applicants have also determined that the amino acids of Table 3 encompass a 7-Angstrom radius around the c-KIT active site. Further it has been determined that the amino acids of Table 4 encompass a 10-Angstrom radius around the c-KIT active site. It is noted that there is one c-KIT molecule in the asymmetric unit, referred to as chain A. Structural coordinates appear in FIG. 3. It is noted that the sequence and structure of the residues in the active site may also be conserved and hence pertinent to other tyrosine protein kinases.

One or more of the sets of amino acids set forth in the tables is preferably conserved in a variant of c-KIT. Hence, c-KIT may optionally comprise a sequence that has at least 55% identity, preferably at least 65%, 78%, 85%, 90%, 95%, 97%, 99% or higher identity with any one of the above sequences (e.g., all of SEQ. ID No. 1 or residues 544-693 and 753-935 of SEQ. ID No. 1) where at least the residues shown in Tables 2, 3, and/or 4 are conserved with the exception of 0, 1, 2, 3, or 4 residues. It should be recognized that one might optionally vary some of the binding site residues in order to determine the effect such changes have on structure or activity.

TABLE 2

Amino Acids encompassed by a 4-Angstrom radius around the c-KIT active site (SEQ. ID No. 1).

| GLN 556 | TRP 557 | LYS 558 |
|---|---|---|
| LEU 595 | VAL 603 | ALA 621 |
| VAL 622 | LYS 623 | GLU 640 |
| VAL 643 | LEU 644 | LEU 647 |
| VAL 668 | THR 670 | TYR 672 |
| CYS 673 | GLY 676 | CYS 788 |
| ILE 789 | HIS 790 | ARG 791 |
| LEU 799 | CYS 809 | ASP 810 |
| PHE 811 | | |

TABLE 3

Amino Acids encompassed by a 7-Angstrom radius around the c-KIT active site (SEQ. ID No. 1).

| LEU 595 | GLY 596 | TYR 553 |
|---|---|---|
| GLU 554 | VAL 555 | GLN 556 |
| TRP 557 | LYS 602 | VAL 603 |

TABLE 3-continued

Amino Acids encompassed by a 7-Angstrom radius around the c-KIT active site (SEQ. ID No. 1).

| VAL 604 | VAL 620 | ALA 621 |
|---|---|---|
| VAL 622 | LYS 623 | MET 624 |
| GLU 640 | VAL 654 | ASN 655 |
| THR 670 | GLU 671 | TYR 672 |
| CYS 673 | CYS 674 | TYR 675 |
| GLY 676 | ASP 677 | LEU 678 |
| ASN 680 | ARG 684 | ASP 792 |
| LYS 558 | VAL 559 | ASN 797 |
| TYR 570 | LEU 799 | LEU 800 |
| ILE 808 | CYS 809 | ASP 810 |
| PHE 811 | GLY 812 | LEU 813 |
| ALA 814 | LEU 637 | VAL 643 |
| LEU 644 | LEU 647 | ILE 653 |
| LEU 656 | VAL 668 | ILE 669 |
| LEU 783 | ASN 787 | CYS 788 |
| ILE 789 | HIS 790 | ARG 791 |

TABLE 4

Amino Acids encompassed by a 10-Angstrom radius around the c-KIT active site (SEQ. ID No. 1).

| LYS 593 | THR 594 | LEU 595 |
|---|---|---|
| GLY 596 | ALA 597 | GLY 598 |
| TYR 553 | GLU 554 | GLY 601 |
| LYS 602 | VAL 603 | VAL 604 |
| GLU 605 | ALA 606 | THR 619 |
| VAL 620 | ALA 621 | VAL 622 |
| LYS 623 | MET 624 | LEU 625 |
| VAL 555 | GLN 556 | TRP 557 |
| ALA 636 | LEU 637 | GLU 640 |
| LEU 644 | ILE 653 | VAL 654 |
| ASN 655 | LEU 656 | LEU 657 |
| VAL 668 | ILE 669 | THR 670 |
| GLU 671 | TYR 672 | CYS 673 |
| CYS 674 | TYR 675 | GLY 676 |
| ASP 677 | LEU 678 | LYS 558 |
| ASN 680 | PHE 681 | ARG 684 |
| HIS 790 | ASP 792 | LEU 793 |
| ALA 794 | ALA 795 | ARG 796 |
| ASN 797 | ILE 798 | LEU 799 |
| LEU 800 | THR 801 | LYS 807 |
| ILE 808 | CYS 809 | ASP 810 |
| PHE 811 | GLY 812 | LEU 813 |
| ALA 814 | VAL 559 | VAL 560 |
| TYR 570 | ILE 571 | ASP 572 |
| PRO 573 | LEU 576 | LEU 589 |
| PHE 591 | MET 638 | SER 639 |
| LEU 641 | LYS 642 | VAL 643 |
| SER 645 | TYR 646 | LEU 647 |
| GLY 648 | HIS 650 | ASN 652 |
| GLY 658 | ALA 659 | THR 666 |
| LEU 667 | MET 757 | GLU 758 |
| GLY 779 | MET 780 | PHE 782 |
| LEU 783 | ALA 784 | LYS 786 |
| ASN 787 | CYS 788 | ILE 789 |
| ARG 791 | HIS 802 | ILE 805 |
| ARG 815 | TYR 846 | THR 847 |
| PHE 848 | ASP 851 | |

With the benefit of the crystal structure and guidance provided by Tables 2, 3 and 4, a wide variety of c-KIT variants (e.g., insertions, deletions, substitutions, etc.) that fall within the above specified identity ranges may be designed and manufactured utilizing recombinant DNA techniques well known to those skilled in the art, particularly in view of the knowledge of the autoinhibited crystal structure provided herein. These modifications can be used in a number of combinations to produce the variants. The present invention is useful for crystallizing and then solving the structure of the range of variants of c-KIT.

Variants of c-KIT may be insertional variants in which one or more amino acid residues are introduced into a predetermined site in the c-KIT sequence. For instance, insertional variants can be fusions of heterologous proteins or polypeptides to the amino or carboxyl terminus of the subunits.

Variants of c-KIT also may be substitutional variants in which at least one residue has been removed and a different residue inserted in its place. Non-natural amino acids (i.e. amino acids not normally found in native proteins), as well as isosteric analogs (amino acid or otherwise) may optionally be employed in substitutional variants. Examples of suitable substitutions are well known in the art, such as the Glu→Asp, Asp→Glu, Ser→Cys, and Cys→Ser for example.

Another class of variants is deletional variants, which are characterized by the removal of one or more amino acid residues from the c-KIT sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution of bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; O-methylisourea, 2,4-pentanedione; and transaminaseN catalyzed reaction with glyoxylate, and N-hydroxysuccinamide esters of polyethylene glycol or other bulky substitutions.

Arginyl residues may be modified by reaction with a number of reagents, including phenylglyoxal, 2,3-butanedione, 1,2-cyclohexanedione, and ninhydrin. Modification of arginine residues requires that the reaction be performed in alkaline conditions because of the high $pK_a$, of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming O-acetyl tyrosyl species and 3-nitro derivatives, respectively. Tyrosyl residues may also be iodinated using $^{125}I$ or $^{131}I$ to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Structure and Molecular Properties*, W.H. Freeman & Co., San Francisco, pp. 79-86, 1983), acetylation of the N-terminal amine and amidation of any C-terminal carboxyl group.

As can be seen, modifications of the nucleic sequence encoding c-KIT may be accomplished by a variety of well-known techniques, such as site-directed mutagenesis (see, Gillman and Smith, *Gene* 8:81-97 (1979) and Roberts, S. et al., *Nature* 328:731-734 (1987)). When modifications are made, these modifications may optionally be evaluated for their affect on a variety of different properties including, for example, solubility, crystallizability and a modification to the protein's structure and activity.

In one variation, the variant and/or fragment of wild-type c-KIT is functional in the sense that the resulting protein is capable of associating with at least one same chemical entity that is also capable of selectively associating with a protein comprising the wild-type c-KIT (e.g., residues 544-693 and 753-935 of SEQ. ID No. 1) since this common associative ability evidences that at least a portion of the native structure has been conserved.

It is noted the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of c-KIT, and the atomic structure coordinates obtained there from, can be used to identify compounds that bind to the native domain. These compounds may affect the activity of the native domain.

Amino acid substitutions, deletions and additions that do not significantly interfere with the three-dimensional structure of c-KIT will depend, in part, on the region where the substitution, addition or deletion occurs in the crystal structure. These modifications to the protein can now be made far more intelligently with the crystal structure information provided herein. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of c-KIT will be apparent to those having skills in the art, particularly in view of the three dimensional structure of c-KIT provided herein.

2. Cloning, Expression and Purification of c-KIT

The gene encoding c-KIT can be isolated from RNA, cDNA or cDNA libraries. In this case, the portion of the gene encoding amino acid residues corresponding to the catalytic and juxtamembrane domains of human c-KIT (SEQ. ID No. 1) was isolated and is shown in SEQ. ID No. 2.

Construction of expression vectors and recombinant proteins from the DNA sequence encoding c-KIT may be performed by various methods well known in the art. For example, these techniques may be performed according to Sambrook et al., Molecular Cloning-A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of c-KIT. Example 1 provides one such expression system.

Once expressed, purification steps are employed to produce c-KIT in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography, (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

c-KIT may optionally be affinity labeled during cloning, preferably with a N-terminal six-histidine tag and rTEV protease cleavage site, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization and Crystals Comprising c-KIT

One aspect of the present invention relates to methods for forming crystals comprising c-KIT as well as crystals comprising c-KIT.

In one embodiment, a method for forming crystals comprising c-KIT is provided comprising forming a crystallization volume comprising c-KIT, one or more precipitants, optionally a buffer, optionally a monovalent and/or divalent salt and optionally an organic solvent; and storing the crystallization volume under conditions suitable for crystal formation.

In yet another embodiment, a method for forming crystals comprising c-KIT is provided comprising forming a crystallization volume comprising c-KIT in solution comprising the components shown in Table 5; and storing the crystallization volume under conditions suitable for crystal formation.

TABLE 5

Precipitant 5-50% w/v of precipitant wherein the precipitant comprises one or more members of the group consisting of PEG MME having a molecular weight range between 1000-10000, PEG having a molecular weight range between 100-10000.

pH pH 4-10. Buffers that may be used include, but are not limited to HEPES, tris, bicine, phosphate, cacodylate, acetate, citrate, PIPES, MES and combinations thereof.

Additives

Optionally 0.05 to 2.5 M additives wherein the additives comprise a monovalent and/or divalent salt (for example, sodium, lithium, magnesium, calcium, and the like)

Protein Concentration 1 mg/ml-50 mg/ml

Temperature

1° C.-25° C.

In yet another embodiment, a method for forming crystals comprising c-KIT is provided comprising forming a crystallization volume comprising c-KIT; introducing crystals comprising c-KIT as nucleation sites, and storing the crystallization volume under conditions suitable for crystal formation.

Crystallization experiments may-optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro, macro and/or streak seeding of crystals may also be performed to facilitate crystallization.

It should be understood that forming crystals comprising c-KIT and crystals comprising c-KIT according to the invention are not intended to be limited to the wild type, full length c-KIT shown in SEQ. ID No. 1, and fragments comprising residues 544-693 and 753-935 of SEQ. ID No. 1. Rather, it should be recognized that the invention may be extended to various other fragments and variants of wild-type c-KIT as described above.

It should also be understood that forming crystals comprising c-KIT and crystals comprising c-KIT according to the invention may be such that c-KIT is optionally complexed with one or more ligands and one or more copies of the same ligand. The ligand used to form the complex may be any ligand capable of binding to c-KIT. In one variation, the ligand is a natural substrate. In another variation, the ligand is an inhibitor, or a substrate or product peptide.

In one particular embodiment, c-KIT crystals have a crystal lattice in the $P2_12_12$ space group. c-KIT crystals may also optionally have unit cell dimensions, +/−5%, of a=44.489 Å b=77.277 Å and c=94.701 Å, $\alpha=\beta=90$. c-KIT crystals also preferably are capable of diffracting X-rays for determination of atomic coordinates to a resolution of 4 Å, 3.5 Å, 3.0 Å or better.

Crystals comprising c-KIT may be formed by a variety of different methods known in the art. For example, crystallizations may be performed by batch, dialysis, and vapor diffusion (sitting drop and hanging drop) methods. A detailed description of basic protein crystallization setups may be found in McRee, D., *Practical Protein Crystallography*, 2nd Ed. (1999), Academic Press Inc. Further descriptions regarding performing crystallization experiments are provided in Stevens, et al. (2000) *Curr. Opin. Struct. Biol.:* 10(5):558-63, and U.S. Pat. Nos. 6,296,673, 5,419,278, and 5,096,676.

In one variation, crystals comprising c-KIT are formed by mixing substantially pure c-KIT with an aqueous buffer containing a precipitant at a concentration just below a concentration necessary to precipitate the protein. One suitable precipitant for crystallizing c-KIT is polyethylene glycol (PEG), which combines some of the characteristics of the salts and other organic precipitants (see, for example, Ward et al., J. Mol. Biol. 98:161, 1975, and McPherson, J. Biol. Chem. 251:6300, 1976).

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of a c-KIT complex were obtained. In order to accomplish this, systematic broad screen crystallization trials were performed on an c-KIT complex using the sitting drop technique. Over 1000 individual trials were performed in which pH, temperature and precipitants were varied. In each experiment, a 100 nL mixture of c-KIT complex and precipitant was placed on a platform positioned over a well containing 100 μL of the precipitating solution. Precipitate and crystal formation was detected in the sitting drops. Fine screening was then carried out for those crystallization conditions that appeared to produce precipitate and/or crystal in the drops.

Based on the crystallization experiments that were performed, a thorough understanding of how different crystallization conditions affect c-KIT crystallization was obtained. Based on this understanding, a series of crystallization conditions were identified that may be used to form crystals comprising c-KIT. These conditions are summarized in Table 5. A particular example of crystallization conditions that may be used to form diffraction quality crystals of the autoinhibited structure of c-KIT is detailed in Example 2. FIG. 2 illustrates crystals of this structure of c-KIT formed using the crystallization conditions provided in Table 5.

One skilled in the art will recognize that the crystallization conditions provided in Table 5 and Example 2 can be varied and still yield protein crystals comprising c-KIT. For example, it is noted that variations on the crystallization conditions described herein can be readily determined by taking the conditions provided in Table 5 and performing fine screens around those conditions by varying the type and concentration of the components in order to determine additional suitable conditions for crystallizing c-KIT, variants of c-KIT, and ligand complexes thereof.

Crystals comprising c-KIT have a wide range of uses. For example, now that crystals comprising autoinhibited c-KIT have been produced, it is noted that crystallizations may be performed using such crystals as a nucleation site within a concentrated protein solution. According to this variation, a concentrated protein solution is prepared and crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising c-KIT according to the present invention, the crystals so formed can be used by this crystallization technique to initiate crystal growth of other c-KIT comprising crystals, including c-KIT complexed to other ligands.

As will be described herein in greater detail, crystals may also be used to perform X-ray or neutron diffraction analysis in order to determine the three-dimensional structure of c-KIT and, in particular, to assist in the identification of its active site. Knowledge of the binding site region allows rational design and construction of ligands including inhibitors. Crystallization and structural determination of c-KIT mutants having altered bioactivity allows the evaluation of whether such changes are caused by general structure deformation or by side chain alterations at the substitution site.

4. X-Ray Data Collection and Structure Determination

Crystals comprising c-KIT may be obtained as described above in Section 3. As described herein, these crystals may then be used to perform X-ray data collection and for structure determination.

In one embodiment, described in Example 2, crystals of c-KIT were obtained where c-KIT has the sequence of residues shown in SEQ. ID No. 3. These particular crystals were used to determine the three dimensional structure of c-KIT. However, it is noted that other crystals comprising c-KIT including different c-KIT variants, fragments, and complexes thereof may also be used.

Diffraction data was collected from cryocooled crystals (100K) of c-KIT at the Advanced Light Source (ALS) beam line 5.0.3 using an ADSC Quantum CCD detector. The diffraction pattern of the c-KIT crystals displayed symmetry consistent with space group $P2_12_12_1$ with unit cell dimensions a=44.489 Å b=77.277 Å and c=94.701 Å, $\alpha=\beta=\gamma=90$ (+/−5%). Data were collected and integrated to 1.8 Å with the HKL2000 program package (Otwinowski, Z. and Minor, W., *Meth. Enzymol.* 276:307 (1997).

The structure solution for c-KIT in the space group P2,212, with unit cell dimensions a=44.489 Å b=77.277 Å and c=94.701 Å, $\alpha=\beta=\gamma<90$ (+/−5%) was obtained by the molecular replacement method using the program AMoRE (Navaza, J. *Acta Crystallogr.* A50:157 (1994)), with the coordinates for activated c-Kit structure (Mol, C. D., et al., *Journal of Biological Chemistry*, in press (2003); PDB code 1 PKG) used as a search model. Using data in the resolution range 15.0 to 3.0 Å, the correct solutions were obtained yielding a correlation coefficient of 0.302 and an R-value of 0.502. All subsequent crystallographic calculations were performed using the CCP4 program package (Collaborative Computational Project, N. The CCP4 Suite: Programs for Protein Crystallography. *Acta Crystallogr.* D50, 760-763 (1994)). The molecular replacement solutions were subjected to rigid body refinement followed by restrained least-squares refinement using the maximum likelihood method as implemented in REFMAC (Murshudov, G. N., Vagin, A. A. and Dodson E. J. *Acta Crystallogr* D53:240 (1997)). The initial refinement resulted in an R-value of 0.420 and an $R_{free}$ value of 0.475 that was improved by cycles of automated refinement with the program ARP/warp as implemented in CCP4 and using data to 1.9 Å resolution. The improved electron density map calculated from a dummy atom ARP/warp model with an R-value of 0.196 and an $R_{free}$ value of 0.319 showed clear differences between the autoinhibited c-KIT structure and the molecular replacement model from which the correct molecular model could be discerned. Multiple rounds of manual fitting of the c-KIT sequence and ordered regions not present in the initial model were performed with Xfit (McRee, D. E., *J. Struct. Biol.* 125:156 (1999)). Manual fitting was interspersed with restrained least-squares refinement in REFMAC against data from 20.0 to 1.8 Å. All stages of refinement were carried with bulk solvent corrections and anisotropic scaling, and excluded 5% of $R_{free}$ reflections for cross-validation. The data collection and data refinement statistics are given in Table 6.

TABLE 6

| Crystal data | |
| --- | --- |
| Space group | $P2_12_12_1$ |
| Unit cell dimensions | a = 44.489 Å |
|  | b = 77.277 Å |
|  | c = 94.701 Å |
| Data collection | |
| X-ray source | ALS BL 5.0.3 |
| Wavelength [Å] | 1.00 |
| Resolution [Å] | 1.80 |
| Observations (unique) | 30651 |
| Redundancy | 4.3 |
| Completeness   overall (outer shell) | 98.6 (92.2)% |
| I/σ(I)              overall (outer shell) | 12.7 (1.9) |
| $R_{symm}^1$    overall (outer shell) | 0.054 (.398) |
| Refinement | |
| Reflections used | 28843 |
| R-factor | 18.83% |
| $R_{free}$ | 23.30% |
| r.m.s bonds | 0.007 Å |
| r.m.s angles | 1.005° |

Structure coordinates were determined for this crystal, where the unit cell dimensions were a=44.489 Å b=77.277 Å and c=94.701 Å, α=β=γ=90, and the resultant set of structural coordinates from the refinement are presented in FIG. 3.

Those of skill in the art understand that a set of structure coordinates (such as those in FIG. 3) for a protein or a protein-complex or a portion thereof, is a relative set of points that define a shape in three dimensions. Thus, it is possible that an entirely different set of structure coordinates could define a similar or identical shape. Moreover, slight variations in the individual coordinates may have little effect on overall shape. In terms of binding pockets, these variations would not be expected to significantly alter the nature of ligands that could associate with those pockets. The term "binding pocket" as used herein refers to a region of the protein that, as a result of its shape, favorably associates with a ligand.

These variations in coordinates may be generated because of mathematical manipulations of the c-KIT structure coordinates. For example, the sets of structure coordinates shown in FIG. 3 could be manipulated by crystallographic permutations of the structure coordinates, fractionalization of the structure coordinates, application of a rotation matrix, integer additions or subtractions to sets of the structure coordinates, inversion of the structure coordinates or any combination of the above.

Alternatively, modifications in the crystal structure due to mutations, additions, substitutions, and/or deletions of amino acids or other changes in any of the components that make up the crystal could also account for variations in structure coordinates. If such variations are within an acceptable standard error as compared to the original coordinates, the resulting three-dimensional shape should be considered to be the same. Thus, for example, a ligand that bound to the active site binding pocket of c-KIT would also be expected to bind to another binding pocket whose structure coordinates defined a shape that fell within the acceptable error.

Various computational methods may be used to determine whether a particular protein or a portion thereof (referred to here as the "target protein"), typically the binding pocket, has a high degree of three-dimensional spatial similarity to another protein (referred to here as the "reference protein") against which the target protein is being compared.

The process of comparing a target protein structure to a reference protein structure may generally be divided into three steps: 1) defining the equivalent residues and/or atoms for the target and reference proteins, 2) performing a fitting operation between the proteins; and 3) analyzing the results. These steps are described in more detail below. All structure comparisons reported herein and the structure comparisons claimed are intended to be based on the particular comparison procedure described below.

Equivalent residues or atoms can be determined based upon an alignment of primary sequences of the proteins, an alignment of their structural domains or as a combination of both. Sequence alignments generally implement the dynamic programming algorithm of Needleman and Wunsch [*J. Mol. Biol.* 48: 442-453, 1970]. For the purpose of this invention the sequence alignment was performed using the publicly available software program MOE (Chemical Computing Group Inc.) package version 2002.3, as described in the accompanying User's Manual. When using the MOE program, alignment was performed in the sequence editor window using the ALIGN option utilizing the following program parameters: Initial pairwise Build-up: ON, Substitution Matrix: Blosum62, Round Robin: ON, Gap Start: 7, Gap Extend: 1, Iterative Refinement: ON, Build-up: TREE-BASED, Secondary Structure: NONE, Structural Alignment: ENABLED, Gap Start: 1, Gap Extend: 0.1

Once aligned, a rigid body fitting operation is performed where the structure for the target protein is translated and rotated to obtain an optimum fit relative to the structure of the reference protein. The fitting operation uses an algorithm that computes the optimum translation and rotation to be applied to the moving structure, such that the root mean square deviation of the fit over the specified pairs of equivalent atoms is an absolute minimum. For the purpose of fitting operations made herein, the publicly available software program MOE (Chemical Computing Group Inc.) v. 2002.3 was used.

The results from this process are typically reported as an RMSD value between two sets of atoms. The term "root mean square deviation" means the square root of the arithmetic mean of the squares of deviations. It is a way to express the deviation or variation from a trend or object. As used herein, an RMSD value refers to a calculated value based on variations in the atomic coordinates of a reference protein from the atomic coordinates of a reference protein or portions of thereof. The structure coordinates for c-KIT, provided in FIG. 3, are used as the reference protein in these calculations.

The same set of atoms was used for initial fitting of the structures and for computing root mean square deviation values. For example, if a root mean square deviation (RMSD) between Cα atoms of two proteins is needed, the proteins in question should be superposed only on the Cα atoms and not on any other set of atoms. Similarly, if an RMSD calculation for all atoms is required, the superposition of two structures should be performed on all atoms.

Based on a review of protein structures deposited in the Protein Databank (PDB), 1IEP was identified as being the most relevant and similar structure relative to the structure coordinates provided herein. Table 7 below provides a series of RMSD values that were calculated by the above described process using the structure coordinates in FIG. 3 as the reference protein and the structure coordinates from PDB code: 1IEP (Mouse Tyrosine Protein Kinase ABL, 1IEP) as the target protein.

TABLE 7

| AA RESIDUES USED TO PERFORM RMSD COMPARISON WITH PDB:1IEP | PORTION OF EACH AA RESIDUE USED TO PERFORM RMSD COMPARISON WITH PDB:1IEP | RMSD [Å] |
|---|---|---|
| Table 2 | alpha-carbon atoms[1] | 0.79 |
| (4 Angstrom set) | main-chain atoms[1] | 0.94 |
|  | all non-hydrogen[2] | 0.82 |
| Table 3 | alpha-carbon atoms[1] | 1.92 |
| (7 Angstrom set) | main-chain atoms[1] | 1.94 |
|  | all non-hydrogen[2] | 1.73 |
| Table 4 | alpha-carbon atoms[1] | 4.37 |
| (10 Angstrom set) | main-chain atoms[1] | 4.22 |
|  | all non-hydrogen[2] | 2.68 |
| 544-693 and 753-935 | alpha-carbon atoms[1] | 3.73 |
| of | main-chain atoms[1] | 3.61 |
| SEQ. ID No. 1 | all non-hydrogen[2] | 2.40 |

[1] the RMSD computed between the atoms of all amino acids that are common to both the target and the reference in the aligned and superposed structure. The amino acids need not to be identical.
[2] the RMSD computed only between identical amino acids, which are common to both the target and the reference in the aligned and superposed structure.

It is noted that mutants and variants of c-KIT as well as other tyrosine protein kinases are likely to have similar structures despite having different sequences. For example, the binding pockets of these related proteins are likely to have similar contours. Accordingly, it should be recognized that the structure coordinates and binding pocket models provided herein have utility for these other related proteins.

Accordingly, in one embodiment, the invention relates to data, computer readable media comprising data, and uses of the data where the data comprises all or a portion of the structure coordinates shown in FIG. 3 or structure coordinates having a root mean square deviation (RMSD) equal to or less than the RMSD value specified in Columns 3, 4 or 5 of Table 1 when compared to the structure coordinates of FIG. 3. the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

As noted, there are many different ways to express the surface contours of the c-KIT structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

5. c-KIT Structure

The present invention is also directed to a three-dimensional crystal structure of c-KIT. This crystal structure may be used to identify binding sites, to provide mutants having desirable binding properties, and ultimately, to design, characterize, or identify ligands that interact with c-KIT as well as other tyrosine protein kinases.

The three-dimensional crystal structure of c-KIT may be generated, as is known in the art, from the structure coordinates shown in FIG. 3 and similar such coordinates.

The final refined coordinates include all amino acid residues from 544-693 and 754-935, including two residues (Thr-Ser) introduced between residues 693 and 754 (FIG. 3). The final coordinate set additionally includes 208 solvent molecules modeled as waters.

Figure 4:
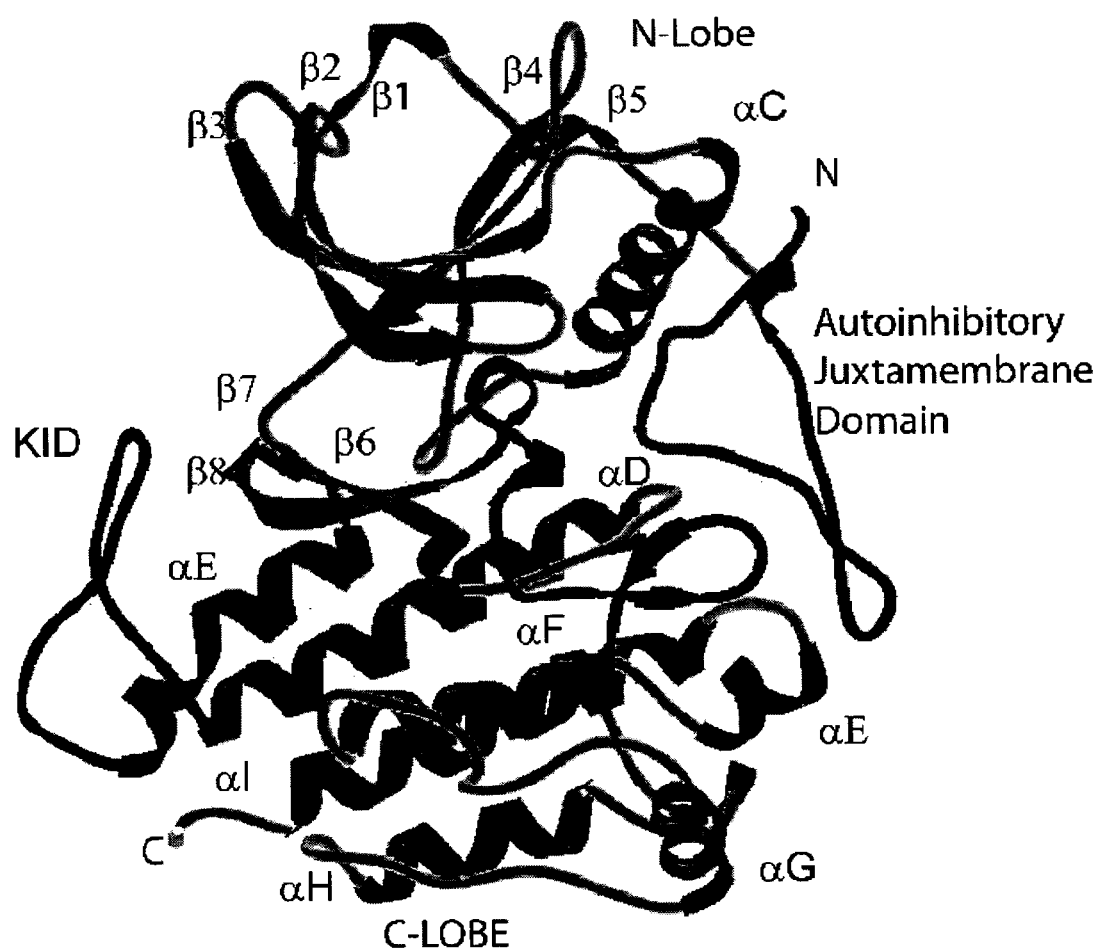
FIG. 4 illustrates a ribbon diagram overview of the structure of c-KIT, highlighting secondary structural elements of the protein.

FIG. 4 illustrates a ribbon diagram overview of the autoinhibited structure of c-KIT, highlighting the secondary structural elements of the protein. As can be seen, the structure exhibits bilobal architecture typical of protein kinase catalytic domains. The smaller N-terminal lobe (residues 586-673) contains a five-stranded anti-parallel β-sheet (β1-β5) and one α-helix (αC). The C-terminal lobe (residues 674-929) contains two short β-strands (β7 and β8) and seven α-helices (αD-αH). Additionally, the structure contains residues 544-585 comprising the autoinhibitory juxtamembrane domain.

Kinases show considerable variability in the relative orientation of the N and C lobes, in the position and orientation of the αC, and in the conformation of the activation loop. This relative orientation of the N- and C-terminal lobes is important in kinase function. A catalytically active conformation is generally a closed structure in which the two lobes clamp together bringing conserved residues into catalytically optimal positions. In particular, in the active conformation, the αC helix becomes parallel with the cleft between the lobes and makes tertiary contacts with the C-lobe. In the inactive conformation observed in the autoinhibited c-Kit kinase structure the two lobes are spaced apart at a much higher angle and the αC helix is rotated away from the C-lobe.

For autoinhibited c-KIT, the activation segment (also known as the activation loop) comprising residues 810-836 is fully ordered. Residues 810-812, known as the Asp-Phe-Gly or kinase DFG motif, are in a conformation consistent with inactive kinase structures.

Figure 5:
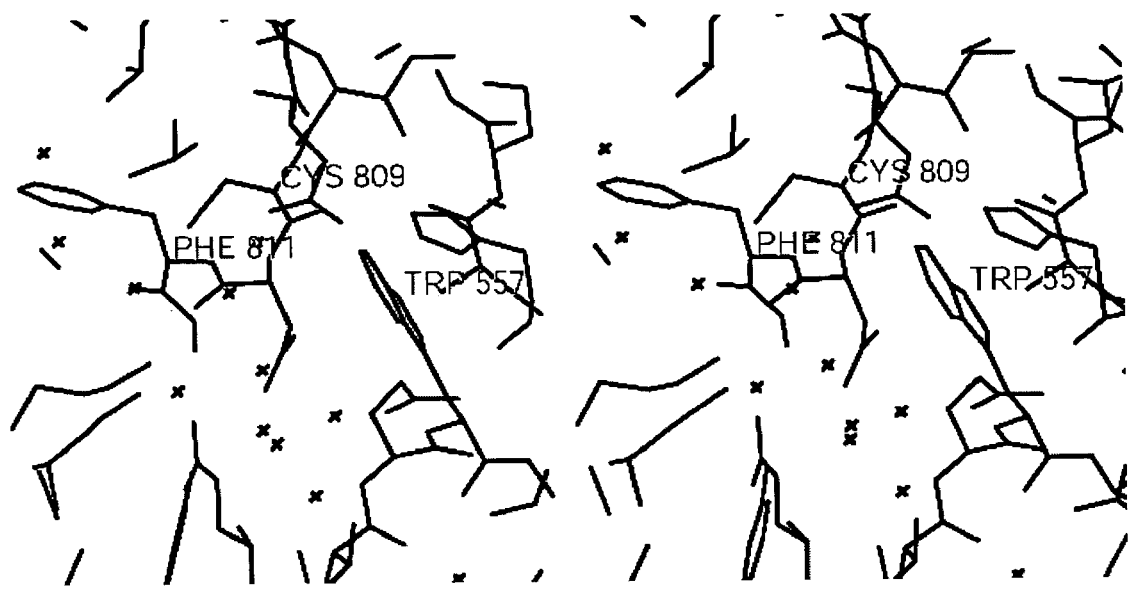
FIG. 5 illustrates the c-KIT binding site of c-KIT based on the determined crystal structure for the molecule in the asymmetric unit corresponding to the coordinates shown in FIG. 3.

FIG. 5 illustrates the binding site of c-KIT based on the determined crystal structure corresponding to the coordinates shown in FIG. 3.

6. c-KIT Active Site and Ligand Interaction

The term "binding site" or "binding pocket", as the terms are used herein, refers to a region of a protein that, as a result of its shape, favorably associates with a ligand or substrate. The term "c-KIT-like binding pocket" refers to a portion of a molecule or molecular complex whose shape is sufficiently similar to the c-KIT binding pockets as to bind common ligands. This commonality of shape may be quantitatively defined based on a comparison to a reference point, that reference point being the structure coordinates provided herein. For example the commonality of shape may be quantitatively defined based on a root mean square deviation (RMSD) from the structure coordinates of the backbone atoms of the amino acids that make up the binding pockets in c-KIT (as set forth in FIG. 3).

The "active site binding pockets" or "active site" of c-KIT refers to the area on the surface of c-KIT where the substrate binds.

FIG. 5 illustrates the ATP binding site of c-KIT based on the determined crystal structure for the molecule in the asymmetric unit corresponding to the structure coordinates shown in FIG. 3. The catalytic site for ATP is located at the interface of the two lobes (FIG. 5).

The ATP binding site of protein kinases is a primary target for the design of small molecule inhibitors. The ATP binding site appears well conserved among protein kinases and involves residues protruding from the β1-β2-β3 sheet, helix C, the loop region linking β5 and the C-lobe, and the catalytic loop. The structure of the ATP binding pocket in the c-KIT complex shows considerable sequence variability with other kinases, which is reflective of diversity among kinase sub-families. The ATP binding cleft shows subtle differences in ATP site architecture that may be explored to confer specificity of inhibition.

In resolving the crystal structure of c-KIT, applicants determined that c-KIT amino acids shown in Table 2 (above) are encompassed within a 4-Angstrom radius around the c-KIT active site and therefore are likely close enough to interact with an active site inhibitor of c-KIT. Applicants have also determined that the amino acids shown in Table 3 (above) are encompassed within a 7-Angstrom radius around the c-KIT active site. Further, the amino acids shown in Table 4 (above) are encompassed within a 10-Angstrom radius around the c-KIT active site. Due to their proximity to the active site, the amino acids in the 4, 7, and/or 10 Angstroms sets are preferably conserved in variants of c-KIT. While it is desirable to largely conserve these residues, it should be recognized however that variants may also involve varying 1, 2, 3, 4 or more of the residues set forth in Tables 2, 3 and 4 in order to evaluate the roles these amino acids play in the binding pocket.

With the knowledge of the c-KIT crystal structure provided herein, Applicants are able to know the contour of an c-KIT binding pocket based on the relative positioning of the 4, 7, and/or 10 Angstroms sets of amino acids. Again, it is noted that it may be desirable to form variants where 1, 2, 3, 4 or more of the residues set forth in Tables 2, 3 and 4 are varied in order to evaluate the roles these amino acids play in the binding pocket. Accordingly, any set of structure coordinates for a protein from any source shall be considered within the scope of the present invention if the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

Accordingly, in various embodiments, the invention relates to data, computer readable media comprising data, and uses of the data where the data comprises structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

As noted above, there are many different ways to express the surface contours of the c-KIT structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

It will be readily apparent to those of skill in the art that the numbering of amino acids in other isoforms of c-KIT may be different than that set forth for c-KIT. Corresponding amino acids in other isoforms of c-KIT are easily identified by visual inspection of the amino acid sequences or by using commercially available homology software programs, as further described below.

7. System for Displaying the Three Dimensional Structure of c-KIT

The present invention is also directed to machine-readable data storage media having data storage material encoded with machine-readable data that comprises structure coordinates for c-KIT. The present invention is also directed to a machine readable data storage media having data storage material encoded with machine readable data, which, when read by an appropriate machine, can display a three dimensional representation of a structure of c-KIT.

All or a portion of the c-KIT coordinate data shown in FIG. 3, when used in conjunction with a computer programmed with software to translate those coordinates into the three-dimensional structure of c-KIT may be used for a variety of purposes, especially for purposes relating to drug discovery. Softwares for generating three-dimensional graphical representations are known and commercially available. The ready use of the coordinate data requires that it be stored in a computer-readable format. Thus, in accordance with the present invention, data capable of being displayed as the three-dimensional structure of c-KIT and/or portions thereof and/or their structurally similar variants may be stored in a machine-readable storage medium, which is capable of displaying a graphical three-dimensional representation of the structure.

For example, in various embodiments, a computer is provided for producing a three-dimensional representation of at least an c-KIT-like binding pocket, the computer comprising:

machine readable data storage medium comprising a data storage material encoded with machine-readable data, the machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

a working memory for storing instructions for processing the machine-readable data, a central-processing unit coupled to the working memory and to the machine-readable data storage medium, for processing the machine-readable data into the three-dimensional representation; and an output hardware coupled to the central processing unit, for receiving the three dimensional representation.

Another embodiment of this invention provides a machine-readable data storage medium, comprising a data storage material encoded with machine readable data which, when used by a machine programmed with instructions for using said data, displays a graphical three-dimensional representation comprising c-KIT or a portion or variant thereof.

In various variations, the machine readable data comprises data for representing a protein based on structure coordinates where the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

According to another embodiment, the machine-readable data storage medium comprises a data storage material encoded with a first set of machine readable data which comprises the Fourier transform of structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data. For example, the Fourier transform of the structure coordinates set forth in FIG. 3 may be used to determine at least a portion of the structure coordinates of other c-KIT-like enzymes, and isoforms of c-KIT.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

Figure 6:
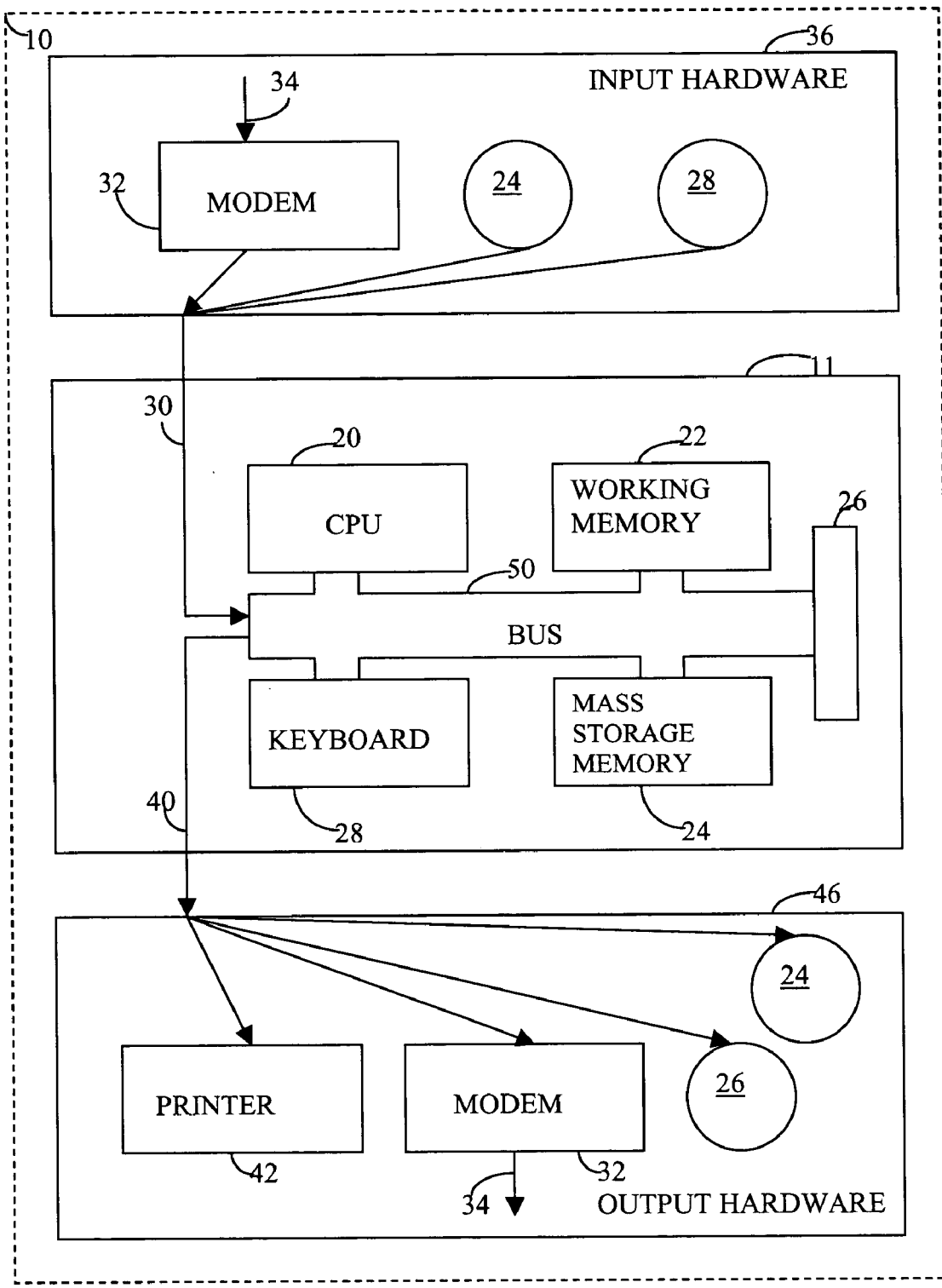
FIG. 6 illustrates a system that may be used to carry out instructions for displaying a crystal structure of c-KIT encoded on a storage medium.

FIG. 6 illustrates an example of a computer system that may be used in combination with storage media according to the present invention. As illustrated, the computer system 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Conventional devices may, similarly implement output hardware 46, coupled to computer 11 by output lines 40. By way of example, output hardware 46 may include CRT display terminal 26 for displaying a graphical representation of a binding pocket of this invention using a program such as MOE as described herein. Output hardware might also include a printer 42, so that hard copy output may be produced, or a disk drive 24, to store system output for later use.

In operation, CPU 20 coordinates the use of the various input and output devices 36, 46 coordinates data accesses from mass storage 24 and accesses to and from working memory 22, and determines the sequence of data processing steps. A number of programs may be used to process the machine-readable data of this invention. Such programs are discussed in reference to using the three dimensional structure of c-KIT described herein.

The storage medium encoded with machine-readable data according to the present invention can be any conventional data storage device known in the art. For example, the storage medium can be a conventional floppy diskette or hard disk. The storage medium can also be an optically readable data storage medium, such as a CD-ROM or a DVD-ROM, or a rewritable medium such as a magneto-optical disk that is optically readable and magneto-optically writable.

8. Uses of the Three Dimensional Structure of c-KIT

The three-dimensional crystal structure of the present invention may be used to identify c-KIT binding sites, be used as a molecular replacement model to solve the structure of unknown crystallized proteins, to design mutants having desirable binding properties, and ultimately, to design, characterize, identify entities capable of interacting with c-KIT and other tyrosine protein kinases, as well as other uses that would be recognized by one of ordinary skill in the art. Such entities may be chemical entities or proteins. The term "chemical entity", as used herein, refers to chemical compounds, complexes of at least two chemical compounds, and fragments of such compounds.

The c-KIT structure coordinates provided herein are useful for screening and identifying drugs that inhibit c-KIT and other tyrosine protein kinases. For example, the structure encoded by the data may be computationally evaluated for its ability to associate with putative substrates or ligands.

Such compounds that associate with c-KIT may inhibit c-KIT, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment of the present invention, a method is provided for evaluating the potential of an entity to associate with c-KIT or a fragment or variant thereof by using all or a portion of the structure coordinates provided in FIG. 3 or functional equivalents thereof. A method is also provided for evaluating the potential of an entity to associate with c-KIT or a fragment or variant thereof by using structure coordinates similar to all or a portion of the structure coordinates provided in FIG. 3 or functional equivalents thereof.

The method may optionally comprise the steps of: creating a computer model of all or a portion of a protein structure (e.g., a binding pocket) using structure coordinates according to the present invention; performing a fitting operation between the entity and the computer model; and analyzing the results of the fitting operation to quantify the association between the entity and the model. The portion of the protein structure used optionally comprises all of the amino acids listed in Tables 2, 3 and 4 that are present in the structure coordinates being used.

It is noted that the computer model may not necessarily directly use the structure coordinates. Rather, a computer model can be formed that defines a surface contour that is the same or similar to the surface contour defined by the structure coordinates.

The structure coordinates provided herein can also be utilized in a method for identifying a ligand (e.g., entities capable of associating with a protein) of a protein comprising an c-KIT-like binding pocket. One embodiment of the method comprises: using all or a portion of the structure coordinates provided herein to generate a three-dimensional structure of an c-KIT-like binding pocket; employing the three-dimensional structure to design or select a potential ligand; synthesizing the potential ligand; and contacting the synthesized potential ligand with a protein comprising an c-KIT-like binding pocket to determine the ability of the potential ligand to interact with protein. According to this method, the structure coordinates used may have a root mean square deviation equal to or less than the RMSD values specified in Columns 3, 4 or 5 of Table 1 when compared to the structure coordinates of FIG. 3 according to the RMSD calculation method set forth herein, provided that the portion of amino acid residues specified in Column 2 of Table 1 of each set of structure coordinates are superimposed and the root mean square deviation is calculated based only on those amino acid residues in the structure coordinates that are also present in the portion of the protein specified in Column 1 of Table 1. The portion of the protein structure used optionally comprises all of the amino acids listed in Tables 1, 2 and/or 3 that are present.

As noted previously, the three-dimensional structure of an c-KIT-like binding pocket need not be generated directly from structure coordinates. Rather, a computer model can be formed that defines a surface contour that is the same or similar to the surface contour defined by the structure coordinates.

A method is also provided for evaluating the ability of an entity, such as a compound or a protein to associate with an c-KIT-like binding pocket, the method comprising: constructing a computer model of a binding pocket defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for c-KIT, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the said binding pocket.

The computer model of a binding pocket used in this embodiment need not be generated directly from structure coordinates. Rather, a computer model can be formed that defines a surface contour that is the same or similar to the surface contour defined by the structure coordinates.

Also according to the method, the method may further include synthesizing the entity; and contacting a protein having an c-KIT-like binding pocket with the synthesized entity.

With the structure provided herein, the present invention for the first time permits the use of molecular design techniques to identify, select or design potential inhibitors of c-KIT, based on the structure of an c-KIT-like binding pocket. Such a predictive model is valuable in light of the high costs associated with the preparation and testing of the many diverse compounds that may possibly bind to the c-KIT protein.

According to this invention, a potential c-KIT inhibitor may now be evaluated for its ability to bind an c-KIT-like binding pocket prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of an c-KIT-like binding pocket may be computationally evaluated using a series of steps in which chemical entities or fragments are screened and selected for their ability to associate with the c-KIT-like binding pockets.

One skilled in the art may use one of several methods to screen entities (whether chemical or protein) for their ability to associate with an c-KIT-like binding pocket. This process may begin by visual inspection of, for example, an c-KIT-like binding pocket on a computer screen based on the c-KIT structure coordinates in FIG. 3 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (P. J. Goodford, "A Computational Procedure for Determining Energetically Favorable Binding Sites on Biologically Important Macromolecules", J. Med. Chem., 28, pp. 849-857 (1985)). GRID is available from Oxford University, Oxford, UK; MCSS (A. Miranker et al., "Functionality Maps of Binding Sites: A Multiple Copy Simultaneous Search Method." Proteins: Structure, Function and Genetics, 11, pp. 29-34 (1991)). MCSS is available from Molecular Simulations, San Diego, Calif.; AUTODOCK (D. S. Goodsell et al., "Automated Docking of Substrates to Proteins by Simulated Annealing", Proteins: Structure, Function, and Genetics, 8, pp. 195-202 (1990)). AUTODOCK is available from Scripps Research Institute, La Jolla, Calif.; & DOCK (I. D. Kuntz et al., "A Geometric Approach to Macromolecule-Ligand Interactions", J. Mol. Biol., 161, pp. 269-288 (1982)). DOCK is available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of c-KIT. This may then be followed by manual model building using software such as MOE, QUANTA or Sybyl [Tripos Associates, St. Louis, Mo].

Useful programs to aid one of skill in the art in connecting the individual chemical entities or fragments include: CAVEAT (P. A. Bartlett et al, "CAVEAT: A Program to Facilitate the Structure-Derived Design of Biologically Active Molecules", in "Molecular Recognition in Chemical and Biological Problems", Special Pub., Royal Chem. Soc., 78, pp. 182-196 (1989); G. Lauri and P. A. Bartlett, "CAVEAT: a Program to Facilitate the Design of Organic Molecules", J. Comput. Aided Mol. Des., 8, pp. 51-66 (1994)). CAVEAT is available from the University of California, Berkeley, Calif.; 3D Database systems such as ISIS (MDL Information Systems, San Leandro, Calif.). This area is reviewed in Y. C. Martin, "3D Database Searching in Drug Design", J. Med. Chem., 35, pp. 2145-2154 (1992); HOOK (M. B. Eisen et al, "HOOK: A Program for Finding Novel Molecular Architectures that Satisfy the Chemical and Steric Requirements of a Macromolecule Binding Site", Proteins: Struct., Funct., Genet., 19, pp. 199-221 (1994). HOOK is available from Molecular Simulations, San Diego, Calif.

Instead of proceeding to build an inhibitor of an c-KIT-like binding pocket in a step-wise fashion one fragment or entity at a time as described above, inhibitory or other c-KIT binding compounds may be designed as a whole or "de novo" using either an empty binding site or optionally including some portion(s) of a known inhibitor(s). There are many de novo ligand design methods including: LUDI (H.-J. Bohm, "The Computer Program LUDI: A New Method for the De Novo Design of Enzyme Inhibitors", J. Comp. Aid. Molec. Design, 6, pp. 61-78 (1992)). LUDI is available from Molecular Simulations Incorporated, San Diego, Calif.; LEGEND (Y. Nishibata et al., Tetrahedron, 47, p. 8985 (1991)). LEGEND is available from Molecular Simulations Incorporated, San Diego, Calif.; LEAPFROG (available from Tripos Associates, St. Louis, Mo.); & SPROUT (V. Gillet et al, "SPROUT: A Program for Structure Generation)", J. Comput. Aided Mol. Design, 7, pp. 127-153 (1993)). SPROUT is available from the University of Leeds, UK.

Other molecular modeling techniques may also be employed in accordance with this invention (see, e.g., Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modem Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once an entity has been designed or selected, for example, by the above methods, the efficiency with which that entity may bind to an c-KIT binding pocket may be tested and optimized by computational evaluation. For example, an effective c-KIT binding pocket inhibitor preferably demonstrates a relatively small difference in energy between its bound and free states (i.e., a small deformation energy of binding). Thus, the most efficient c-KIT binding pocket inhibitors should preferably be designed with deformation energy of binding of not greater than about 10 kcal/mole, more preferably, not greater than 7 kcal/mole. c-KIT binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to an c-KIT binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. COPYRGT.1995); AMBER, version 4.1 (P. A. Kollman, University of California at San Francisco, COPYRGT 1995); QUANTA/CHARMM (Molecular Simulations, Inc., San Diego, Calif. COPYRGT.1995); Insight II/Discover (Molecular Simulations, Inc., San Diego, Calif. COPYRGT. 1995); DelPhi (Molecular Simulations, Inc., San Diego, Calif COPYRGT. 1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by this invention, is the computational screening of small molecule databases for chemical entities or compounds that can bind in whole, or in part, to an c-KIT binding pocket. In this screening, the quality of fit of such entities to the binding site may be judged either by shape complementarities or by estimated interaction energy [E. C. Meng et al., J. Comp. Chem., 13, 505-524 (1992)].

According to another embodiment, the invention provides compounds that associate with an c-KIT-like binding pocket produced or identified by various methods set forth above.

The structure coordinates set forth in FIG. 3 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIG. 3 as a molecular replacement model.

By using molecular replacement, all or part of the structure coordinates of the c-KIT provided by this invention (and set forth in FIG. 3) can be used to determine the structure of another crystallized molecule or molecular complex more quickly and efficiently than attempting an ab initio structure determination. One particular use includes use with other tyrosine protein kinases. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of c-KIT according to FIG. 3 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55-77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of c-KIT can be resolved by this method.

In one embodiment, the method of molecular replacement is utilized to obtain structural information about the present invention and any other c-KIT-like molecule. The structure coordinates of c-KIT, as provided by this invention, are particularly useful in solving the structure of other isoforms of c-KIT or c-KIT complexes.

The structure coordinates of c-KIT as provided by this invention are useful in solving the structure of c-KIT variants that have amino acid substitutions, additions and/or deletions (referred to collectively as "c-KIT mutants", as compared to naturally occurring c-KIT). These c-KIT mutants may optionally be crystallized in co-complex with a ligand, such as an inhibitor, substrate analogue or a suicide substrate. The crystal structures of a series of such complexes may then be solved by molecular replacement and compared with that of c-KIT. Potential sites for modification within the various binding sites of the enzyme may thus be identified. This information provides an additional tool for determining the most efficient binding interactions such as, for example, increased hydrophobic interactions, between c-KIT and a ligand. It is noted that the ligand may be the protein's natural ligand or may be a potential agonist or antagonist of a protein.

All of the complexes referred to above may be studied using well-known X-ray diffraction techniques and may be refined versus 1.5-3A resolution X-ray data to an R value of about 0.22 or less using computer software, such as X-PLOR [Yale University, COPYRIGHT.1992, distributed by Molecular Simulations, Inc.; see, e.g., Blundell & Johnson, supra; Meth. Enzymol., Vol. 114 & 115, H. W. Wyckoff et al., eds., Academic Press (1985)]. This information may thus be used to optimize known c-KIT inhibitors, and more importantly, to design new c-KIT inhibitors.

The structure coordinates described above may also be used to derive the dihedral angles, phi and psi, that define the conformation of the amino acids in the protein backbone. As will be understood by those skilled in the art, the $phi_n$ angle refers to the rotation around the bond between the alpha-carbon and the nitrogen, and the $psi_n$ angle refers to the rotation around the bond between the carbonyl carbon and the alpha-carbon. The subscript "n" identifies the amino acid whose conformation is being described [for a general reference, see Blundell and Johnson, Protein Crystallography, Academic Press, London, 1976].

9. Uses of the Crystal and Diffraction Pattern of c-KIT

Crystals, crystallization conditions and the diffraction pattern of c-KIT that can be generated from the crystals also have a range of uses. One particular use relates to screening entities that are not known ligands of c-KIT for their ability to bind to c-KIT. For example, with the availability of crystallization conditions, crystals and diffraction patterns of c-KIT provided according to the present invention, it is possible to take a crystal of c-KIT; expose the crystal to one or more entities that may be a ligand of c-KIT; and determine whether a ligand/c-KIT complex is formed. The crystals of c-KIT may be exposed to potential ligands by various methods, including but not limited to, soaking a crystal in a solution of one or more potential ligands or co-crystallizing c-KIT in the presence of one or more potential ligands. Given the structure coordinates provided herein, once a ligand complex is formed, the structure coordinates can be used as a model in molecular replacement in order to determine the structure of the ligand complex.

Once one or more ligands are identified, structural information from the ligand/c-KIT complex(es) may be used to design new ligands that bind tighter, bind more specifically, have better biological activity or have better safety profile than known ligands.

In one embodiment, a method is provided for identifying a ligand that binds to c-KIT comprising: (a) attempting to crystallize a protein that comprises a sequence with 55%, 65%, 78%, 85%, 90%, 95%, 97%, 99% or greater identity with SEQ. ID No. 3 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to c-KIT comprising: soaking a crystal of a protein that comprises a sequence with 55%, 65%, 78%, 85%, 90%, 95%, 97%, 99% or greater identity with SEQ. ID No. 3 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-c-KIT complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

EXAMPLES

Example 1

Expression and Purification of c-KIT

This example describes cloning, expression and purification of c-KIT. It should be noted that a variety of other expression systems and hosts are also suitable for the expression of c-KIT, as would be readily appreciated by one of skill in the art.

The portion of the gene encoding residues 544-935 (from SEQ. ID No. 1), which corresponds to the catalytic domain of human c-KIT, was cloned into a modified pFastBacHTc vector (also known as pSXB1) at the BamHI and XbaI sites. The region corresponding to amino acid residues 694-753 (SEQ. ID No. 1) or nucleotide sequence 451-630 (SEQ. ID No. 2) was deleted by using inverse PCR, which generated an additional Thr-Ser residues at positions 182-183 (SEQ. ID No. 3). Expression from this vector produced the recombinant c-KIT catalytic domain with a 6x-histidine tag at the N-terminus followed by a rTEV protease cleavage sequence to facilitate tag removal (the excised 6x-Histidine tag and rTEV protease cleavage site sequences are underlined in SEQ. ID No. 3). Recombinant baculovirus genomic DNAs incorporating the c-KIT catalytic domain cDNA sequences were generated by transposition using the Bac-to-Bac system (Invitrogen). Infectious viral particles were obtained by transfection of a 2 mL adherent culture of *Spodoptera frugiperda* Sf9 insect cells with the recombinant viral genomic DNA. Growth in ESF 921 protein free medium (Expression Systems) was for 3 days at 27° C. The resulting Passagxe 0 viral supernatant was used to obtain Passage 1 high titer viral stock (HTS) by infection of a 30 mL adherent culture of *Spodoptera frugiperda* Sf9 insect cells grown under similar conditions. Passage 1 HTS was used in turn to infect a 100 mL suspension culture of *Spodoptera frugiperda* Sf9 insect cells in order to generate Passage 2 HTS.

Passage 2 HTS was used to infect a 5-liter culture of *Spodoptera frugiperda* Sf9 insect cells (at a density of approx. $3 \times 10^6$ cells/mL) in a 10 liter Wave BioReactor grown in ESF-921 serum-free medium at a multiplicity of infection (moi) of approximately 5 (empirical value based on usual HTS viral counts). Cell growth/infection proceeded for two days after which time the cells were pelleted by centrifugation and the cell pellet stored at −80° C. until required. Frozen cell pellets from two such 5-liter cultures were removed from the −80° C. freezer and each suspended in 150 mL of Lysis Buffer (50 mM Tris-HCl, pH 7.9, 200 mM NaCl, 0.25 mM TCEP, 1 mM PMSF and 2 'Complete-EDTA' Roche Protease Inhibitor tablets). The suspensions were stirred for 45 min at 4° C. followed by centrifugation at 7,000 g for 1 h. To each supernatant were added 8 mL of a 50% slurry of ProBond (InVitrogen) resin that had been equilibrated in Lysis Buffer without protease inhibitors. The suspensions were mixed for 90 min followed by centrifugation at 640 g for 5 min. The supernatants were discarded and the resin pellets washed three times with 50 mM potassium phosphate, pH 7.9, 400 mM NaCl, 0.25 mM TCEP and 1 ug/mL leupeptin. Each resin sample was transferred to an OMNI chromatography column (10 cm×1.5 cm diameter) at 4° C. and washed with 50 column volumes of 50 mM potassium phosphate, pH 7.9, 400 mM NaCl, 20 mM imidazole-HCl, pH 7.9, 0.25 mM TCEP and 1 ug/mL leupeptin. The columns were subsequently washed with 5 column volumes of 50 mM Tris-HCl, pH 7.9, 400 mM NaCl, 0.25 mM TCEP and 1 ug/mL leupeptin. Target elution was effected by the addition of 50 mM Tris-HCl, pH 7.9, 400 mM NaCl, 200 mM imidazole-HCl, pH 7.9, 0.25 mM TCEP, 1 ug/mL leupeptin. The eluates were pooled (the yield at this stage was 25.3 mg total protein in 36 mL) and the polyhistidine purification tag removed by cleavage overnight with 100u/mL TEV protease during dialysis against 50 mM Tris-HCl, pH 7.9, 400 mM NaCl, 20 mM imidazole-HCl, pH 7.9, 0.25 mM TCEP and 1 ug/mL leupeptin at 4° C. The TEV protease-treated sample was passed by gravity flow through an 8 mL bed volume of ProBond chelating resin charged with Ni that had been equilibrated in 50 mM Tris-HCl, pH 7.9, 400 mM NaCl, 20 mM imidazole-HCl, pH 7.9, 0.25 mM TCEP and 1 ug/mL leupeptin at 4° C. The unbound flow-through material was concentrated and buffer-exchanged into 25 mM Tris-HCl buffer, pH 7.6, 250 mM NaCl, 5 mM DTT and 1 mM EDTA-NaOH, pH 8.0, by using Vivaspin centrifugal concentrators. Following three five-fold dilution buffer-exchanges, the purified c-KIT was concentrated to 10.6 mg/mL with a total volume of 1.68 mL (17.8 mg purified c-KIT). The purified protein had the correct molecular mass as determined by mass spectrograph (MS) analysis (38,705 expected and 38,700 observed), was monomeric by analytical size-exclusion chromatography (SEC) and exhibited a major band by both isoelectric focusing (IEF) and by sodium-dodecyl-sulfate polyacrylamide gel electrophoresis (SDS-PAGE) analyses.

Example 2

Crystallization of c-KIT

This example describes the crystallization of c-KIT. It is noted that the precise crystallization conditions used may be further varied, for example by performing a fine screen based on these crystallization conditions.

c-KIT protein samples (corresponding to residues 32-365 of SEQ. ID No. 3) were used to obtain protein crystals after an extensive and broad screen of conditions, followed by a fine screen of crystallization conditions. Diffraction quality crystals were grown in 100 nL sitting droplets using the vapor diffusion method. 50 nL comprising the c-KIT-ATP complex (10.6 mg/mL) was mixed with 50 nL from a reservoir solution (100 µL) comprising: 13% PEG 8000; and 0.1M HEPES buffer pH=7.0. The resulting solution was incubated at 20° C. Crystals typically appeared after 3-5 days and grew to a maximum size within 7-10 days. Single crystals were transferred, briefly, into a cryoprotecting solution containing the reservoir solution supplemented with 25% v/v ethylene glycol. Crystals were then flash frozen by immersion in liquid nitrogen and then stored under liquid nitrogen. A crystal of autoinhibited c-KIT produced as described is illustrated in FIG. 2.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, papers, and books cited in this application are incorporated herein in their entirety.

We claim:

1. A composition comprising a c-KIT tyrosine kinase (c-KIT) protein in crystalline form wherein the protein consists of SEQ ID NO:3, and wherein the protein crystal has a crystal lattice in a $P2_12_12$ space group and unit cell dimensions, +/−5%, of a=44.489 Å b=77.277 Å and c=94.701 Å, $\alpha=\beta=\gamma=90$.

2. A composition according to claim 1 wherein the protein crystal diffracts X-rays for a determination of structure coordinates to a resolution less than 3.0 Angstroms.

3. A method for forming a crystal of a c-KIT tyrosine kinase (c-KIT) protein comprising:
   forming a crystallization volume comprising a precipitant solution and a protein that consists of SEQ ID NO:3, and wherein the protein crystal has a crystal lattice in a $P2_12_12$ space group and unit cell dimensions, +/−5%, of a=44.489 Å b=77.277 Å and c=94.701 Å, $\alpha=\beta=\gamma=90$; and
   storing the crystallization volume under conditions suitable for crystal formation until a crystal is formed.

4. A method according to claim 3 wherein the protein crystal diffracts X-rays for a determination of structure coordinates to a resolution less than 3.0 Angstroms.

5. A non-crystalline protein consisting of SEQ ID NO:3.

6. An isolated noncrystalline protein consisting of residues 544-693 and 753-935 of SEQ ID NO:1.

7. The protein according to claim 6 where the protein is expressed from a nucleic acid molecule that consists of SEQ ID NO:2.

8. A non-crystalline protein consisting of amino acids 544-693 and 753-935 of SEQ ID NO:1.

9. An isolated non-crystalline protein consisting of SEQ ID NO:3.

10. A method for obtaining a three dimensional structure of a c-KIT tyrosine kinase (c-KIT) protein comprising the steps of:
   (a) obtaining a crystal of a protein whose sequence consists of SEQ ID NO:3, wherein the protein crystal has a crystal lattice in a $P2_12_12$ space group and unit cell dimensions, +/−5%, of a=44.489 Å b=77.277 Å and c=94.701 Å, $\alpha=\beta=\gamma=90$;
   (b) using the crystal obtained in step (a) to obtain an x-ray diffraction pattern; and
   (c) solving the three dimensional structure of the protein from the diffraction pattern obtained in step (b), thereby obtaining the three dimensional structure of the protein.

11. A method for identifying a compound that binds to a c-KIT tyrosine kinase (c-KIT) protein comprising the steps of:
   (a) obtaining a crystal of a protein whose sequence consists of SEQ ID NO:3, wherein the protein crystal has a crystal lattice in a $P2_12_12$ space group and unit cell dimensions, +/−5%, of a=44.489 Å b=77.277 Å and c=94.701 Å, $\alpha=\beta=\gamma=90$;
   (b) using the crystal obtained in step (a) to obtain an x-ray diffraction pattern;
   (c) solving the three dimensional structure of the protein from the diffraction pattern obtained in step (b), thereby obtaining the three dimensional structure of the protein; and
   (d) identifying one or more compounds that binds to the protein based on the three dimensional structure.

12. The method according to claim 11, further comprising the step of:
   contacting one or more compounds identified in step (d) with the protein whose sequence consists of SEQ ID NO:3.

13. The method according to claim 12, further comprising the step of:
   measuring an activity of the protein whose sequence consists of SEQ ID NO:3, when the protein is contacted with the one or more compounds.

14. The method according to claim 13, further comprising the step of:
   comparing activities of the protein whose sequence consists of SEQ ID NO:3, when the protein is in the presence of and in the absence of the one or more compounds.

15. The method according to claim 11, further comprising the steps of:
   contacting one or more compounds identified in step (d) with a cell that expresses a protein whose sequence consists of SEQ ID NO:3; and
   detecting whether a phenotype of the cell changes when the one or more compounds are present.

* * * * *